US011136304B2

(12) United States Patent
Bhogle et al.

(10) Patent No.: US 11,136,304 B2
(45) Date of Patent: Oct. 5, 2021

(54) SALTS OF A HETEROCYCLIC COMPOUND AND CRYSTALLINE FORMS, PROCESSES FOR PREPARING, THERAPEUTIC USES, AND PHARMACEUTICAL COMPOSITIONS THEREOF

(71) Applicant: Sunovion Pharmaceuticals Inc., Marlborough, MA (US)

(72) Inventors: Nandkumar Nivritti Bhogle, North Reading, MA (US); Takahiko Hashizuka, Matsubara (JP); Robert Joseph Prytko, Millbury, MA (US); John R. Snoonian, Bolton, MA (US); Harold Scott Wilkinson, Westboro, MA (US); Haitao Zhang, Shrewsbury, MA (US)

(73) Assignee: Sunovion Pharmaceuticals Inc., Marlborough, MA (US)

( * ) Notice: Subject to any disclaimer, the term of this patent is extended or adjusted under 35 U.S.C. 154(b) by 0 days.

(21) Appl. No.: 16/817,749

(22) Filed: Mar. 13, 2020

(65) Prior Publication Data
US 2020/0290987 A1    Sep. 17, 2020

Related U.S. Application Data

(60) Provisional application No. 62/818,256, filed on Mar. 14, 2019.

(51) Int. Cl.
*C07D 311/76* (2006.01)

(52) U.S. Cl.
CPC ........ *C07D 311/76* (2013.01); *C07B 2200/13* (2013.01)

(58) Field of Classification Search
None
See application file for complete search history.

(56) References Cited

U.S. PATENT DOCUMENTS

| | | |
|---|---|---|
| 3,438,995 A | 4/1969 | Faust et al. |
| 3,470,179 A | 9/1969 | Ott |
| 3,536,809 A | 10/1970 | Applezweig |
| 3,549,624 A | 12/1970 | Conover et al. |
| 3,551,427 A | 12/1970 | Sandoz |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,021,451 A | 5/1977 | Dobson et al. |
| 4,021,452 A | 5/1977 | Floyd |
| 4,036,842 A | 7/1977 | Dobson et al. |
| 4,066,648 A | 1/1978 | Oka et al. |
| 4,127,665 A | 11/1978 | Sarges et al. |
| 4,337,343 A | 6/1982 | Maillard et al. |
| 4,351,942 A | 9/1982 | Dobson et al. |
| 4,500,543 A | 2/1985 | Debernardis et al. |
| 4,556,656 A | 12/1985 | McCall |
| 4,904,300 A | 2/1990 | Lutz |
| 4,963,568 A | 10/1990 | Schoenleber et al. |
| 4,994,486 A | 2/1991 | Schoenleber et al. |
| 4,999,359 A | 3/1991 | Vecchietti et al. |
| 5,032,598 A | 7/1991 | Baldwin et al. |
| 5,041,451 A | 8/1991 | Colle et al. |
| 5,059,595 A | 10/1991 | Le Grazie |
| 5,073,543 A | 12/1991 | Marshall et al. |
| 5,109,008 A | 4/1992 | Scopes et al. |
| 5,120,548 A | 6/1992 | McClelland et al. |
| 5,134,127 A | 7/1992 | Stella et al. |
| 5,288,749 A | 2/1994 | Meyer et al. |
| 5,304,657 A | 4/1994 | Toki et al. |
| 5,354,556 A | 10/1994 | Sparks et al. |
| 5,391,556 A | 2/1995 | Heckel et al. |
| 5,393,759 A | 2/1995 | Combourieu et al. |
| 5,464,834 A | 11/1995 | Peligion et al. |
| 5,532,203 A | 7/1996 | Fory et al. |
| 5,532,233 A | 7/1996 | Weber et al. |
| 5,591,767 A | 1/1997 | Mohr et al. |
| 5,621,133 A | 4/1997 | Deninno et al. |
| 5,639,476 A | 6/1997 | Oshlack et al. |
| 5,646,173 A | 7/1997 | Bos et al. |
| 5,656,658 A | 8/1997 | Hammarberg et al. |
| 5,674,533 A | 10/1997 | Santus et al. |
| 5,684,020 A | 11/1997 | Peligion et al. |
| 5,733,566 A | 3/1998 | Lewis |
| 6,031,099 A | 2/2000 | Moltzen et al. |
| 6,235,774 B1 | 5/2001 | Fagrig et al. |
| 6,262,044 B1 | 7/2001 | Moller et al. |
| 6,313,309 B1 | 11/2001 | Baxter et al. |

(Continued)

FOREIGN PATENT DOCUMENTS

| | | |
|---|---|---|
| AU | 2010325925 A1 | 6/2011 |
| AU | 2016200448 A1 | 2/2016 |
| CA | 2031684 | 6/1991 |
| CA | 2323493 | 9/1999 |
| CA | 2787416 A1 | 6/2011 |
| CN | 1300291 A | 6/2001 |
| CN | 101228121 A | 7/2008 |
| CN | 101468986 | 7/2009 |
| CN | 101468987 | 7/2009 |
| CN | 101759710 | 6/2010 |
| CN | 102731574 | 10/2012 |

(Continued)

OTHER PUBLICATIONS

Morissette et al., Advanced Drug Delivery Reviews, 56, pp. 275-300 (Year: 2004).*

(Continued)

*Primary Examiner* — Zinna Northington Davis
(74) *Attorney, Agent, or Firm* — Heslin Rothenberg Farley & Mesiti P.C.

(57) ABSTRACT

The present disclosure relates to salts of (R)-1-(8-fluoroisochroman-1-yl)-N-methylmethanamine, crystalline forms thereof, and methods of preparation thereof, which are useful in the treatment of CNS disorders.

22 Claims, 47 Drawing Sheets

(56) References Cited

U.S. PATENT DOCUMENTS

| | | | |
|---|---|---|---|
| 6,436,943 B1 | 8/2002 | Stoltefuss et al. | |
| 6,503,913 B1 | 1/2003 | Goldmann et al. | |
| 7,019,026 B1 | 3/2006 | Andersen et al. | |
| 7,282,499 B2 | 10/2007 | Arjona et al. | |
| 7,297,704 B2 | 11/2007 | Sabb et al. | |
| 7,414,068 B2 | 8/2008 | Lim et al. | |
| 7,544,717 B2 | 6/2009 | Hom et al. | |
| 7,745,462 B2 | 6/2010 | Fairhurst et al. | |
| 7,884,109 B2 | 2/2011 | Ohlmeyer et al. | |
| 8,227,625 B2 | 7/2012 | Corbera-Arjona et al. | |
| 8,710,245 B2 | 4/2014 | Shao et al. | |
| 9,216,975 B2 | 12/2015 | Napoletano et al. | |
| 10,196,403 B2 * | 2/2019 | Hanania | C07D 313/08 |
| 10,336,732 B2 | 7/2019 | Xie et al. | |
| 2003/0073687 A1 | 4/2003 | Bebbington et al. | |
| 2003/0149057 A1 | 8/2003 | Want et al. | |
| 2004/0180883 A1 | 9/2004 | Gilmore et al. | |
| 2004/0220402 A1 | 11/2004 | Chow et al. | |
| 2005/0032873 A1 | 2/2005 | Hatzenbuhler et al. | |
| 2005/0075366 A1 | 4/2005 | Heidelbaugh et al. | |
| 2005/0187281 A1 | 8/2005 | Hinze et al. | |
| 2005/0239832 A1 | 10/2005 | John et al. | |
| 2005/0267199 A1 | 12/2005 | Hom et al. | |
| 2006/0047127 A1 | 3/2006 | Arjona | |
| 2006/0148872 A1 | 7/2006 | Chow et al. | |
| 2006/0258714 A1 | 11/2006 | Heffernan et al. | |
| 2007/0032481 A1 | 2/2007 | Dvorak et al. | |
| 2007/0072926 A1 | 3/2007 | Chow et al. | |
| 2007/0185144 A1 | 8/2007 | Zhong et al. | |
| 2008/0081910 A1 | 4/2008 | Saab et al. | |
| 2008/0113961 A1 | 5/2008 | Nishi et al. | |
| 2008/0255239 A1 | 10/2008 | Chow et al. | |
| 2008/0306082 A1 | 12/2008 | Dahnke et al. | |
| 2009/0069305 A1 | 3/2009 | Gaul et al. | |
| 2009/0118283 A1 | 5/2009 | Defert et al. | |
| 2009/0318690 A1 | 12/2009 | Sasaki et al. | |
| 2010/0035887 A1 | 2/2010 | Ricciardi | |
| 2010/0178299 A1 | 7/2010 | Sitkovsky et al. | |
| 2010/0197714 A1 | 8/2010 | Wunsch et al. | |
| 2012/0171199 A1 | 7/2012 | Dobson et al. | |
| 2012/0295881 A1 | 11/2012 | Lange et al. | |
| 2013/0109677 A1 | 5/2013 | Shao et al. | |
| 2014/0256712 A1 | 9/2014 | Shao et al. | |
| 2015/0031709 A1 | 1/2015 | Campbell et al. | |
| 2016/0083399 A1 | 3/2016 | Shao et al. | |
| 2016/0264597 A1 | 9/2016 | Chytil et al. | |
| 2017/0001987 A1 | 1/2017 | Xie et al. | |
| 2018/0028492 A1 | 2/2018 | Powel et al. | |
| 2018/0030064 A1 | 2/2018 | Xie et al. | |
| 2018/0057506 A1 | 3/2018 | Chytil et al. | |
| 2018/0093974 A1 | 4/2018 | Xie et al. | |
| 2018/0118727 A1 | 5/2018 | Campbell et al. | |
| 2019/0038594 A1 | 2/2019 | Bowen et al. | |

FOREIGN PATENT DOCUMENTS

| | | |
|---|---|---|
| CN | 104193761 A | 12/2014 |
| DE | 2624693 | 7/1977 |
| DE | 3827727 | 2/1990 |
| DE | 4104257 | 8/1992 |
| EP | 0021940 | 1/1981 |
| EP | 333427 A1 | 9/1989 |
| EP | 03589557 | 3/1990 |
| EP | 366327 A1 | 5/1990 |
| EP | 368175 | 5/1990 |
| EP | 370732 A2 | 5/1990 |
| EP | 416740 | 3/1991 |
| EP | 0431421 | 6/1991 |
| EP | 431945 A2 | 6/1991 |
| EP | 483647 A1 | 5/1992 |
| EP | 0518805 A1 | 12/1992 |
| EP | 555824 A1 | 8/1993 |
| EP | 574313 A1 | 12/1993 |
| EP | 600836 A2 | 7/1994 |
| EP | 745598 A1 | 12/1996 |
| EP | 1634873 A1 | 3/2006 |
| EP | 1829869 A1 | 9/2007 |
| EP | 1982714 A1 | 10/2008 |
| EP | 1982987 A1 | 10/2008 |
| EP | 2377850 A1 | 10/2011 |
| FR | 2875230 A1 | 3/2017 |
| GB | 984365 | 2/1965 |
| GB | 1552004 | 9/1979 |
| JP | 5283846 | 7/1977 |
| JP | S567772 A | 1/1981 |
| JP | 01006267 | 1/1989 |
| JP | H2243691 | 9/1990 |
| JP | H03163068 B2 | 7/1991 |
| JP | H03223277 B2 | 10/1991 |
| JP | 049367 | 1/1992 |
| JP | H0570453 | 3/1993 |
| JP | 2003261566 A | 9/2003 |
| JP | 2004269449 A | 9/2004 |
| JP | 2005145859 A | 6/2005 |
| JP | 2006117568 A | 5/2006 |
| JP | 2008540369 A | 11/2008 |
| JP | 2014214130 A | 11/2014 |
| JP | 2015227348 A | 12/2015 |
| MX | 2012006326 A | 10/2012 |
| RU | 2128649 C1 | 4/1999 |
| SG | 181498 A1 | 7/2012 |
| WO | 9108205 A1 | 6/1991 |
| WO | 9203434 | 3/1992 |
| WO | 9214465 | 9/1992 |
| WO | 9215592 A1 | 9/1992 |
| WO | 9400441 A1 | 1/1994 |
| WO | 9604287 A1 | 2/1996 |
| WO | 9638435 | 12/1996 |
| WO | 9901437 | 1/1999 |
| WO | 9946237 A1 | 9/1999 |
| WO | 9946267 A1 | 9/1999 |
| WO | 0000487 | 1/2000 |
| WO | 2000023445 | 4/2000 |
| WO | 2000035915 | 6/2000 |
| WO | 2000043397 | 7/2000 |
| WO | 2000068230 | 11/2000 |
| WO | 2000078742 | 12/2000 |
| WO | 200119831 A1 | 3/2001 |
| WO | 2001017516 | 3/2001 |
| WO | 0132610 | 5/2001 |
| WO | 0132655 | 5/2001 |
| WO | 200132610 A1 | 5/2001 |
| WO | 200132655 A1 | 5/2001 |
| WO | 0162233 | 8/2001 |
| WO | 0172745 | 10/2001 |
| WO | 2002012189 | 2/2002 |
| WO | 2002022614 | 3/2002 |
| WO | 2002066443 A2 | 8/2002 |
| WO | 0180893 | 10/2002 |
| WO | 02083667 | 10/2002 |
| WO | 2002102387 A1 | 12/2002 |
| WO | 2003006455 A1 | 1/2003 |
| WO | 2003035065 A1 | 5/2003 |
| WO | 2003092374 | 11/2003 |
| WO | 2004004726 A1 | 1/2004 |
| WO | 2004035812 A2 | 4/2004 |
| WO | 2004066912 A2 | 8/2004 |
| WO | 2004078723 A1 | 9/2004 |
| WO | 2004082687 A1 | 9/2004 |
| WO | 2004087680 A1 | 10/2004 |
| WO | 2004089913 A1 | 10/2004 |
| WO | 2004112719 A1 | 12/2004 |
| WO | 2005035518 A1 | 4/2005 |
| WO | 2005072412 A2 | 8/2005 |
| WO | 2005073236 A2 | 8/2005 |
| WO | 2005079800 A1 | 9/2005 |
| WO | 2005087779 A1 | 9/2005 |
| WO | 2005111025 A1 | 11/2005 |
| WO | 2006014135 A1 | 2/2006 |
| WO | 2006014136 A1 | 2/2006 |
| WO | 2006015259 A2 | 2/2006 |
| WO | 2006030124 | 3/2006 |
| WO | 2006053274 A2 | 5/2006 |
| WO | 2006066172 | 6/2006 |

(56) References Cited

FOREIGN PATENT DOCUMENTS

| | | |
|---|---|---|
| WO | 2006089053 | 8/2006 |
| WO | 2006117305 | 11/2006 |
| WO | 2007001939 A1 | 1/2007 |
| WO | 2007002681 A2 | 1/2007 |
| WO | 2007006546 A1 | 1/2007 |
| WO | 2007095586 A2 | 8/2007 |
| WO | 2007102999 A2 | 9/2007 |
| WO | 2007120594 A1 | 10/2007 |
| WO | 2007126041 A1 | 11/2007 |
| WO | 2008011560 | 1/2008 |
| WO | 2008042422 A2 | 4/2008 |
| WO | 2008048981 A2 | 4/2008 |
| WO | 2008058342 A1 | 5/2008 |
| WO | 2008119689 A1 | 10/2008 |
| WO | 2008125348 | 10/2008 |
| WO | 2008155132 A1 | 12/2008 |
| WO | 2009009550 A1 | 1/2009 |
| WO | 2009057974 A2 | 5/2009 |
| WO | 2009067202 A1 | 5/2009 |
| WO | 2009068467 A1 | 6/2009 |
| WO | 2009072621 A1 | 6/2009 |
| WO | 2009085256 A1 | 7/2009 |
| WO | 2010053583 A2 | 5/2010 |
| WO | 2010090716 | 8/2010 |
| WO | 2010092180 A1 | 8/2010 |
| WO | 2010092181 A1 | 8/2010 |
| WO | 2011017389 | 2/2011 |
| WO | 2011036889 A1 | 3/2011 |
| WO | 2011060035 A1 | 5/2011 |
| WO | 2011060217 A1 | 5/2011 |
| WO | 2011069063 A2 | 6/2011 |
| WO | 2011081205 A1 | 7/2011 |
| WO | 2011133729 A2 | 10/2011 |
| WO | 2012020133 A1 | 2/2012 |
| WO | 2012122340 A1 | 9/2012 |
| WO | 2013010453 A1 | 1/2013 |
| WO | 2013067248 A1 | 5/2013 |
| WO | 2013119895 | 8/2013 |
| WO | 2013192346 A1 | 12/2013 |
| WO | 2014078454 | 5/2014 |
| WO | 2014106238 A1 | 7/2014 |
| WO | 2006066950 A2 | 6/2016 |
| WO | 2018023072 A2 | 2/2018 |
| WO | 2011094740 | 8/2018 |
| ZA | 9102744 A | 2/1992 |

OTHER PUBLICATIONS

Shklyaeva et al. "2-Amino-6-(3,4-ethylenedioxythiophen-2-yl)-4-(2-thienyl)-pyrimidine: Synthesis and Properties", Russian Journal of Organic Chemistry, 46(6), pp. 938-940. 2010.
Sridhar et al. "Synthesis and Anticancer Activity of Some Novel Pyrimidine Derivatives", International Journal of Pharmaceutical Sciences and Research, 2(10), pp. 2562-2565. 2011.
Stanetty et al. "Heterocyclische Spiroverbindungen Spiroverbindungen: Spiro [benzo[b]thiophen-4(5H),3'-pyrrolidine]", Arch. Pharm., 317, pp. 168-176 with English Abstract. 1984.
US Food and Drug Administration, "Highlights of Prescribing Information: Abilify", FDA Label, 84 pages. Dec. 2014.
Michaeljfox.org [online] "Parkinson's Disease" retrieved on Dec. 28, 2018 from URL <https://www.michaeljfox.org/understanding-parkinsons/living-with-pd/topic.php?causes>, 5 pages. May 2007.
Toffano et al. "Asymmetric Routes Towards Polyfunctionalized Pyrrolidines: Application to the Synthesis of Alkaloid Analogues", Tetrahedron: Asymmetry, 14, pp. 3365-3370. 2003.
Torrado et al. "Novel Selective and Potent 5-HT Reuptake Inhibitors with 5-HT1D Antagonist Activity: Chemistry and Pharmacological Evaluation of a Series of Thienopyran Derivatives", Bioorganic & Medicinal Chemistry, 12(20), pp. 5277-5295. 2004.
Trehan, "A New Synthesis of 13-aza-18-nor-17-oxo-A-nor-3-thiaestra-1,5(10),9(11)-triene", Retrieved from STN Database Accession No. 1986:225089 & Indian Journal of Chemistry, Section 6: Organic Chemistry Including Medicinal Chemistry 24B(6), pp. 659-661. 1985.
Trehan "Synthesis of 2,3,13-Triaza-18-nor-17-oxo-3-phenyl-A-nor-estra-1,5(10),9(11)-triene & 2,3,13-Trizaz-7,7-dimethyl-18-nor-17-oxo-3-phenyl-A-nor-estra-1 ,5(10),9(11)-triene", Indian Journal of Chemistry, 19B, pp. 243-245. 1980.
UPMC.com [online], "Find the Best Epilepsy Treatment for You", retrieved on Mar. 16, 2019 from URL <https://share.upmc.com/2015/05/epilepsy-treatment/>, 5 pages. May 23, 2015.
Van Der Stoel et al. "Di-TT-methane Rearrangement of 4-Heteroaryl-1,4(or 3,4)-dihydropyrimidines", Journal of the Chemistry Society, Perkin Transactions 1, pp. 2393-2396. Nov. 2, 1978.
Vecchietti et al. "(1S)-1-(Aminomethyl)-2-(arylacety1)-1,2,3,4-tetrahydroisoquinoline and Heterocycle-Condensed Tetrahydropyridine Derivatives: Members of a Novel Class of Very Potent K Opioid Analgesics", Journal of Medicinal Chemistry, 34(8), pp. 2624-2633. 1991.
Walker et al. "Sigma Receptors: Biology and Function", Pharmacological Reviews, 42(4), pp. 355-402. 1990.
Weis et al. "The Crystal and Molecular Structure of 4,6,6-trimethyl-2-phenyl-1,6-dihydropyrimidine", Heterocycles, 19 (3), 6 pages. 1982.
Werber et al. "The Beneficial Effect of Cholinesterase Inhibitors on Patients Suffering from Parkinson's Disease and Dementia", J Neural Transm., 108, pp. 1319-1325. Jun. 27, 2001.
Wilkinson et al. "Cholinesterase Inhibitors Used in the Treatment of Alzheimer's Disease", Drug Aging, 21(7), pp. 453-478. 2004.
Williams et al. "Emerging Molecular Approaches to Pain Therapy", Journal of Medicinal Chemistry, 42(9), pp. 1481-1500. 1999.
Winhusen et al. "A Placebo-Controlled Screening Trial of Tiagabine, Sertraline and Donepezil as Cocaine Dependence Treatments", Addiction, 100(suppl.1) pp. 68-77. 2005.
Xi et al. "Preparation of Partially Substituted 1-Halo-and 1,4-Dihalo-1,3-Dienes via Reagent-Controlled Desilyation of Halogenated 1,3-Dienes", Journal of Organic Chemistry, 71, pp. 3154-3158. 2006.
CAS Registry No. 1071058-54-2, 4 pages. Nov. 6, 2008.
CAS Registry No. 40196-93-8, 2 pages. Nov. 16, 1984.
CAS Registry No. 40196-92-7, 2 pages. Nov. 16, 1984.
CAS Registry No. 1027834-86-1, 4 pages. Jun. 13, 2008.
Datta et al. "Studies in Sulphur Heterocycles. Part 5. Further Use of 6,7-Dihydrobenzo[b]thiophen-4[5H]-one in the Synthesis of Substituted Benzo[b]thiophene Derivatives", J. Chem Research (S), pp. 72-73. 1988.
Davis et al. "Benzothiophene Containing Rho Kinase Inhibitors: Efficacy in an Animal Model of Glaucoma", Bioorganic & Medicinal Chemistry Letters, 20(11), pp. 3361-3366. Jun. 1, 2010.
Devani et al. "Synthesis of 2-Aminothiophenes & Trieno[2,3-d]pyrimidines", Indian Journal of Chemistry, 14B, pp. 357-360. May 1976.
Frohlich et al. "A Novel Synthesis of 3,3-(Spiro)Substituted Azetidines", Heterocycles, 37(3), pp. 1879-1891. 1994.
Google.com [online] "Parkinson's Disease—Symptoms, Diagnosis and Treatment", retrieved on Dec. 28, 2018 from URL <https:www.google.com/search?q=Parkinson+disease+treatment&source=INT&tbs+cdr%3A1%2Ccd_max%3A2%2F2012&tbm=>, 2 pages. Jan. 22, 2006.
Hopkinsmedicine.org [online] "Treatment For Tourette Syndrome: Johns Hopkins Pediatric Neurology", retrieved on Dec. 28, 2018 from URL <https://www.hopkinsmedicine.org/neurology_neurosurgery/centers_clinics/pediatric-neurology/conditions/tourettes_syndrome/treatment.html>, 1 page. Apr. 2006.
Mayoclinic.org [online] "Fibromyalgia Treatment: Is Neurontin Effective?", retrieved on Oct. 18, 2019 from URL <https://www.mayoclinic.org/diseases-conditions/fibromyalgia/expert-answers/fibromyalgia-treatment/faq-20058273>, 3 pages. Jul. 2009.
Debernardis et al. "Conformationally Defined Adrenergic Agents. 4. 1-(Aminomethyl)phthalans: Synthesis and Pharmacological Consequences of the Phtalan Ring Oxygen Atom", Journal of Medicinal Chemistry, 30, pp. 178-184. 1987.

(56) References Cited

OTHER PUBLICATIONS

Dehaven-Hudkins et al. "Characterization of the Binding of [3H](+)pentazocine to σ Recognition Sites in Guinea Pig Brain", European Journal of Pharmacology-Molecular Pharmacology Section 227, pp. 371-378. 1992.
Deninno et al. "Synthesis and Dopaminergic Activity of 3-Substituted 1-(Aminomethyl)-3,4-dihydro-5,6-dihydroxy-1H-2-benzopyrans: Characterization of an Auxiliary Binding Region in the D1 Receptor", Jounral of Medicinal Chemistry, 34, pp. 2561-2569. 1991.
Disabled World Towards Tomorrow, "Neurological Disorders: Types, Research & Treatment" URL: https://www/disabled-world.com/health/neurology, 5 pages. Nov. 1, 2017.
Dobson et al. "Pyrano Hetercycles I. The Syntheses of Isochromans and the Novel Thieno[3,2-c]pyran, Benzothieno [3,2-c]pyran, and Pyrano[4,3-b]benzofuran Systems", Journal of Heterocyclic Chemistry, 12(3), pp. 591-594. 1975.
Ellis "Affective Disorders (Mood Disorders)", Healthline Part 1 of 7 Overview; URL: http://www.healthline.com/health/affective-disorders, 5 pages. Downloaded Jul. 25, 2015.
Emedicine Health, "Brain Cancer: Get Facts on Treatment, Causes and Symptoms", URL: https://www.emedicinehealth.com/brain_cancer/article_em.htm?pf=2; 15 pages. Downloaded 2015.
EP Application No. 13747266.8, Communication Pursuant to Article 94(63) EPC, dated Dec. 21, 2017.
EP Application No. 13747266.8, Partial Supplementary European Search Report, 11 pages, dated Aug. 14, 2015.
EP Application No. 10835185.9. Extended European Search Report, 15 pages, dated Apr. 4, 2013.
EP Application No. 13747266.8, Communication Pursuant to Article 94(3), dated Nov. 18, 2016.
Gaur et al. "CoMFA and CoMSIA Studies on a set of Benzyl Piperazines, Piperadines, Pyrazinopyridoindoles, Pyrazinoisoquinolines and Semi Rigid Analogs of Diphenydramine", Medicinal Chemistry Research, 13(8-9), pp. 746-757. 2004.
Ghaemi et al. "Does Olanzapine have Antidepressant Properies? A Retrospective Preliminary Study", Bipolar Disorders, 2, pp. 196-199. 2000.
Girke "Elektrophile AromatischeSubstitutionsreaktionen Mit Protonierten 1 ,3-Diazinen II. Darstellung und Eigenschaften 4-arylsubstituierter 3,4-Dichrochinazolin-Derivate", European Journal of Inorganic Chemistry, 112(4), pp. 1348-1358. English Abstract and Machine Translation of entire reference, 24 pages] 1979.
Gleason et al. "Blockade of Phencyclidine-Induced Hyperlocomtion by Olanzapine, Clozapine and Serotonin Receptor Subtype Selective Antagonists in Mice", Psychopharmacology, 129, pp. 79-84. 1997.
Gould "Salt Selection for Basic Drugs", International Journal of Pharmaceutics, 33, pp. 201-217. 1986.
Grilliot et al. "Guanidinium Carboxylates: Preparation of 3-Carboxyoctahydro-9aH-Pyrimidin-9a-Ylium Chloride", Heterocycles, 39(2), pp. 435-438. 1994.
Gronowitz et al. "The Reaction of 5-Bromo-and 2-Bromopyrimidine with Organolithium Compounds", Acta Chemica Scandinavica 19(7), pp. 1741-1748. 1965.
Hanner et al. "Purification, Molecular Cloning, and Expression of the Mammalian Sigma1-Binding Site", Proc. Natl. Aca. Sci. 93, pp. 8072-8077. 1996.
Hayakawa et al. "Addition Reactions of (Phenylsulfonyl)propadiene with 1-Pryrrolidinyl Enamines of Cyclic Ketones: Syntheses and Reactions of 1,3-Dienes Possessing an Allyl Sulfone Moiety", Journal of Organic Chemistry, 51, pp. 5100-5105. 1986.
Hejl et al. "Prepulse Inhibition in Patients with Alzheimer's Disease", Neruobiology of Aging, 25, pp. 1045-1050. 2004.
Horig et al. "From Bench to Clinic and Back: Perspective on the 1st IQPC Translational Research Conference" Journal of Translational Medicine, 2:44, 8 pages. 2004.
Huang et al. "Thiation Reactions of Some Active Carbonyl Compounds with Sulfur Transfer Reagents", The Journal of Organic Chemistry, 52(2), pp. 169-172. 1987.

Ingebrigsten et al. "Palladium-Catalysed Synthesis of Pyrimidines", Heterocycles, 65(11), pp. 2593-2603. 2005.
International Search Report and Written Opinion in International Application No. PCT/US2010/058884, dated Aug. 25, 2011.
International Preliminary Report on Patentability in International Application No. PCT/US2017/044511, 7 pages, dated Jan. 29, 2019.
International Prelminary Report on Patentability in International Application No. PCT/US2017/044517, 5 pages, dated Jan. 29, 2019.
International Preliminary Report on Patentability in International Application No. PCT/US2013/025260, 8 pages, dated Aug. 12, 2014.
International Search Report and Written Opinion in International Application No. PCT/US2013/025260, 10 pages, dated Apr. 17, 2013.
International Search Report and Written Opinion in International Application No. PCT/US2017/044511, 11 pages, dated Dec. 21, 2017.
International Search Report and Written Opinion in International Application No. PCT/US2017/044517, 5 pages, dated Jan. 11, 2018.
International Search Report and Written Opinion in International Application No. PCT/US2018/044854, 21 pages, dated Apr. 10, 2018.
Ito et al. "A Mediium-Term Rat Live Bioassy for Rapid in vivo Detection of Carcinogenic Potential of Chemicals", Cancer Science, 94(1), pp. 3-8. 2003.
International Search Report and Written Opinion in International Application No. PCT/US2016/017527, 8 pages, dated Apr. 13, 2016.
International Search Report and Written Opinion in International Application No. PCT/US2016/017539, 8 pages, dated May 2, 2016.
Kumar et al. "Phenethylamine in a Semi-Rigid Framework: Synthesis & Biological Activity of N-Substituted I-Aminomethyl-5,6-& 6,7-dimethoxyisochromans", Indian Journal of Chemistry 16B, pp. 793-796. 1978.
Jacobs et al. "1-Imidizolyl(alkyl)-Substituted Di-and Tetrahydroquinolines and Analogues: Syntheses and Evaluation of Dual Inhibitors of Thromboxane A2 Synthase and Aromatase", Journal of Medicinal Chemistry, 43(9), pp. 1841-1851. 2000.
Jaskowska et al. "N-Alkylation of Imides Using Phase Transfer Catalysts Under Solvent-Free Conditions", Journal Heterocyclic Chemistry, 45, pp. 1371-1375. 2008.
Jentsch et al. "The Neuropsychopharmacology of Phencyclidine: From NMDA Receptor Hypofunction to the Dopamine Hypothesis of Schizophrenia" Neuropsychopharmacology, 20(3), pp. 201-225. 1999.
Office Action in JP Application No. 2012-542219, 9 pages, including translation, dated Nov. 21, 2014.
Notice of Reasons for Rejection in JP Application No. 2014-556702 with translation, 10 pages, dated Jul. 19, 2016.
Notice of Reasons for Rejection in JP Application No. 2014-556702, with translation, 5 pages, dated Mar. 14, 2017.
Kapur et al. "NMDA Receptor Antagonists Ketamine and PCP Have Direct Effects on the Dopamine D2 and Serotonin 5-HT2 Receptors-Implications for Models of Schizophrenia" Molecular Psychiatry, 7, pp. 837-844. 2002.
Karran et al. "The Amyloid Cascade Hypothesis for Alzheimer's Disease: An Appraisal for the Development of Therapeutics", Nature, 10, pp. 698-712. 2011.
Katsuki et al. "Excitotoxic Degeneration of Hypthalamic Orexin Neurons in Slice Culture", Neurobiology of Disease, 15, pp. 61-69. 2004.
Korneev et al. CAS STN Abstract, RN 1202851-83-9. 2017.
Kostin et al. "Lack of Hypocretin Attenuates Behavorial Changes Produced by Glutamatergic Activation of hte Perifornical-Lateral Hypthalamic Area", Sleep, 37(5), pp. 1011-1020. 2014.
Krogsgaard-Larsen et al. Textbook of Drug Design and Discovery, Madsen, U (Ed.). Third Edition, London and New York, Taylor & Francis. 2002.
Kumar et al. "Catecholamines in a Semi-Rigid Framework: Synthesis & Biological Activity of N-Substituted I-Aminomethyl-5,6-& 6,7-dihydroxyisochromans", Indian Journal of Chemistry 26B, pp. 47-51. 1987.
The List of Search Results of CAPLUS, 102 pages. Apr. 6, 2016.

(56) References Cited

OTHER PUBLICATIONS

Extended European Search Report in EP Application No. 17835385.0, dated Feb. 26, 2020.
Bonner et al. "Mapping the Catechol Binding Site in Dopamine D1 Receptors: Synthesis and Evaluation of Two Parallel Series of Bicyclic Dopamine Analogues", Chemmedchem, vol. 6, No. 6, pp. 1024-1040. Jun. 6, 2011.
Niozawa et al. "Benzopyran Derivatives as Inhibitors for the Formation of Active Oxygen", Chemical Abstract Service, Database Accession No. 1989:553630. 1989.
Ahmad et al. "A Convenient Entry into the Rhoeadan Skeleton. Total Synthesis of (±)-cis-alpinigenine", Canadian Journal of Chemistry, 60(12):2678-2686. 1982.
Adaa.org [Online], "Treatment" retrieved on Mar. 16, 2019 from URL <https://adaa.org/understanding-anxiety/depression/treatment>, 5 pages. Jan. 29, 2009.
Akdemir et al. "Identification of Novel A7 Nicotinic Receptor Ligands by in Silico Screening Against the Crystal Structure of a Chimeric A7 Receptor Ligand Binding Domain", Bioorganic and Medicinal Chemistry, 20: pp. 5992-6002. 2012.
American Chemical Society, STN Database RN 63463-05-8. Nov. 16, 1984.
Answer Summary from the search of CAPLUS. 29 pages. Apr. 21, 2016.
Antosz et al. The Structure and Chemistry of Actinobolin:, Journal of American Chemical Society, 92 (16):4933-4942. 1970.
Examination Report No. 2 in AU Application No. 2013216935, dated Aug. 1, 2017.
Bakshi et al. "Antagonism of Phencyclidine-Induced Deficits in Prepulse Inhibition by the Putative Atypical Antipsychotic Olanzapine", Psychopharamcology, 122(2), pp. 198-201. 1995.
Berardi et al. "4-(Tetralin-1-yl)and-4-(Naphthalen-lyl)alkyl Derivatives of 1-Cyclohexylpiperazine as σ Receptor Ligands with Agonists σ2 Activity", Journal of Medicinal Chemistry, American Chemical Society, 47(9):2308-2317. 2004.
Berardi et al. "A Multireceptorial Binding Reinvestigation on an Extended Class of a Ligands: N-[ω-(Indan-1-yl and Tetralin-1-yl)alkyl] Derivatives of 3,3-Dimethylpiperdine Reveal High Affinities Towards σ1 and EBP sites", Bioorganic & Medicinal Chemistry, 9(5), pp. 1325-1335. 2001.
Berge et al. "Pharmaceuticals Salts" Journal of Pharmaceutical Sciences, 66(1), 1-19. 1977.
Bianchi et al. "Model Studies Towards Stephaoxocanes: Construction of the 2-oxo-4azaphenalene Core of Stephaoxocanidine and Eletefine", European Journal of Organic Chemistry, 24, pp. 4731-4736. 2003.
Boger et al. "Thermal Cycloaddition of 1,3,5-Triazine with Enamines: Regiospecific Pyrimidine Annulation", Journal of Organic Chemistry, 47, pp. 2673-2675. 1982.
Bohme et al. "Homoisochroman-Derivative Mit Basischer Seitenkette in 1-Stellung", Archiv der Pharmazie 306, pp. 948-953. English Abstract. 1973.
Bohme et al. "The Aminomethylation of 1-Cyano-lsochromane and 1-Cyano-lsothlochromane", Arch Pharm (Weinheim), 307(4), pp. 287-290, with English Translation. 1974.
CAPLUS Search Results, 19 Pages. Apr. 21, 2016.
CAS Database Registry 444792-99-8 (XP-002742897), 1 page. Aug. 24, 2002.
CAS Database Registry 444793-00-4 (XP-002742898), 1 page. Aug. 24, 2002.
CAS Database Registry 444793-01-5 (XP-002742896), 1 page. Aug. 24, 2002.
CAS Database Registry 46490-93-1 (XP-002742899), 1 page. Nov. 16, 1984.
CAS Database Registry 738532-48-4 (XP-002742900), 1 page. Sep. 3, 2004.
CAS Database Registry Accession No. 1022058-43-0. May 23, 2008.
CAS Database Registry Accession No. 1022339-80-5. May 25, 2008.
CAS Database Registry Accession No. 1022468-83-2. May 25, 2008.
CAS Database Registry Accession No. 1022813-67-7. May 27, 2008.
CAS Database Registry Accession No. 1023480-64-9. May 29, 2008.
CAS Database Registry Accession No. 1024262-27-8. Jun. 1, 2008.
CAS Database Registry Accession No. 359452-84-9. Sep. 28, 2001.
CAS Database Registry Accession No. 359452-83-8. Sep. 28, 2001.
CAS Database Registry Accession Nos. 131022-75-8, 1310059-007-4, 1310059-06-3, 1310059-08-5 and 1310059-09-6 as cited in the Japanese Office Action for Japanese Application No. 2014-556702, dated Mar 14, 2017.
Dammacco et al. "Lithiation of N-Alkyl-(o-totyl)aziridine: Stereoselective Synthesis of Isochromans", Journal of Organic Chemistry, 74, pp. 6319-6322, with supplemental material pp. S1-S34. 2009.
CAS Database Registry Accession No. 340968-07-2. Jun. 14, 2001.
CAS Database Registry Accession No. 359452-60-1. Sep. 28, 2001.
CAS Database Registry No. 1027177-28-1. Jun. 11, 2008.
CAS Database Registry No. 1935196-69-2. Jun. 20, 2016.
CAS Registry No. 724648-33-5; STN entry date Sep. 10, 2004; Chemical Name: Quinazoline, 4-benzo[b]thien-2-yl-1,4-dihydro- (cited Aug. 1, 2017, obtained from https://sscifinder.cas.org on Aug. 10, 2017). Sep. 10, 2004.
CAS Registry No. 736880-30-1; STN entry date Sep. 1, 2004; Chemical name: Quinazoline, 4-benzo[b]thien-2-yl-1,4-dihydro-2-methyl-(cited Aug. 1, 2017, obtained from https://scifinder.cas.org on Aug. 10, 2017). Sep. 1, 2004.
CAS Registry No. 775528-08-0; STN entry date Nov. 7, 2004; Chemical name: Quinazoline, 4-benzo[b]thien-2-yl-1,4-dihydro-methyl (cited Aug. 1, 2017, obtained from https://scifindercas.org on Aug. 10, 2017). Nov. 7, 2004.
CAS Registry No. 790156-85-3; STN entry date Nov. 28, 2004; Chemical Name: Quinazoline, 4-benzo[b]thien-2-yl-1,4-dihydro- (cited Aug. 1, 2017, obtained from https://scifinder.cas.org on Aug. 10, 2017). Nov. 28, 2004.
CAS Registry No. 933704-21-3. Apr. 30, 2007.
CAS Registry No. 1541037-08-04. Feb. 10, 2014.
CDC.gov, "Treatment of ADHD" [retrieved Mar. 16, 2019] retrieved from URL <https://www.cdc.gov/ncbddd/adhd/treatment.html>, 8 pages. Jan. 30, 2016.
Chemical Abstracts STN Registry datadase, record for RN 1784628-34-7. Jun. 19, 2015.
Chihara et al. "Preparation of Benzothiiophene Derivatives as Blood Platelet Aggregation Inhibitors", Retrieved from STN Database Accession No. 1992:128652 and JP03223277a, Yoshitomi Pharmaceutical Industries Ltd. Oct. 2, 1991.
CN Office Action in Application No. 20141033332.1 with translation, dated Nov. 2, 2015.
Corbera et al. "A Medicinal-Chemistry-Guided Approach to Selective and Druglike Sigma 1 Ligands", ChemMedChem, 1(1), pp. 140-154. 2006.
Langa et al. "Generation and Phenotypic Analsis of Sigma Receptor Type 1 (σ1) Knockout Mice", European Journal of Neuroscience, 18, pp. 2188-2196. 2003.
Lima et al. "Bioisosterism: A Useful Strategy for Molecular Modification and Drug Design", Current Medicinal Chemistry, 12, pp. 23-49. 2005.
Lindvall et al. "Stem Cells for the Treatment of Neurological Disorders", Nature, 441, pp. 1094-1096. 2006.
Lowry et al. "Protein Measurement with the Folin Phenol Reagent", Journal Biochemistry, 193, p. 265-275. 1951.
Macchia et al. "Conformationally Restrained Analogs of Sympathomimetic Catecholamines, Synthesis, Conformational Analysis, and Adrenergic Activity of Isochroman Derivatives", Journal of Medicinal Chemistry, 36, pp. 3077-3086. 1993.
Maier et al. "Novel Spiropiperdines as Highly Potent and Subtype Selective σ-Receptor Ligands. Part 1", Journal of Medicinal Chemistry, 45, pp. 438-448. 2002.
Maier et al. "Novel σ Receptor Ligands, Part 2. SAR of Spiro[[2]benxopyran-1,4-piperdines] and Spiro [[2]benzofuran-1,4'-piperdines] with Carbon Substituents in Position 3", Journal Medicinal Chemistry, 45, pp. 4923-4930. 2002.

(56) References Cited

OTHER PUBLICATIONS

Marcus et al. "The Efficacy and Safety of Aripiprazole as Adjunctive Therapy in Major Depressive Disorder. A Second Multicenter, Randomized, Double-Blind, Placebo-Controlled Study", Journal of Clinical Psychopharmacology, 28(2), pp. 156-165. 2008.
Mashkovskiy, Drugs, Moscow, New Wave, LLC, vol. 1, p. 11 with translation, 4 pages total. 2002.
Mayo Clinic Symptoms and Causes, "Seasonal Affective Disorder (SAD)", URL: https://www.mayoclinic.org/diseases-conditions/seasonal-affective-disorders/symptoms-causes; 2 pages. Downloaded 2015.
Mokrosz et al. "Structure-Activity Relationship Studies of CNS Agents. Part 14:3 Structural Requirements for the 5-HT1A and 5-HT2A Receptor of Simple 1-(2-pyrimidinyl)piperazine Derivatives", Pharmazie, 49(H11) 6 pages. 1994.
Moreno et al. "Preclinical Models of Antipsychotic Drug Action", International Journal of Neuropsychopharmacology, 16, pp. 2131-2144. 2013.
Movassaghi et al. "Single-Step Synthesis of Pyrimidine Derivatives", Journal of American Chemical Society, 128, pp. 14254-14255. 2006.
Examination Report in MX Application No. MX/a/2012/006326, 6 pages, with translation, dated Jul. 4, 2013.
Nakashima et al. "Regulation of Folding and Photochromic Reactivity of Terarylenes Through a Host-Guest Interaction", Chem. European Journal, 17, pp. 10951-10957. 2011.
Nemade et al. "Schizophrenia Medication Treatment Options", Retrieved on Mar. 16, 2019 from URL <https://www.mentalhelp.net/articles/schizophrenia-medication-treatment-options/>, 6 pages. Feb. 15, 2006.
Nimh.nih.com [online] "Bipolar Disorder" retrieved on Mar. 16, 2019 from URL <https://www.nimh.nih.gov/health/topics/bipolar-disorder/index/shtml>, 13 pages. Jan. 2016.
Nimh.nih.com [online] "Obsessive-Compulsive Disorder" retrieved on Mar. 16, 2019 from URL <https://www.nimh.nih.gov/health/topics/obsessive-compulsive-disorder-ocd/index.shtml>, 10 pages. Jan. 2016.
Nishimura et al. "Syntheses and Activities of some Bactobolin Derivatives", Jounal of Antibiotics, 45(5), pp. 735-741. 1992.
Nordquist et al. "Effects of Aripiprazole/OPC-14597 on Motor Activity, Pharmacological Models of Psychosis, and Brain Activity in Rats", Neuropharmacology, 54, pp. 405-416. 2008.
First Examination Report in NZ Application No. 600008, 3 pages, dated Mar. 11, 2013.
Examination Report in NZ Application No. 626068, 3 pages, dated Oct. 8, 2015.
Examination Report in NZ Application No. 711802, 5 pages, dated Oct. 8, 2015.
Papillion et al. "Structure-Activity Relationships, Pharmacokinetics and in Vivo Activity of CYP11B2 and CYP11B1 Inhibitors", Journal of Medicinial Chemistry, 58, pp. 4749-4770. 2015.
Pittenger et al. "The NMDA Receptors as a Therapeutic Target in Major Depressive Disorder", CNS & Neurological Disorders—Drug Targets, 6(2), pp. 101-115. 2007.
Pubchem CID 12175079, p. 3 compound, accessed Nov. 13, 2017, 9 pages. Feb. 7, 2007.
Quirion et al. "A Proposal for the Classification of Sigma Binding Sites", Trends in Pharmacology Science, 13, pp. 85-86. 1992.
Quiroz et al. "A Practical Method for the Synthesis of Pyrrolizidine, Indolizidine and Pyrroloazepinolizidine Nucleus", Tetrahedron Letters, 48, pp. 1571-1575. 2007.
Radesca et al. "Synthesis and Receptor Binding of Enantiomeric N-Substituted cis-N-[2-(3,4-Dichlorophenyl)ethyl]-1-(1-pyrrolidinyl) cyclohexylamines as High-Affinity σ Receptor Ligands", Journal of Medicinal Chemistry, 34, pp. 3058-3065. 1991.
Ram et al. "Synthesis & Structure-Activity Relationships of 1-Substituted-Aminomethyl-3-Phenyl/Methyl-1,3-Dihydroisobenzofurans & 4-Substituted-Amino-1-Phenyl/Methylisochromans—A New Class of Antihistaminics", Indian Journal of Chemistry, Section B: Organic Chemistry including Medicinal Chemistry, 23B(12), pp. 1261-1267. 1984.
Ross et al. "α2 Adrenoceptor Agonists as Potential Analgesic Agents. 2. Discovery of 4-(4-Imidazo)-1,3-dimethyl-6,7-dihydrothianaphthene as a High-Affinity Ligand for the α2D Adreneric Receptor", J. Med. Chem., 43, pp. 1423-1426. 2000.
Rekka et al. "Structural Features of Some Diphenhydramine Analogs that Determine the Interaction with Rat Liver Cytochrome P-450", Agents and Actions, 27(1-2), pp. 184-187. 1989.
Ross et al. "Potential Anticancer Agents. XVIII. Synthesis of Substituted 4,5-Trimethylenepyrimidines", Journal of American Chemical Society, 84(12), pp. 3108-3114. 1959.
Sakai et al. "Facile and Efficient Synthesis of Polyfunctionalized Benzofurans: Three-Component Coupling Reactions from an Alkynylsilane, an o-Hydroxybenzaldehyde Derivative, and a Secondary Amine by a Cu(I)-Cu(ll) Cooperative Calatytic System", 49, pp. 3437-3440. 2008.
Salomone et al. "Preparation of Polysubstituted Isochromomanes by Addition of ortho-Lithiated Aryloxiranes to Enaminones", Journal of Organic Chemistry, 78, pp. 11059-11065. 2013.
Saxena et al. "Synthesis of Some Substituted Pyrazinopyridoindoles and 3D QSAR Studies along with Related Compounds: Piperazines, Piperidines, Pyrazinoisoquinolines and Diphenhydramine and its Semi-Rigid Analogs as Antihistamines (H1)" Bioorganic & Medicinal Chemistry 14, pp. 8249-8258. 2006.
Schafer "Failure is an Option: Learning from Unsuccessful Proof-of-Concept Trials", Drug Discovery Today, 13 (21/22), pp. 913-916. 2008.
Schmitz et al. "Hippocampal Neuron Loss Exceeds Amyloid Plaque Load in a Transgenic Mouse Model of Alzheimers Disease", American Journal of Pathology, 164(4), pp. 1495-1502. 2004.
Schow et al. "Novel Sigma Receptor Ligands 2", Bioorganic & Medicinial Chemistry Letters, 3(2), pp. 221-224. 1993.
Written Opinion in SG Application No. 201204089-5, 12 pages, dated Sep. 20, 2013.
Search Report & Written Opinion in SG Application No. 10201401661, 10 pages, dated Jun. 15, 2015.
Snyder et al. "Receptor Mechanisims in Antipsychotic Drug Action: Focus on Sigma Receptors", Journal of Neuropsychiatry, 1(1), pp. 7-15. 1989.
Steliou et al. "Group 14 Metal Assisted Carbon-Sulfur Bond Formation", Journal of Organic Chemistry, 50(24), pp. 4969-4971. 1985.
Strekowski et al. "Synthesis of 2-Chloro-4,6-di(heteroaryl)pyrimidines", Journal of Heterocyclic Chemistry, 27, pp. 1393-1400. 1990.
Swerdlow et al. "Seroquel Restores Sensorimotor Gating in Phencyclidine-Treated Rats", Journal of Pharmacology and Experimetnal Therapeutics, vol. 279, No. 3, pp. 1290-1299. Dec. 1996.
Medicinenet.com [online] "Alzheimer's Disease Treatment, Symptoms, Stages & Life Expectancy", retrieved on Dec. 28, 2018 from URL <https://www.medicinenet.com/alzheimers_disease_causes_stages_and_symptoms/article.htm#alzheimers_disease_medications>, 16 pages. Jul. 2007.
Medlineplus.gov [online] "Symptoms, Diagnosis and Treatment: Alzheimer's Disease", Retrieved Dec. 28, 2018 from URL ,https://medlineplus.gov/magazine/issues/fall10/articles/fall10pg19.html>, 5(3), p. 19. 2010.
Pubchem CID 4878038 accessed Feb. 22, 2019, 12 pages. Sep. 17, 2005.
Pubchem CID 4878041 accessed Feb. 22, 2019, 14 pages. Sep. 17, 2005.
Ghasemi et al. "The Role of NMDA Receptors in the Pathophysiology and Treatment of Mood Disorders", Neuroscience and Biobehavioral Reviews, 47, pp. 336-358. 2014.
Written Opinion of International Application No. PCT/US2020/022642, dated Aug. 5, 2020.
International Search Report of International Application No. PCT/US2020/022642, dated Aug. 5, 2020.
Bastin et al. "Salt Selection and Optimisation Procedures for Pharmaceutical New Chemical Entities", Organic Process Research & Development, vol. 4, pp. 427-435. 2000.
RN 1823425-66-6, 12 compounds, Database Registry Online. Dec. 6, 2015.

(56) References Cited

OTHER PUBLICATIONS

RN 748090-37-1, 5 compounds, Database Registry Online. Sep. 19, 2004.
Pubchem Database Accession No. 13864381. Feb. 8, 2007.
Pubchem Database Accession No. 96583975. Dec. 11, 2015.
Pubchem Database Accession No. 91045524. Mar. 17, 2015.
Pubchem Database Accession No. 15696482. Feb. 12, 2007.
Pubchem Database Accession No. 209070. Aug. 9, 2005.
Pubchem Database Accession No. 23504851. Dec. 6, 2007.

* cited by examiner

SALTS OF A HETEROCYCLIC COMPOUND AND CRYSTALLINE FORMS, PROCESSES FOR PREPARING, THERAPEUTIC USES, AND PHARMACEUTICAL COMPOSITIONS THEREOF

CROSS REFERENCE TO RELATED APPLICATIONS

This application claims priority from U.S. provisional application 62/818,256, filed Mar. 14, 2019, the entire disclosure of which is hereby incorporated herein by reference.

FIELD

This application relates to salts of (R)-1-(8-fluoroisochroman-1-yl)-N-methylmethanamine (Compound 1), and crystalline forms, processes for preparing, therapeutic uses, and pharmaceutical compositions thereof.

BACKGROUND

Central nervous system diseases and disorders affect a wide range of the population with differing severity. Neurological and psychiatric diseases and disorders include major depression, schizophrenia, bipolar disorder, obsessive compulsive disorder (OCD), panic disorder, and posttraumatic stress disorder (PTSD), among others. These diseases and disorders affect a person's thoughts, mood, behavior and social interactions and can significantly impair daily functioning. See, e.g., *Diagnostic and Statistical Manual of Mental Disorders*, 4$^{th}$ Ed., American Psychiatric Association (2000) ("DSM-IV-TR"); *Diagnostic and StatisticalManual of Mental Disorders*, 5$^{th}$ Ed., American Psychiatric Association (2013) ("DSM-5"). Furthermore, neuropsychiatric symptoms such as apathy, depression, anxiety, cognitive impairment, psychosis, aggression, agitation, impulse control and sleep disruption are now recognized as core impairments of neurological diseases and disorders such as Alzheimer's and Parkinson's diseases.

Various drugs are currently being developed for the treatment of CNS disorders. For example, (R)-1-(8-fluoroisochroman-1-yl)-N-methylmethanamine, which is reported in U.S. Pat. No. 10,196,403, the entirety of which is incorporated herein by reference, is useful in the treatment of CNS disorders. There is a need for salts and new forms of (R)-1-(8-fluoroisochroman-1-yl)-N-methylmethanamine for facilitating the manufacture of safe, effective, and high quality drug products.

SUMMARY

Provided herein are salts of (R)-1-(8-fluoroisochroman-1-yl)-N-methylmethanamine and crystalline forms thereof. Compound (R)-1-(8-fluoroisochroman-1-yl)-N-methylmethanamine (Compound 1) has the following structure:

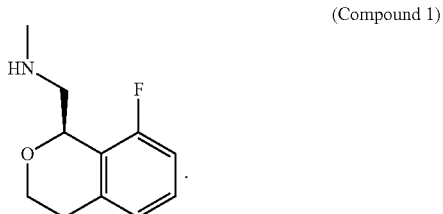

(Compound 1)

In some embodiments, provided are processes of preparing (R)-1-(8-fluoroisochroman-1-yl)-N-methylmethanamine (Compound 1), or salts or crystalline forms thereof.

In some embodiments, provided are methods of using (R)-1-(8-fluoroisochroman-1-yl)-N-methylmethanamine (Compound 1), or salts or crystalline forms thereof, in the treatment of CNS disorders.

In some embodiments, provided are pharmaceutical compositions comprising (R)-1-(8-fluoroisochroman-1-yl)-N-methylmethanamine (Compound 1), or salts or crystalline forms thereof, as described herein, and one or more pharmaceutically acceptable excipients.

DETAILED DESCRIPTION

Figure 1:
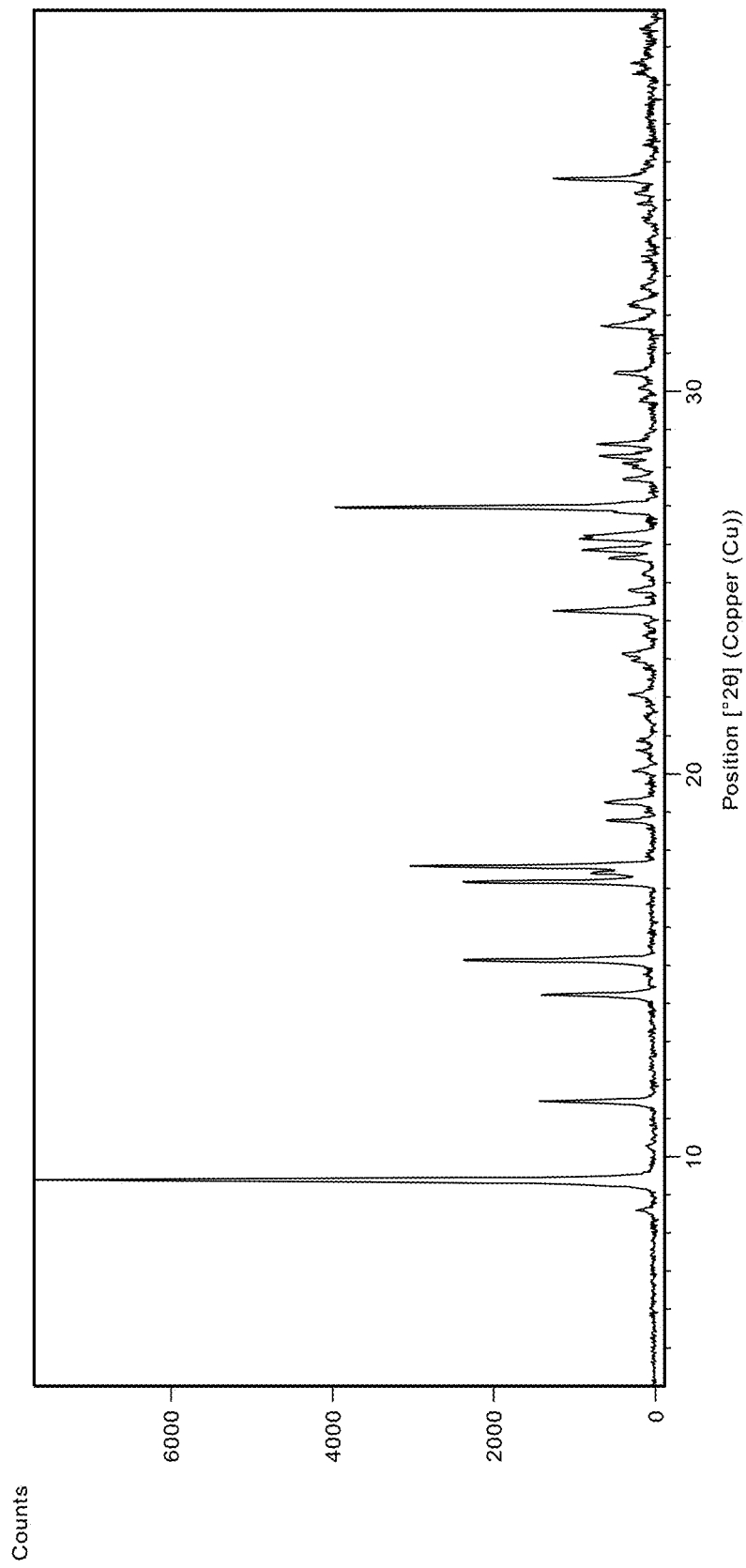
FIG. 1 shows an X-ray powder diffraction (XRPD) pattern of Compound 1 Hydrochloride Form HA.

The methods of the disclosure relate to the use of compounds and compositions disclosed herein to treat neurological or psychiatric diseases, disorders or impairments. In some embodiments, the neurological or psychiatric disease or disorder is depression, bipolar disorder, pain, schizophrenia, obsessive compulsive disorder, psychostimulation, addiction, social disorder, attention deficit hyperactivity disorder, an anxiety disorder, a movement disorder, epilepsy, autism, Alzheimer's disease, Parkinson's disease or cognitive impairments. In one embodiment, the disease or disorder is depression, particularly treatment-resistant depression (TRD), major depressive disorder (MDD), unipolar depression, bipolar depression or depression associated with another disease or disorder. In some embodiments, the impairments in neurological diseases or disorders such as Alzheimer's and Parkinson's diseases include neuropsychiatric symptoms such as apathy, depression, anxiety, cognitive impairment, psychosis, aggression, agitation, impulse control disorders, and/or sleep disorders.

The description herein sets forth details to provide an understanding of various embodiments of the disclosure, and is made with the understanding that the provided disclosures are an exemplification of the claimed subject matter without intending to limit the claims to specific embodiments. Accordingly, specific embodiments disclosed herein may be combined with other specific embodiments disclosed herein, including specific embodiments under various headings, which are provided for convenience and organization, but are not to be construed to limit the claims in any way.

All published documents cited herein are hereby incorporated by reference in their entirety.

Definitions

Unless defined otherwise, all technical and scientific terms used herein have the same meaning as commonly understood by one of ordinary skill in the art.

As used herein, the singular forms "a", "an" and "the" are intended to include the plural forms as well, unless the context clearly indicates otherwise.

As used herein, and unless otherwise specified, the term "about", when used in connection with a numeric value or range of values which is provided to describe a particular solid form (e.g., a specific temperature or temperature range, such as describing a melting, dehydration, or glass transition; a mass change, such as a mass change as a function of temperature or humidity; a solvent or water content, in terms of, for example, mass or a percentage; or a peak position, such as in analysis by, for example, $^{13}$C NMR, DSC, TGA and XRPD), indicate that the value or range of values may deviate to an extent deemed reasonable to one of ordinary skill in the art while still describing the particular solid form. Specifically, the term "about", when used in this context, indicates that the numeric value or range of values may vary by 5%, 4%, 3%, 2%, 1%, 0.9%, 0.8%, 0.7%, 0.6%, 0.5%, 0.4%, 0.3%, 0.2% or 0.1% of the recited value or range of values while still describing the particular solid form. In some embodiments, the values can vary by about 5%. The term "about", when used in reference to a degree 2-theta value refers to +0.3 degrees 2-theta or ±0.2 degrees 2-theta. In some embodiments, "about" refers to a degree 2-theta value of ±0.2 degrees 2-theta. In some embodiments, "about" refers to a temperature of +3° C.

As used herein, the phrase "alkali metal bicarbonate," employed alone or in combination with other terms, refers to a base having formula M(HCO$_3$), wherein M refers to an alkali metal (e.g. lithium, sodium, or potassium). Example alkali metal bicarbonate include, but are not limited to, lithium bicarbonate, sodium bicarbonate, and potassium bicarbonate.

As used herein, the phrase "alkali metal alkoxide," employed alone or in combination with other terms, refers to a base having formula M(O-alkyl), wherein M refers to an alkali metal (e.g. lithium, sodium, or potassium). Examples alkali metal alkoxide include, but are not limited to lithium alkoxide, sodium alkoxide, and potassium alkoxide.

As used herein, the phrase "metal hydroxide base," employed alone or in combination with other terms, refers to a base having formula MOH, wherein M refers to a metal such as an alkali metal (e.g. lithium, sodium, or potassium). Example alkali metal hydroxide bases include, but are not limited to lithium hydroxide, sodium hydroxide, and potassium hydroxide.

As used herein, the terms "comprising" and "including" or grammatical variants thereof are to be taken as specifying the stated features, integers, steps or components but do not preclude the addition of one or more additional features, integers, steps, components or groups thereof. These terms encompass the term "consisting of".

The expressions, "ambient temperature" and "room temperature," as used herein, are understood in the art, and refer generally to a temperature, e.g., a reaction temperature, that is about the temperature of the room in which the reaction is carried out, for example, a temperature from about 20° C. to about 30° C.

As used herein, the term "amorphous" or "amorphous form" is intended to mean that the substance, component, or product in question is not crystalline as determined, for instance, by XRPD or where the substance, component, or product in question, for example is not birefringent when viewed microscopically. For example, amorphous means essentially without regularly repeating arrangement of molecules or lacks the long range order of a crystal, i.e., amorphous form is non-crystalline. An amorphous form does not display a defined x-ray diffraction pattern with sharp maxima. In certain embodiments, a sample comprising an amorphous form of a substance can be substantially free of other amorphous forms and/or crystalline forms. For example, an amorphous substance can be identified by an XRPD spectrum having an absence of readily distinguishable reflections.

As used herein, the term "chemical purity" or "purity" refers to a measurement of purity compound. In some embodiments, the compound described herein can be isolated with a purity of at least about 80%, about 85%, about 90%, about 95%, about 96%, about 97%, about 98%, or about 99%. In some embodiments, the compound described herein can be isolated with an enantiomeric purity greater than about 90%. In some embodiments, the compound described herein can be isolated with an enantiomeric purity greater than about 95%. In some embodiments, the compound described herein can be isolated with an enantiomeric purity greater than about 99%. The measurement can be determined by methods well-known in the art, e.g., by elemental analysis, column chromatography, NMR spectroscopy, and the like.

As used herein, the term "crystalline" or "crystalline form" refers to a crystalline solid form of a chemical compound, including, but not limited to, a single-component or multiple-component crystal form, e.g., including solvates, hydrates, clathrates, and a co-crystal. For example, crystalline means having a regularly repeating and/or ordered arrangement of molecules, and possessing a distinguishable crystal lattice. The term "crystalline form" is meant to refer to a certain lattice configuration of a crystalline substance. Different crystalline forms of the same substance typically have different crystalline lattices (e.g., unit cells), typically have different physical properties attributed to their different crystalline lattices, and in some instances, have different water or solvent content. The different crystalline lattices can be identified by solid state characterization methods such as by X-ray powder diffraction (XRPD). Other characterization methods such as differential scanning calorimetry (DSC), thermogravimetric analysis (TGA), dynamic vapor sorption (DVS), and the like further help identify the crystalline form as well as help determine stability and solvent/water content.

As used herein, the term "% crystallinity" or "crystalline purity," means percentage of a crystalline form in a preparation or sample, which may contain other forms such as an amorphous form of the same compound, or at least one other crystalline form of the compound, or mixtures thereof. In some embodiments, the crystalline forms can be isolated with a purity of at least about 80%, about 85%, about 90%, about 95%, about 96%, about 97%, about 98%, or about 99%. In some embodiments, the crystalline forms can be isolated with a purity greater than about 90%. In some embodiments, the crystalline forms can be isolated with a purity greater than about 95%. In some embodiments, the crystalline forms can be isolated with a purity greater than about 99%.

As used herein, "delaying" development of a disorder mean to defer, hinder, slow, stabilize, and/or postpone development of the disorder. Delay can be of varying lengths of time, depending on the history of the disease and/or the individual being treated.

As used herein, the term "disorder" or specifically identified disorders disclosed herein, (e.g. CNS disorders) refer to the disorder as defined in the Diagnostic and Statistical Manual of Mental Disorders, Fifth Edition (DSM-5).

As used herein, the term "enantiomeric purity" refers to a measurement of purity for a chiral compound. In some embodiments, the compound described herein can be isolated with an enantiomeric purity of at least about 80%, about 85%, about 90%, about 95%, about 96%, about 97%, about 98%, or about 99%. In some embodiments, the compound described herein can be isolated with an enantiomeric purity greater than about 99%. In some embodiments, the compound described herein can be isolated with an enantiomeric purity greater than about 90%. In some embodiments, the compound described herein can be isolated with an enantiomeric purity greater than about 95%. The measurement can be determined by methods well-known in the art, e.g., by specific optical rotation, chiral column chromatography, NMR spectroscopy, and the like.

The term "hydrate," as used herein, is meant to refer to a solid form (e.g., crystalline form) of Compound 1 and its salts that includes water. The water in a hydrate can be present in a stoichiometric amount with respect to the amount of salt in the solid, or can be present in varying amounts, such as can be found in connection with channel hydrates.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas. As used herein, the term "organic solvent" refers to carbon-based solvents (i.e., they contain carbon in their structure) that are employed to dissolve or disperse one or more compounds described herein.

Suitable solvents can include halogenated solvents such as carbon tetrachloride, bromodichloromethane, dibromochloromethane, bromoform, chloroform, bromochloromethane, dibromomethane, butyl chloride, dichloromethane (methylene chloride), tetrachloroethylene, trichloroethylene, 1,1,1-trichloroethane, 1,1,2-trichloroethane, 1,1-dichloroethane, 2-chloropropane, I,I,I-trifluorotoluene, 1,2-dichloroethane, 1,2-dibromoethane, hexafluorobenzene, 1,2,4-trichlorobenzene, 1,2-dichlorobenzene, chlorobenzene, fluorobenzene, mixtures thereof and the like.

Suitable solvents can include ether solvents include dimethoxymethane, tetrahydrofuran, 1,3-dioxane, 1,4-dioxane, furan, tetrahydrofuran (THF), diethyl ether, ethylene glycol dimethyl ether, ethylene glycol diethyl ether, diethylene glycol dimethyl ether (diglyme), diethylene glycol diethyl ether, triethylene glycol dimethyl ether, anisole, tert-butyl methyl ether, mixtures thereof and the like.

Suitable solvents can include protic solvents (e.g., polar protic solvents) can include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, iso-butyl alcohol, tert-butyl alcohol, 2-ethoxyethanol, diethylene glycol, 1-, 2-, or 3-pentanol, neo-pentyl alcohol, tert-pentyl alcohol, diethylene glycol monomethyl ether, diethylene glycol monoethyl ether, cyclohexanol, benzyl alcohol, phenol, or glycerol.

Suitable solvents can include aprotic solvents can include, by way of example and without limitation, N,N-dimethylformamide (DMF), N,N-dimethylacetamide (DMA), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable solvents can include hydrocarbon solvents include benzene, cyclohexane, pentane, hexane, toluene, cycloheptane, methylcyclohexane, heptane, ethylbenzene, m-, o-, or p-xylene, octane, indane, nonane, or naphthalene.

As used herein, the term "peak" or "characteristic peak" refers to a reflection having a relative height/intensity of at least about 3% of the maximum peak height/intensity.

As used herein, "pharmaceutically acceptable" or "physiologically acceptable" refer to compounds (e.g., solid forms), compositions, dosage forms and other materials, which are useful in preparing a pharmaceutical composition that is suitable for veterinary or human pharmaceutical use.

The term "pharmaceutically acceptable excipient" refers to a non-toxic binder, filler, adjuvant, carrier, excipient, glidant, sweetening agent, diluent, preservative, dye/colorant, flavor enhancer, surfactant, wetting agent, dispersing agent, suspending agent, stabilizer, isotonic agent, solvent, emulsifier, anti-caking agent, flavor, desiccant, plasticizer, vehicle, disintegrant, or lubricant that does not destroy the pharmacological activity of the compound with which it is formulated. Pharmaceutically acceptable excipients that can be used in the compositions include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

As used herein, "prevention" or "preventing" refers to a regimen that protects against the onset of the disorder such that the clinical symptoms of the disorder do not develop. Accordingly, "prevention" relates to administration of a therapy, including administration of a compound disclosed herein, to a subject before signs of the diseases are detectable in the subject (for example, administration of a compound disclosed herein to a subject in the absence of a detectable syndrome of the disorder). The subject may be at risk of developing the disorder. As used herein, an "at risk" subject is one who is at risk of developing a disorder to be treated. This may be shown, for example, by one or more risk factors, which are measurable parameters that correlate with development of a disorder and are known in the art.

Preparation of compounds can involve the protection and deprotection of various chemical groups. The need for protection and deprotection, and the selection of appropriate protecting groups (PG) can be readily determined by one skilled in the art. The chemistry of protecting groups can be found, for example, in Wuts and Greene, *Greene's Protective Groups in Organic Synthesis*, 4$^{th}$ Ed., John Wiley & Sons: New York, 2006, which is incorporated herein by reference in its entirety. Preparation of compounds can also include leaving group (LG), which is a molecular fragment that leaves in bond cleavage. Leaving groups can be anions or neutral fragment and is able to stabilize the additional electron density that results from bond cleavage. Typical leaving groups are halides such as Cl, Br, and I, and sulfonate esters such as tosylate (TsO), triflate (TfO), mesylate (MsO), and the like.

As used herein, the term "reacting," "contacting" or "treating" when describing a certain process is used as known in the art and generally refers to the bringing together of chemical reagents in such a manner so as to allow their interaction at the molecular level to achieve a chemical or physical transformation. In some embodiments, the reacting involves two reagents, wherein one or more equivalents of second reagent are used with respect to the first reagent. The reacting steps of the processes described herein can be conducted for a time and under conditions suitable for preparing the identified product.

As used herein, the term "salt" refers to a substance that results from the combination of a compound and an acid or a base. For example, the free base Compound 1 can be combined with the desired acid in a solvent or in a melt to generate a salt of Compound 1. In some embodiments, acid addition salt of Compound 1 can be converted to a different acid addition salt by anion exchange. Salts which are prepared in a solvent system can be isolated by precipitation from the solvent. Precipitation and/or crystallization can be induced, for example, by evaporation, reduction of temperature, addition of anti-solvent, or combinations thereof.

As used herein, the term "solid form" refers to a compound provided herein in either an amorphous state or a crystalline state (e.g., crystalline form), whereby a compound provided herein in a crystalline state may optionally include solvent or water within the crystalline lattice, for example, to form a solvated or hydrated crystalline form. In some embodiments, the compound provided herein is in a crystalline state as described herein.

A "solvate" as used herein is formed by the interaction of a solvent and a compound.

As used herein, the term "subject," to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys. The "subject" may have independently been diagnosed with a disorder as defined herein, may currently be experiencing symptoms associated with disorders or may have experienced symptoms in the past, may be at risk of developing a disorder, or may be reporting one or more of the symptoms of a disorder, even though a diagnosis may not have been made. In some embodiments, the subject is a human who may have independently been diagnosed with a disorder as defined herein, may currently be experiencing symptoms associated with disorders or may have experienced symptoms in the past, may be at risk of developing a disorder, or may be reporting one or more of the symptoms of a disorder, even though a diagnosis may not have been made.

As used herein, the term "substantially" when referring to a characteristic figure of a crystal form, such as an XRPD pattern, a DSC thermogram, a TGA thermogram, or the like, means that a subject figure can be non-identical to the reference depicted herein, but it falls within the limits of experimental error and thus can be deemed as derived from the same crystal form as disclosed herein, as judged by a person of ordinary skill in the art. For example, the term "substantially" as used in the context of XRPD herein is meant to encompass variations disclosed herein (e.g., instrument variation, measurement variation, etc.).

As used herein, the term "substantially amorphous" means a majority of the weight of a sample or preparation (e.g., of a salt of Compound 1) is amorphous and the remainder of the sample is a crystalline form of the same compound. In some embodiments, a substantially amorphous sample has less than about 5% crystallinity (e.g., about 95% of the non-crystalline form of the same compound), preferably less than about 4% crystallinity (e.g., about 96% of the non-crystalline form of the same compound), more preferably less than about 3% crystallinity (e.g., about 97% of the non-crystalline form of the same compound), even more preferably less than about 2% crystallinity (e.g., about 98% of the non-crystalline form of the same compound), still more preferably less than about 1% crystallinity (e.g., about 99% of the non-crystalline form of the same compound), and most preferably about 0% crystallinity (e.g., about 100% of the non-crystalline form of the same compound). In some embodiments, the term "fully amorphous" means less than about 99% or about 0% crystallinity.

As used herein, the term "substantially crystalline," means a majority of the weight of a sample or preparation (e.g., of a salt of Compound 1) is crystalline and the remainder of the sample is a non-crystalline form (e.g., amorphous form) of the same compound. In some embodiments, a substantially crystalline sample has at least about 95% crystallinity (e.g., about 5% of the non-crystalline form of the same compound), preferably at least about 96% crystallinity (e.g., about 4% of the non-crystalline form of the same compound), more preferably at least about 97% crystallinity (e.g., about 3% of the non-crystalline form of the same compound), even more preferably at least about 98% crystallinity (e.g., about 2% of the non-crystalline form of the same compound), still more preferably at least about 99% crystallinity (e.g., about 1% of the non-crystalline form of the same compound), and most preferably about 100% crystallinity (e.g., about 0% of the non-crystalline form of the same compound). In some embodiments, the term "fully crystalline" means at least about 99% or about 100% crystallinity.

The term "substantially isolated" is meant that the compound is at least partially or substantially separated from the environment in which it was formed or detected. Partial separation can include, e.g., a composition enriched in the compound, salts, hydrates, solvates, or solid forms provided herein. Substantial separation can include compositions containing at least about 50%, at least about 60%, at least about 70%, at least about 80%, at least about 90%, at least about 95%, at least about 97%, or at least about 99% by weight of the compound, salts, hydrates, solvates, or solid forms provided herein.

As used herein, the term "therapeutically effective amount" or "effective amount" refers to an amount that is effective to elicit the desired biological or medical response, including the amount of a compound that, when administered to a subject for treating a disorder, is sufficient to effect such treatment of the disorder. The effective amount will vary depending on the compound, the disorder, and its severity, and the age, weight, etc. of the subject to be treated. The effective amount may be in one or more doses (for example, a single dose or multiple doses may be required to achieve the desired treatment endpoint). An effective amount may be considered to be given in an effective amount if, in conjunction with one or more other agents, a desirable or beneficial result may be or is achieved. Suitable doses of any co-administered compounds may optionally be lowered due to the combined action, additive or synergistic, of the compound.

As used herein, the terms "treatment," "treat," and "treating" refer to an approach for obtaining beneficial or desired results including, but not limited to, therapeutic benefit. Therapeutic benefit includes eradication and/or amelioration of the underlying disorder being treated; it also includes the eradication and/or amelioration of one or more of the symptoms associated with the underlying disorder such that an improvement is observed in the subject, notwithstanding that the subject may still be afflicted with the underlying disorder. In some embodiments, "treatment" or "treating" includes one or more of the following: (a) inhibiting the disorder (for example, decreasing one or more symptoms resulting from the disorder, and/or diminishing the extent of the disorder); (b) slowing or arresting the development of one or more symptoms associated with the disorder (for example, stabilizing the disorder and/or delaying the worsening or progression of the disorder); and/or (c) relieving the disorder (for example, causing the regression of clinical symptoms, ameliorating the disorder, delaying the progression of the disorder, and/or increasing quality of life). In some embodiments, treatment can be administered after one or more symptoms have developed. In other embodiments, treatment can be administered in the absence of symptoms. For example, treatment can be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

As used herein, the term "treatment-resistant depression," which is also known as "treatment-refractory depression," refers to major depressive disorder (MDD) situations where the subject shows inadequate responses to treatment with at least two antidepressants (e.g., standard antidepressant treatments that are commercially available). Inadequate response can be no response. Inadequate response can also be when the subject does not show full remission of symptoms, or when the physician or clinician does not deem the subject's response to be adequate. Treatment-resistant depression symptoms can range from mild to severe. Factors that can contribute to inadequate response include, but not limited to, early discontinuation of treatment, insufficient dosage of medication, patient noncompliance, misdiagnosis, and concurrent psychiatric disorders.

EtOAc (ethyl acetate); g (gram(s)); h (hour(s)); HCl (hydrochloric acid); M (molar); MeCN (acetonitrile); MeOH (methanol); mg (milligram(s)); min. (minutes(s)); mL (milliliter(s)); mmol (millimole(s)); $NaHCO_3$ (sodium bicarbonate); NaOH (sodium hydroxide); nM (nanomolar);

Ph (phenyl); g (microgram(s)); L (microliter(s)); M (micromolar); wt % (weight percent).

Salts and Crystalline Forms Thereof

Provided herein are salts of (R)-1-(8-fluoroisochroman-1-yl)-N-methylmethanamine (Compound 1), and crystalline forms thereof. Compound (R)-1-(8-fluoroisochroman-1-yl)-N-methylmethanamine (Compound 1) has the structure:

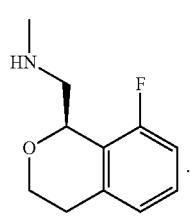

Compound 1

Compound 1 is described in U.S. patent application Ser. No. 15/663,688 (allowed), the entirety of which is incorporated herein by reference.

Compound 1 (R)-1-(8-fluoroisochroman-1-yl)-N-methylmethanamine is named or identified using other commonly recognized nomenclature systems. For example, the compound may be named or identified with common names, systematic names, or non-systematic names. The nomenclature systems that are commonly recognized in the art of chemistry include, but are not limited to, Chemical Abstract Service (CAS) and International Union of Pure and Applied Chemistry (IUPAC). The IUPAC name provided by ChemDraw Professional 15.0 has been used herein for Compound 1.

Compound 1 may be prepared as a salt. In some embodiments, Compound 1 may be prepared as a pharmaceutically acceptable salt. Non-limiting examples of pharmaceutically acceptable salts include malates, tartrates, citrates, phosphates, sulfates, pyrosulfates, bisulfates, sulfites, bisulfites, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, tosylates, xylenesulfonates, naphthalene-1-sulfonates, naphthalene-2-sulfonates, phenylacetates, phenylpropionates, phenylbutyrates, lactates, gamma-hydroxybutyrates, glycolates, and mandelates. Lists of other suitable pharmaceutically acceptable salts are found in Remington: The Science and Practice of Pharmacy, 21st Edition, Lippincott Williams and Wilkins, Philadelphia, Pa., 2006.

In some embodiments, the salt is a hydrochloric acid salt of Compound 1. The hydrochloric acid salt form of Compound 1 is referred to herein as "Compound 1 Hydrochloride." An alternative name for the salt is (R)-1-(8-fluoroisochroman-1-yl)-N-methylmethanamine hydrochloride or (R)-1-(8-fluoroisochroman-1-yl)-N-methylmethanamine hydrochloric acid salt.

In some embodiments, the salt is a phosphoric acid salt of Compound 1. The phosphoric acid salt form of Compound 1 is referred to herein as "Compound 1 Phosphate." An alternative name for the salt is (R)-1-(8-fluoroisochroman-1-yl)-N-methylmethanamine phosphate or (R)-1-(8-fluoroisochroman-1-yl)-N-methylmethanamine phosphoric acid salt.

In some embodiments, the salt is a L-tartaric acid salt of Compound 1. The L-tartaric acid salt form of Compound 1 is referred to herein as "Compound 1 L-Tartrate." An alternative name for the salt is (R)-1-(8-fluoroisochroman-1-yl)-N-methylmethanamine or (R)-1-(8-fluoroisochroman-1-yl)-N-methylmethanamine L-tartaric acid salt.

In some embodiments, the salt is a D-tartaric acid salt of Compound 1. The D-tartaric acid salt form of Compound 1 is referred to herein as "Compound 1 D-Tartrate." An alternative name for the salt is (R)-1-(8-fluoroisochroman-1-yl)-N-methylmethanamine D-tartrate or (R)-1-(8-fluoroisochroman-1-yl)-N-methylmethanamine D-tartaric acid salt.

In some embodiments, the salt is a fumaric acid salt of Compound 1. The fumaric acid salt form of Compound 1 is referred to herein as "Compound 1 Fumarate." An alternative name for the salt is (R)-1-(8-fluoroisochroman-1-yl)-N-methylmethanamine fumarate or (R)-1-(8-fluoroisochroman-1-yl)-N-methylmethanamine fumaric acid salt.

In some embodiments, the salt is a citric acid salt of Compound 1. The citric acid salt form of Compound 1 is referred to herein as "Compound 1 Citrate." An alternative name for the salt is (R)-1-(8-fluoroisochroman-1-yl)-N-methylmethanamine citrate or (R)-1-(8-fluoroisochroman-1-yl)-N-methylmethanamine citric acid salt.

In some embodiments, the salt is a succinic acid salt of Compound 1. The succinic acid salt form of Compound 1 is referred to herein as "Compound 1 Succinate." An alternative name for the salt is (R)-1-(8-fluoroisochroman-1-yl)-N-methylmethanamine succinate or (R)-1-(8-fluoroisochroman-1-yl)-N-methylmethanamine succinic acid salt.

In some embodiments, the salt is a glutaric acid salt of Compound 1. The citric acid salt form of Compound 1 is referred to herein as "Compound 1 Glutarate." An alternative name for the salt is (R)-1-(8-fluoroisochroman-1-yl)-N-methylmethanamine glutarate or (R)-1-(8-fluoroisochroman-1-yl)-N-methylmethanamine glutaric acid salt.

In some embodiments, the salt is a L-malic acid salt of Compound 1. The L-malic acid salt form of Compound 1 is referred to herein as "Compound 1 L-malate." An alternative name for the salt is (R)-1-(8-fluoroisochroman-1-yl)-N-methylmethanamine L-malate or (R)-1-(8-fluoroisochroman-1-yl)-N-methylmethanamine L-malic acid salt.

In some embodiments, the salt is a benzenesulfonic acid salt of Compound 1. The benzenesulfonic acid salt form of Compound 1 is referred to herein as "Compound 1 Besylate." An alternative name for the salt is (R)-1-(8-fluoroisochroman-1-yl)-N-methylmethanamine besylate or (R)-1-(8-fluoroisochroman-1-yl)-N-methylmethanamine benzenesulfonic acid salt.

In some embodiments, the salt is a p-toluenesulfonic acid salt of Compound 1. The p-toluenesulfonic acid salt form of Compound 1 is referred to herein as "Compound 1 Tosylate." An alternative name for the salt is (R)-1-(8-fluoroisochroman-1-yl)-N-methylmethanamine tosylate or (R)-1-(8-fluoroisochroman-1-yl)-N-methylmethanamine p-toluenesulfonic acid salt.

The salts described herein can have about half, about 1, about 2, about 3 equivalents, etc. of acid to Compound 1. In some embodiments, the salts described herein comprises about half equivalent of acid to Compound 1. In some embodiments, the salts described herein comprise about 1 equivalent of acid to Compound 1. In some embodiments, the salts described herein comprise about 2 equivalents of acid to Compound 1. In some embodiments, the salts described herein comprise about 3 equivalents of acid to Compound 1. A person skilled in the art would recognize that there is an equilibrium between the acid and Compound 1 in which the protons may reside, which depends on the conditions (e.g., solvents, temperature, etc.) and the strength of the acids. For example, in some conditions, the acid becomes a counter-anion by losing one or more protons to Compound 1, and Compound 1 becomes a counter-cation. In some conditions, the protons of the acids may form a weak interaction with the basic sites of Compound 1 and thus, the protons are shared between the acid and Compound 1.

The salts described herein can have less than about 1, about 2, about 3, about 4, about 5, or greater than about 6 equivalents of solvent or hydrate to the salt. In some embodiments, the salts described have less than about 1 equivalent of solvent or hydrate to the salt. In some embodiments, the salts described have less than about 1 equivalent of hydrate to the salt. In some embodiments, the salts described have about 2 equivalents of solvent or hydrate to the salt. In some embodiments, the salts described have about 2 equivalent of hydrate to the salt. In some embodiments, the salts described have about 3 equivalents of solvent or hydrate to the salt. In some embodiments, the salts described have about 3 equivalents of hydrate to the salt.

In some embodiments, the salts described herein are anhydrous.

Salts of Compound 1 can be isolated as one or more crystalline forms. Different crystalline forms of the same substance may have different bulk properties relating to, for example, hygroscopicity, solubility, stability, and the like. Crystalline forms with high melting points may have good thermodynamic stability, which may be advantageous in prolonging shelf-life drug formulations containing the crystalline form. Crystalline forms with lower melting points may be less thermodynamically stable, but may be advantageous in having increased water solubility, which may translate to increased drug bioavailability. Crystalline forms that are weakly hygroscopic may be desirable for stability to heat or humidity and may be resistant to degradation during long storage. The crystalline forms described herein have many advantages, for example they have desirable properties. Moreover, the crystalline forms disclosed herein may be useful for improving the performance characteristics of a pharmaceutical product such as dissolution profile, shelf-life and bioavailability.

Different crystalline forms of a particular substance, such as Compound 1 as described herein, can include both anhydrous forms of that substance and solvated/hydrated forms of that substance, where each of the anhydrous forms and solvated/hydrated forms are distinguished from each other by different XRPD patterns, or other solid state characterization methods, thereby signifying different crystalline lattices. In some instances, a single crystalline form (e.g., identified by a unique XRPD pattern) can have variable water or solvent content, where the lattice remains substantially unchanged (as does the XRPD pattern) despite the compositional variation with respect to water and/or solvent.

An XRPD pattern of reflections (peaks) is typically considered a fingerprint of a particular crystalline form. It is well known that the relative intensities of the XRPD peaks can widely vary depending on, inter alia, the sample preparation technique, crystal size distribution, filters used, the sample mounting procedure, and the particular instrument employed. In some instances, new peaks can be observed or existing peaks may disappear, depending on the type of the machine or the settings (for example, whether a Ni filter is used or not). Moreover, instrument variation and other factors can affect the 2-theta (2θ) values. Thus, peak assignments, such as those reported herein, can vary by plus or minus (±) about 0.2° (2-theta) or about 0.3° (2-theta).

In the same way, temperature readings in connection with DSC, TGA, or other thermal experiments can vary about +3° C. depending on the instrument, particular settings, sample preparation, etc. Accordingly, a crystalline form reported herein having a DSC thermogram "substantially" as shown in any of the Figures is understood to accommodate such variation.

Crystalline forms of a substance can be obtained by a number of methods, as known in the art. Such methods include, but are not limited to, melt recrystallization, melt cooling, solvent recrystallization, recrystallization in confined spaces such as, e.g., in nanopores or capillaries, recrystallization on surfaces or templates such as, e.g., on polymers, recrystallization in the presence of additives, such as, e.g., co-crystal counter-molecules, desolvation, dehydration, rapid evaporation, rapid cooling, slow cooling, vapor diffusion, sublimation, exposure to moisture, grinding and solvent-drop grinding.

Compound 1 and its salts can be prepared in batches referred to as batches, samples, or preparations. The batches, samples, or preparations can include Compound 1 and its salts in any of the crystalline or non-crystalline forms described herein, including hydrated and non-hydrated forms, and mixtures thereof.

Compounds provided herein (e.g., salts of Compound 1) can also include all isotopes of atoms occurring in the intermediates or final compounds. Isotopes include those atoms having the same atomic number but different mass numbers. For example, isotopes of hydrogen include tritium and deuterium. One or more constituent atoms of the compounds provided herein can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7 or 8 deuterium atoms. Synthetic methods for including isotopes into organic compounds are known in the art. Examples of isotopes that can be incorporated into the compounds disclosed herein include isotopes of hydrogen, carbon, nitrogen, oxygen, phosphorus, fluorine, chlorine, and iodine (e.g., $^{2}H$, $^{3}H$, $^{11}C$, $^{13}C$, $^{14}C$, $^{13}N$, $^{15}N$, $^{15}O$, $^{18}O$, $^{31}P$, $^{32}P$, $^{35}S$, $^{18}F$, $^{36}Cl$, $^{123}I$, and $^{125}I$).

In some embodiments, Compound 1 or its salts and crystalline forms thereof are substantially isolated.

Compound 1 can be observed and/or isolated as various salt forms and polymorphs thereof, including, e.g., hydrochloride salt (form HA and form HB), phosphate salt, L-tartrate salt (form LA, form LB, and form LC), D-tartrate salt, fumarate (form FA and form FB), citrate, succinate, glutarate, L-malate, besylate, and tosylate.

Compound 1 Hydrochloride

In some embodiments, provided is (R)-1-(8-fluoroisochroman-1-yl)-N-methylmethanamine hydrochloride (Compound 1 Hydrochloride). In some embodiments, Compound 1 Hydrochloride is crystalline.

Compound 1 Hydrochloride can be prepared according to the procedure provided in U.S. Pat. No. 10,196,403. In some embodiments, provided is Compound 1 Hydrochloride prepared by isolating Compound 1 Hydrochloride Form HA from a mixture of Compound 1, HCl, and S1, wherein S1 is a solvent. In some embodiments, S1 is an organic solvent. In some embodiments, S1 is $C_{1-6}$ alkyl alcohol. In some embodiments, S1 is ether. In some embodiments, S1 is $C_{1-6}$ alkyl acetate. In some embodiments, S1 is methanol. In some embodiments, S1 is THF. In some embodiments, S1 is ethyl acetate.

Compound 1 Hydrochloride Form HA

In some embodiments, provided is (R)-1-(8-fluoroisochroman-1-yl)-N-methylmethanamine hydrochloride Form HA (Compound 1 hydrochloride Form HA). In some embodiments, Compound 1 Hydrochloride Form HA is crystalline.

In some embodiments, Compound 1 Hydrochloride Form HA has characteristic XRPD peak in terms of 2θ selected from 9.4°±0.2°, 11.4°±0.2°, and 15.1°±0.2°. In some embodiments, Compound 1 Hydrochloride Form HA has a characteristic XRPD peak in terms of 2θ at 9.4°±0.2°. In some embodiments, Compound 1 Hydrochloride Form HA has a characteristic XRPD peak in terms of 2θ at 11.4°±0.2°. In some embodiments, Compound 1 Hydrochloride Form HA has a characteristic XRPD peak in terms of 2θ at 15.10°±0.2°.

In some embodiments, Compound 1 Hydrochloride Form HA has characteristic XRPD peaks in terms of 2θ selected from 9.4°±0.2°, 11.4°±0.2°, 15.1°±0.2°, 17.2°±0.2°, and 17.6°±0.2°. In some embodiments, Compound 1 Hydrochloride Form HA has at least one characteristic XRPD peak in terms of 2θ selected from 9.4°±0.2°, 11.4°±0.2°, 15.10°±0.2°, 17.2° °±0.2°, and 17.6°±0.2°.

In some embodiments, Compound 1 Hydrochloride Form HA has at least one characteristic XRPD peak in terms of 2θ selected from 9.4°±0.2°, 11.4°±0.2°, 14.2°±0.2°, 15.1°±0.2°, 17.2°±0.2°, 17.6°±0.2°, and 27.0°±0.2°. In some embodiments, Compound 1 Hydrochloride Form HA has at least one characteristic XRPD peak in terms of 2θ selected from 9.4°±0.2°, 11.4°±0.2°, 14.2°±0.2°, 15.1°±0.2°, 17.2°±0.2°, 17.6°±0.2°, 18.8°±0.2°, 19.2°±0.2°, 24.3°±0.2°, and 27.0°±0.2°.

In some embodiments, Compound 1 Hydrochloride Form HA has at least two characteristic XRPD peaks in terms of 2θ selected from 9.4°±0.2°, 11.4°±0.2°, 14.2°±0.2°, 15.1°±0.2°, 17.2°±0.2°, 17.6°±0.2°, and 27.0°±0.2°. In some embodiments, Compound 1 Hydrochloride Form HA has at least two characteristic XRPD peaks in terms of 2θ selected from 9.4°±0.2°, 11.4°±0.2°, 14.2°±0.2°, 15.1°±0.2°, 17.2°±0.2°, 17.6°±0.2°, 18.8°±0.2°, 19.2°±0.2°, 24.3°±0.2°, and 27.0°±0.2°.

In some embodiments, Compound 1 Hydrochloride Form HA has at least three characteristic XRPD peaks in terms of 2θ selected from 9.4°±0.2°, 11.4°±0.2°, 14.2°±0.2°, 15.1°±0.2°, 17.2°±0.2°, 17.6°±0.2°, and 27.0°±0.2°. In some embodiments, Compound 1 Hydrochloride Form HA has at least three characteristic XRPD peaks in terms of 2θ selected from 9.4°±0.2°, 11.4°±0.2°, 14.2°±0.2°, 15.1°±0.2°, 17.2°±0.2°, 17.6°±0.2°, 18.8°±0.2°, 19.2°±0.2°, 24.3°±0.2°, and 27.0°±0.2°.

In some embodiments, Compound 1 Hydrochloride Form HA has an XRPD pattern with characteristic peaks as substantially shown in FIG. 1 (FIG. 1).

Figure 2:
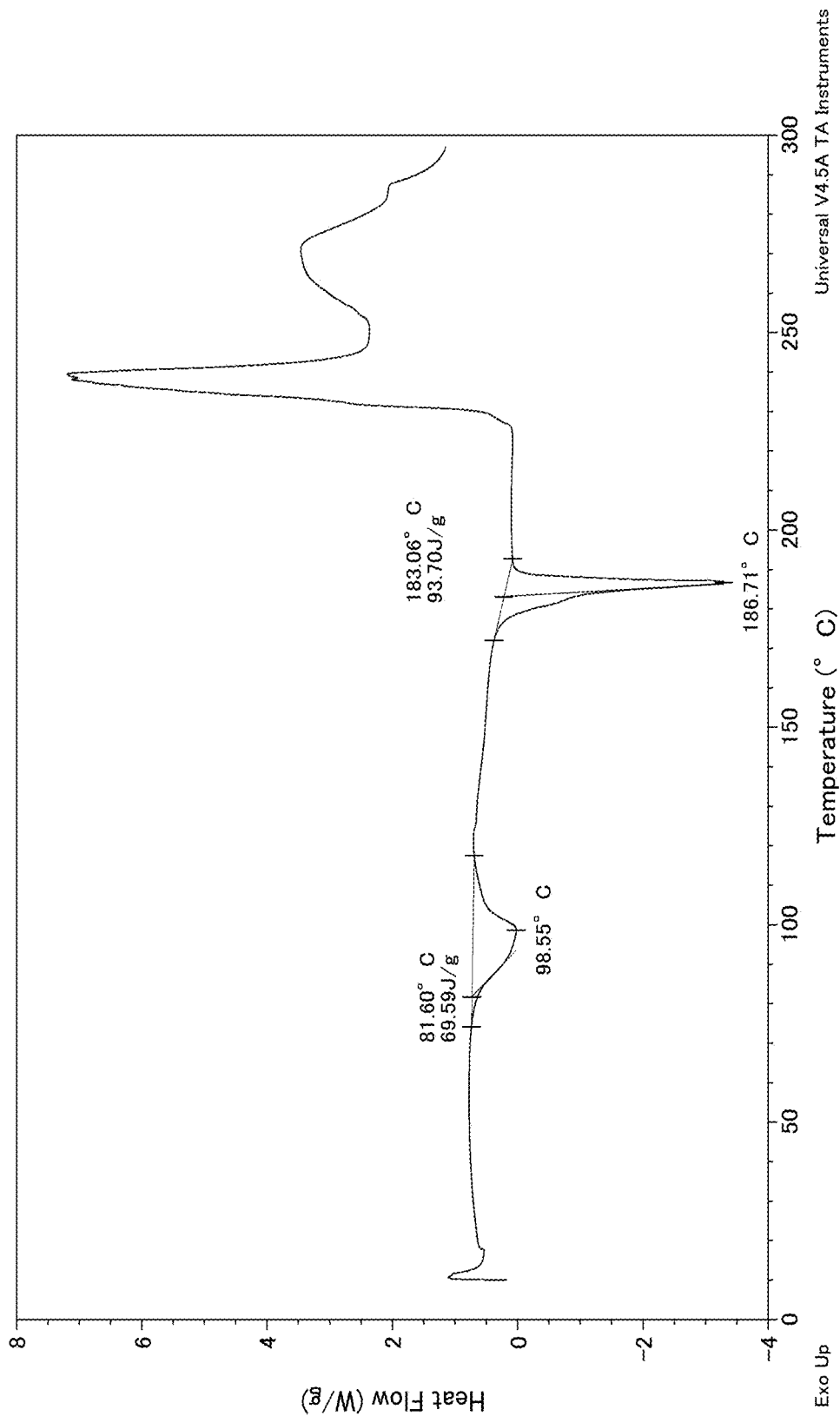
FIG. 2 shows a differential scanning calorimetry (DSC) thermogram of Compound 1 Hydrochloride Form HA.
Figure 3:
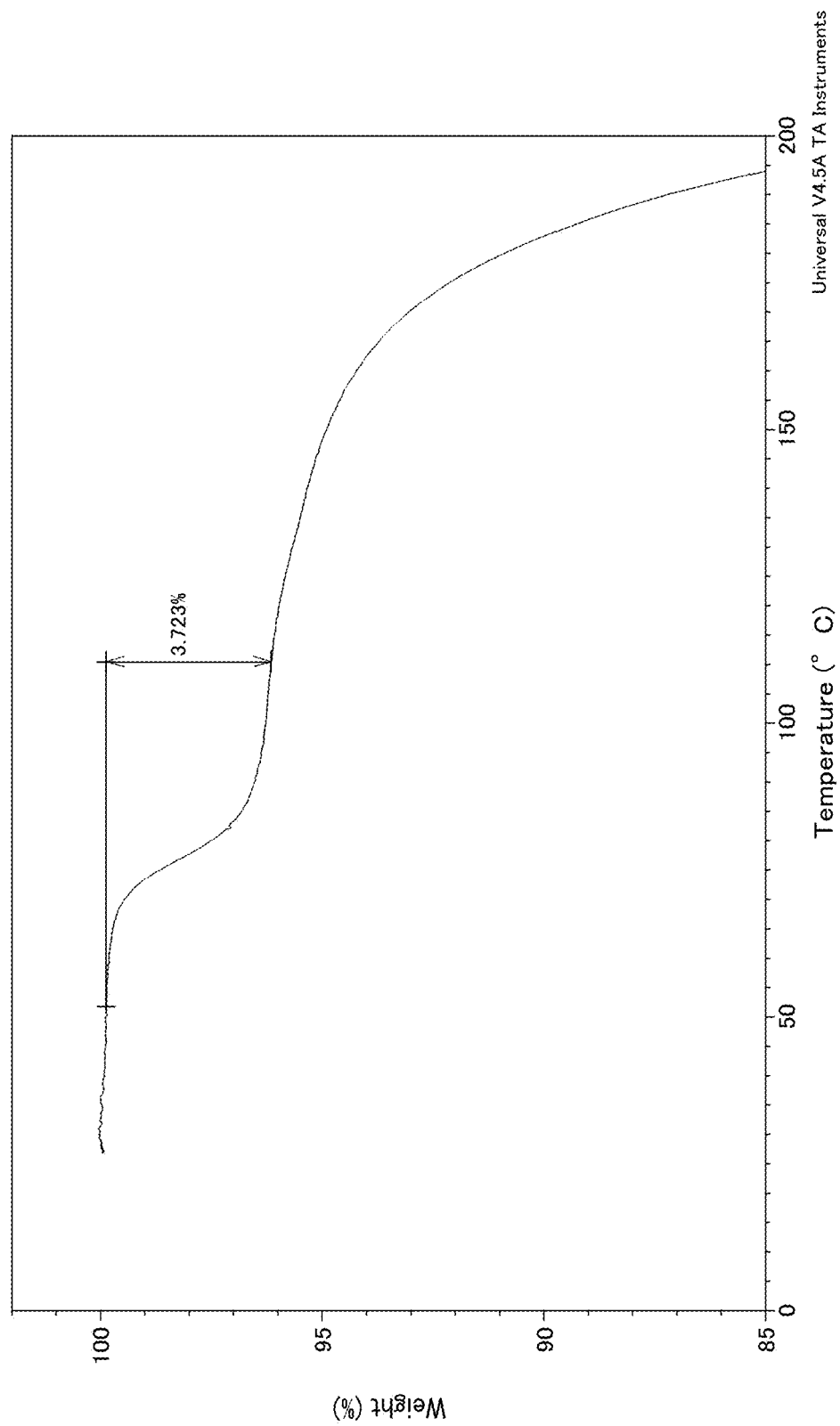
FIG. 3 shows a thermogravimetric analysis (TGA) thermogram of Compound 1 Hydrochloride Form HA.
Figure 4:
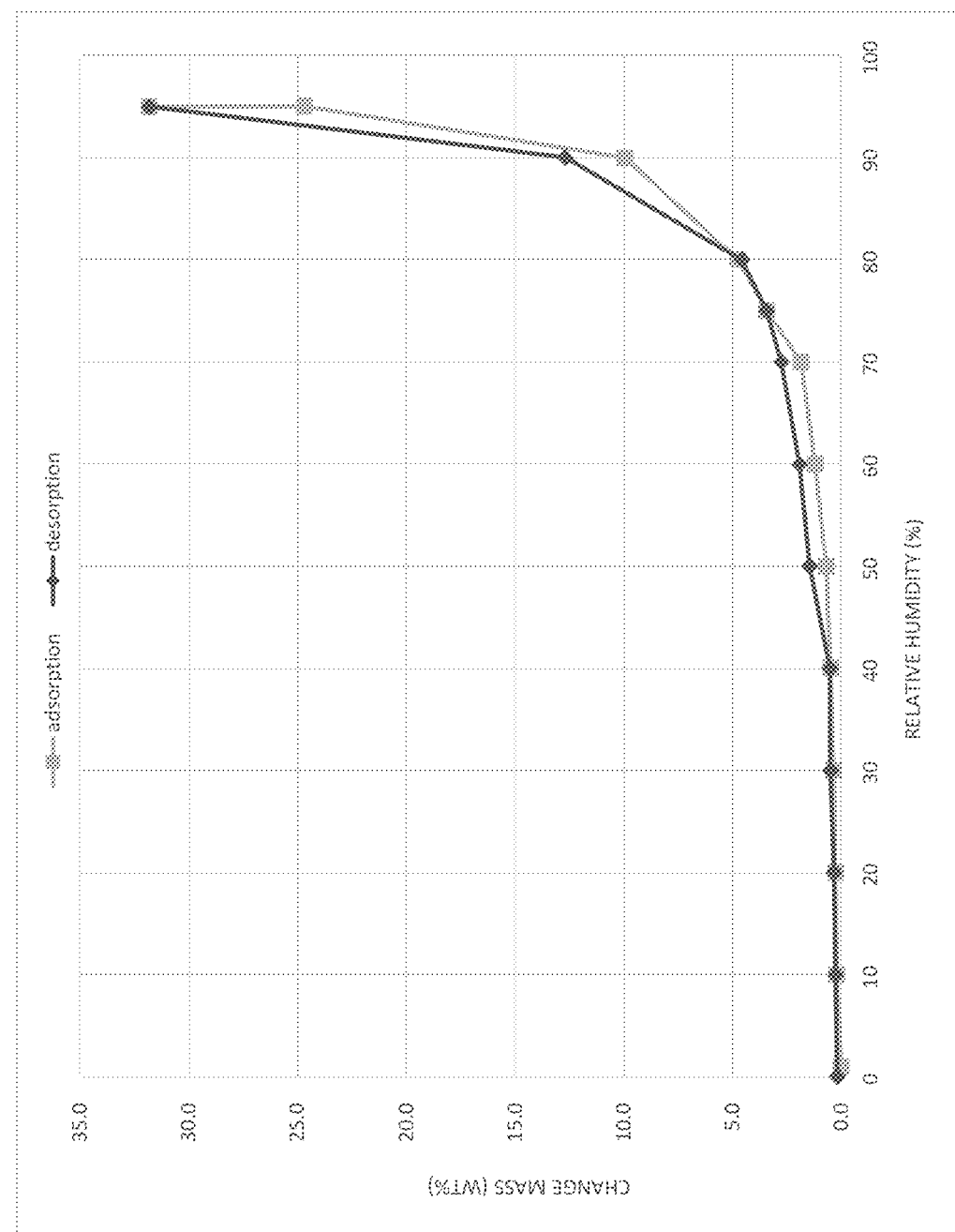
FIG. 4 shows a dynamic vapor sorption (DVS) isotherm of Compound 1 Hydrochloride Form HA.

In some embodiments, Compound 1 Hydrochloride Form HA has endotherm peaks at temperatures of about 99° C. and about 187° C. In some embodiments, Compound 1 Hydrochloride Form HA has an endotherm peak at a temperature of about 99° C. In some embodiments, Compound 1 Hydrochloride Form HA has an endotherm peak at a temperature of about 187° C. In some embodiments, Compound 1 Hydrochloride Form HA has a DSC thermogram substantially as depicted in FIG. 2 (FIG. 2). In some embodiments, Compound 1 Hydrochloride Form HA has a TGA thermogram substantially as depicted in FIG. 3 (FIG. 3). In some embodiments, Compound 1 Hydrochloride Form HA has a DVS isotherm substantially as depicted in FIG. 4 (FIG. 4).

In some embodiments, Compound 1 Hydrochloride Form HA has characteristic XRPD peaks in terms of 2θ selected from 9.4°±0.2°, 11.4°±0.2°, and 15.1°±0.2°; and has endotherm peaks at temperatures of about 99° C. and about 187° C. In some embodiments, Compound 1 Hydrochloride Form HA has characteristic XRPD peaks in terms of 2θ selected from 9.4°±0.2°, 11.4±0.2°, and 15.10°±0.2°; and an endotherm peak at a temperature of about 99° C. In some embodiments, Compound 1 Hydrochloride Form HA has characteristic XRPD peaks in terms of 2θ selected from 9.4°±0.2°, 11.4±0.2°, and 15.10°±0.2°; and an endotherm peak at a temperature of about 187° C. In some embodiments, Compound 1 Hydrochloride Form HA has characteristic XRPD peaks in terms of 2θ selected from 9.4°±0.2°, 11.4±0.2°, and 15.1°±0.2°; and a DSC thermogram substantially as depicted in FIG. 2 (FIG. 2). In some embodiments, Compound 1 Hydrochloride Form HA has characteristic XRPD peaks in terms of 2θ selected from 9.4°±0.2°, 11.4±0.2°, and 15.1°±0.2°; and a DVS isotherm substantially as depicted in FIG. 4 (FIG. 4).

In some embodiments, Compound 1 Hydrochloride Form HA can be isolated with a crystalline purity of at least about 80%, about 85%, about 90%, about 95%, about 96%, about 97%, about 98%, or about 99%. In some embodiments, Compound 1 Hydrochloride Form HA can be isolated with a crystalline purity greater than about 99%. In some embodiments, Compound 1 Hydrochloride Form HA can be isolated with a crystalline purity greater than about 99.9%.

In some embodiments, provided is Compound 1 Hydrochloride Form HA prepared by isolating Compound 1 Hydrochloride Form HA from a mixture of Compound 1, HCl, and S1, wherein S1 is a solvent. In some embodiments, S1 is an organic solvent. In some embodiments, S1 is ether. In some embodiments, S1 is $C_{1-6}$ alkyl acetate. In some embodiments, S1 is THF. In some embodiments, S1 is ethyl acetate.

Compound 1 Hydrochloride Form HB

In some embodiments, provided is (R)-1-(8-fluoroisochroman-1-yl)-N-methylmethanamine Hydrochloride Form HB (Compound 1 hydrochloride Form HB). In some embodiments, Compound 1 Hydrochloride HB is crystalline.

In some embodiments, Compound 1 Hydrochloride Form HB has characteristic XRPD peaks in terms of 2θ selected from 8.6°±0.2°, 9.6°±0.2°, and 10.3°±0.2°. In some embodiments, Compound 1 Hydrochloride Form HB has a characteristic XRPD peak in terms of 2θ at 8.6°±0.2°. In some embodiments, Compound 1 Hydrochloride Form HB has a characteristic XRPD peak in terms of 2θ at 9.6°±0.2°. In some embodiments, Compound 1 Hydrochloride HB has a characteristic XRPD peak in terms of 2θ at 10.3°±0.2°.

In some embodiments, Compound 1 Hydrochloride Form HB has characteristic XRPD peaks in terms of 2θ selected from 8.6°±0.2°, 9.6°±0.2°, 10.3°±0.2°, and 17.3°±0.2°. In some embodiments, Compound 1 Hydrochloride Form HB has at least one characteristic XRPD peak in terms of 2θ selected from 8.6°±0.2°, 9.6°±0.2°, 10.3°±0.2°, and 17.3°±0.2°.

In some embodiments, Compound 1 Hydrochloride Form HB has at least one characteristic XRPD peak in terms of 2θ selected from 8.6°±0.2°, 9.6°±0.2°, 10.3°±0.2°, 12.6°±0.2°, 14.7°±0.2°, 17.3°±0.2°, and 23.8°±0.2°. In some embodiments, Compound 1 Hydrochloride Form HB has at least one characteristic XRPD peak in terms of 2θ selected from 8.6°±0.2°, 9.6°±0.2°, 10.3°±0.2°, 12.6°±0.2°, 14.7°±0.2°, 16.5°±0.2°, 17.3°±0.2°, 18.3°±0.2°, 23.8°±0.2°, 24.4°±0.2°, 26.9°±0.2°, and 27.1°±0.2°.

In some embodiments, Compound 1 Hydrochloride Form HB has at least two characteristic XRPD peaks in terms of 2θ selected from 8.6°±0.2°, 9.6°±0.2°, 10.3°±0.2°, 12.6°±0.2°, 14.7°±0.2°, 17.3°±0.2°, and 23.8°±0.2°. In some embodiments, Compound 1 Hydrochloride Form HB has at least two characteristic XRPD peaks in terms of 2θ selected from 8.6°±0.2°, 9.6°±0.2°, 10.3°±0.2°, 12.6°±0.2°, 14.7°±0.2°, 16.5°±0.2°, 17.3°±0.2°, 18.3°±0.2°, 23.8°±0.2°, 24.4°±0.2°, 26.9°±0.2°, and 27.1°±0.2°.

In some embodiments, Compound 1 Hydrochloride Form HB has at least three characteristic XRPD peaks in terms of 2θ selected from 8.6°±0.2°, 9.6°±0.2°, 10.3°±0.2°, 12.6°±0.2°, 14.7°±0.2°, 17.3°±0.2°, and 23.8°±0.2°. In some embodiments, Compound 1 Hydrochloride Form HB has at least three characteristic XRPD peaks in terms of 2θ selected from 8.6°±0.2°, 9.6°±0.2°, 10.3°±0.2°, 12.6°±0.2°, 14.7°±0.2°, 16.5°±0.2°, 17.3°±0.2°, 18.3°±0.2°, 23.8°±0.2°, 24.4°±0.2°, 26.9°±0.2°, and 27.1°±0.2°.

Figure 5:
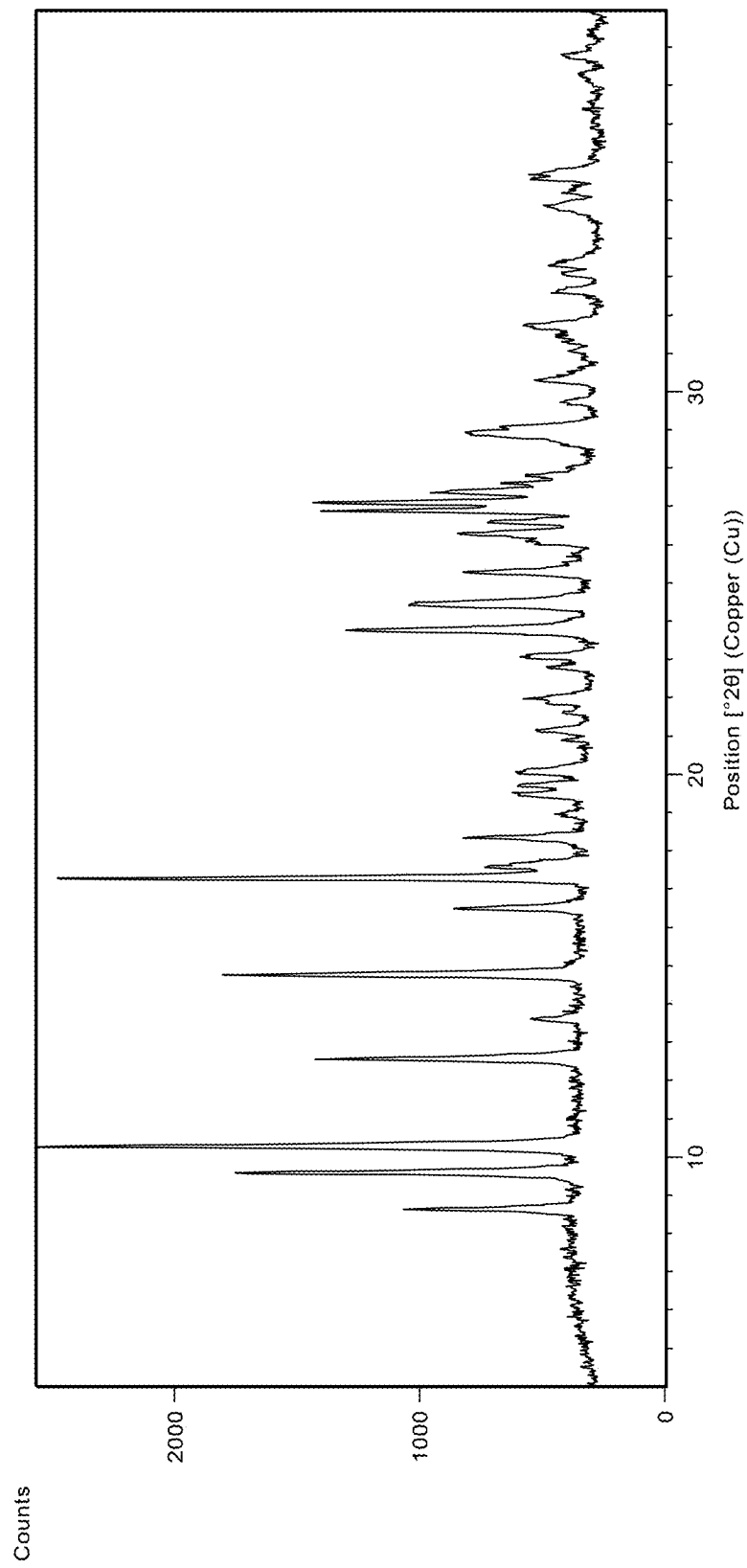
FIG. 5 shows an XRPD pattern of Compound 1 Hydrochloride Form HB.

In some embodiments, Compound 1 Hydrochloride Form HB has an XRPD pattern with characteristic peaks as substantially shown in FIG. 5 (FIG. 5).

In some embodiments, Compound 1 Hydrochloride Form HB can be isolated with a crystalline purity of at least about 80%, about 85%, about 90%, about 95%, about 96%, about 97%, about 98%, or about 99%. In some embodiments, Compound 1 Hydrochloride Form HB can be isolated with a crystalline purity greater than about 99%. In some embodiments, Compound 1 Hydrochloride Form HB can be isolated with a crystalline purity greater than about 99.9%.

In some embodiments, provided is Compound 1 hydrochloride Form HB prepared by isolating Compound 1 hydrochloride Form HA from a mixture of Compound 1, HCl, and S1, wherein S1 is a solvent. In some embodiments, S1 comprises water. In some embodiments, Form HB is prepared by exposing Form HA to high humidity. In some embodiments, Form HB is prepared by exposing Form HA to about 75% relative humidity.

Compound 1 Phosphate

In some embodiments, provided is (R)-1-(8-fluoroisochroman-1-yl)-N-methylmethanamine Phosphate. In some embodiments, Compound 1 Phosphate is crystalline.

In some embodiments, Compound 1 Phosphate has characteristic XRPD peaks in terms of 2θ selected from 4.6°±0.2°, 9.10°±0.2°, and 18.2°±0.2°. In some embodiments, Compound 1 Phosphate has a characteristic XRPD peak in terms of 2θ at 4.6°±0.2°. In some embodiments, Compound 1 Phosphate has a characteristic XRPD peak in terms of 2θ at 9.1°±0.2°. In some embodiments, Compound 1 Phosphate has a characteristic XRPD peak in terms of 2θ at 18.2°±0.2°.

In some embodiments, Compound 1 Phosphate has characteristic XRPD peaks in terms of 2θ selected from 4.6°±0.2°, 9.10°±0.2°, 18.2°±0.2°, and 22.8°±0.2°. In some embodiments, Compound 1 Phosphate has at least one characteristic XRPD peak in terms of 2θ selected from 4.6°±0.2°, 9.1°±0.2°, 18.2°±0.2°, and 22.8°±0.2°.

In some embodiments, Compound 1 Phosphate has at least one characteristic XRPD peak in terms of 2θ selected from 4.6°±0.2°, 9.1°±0.2°, 15.7°±0.2°, 18.2°±0.2°, 22.3°±0.2°, 22.8°±0.2°, and 24.8°±0.2°. In some embodiments, Compound 1 Phosphate has at least one characteristic XRPD peak in terms of 2θ selected from 4.6°±0.2°, 9.1°±0.2°, 15.7°±0.2°, 18.2°±0.2°, 19.1°±0.2°, 22.3°±0.2°, 22.8°±0.2°, 24.8°±0.2°, 26.0°±0.2°, 27.4°±0.2°, and 30.1°±0.2°.

In some embodiments, Compound 1 Phosphate has at least two characteristic XRPD peaks in terms of 2θ selected from 4.6°±0.2°, 9.1°±0.2°, 15.7°±0.2°, 18.2°±0.2°, 22.3°±0.2°, 22.8°±0.2°, and 24.8°±0.2°. In some embodiments, Compound 1 Phosphate has at least two characteristic XRPD peaks in terms of 2θ selected from 4.6°±0.2°, 9.1°±0.2°, 15.7°±0.2°, 18.2°±0.2°, 19.1°±0.2°, 22.3°±0.2°, 22.8°±0.2°, 24.8°±0.2°, 26.0°±0.2°, 27.4°±0.2°, and 30.1°±0.2°.

In some embodiments, Compound 1 Phosphate has at least three characteristic XRPD peaks in terms of 2θ selected from 4.6°±0.2°, 9.1°±0.2°, 15.7°±0.2°, 18.2°±0.2°, 22.3°±0.2°, 22.8°±0.2°, and 24.8°±0.2°. In some embodiments, Compound 1 Phosphate has at least three characteristic XRPD peaks in terms of 2θ selected from 4.6°±0.2°, 9.10°±0.2°, 15.7°±0.2°, 18.2°±0.2°, 19.1°±0.2°, 22.3°±0.2°, 22.8°±0.2°, 24.8°±0.2°, 26.0°±0.2°, 27.4°±0.2°, and 30.1°±0.2.

Figure 6:
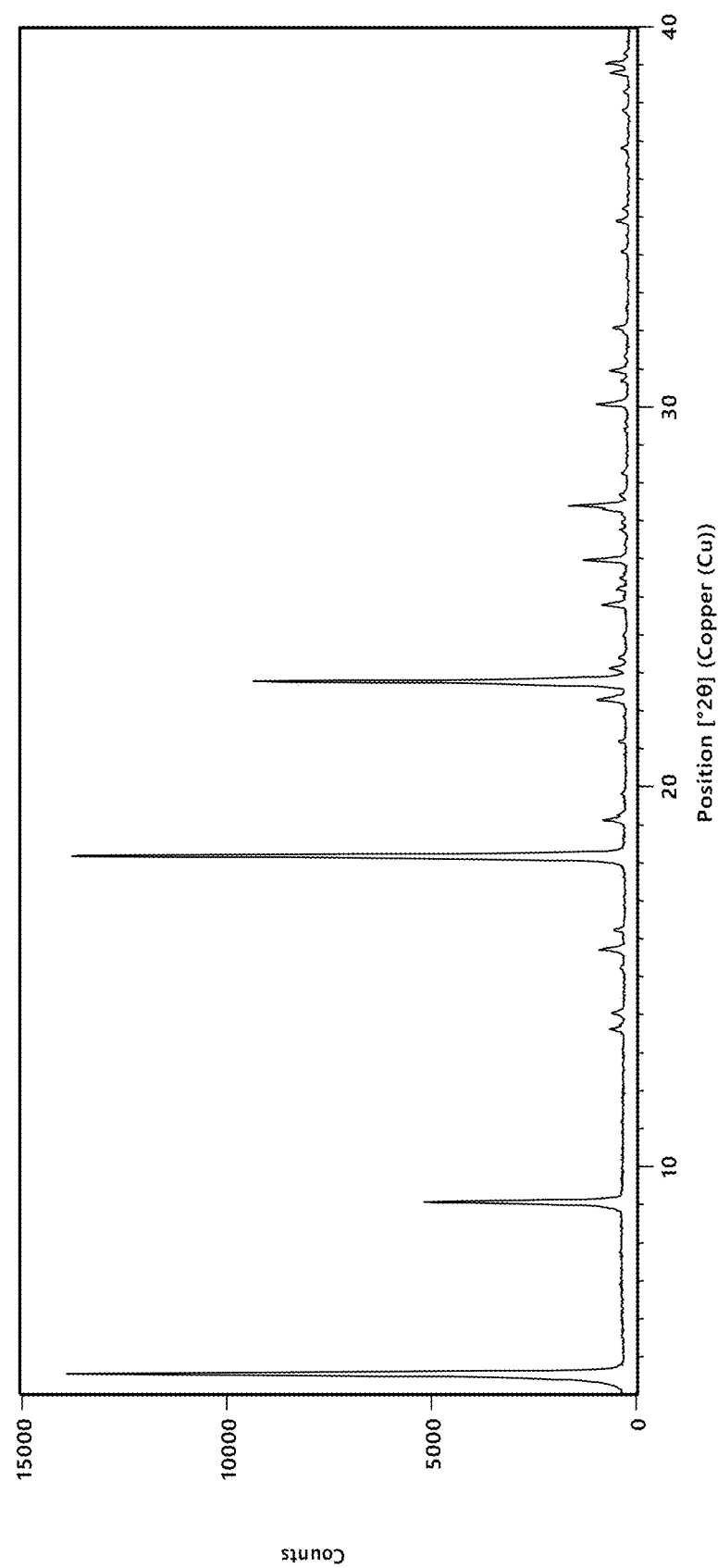
FIG. 6 shows an XRPD pattern of Compound 1 Phosphate.

In some embodiments, Compound 1 Phosphate has an XRPD pattern with characteristic peaks as substantially shown in FIG. 6 (FIG. 6).

Figure 7:
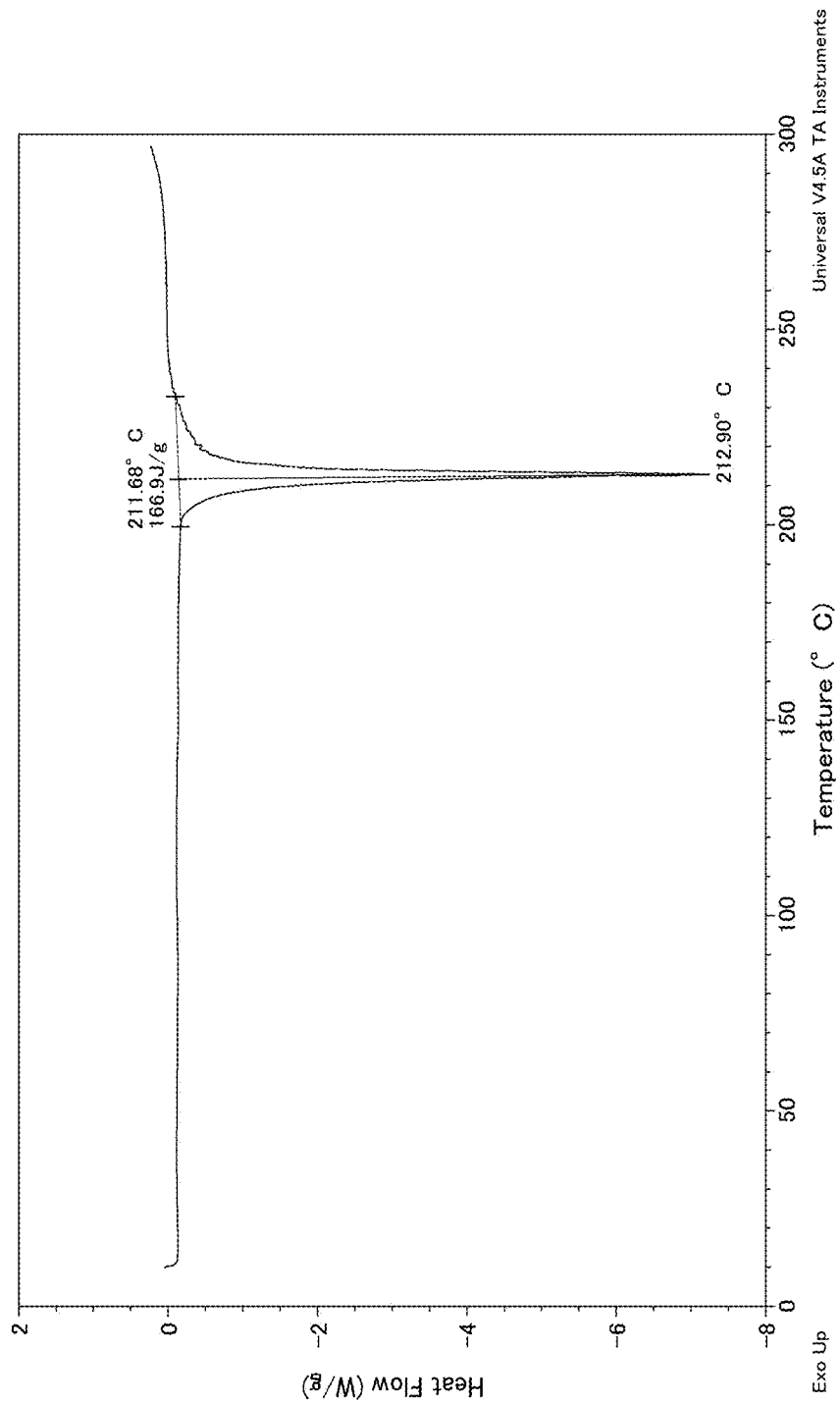
FIG. 7 shows a DSC thermogram of Compound 1 Phosphate.
Figure 8:
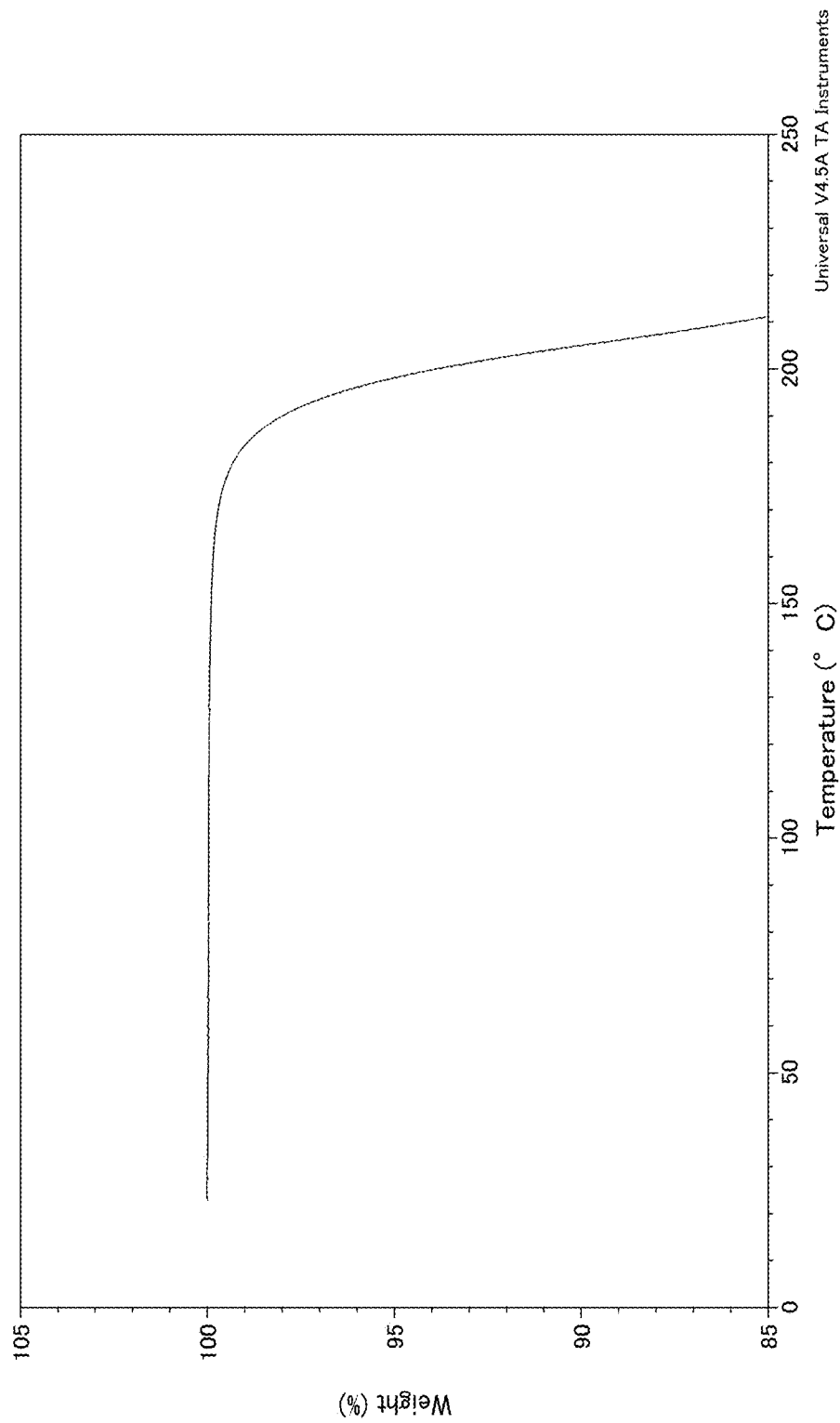
FIG. 8 shows a TGA thermogram of Compound 1 Phosphate.
Figure 9:
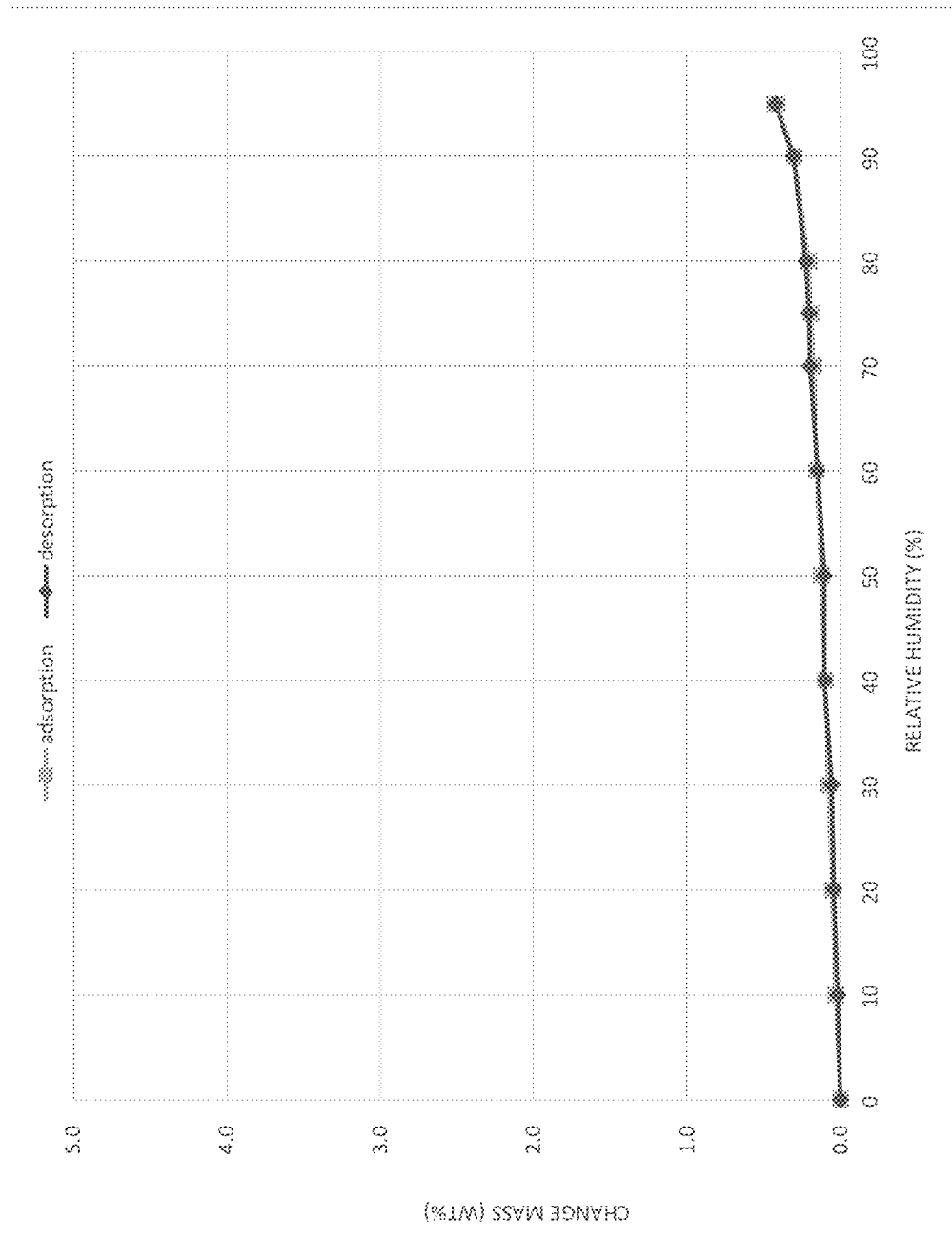
FIG. 9 shows a DVS isotherm of Compound 1 Phosphate.

In some embodiments, Compound 1 Phosphate has an endotherm peak at a temperature of about 213° C. In some embodiments, Compound 1 Phosphate has a DSC thermogram substantially as depicted in FIG. 7 (FIG. 7). In some embodiments, Compound 1 Phosphate has a TGA thermogram substantially as depicted in FIG. 8 (FIG. 8). In some embodiments, Compound 1 Phosphate has a DVS isotherm substantially as depicted in FIG. 9 (FIG. 9).

In some embodiments, Compound 1 Phosphate has at least one characteristic XRPD peak in terms of 2θ selected from 4.6°±0.2°, 9.1°±0.2°, 18.2°±0.2°, and 22.8°±0.2°; and an endotherm peak at a temperature of about 213° C. In some embodiments, Compound 1 Phosphate has at least one characteristic XRPD peak in terms of 2θ selected from 4.60°±0.2°, 9.1°±0.2°, 18.2°±0.2°, and 22.8°±0.2°; and a DSC thermogram substantially as depicted in FIG. 7 (FIG. 7). In some embodiments, Compound 1 Phosphate has at least one characteristic XRPD peak in terms of 2θ selected from 4.6°±0.2°, 9.1°±0.2°, 18.2°±0.2°, and 22.8°±0.2°; and a DVS isotherm substantially as depicted in FIG. 9 (FIG. 9).

In some embodiments, Compound 1 Phosphate can be isolated with a crystalline purity of at least about 80%, about 85%, about 90%, about 95%, about 96%, about 97%, about 98%, or about 99%. In some embodiments, Compound 1 Phosphate can be isolated with a crystalline purity greater than about 99%. In some embodiments, Compound 1 phosphate can be isolated with a crystalline purity greater than about 99.9%.

In some embodiments, provided is Compound 1 phosphate prepared by isolating Compound 1 phosphate from a mixture of Compound 1, phosphoric acid, and S1, wherein S1 is a solvent. In some embodiments, S1 is an organic solvent. In some embodiments, S1 is $C_{1-6}$ alkyl alcohol. In some embodiments, S1 is ether. In some embodiments, S1 is $C_{1-6}$ alkyl acetate. In some embodiments, S1 is a mixture of organic solvents. In some embodiments, S1 is a mixture of $C_{1-6}$ alkyl alcohol and $C_{1-6}$ alkyl acetate. In some embodiments, S1 is THF. In some embodiments, S1 is ethyl acetate. In some embodiments, S1 is a mixture of methanol and acetone. In some embodiments, S1 is a mixture of methanol and ethyl acetate.

Compound 1 L-Tartrate

In some embodiments, provided is (R)-1-(8-fluoroisochroman-1-yl)-N-methylmethanamine L-tartrate (Compound 1 L-Tartrate). In some embodiments, Compound 1 L-Tartrate is crystalline.

In some embodiments, provided is Compound 1 L-Tartrate prepared by isolating Compound 1 L-Tartrate from a mixture of Compound 1, tartaric acid, and S1, wherein S1 is a solvent. In some embodiments, S1 is an organic solvent. In some embodiments, S1 is $C_{1-6}$ alkyl alcohol. In some embodiments, S1 is ether. In some embodiments, S1 is $C_{1-6}$ alkyl acetate. In some embodiments, S1 is $C_{1-6}$ alkyl ketone. In some embodiments, S1 is a mixture of $C_{1-6}$ alkyl alcohol and $C_{1-6}$ alkyl ketone. In some embodiments, S1 is a mixture of $C_{1-6}$ alkyl alcohol and $C_{1-6}$ alkyl acetate. In some embodiments, S1 is methanol. In some embodiments, S1 is THF. In some embodiments, S1 is ethyl acetate. In some embodiments, S1 is a mixture of methanol and acetone. In some embodiments, S1 is a mixture of methanol and ethyl acetate.

Compound 1 L-Tartrate Form LA

In some embodiments, provided is (R)-1-(8-fluoroisochroman-1-yl)-N-methylmethanamine L-Tartrate Form LA (Compound 1 L-Tartrate Form LA). In some embodiments, Compound 1 L-Tartrate Form LA is crystalline.

In some embodiments, Compound 1 L-Tartrate Form LA has characteristic XRPD peaks in terms of 2θ selected from 12.1°±0.2°, 18.1°±0.2°, and 24.2°±0.2°. In some embodiments, Compound 1 L-Tartrate Form LA has a characteristic XRPD peak in terms of 2θ at 12.1°±0.2°. In some embodiments, Compound 1 L-Tartrate Form LA has a characteristic XRPD peak in terms of 2θ at 18.1°±0.2°. In some embodiments, Compound 1 L-Tartrate Form LA has a characteristic XRPD peak in terms of 2θ at 24.2°±0.2°.

In some embodiments, Compound 1 L-Tartrate Form LA has at least one characteristic XRPD peak in terms of 2θ selected from 12.1°±0.2°, 15.0°±0.2°, 16.4°±0.2°, 16.9°±0.2°, 17.1°±0.2°, 18.10°±0.2°, 23.9°±0.2°, and 24.2°±0.2°. In some embodiments, Compound 1 L-Tartrate Form LA has at least one characteristic XRPD peak in terms of 2θ selected from 12.1°±0.2°, 15.0°±0.2°, 16.4°±0.2°, 16.9°±0.2°, 17.1°±0.2°, 18.1°±0.2°, 19.3°±0.2°, 23.9°±0.2°, 24.2°±0.2°, 24.8°±0.2°, and 27.2°±0.2°.

In some embodiments, Compound 1 L-Tartrate Form LA has at least two characteristic XRPD peaks in terms of 2θ selected from 12.1°±0.2°, 15.0°±0.2°, 16.4°±0.2°, 16.9°±0.2°, 17.1°±0.2°, 18.10°±0.2°, 23.9°±0.2°, and 24.2°±0.2°. In some embodiments, Compound 1 L-Tartrate Form LA has at least two characteristic XRPD peaks in terms of 2θ selected from 12.1°±0.2°, 15.0°±0.2°, 16.4°±0.2°, 16.9°±0.2°, 17.1°±0.2°, 18.1°±0.2°, 19.3°±0.2°, 23.9°±0.2°, 24.2°±0.2°, 24.8°±0.2°, and 27.2°±0.2°.

In some embodiments, Compound 1 L-Tartrate Form LA has at least three characteristic XRPD peaks in terms of 2θ selected from 12.1°±0.2°, 15.0°±0.2°, 16.4°±0.2°, 16.9°±0.2°, 17.1°±0.2°, 18.10°±0.2°, 23.9°±0.2°, and 24.2°±0.2°. In some embodiments, Compound 1 L-Tartrate Form LA has at least three characteristic XRPD peaks in terms of 2θ selected from 12.1°±0.2°, 15.0°±0.2°, 16.4°±0.2°, 16.9°±0.2°, 17.1°±0.2°, 18.1°±0.2°, 19.3°±0.2°, 23.9°±0.2°, 24.2°±0.2°, 24.8°±0.2°, and 27.2°±0.2°.

Figure 10:
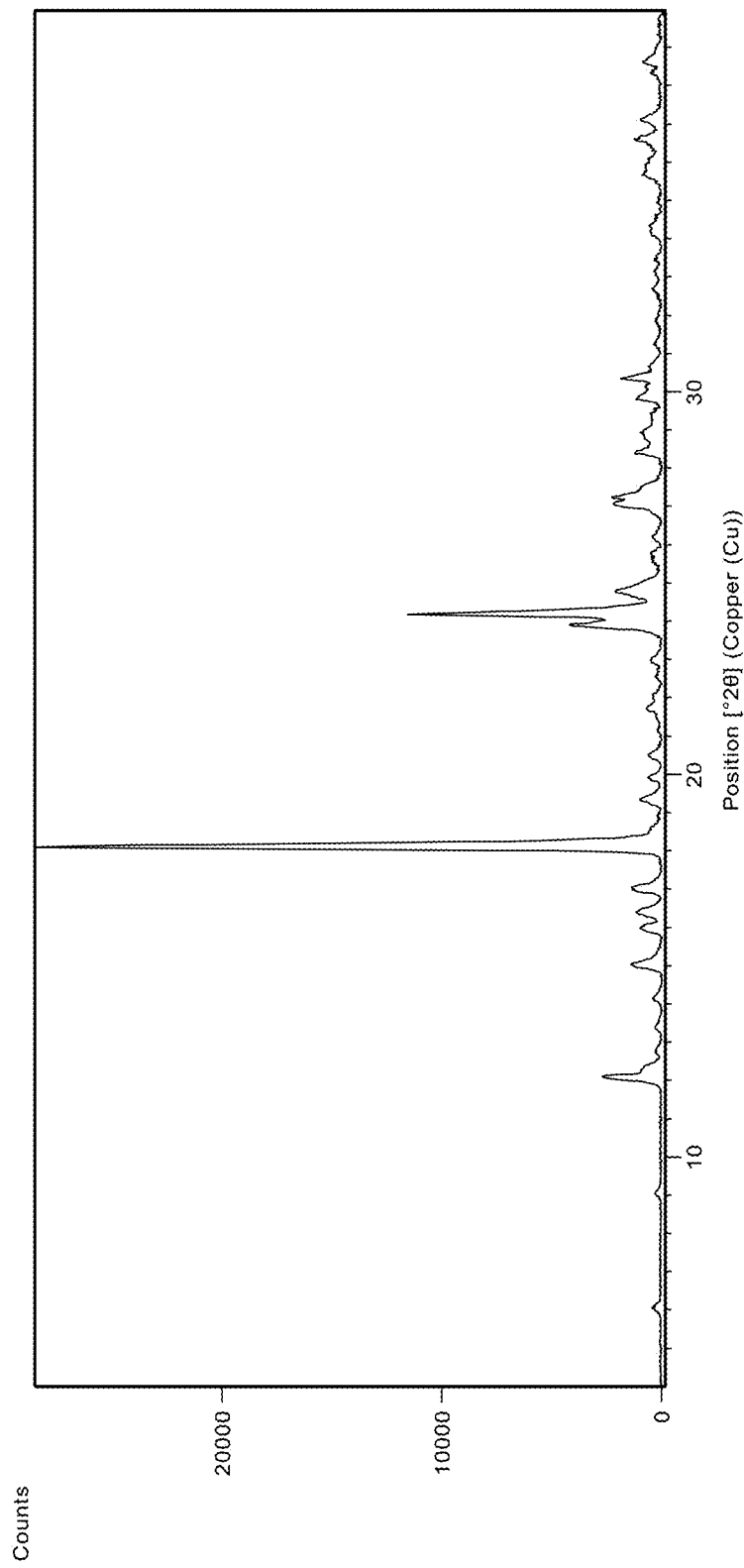
FIG. 10 shows an XRPD pattern of Compound 1 L-Tartrate Form LA.

In some embodiments, Compound 1 L-Tartrate Form LA has an XRPD pattern with characteristic peaks as substantially shown in FIG. 10 (FIG. 10).

Figure 11:
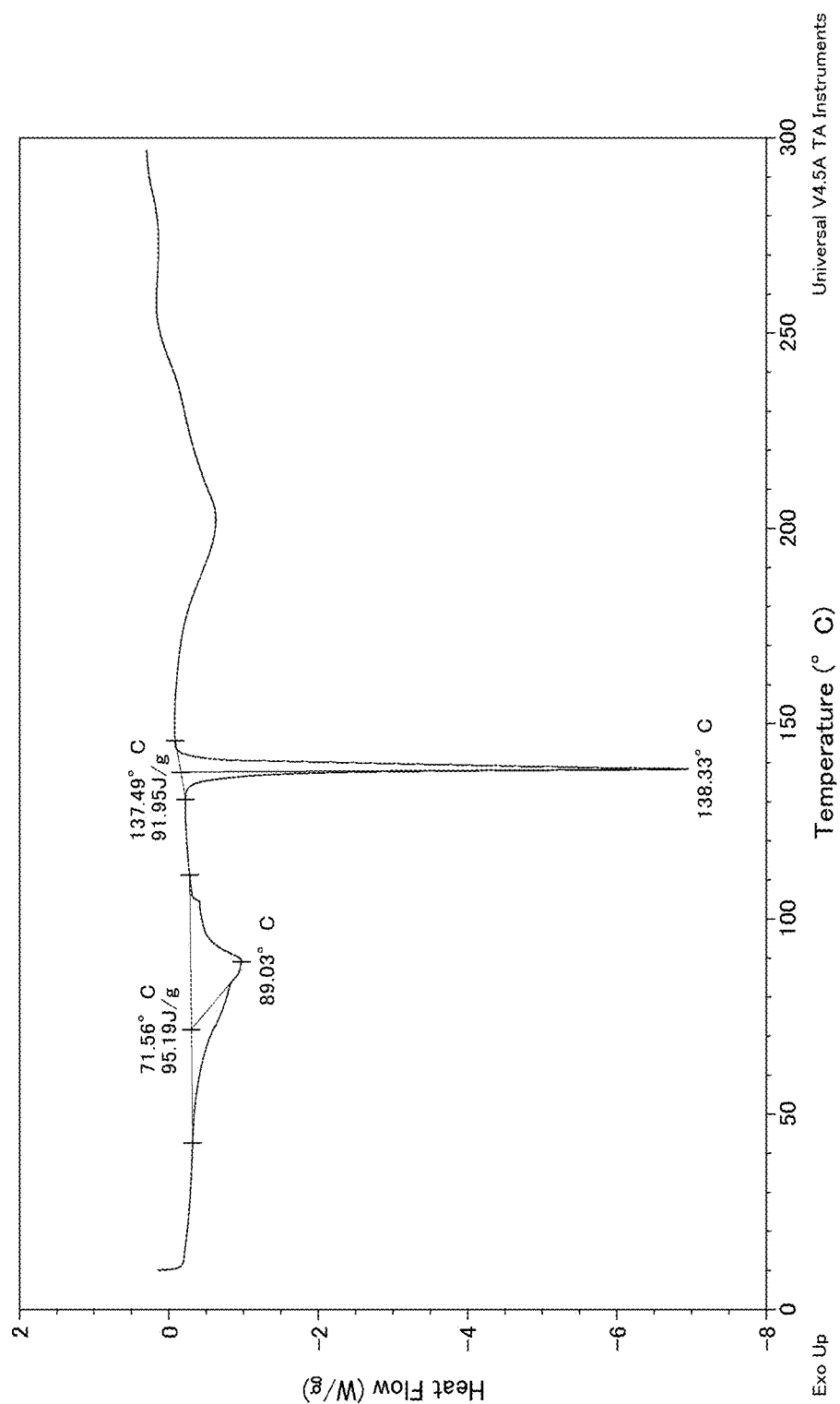
FIG. 11 shows a DSC thermogram of Compound 1 L-Tartrate Form LA.
Figure 12:
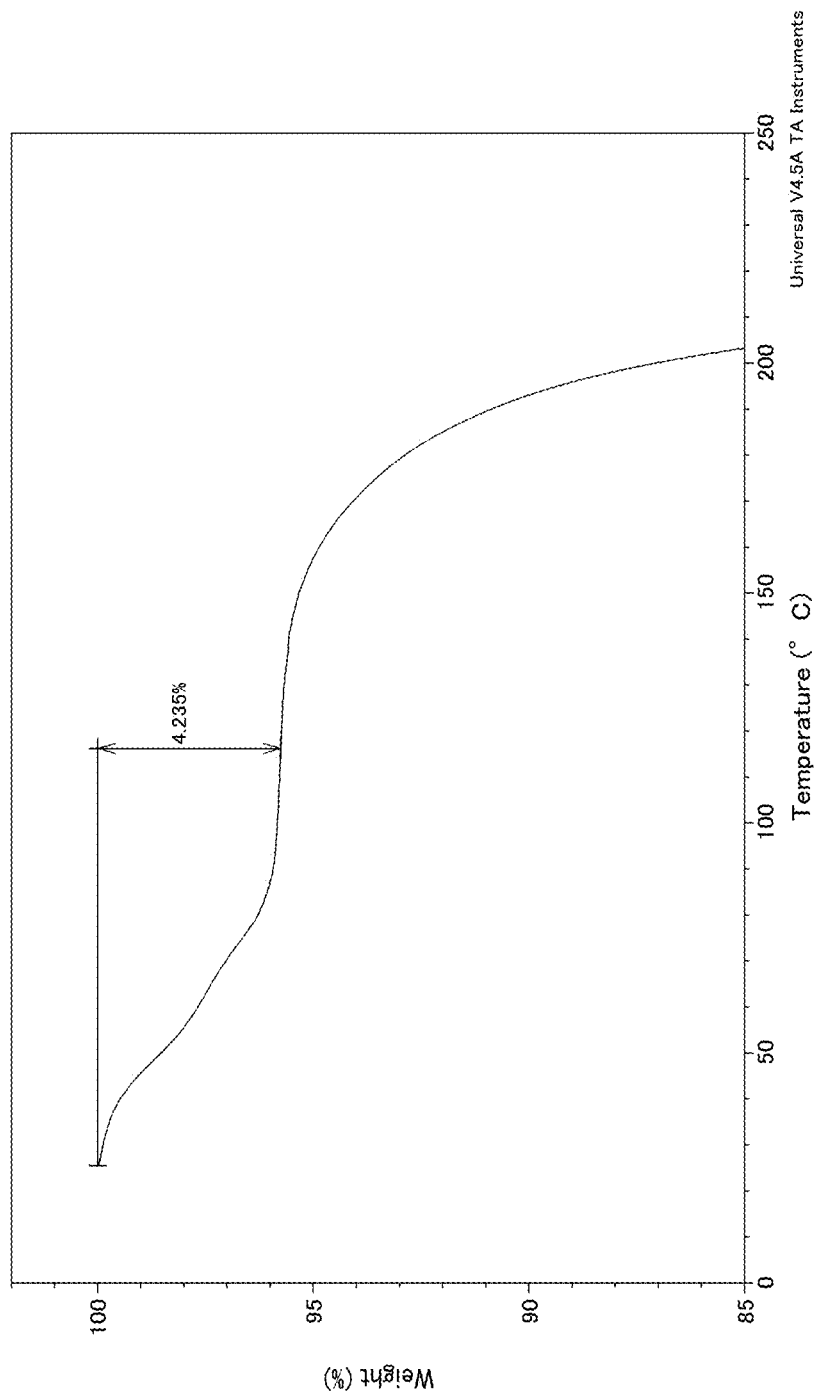
FIG. 12 shows a TGA thermogram of Compound 1 L-Tartrate Form LA.
Figure 13:
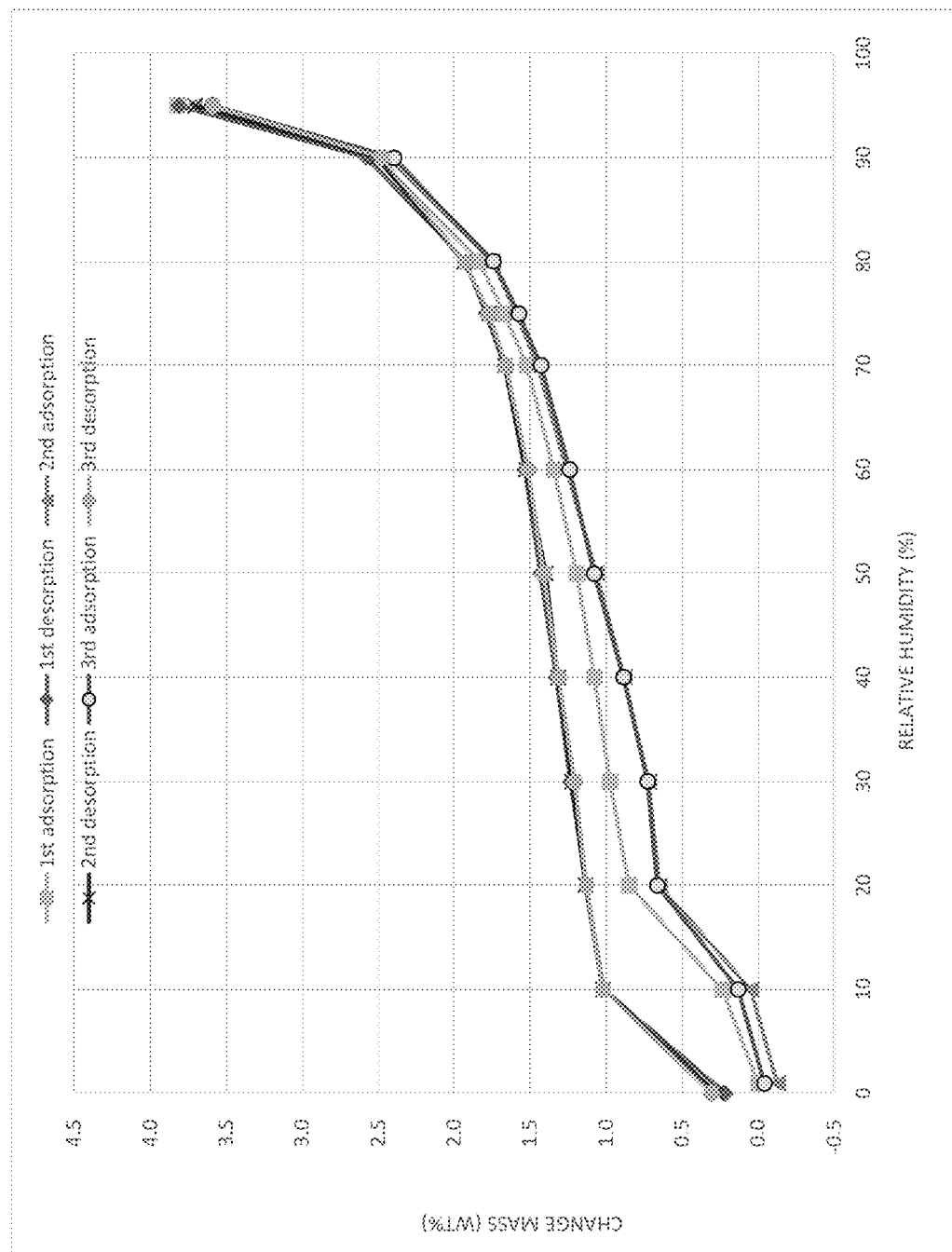
FIG. 13 shows a DVS isotherm of Compound 1 L-Tartrate Form LA.

In some embodiments, Compound 1 L-Tartrate Form LA has endotherm peaks at temperatures of about 89° C. and about 138° C. In some embodiments, Compound 1 L-Tartrate Form LA has an endotherm peak at a temperature of about 89° C. In some embodiments, Compound 1 L-Tartrate Form LA has an endotherm peak at a temperature of about 138° C. In some embodiments, Compound 1 L-Tartrate Form LA has a DSC thermogram substantially as depicted in FIG. 11 (FIG. 11). In some embodiments, Compound 1 L-Tartrate Form LA has a TGA thermogram substantially as depicted in FIG. 12 (FIG. 12). In some embodiments, Compound 1 L-Tartrate Form LA has a DVS isotherm substantially as depicted in FIG. 13 (FIG. 13).

In some embodiments, Compound 1 L-Tartrate Form LA has at least one characteristic XRPD peak in terms of 2θ selected from 12.1°±0.2°, 18.1°±0.2°, and 24.2°±0.2°; and has endotherm peaks at temperatures of about 89° C. and about 138° C. In some embodiments, Compound 1 L-Tartrate Form LA has at least one characteristic XRPD peak in terms of 2θ selected from 12.1°±0.2°, 18.1°±0.2°, and 24.2°±0.2°; and an endotherm peak at a temperature of about 89° C. In some embodiments, Compound 1 L-Tartrate Form LA has at least one characteristic XRPD peak in terms of 2θ selected from 12.1°±0.2°, 18.1°±0.2°, and 24.2°±0.2°; and an endotherm peak at a temperature of about 138° C. In some embodiments, Compound 1 L-Tartrate Form LA has at least one characteristic XRPD peak in terms of 2θ selected from 12.1°±0.2°, 18.1°±0.2°, and 24.2°±0.2°; and a DSC thermogram substantially as depicted in FIG. 11 (FIG. 11). In some embodiments, Compound 1 L-Tartrate Form LA has at least one characteristic XRPD peak in terms of 2θ selected from 12.1°±0.2°, 18.1°±0.2°, and 24.2°±0.2°; and a DVS isotherm substantially as depicted in FIG. 13 (FIG. 13).

In some embodiments, Compound 1 L-Tartrate Form LA can be isolated with a crystalline purity of at least about 80%, about 85%, about 90%, about 95%, about 96%, about 97%, about 98%, or about 99%. In some embodiments, Compound 1 L-Tartrate Form LA can be isolated with a crystalline purity greater than about 99%. In some embodiments, Compound 1 L-Tartrate Form LA can be isolated with a crystalline purity greater than about 99.9%.

In some embodiments, provided is Compound 1 L-tartrate Form LA prepared by isolating Compound 1 L-tartrate Form LA from a mixture of Compound 1, L-tartaric acid, and S1, wherein S1 is a solvent. In some embodiments, S1 is an organic solvent. In some embodiments, S1 is ether. In some embodiments, S1 is $C_{1-6}$ alkyl acetate. In some embodiments, S1 is THF. In some embodiments, S1 is ethyl acetate.

Compound 1 L-Tartrate Form LB

In some embodiments, provided is (R)-1-(8-fluoroisochroman-1-yl)-N-methylmethanamine L-Tartrate Form LB (Compound 1 L-tartrate Form LB). In some embodiments, Compound 1 L-Tartrate Form LB is crystalline.

In some embodiments, Compound 1 L-Tartrate Form LB has characteristic XRPD peaks in terms of 2θ selected from 18.7°±0.2°, 25.0°±0.2°, and 31.4°±0.2°. In some embodiments, Compound 1 L-Tartrate Form LB has a characteristic XRPD peak in terms of 2θ at 18.7°±0.2°. In some embodiments, Compound 1 L-Tartrate Form LB has a characteristic XRPD peak in terms of 2θ at 25.0°±0.2°. In some embodiments, Compound 1 L-Tartrate Form LB has a characteristic XRPD peak in terms of 2θ at 31.4°±0.2°.

In some embodiments, Compound 1 L-Tartrate Form LB has at least one characteristic XRPD peak in terms of 2θ selected from 6.3°±0.2°, 12.5°±0.2°, 18.1°±0.2°, 18.70°±0.2°, 23.9°±0.2°, 25.0°±0.2°, and 31.4°±0.2°. In some embodiments, Compound 1 L-Tartrate Form LB has at least one characteristic XRPD peak in terms of 2θ selected from 6.3°±0.2°, 12.5°±0.2°, 18.1°±0.2°, 18.7°±0.2°, 20.0°±0.2°, 23.9°±0.2°, 24.2°±0.2°, 25.0°±0.2°, and 31.4°±0.2°.

In some embodiments, Compound 1 L-Tartrate Form LB has at least two characteristic XRPD peaks in terms of 2θ selected from 6.3°±0.2°, 12.5°±0.2°, 18.1°±0.2°, 18.7°±0.2°, 23.9°±0.2°, 25.0°±0.2°, and 31.4°±0.2°. In some embodiments, Compound 1 L-Tartrate Form LB has at least two characteristic XRPD peaks in terms of 2θ selected from 6.3°±0.2°, 12.5°±0.2°, 18.1°±0.2°, 18.7°±0.2°, 20.0°±0.2°, 23.9°±0.2°, 24.2°±0.2°, 25.0°±0.2°, and 31.4°±0.2°.

In some embodiments, Compound 1 L-Tartrate Form LB has at least three characteristic XRPD peaks in terms of 2θ selected from 6.3°±0.2°, 12.5°±0.2°, 18.1°±0.2°, 18.7°±0.2°, 23.9°±0.2°, 25.0°±0.2°, and 31.4°±0.2°. In some embodiments, Compound 1 L-Tartrate Form LB has at least three characteristic XRPD peaks in terms of 2θ selected from 6.3°±0.2°, 12.5°±0.2°, 18.1°±0.2°, 18.7°±0.2°, 20.0°±0.2°, 23.9°±0.2°, 24.2°±0.2°, 25.0°±0.2°, and 31.4°±0.2.

Figure 14:
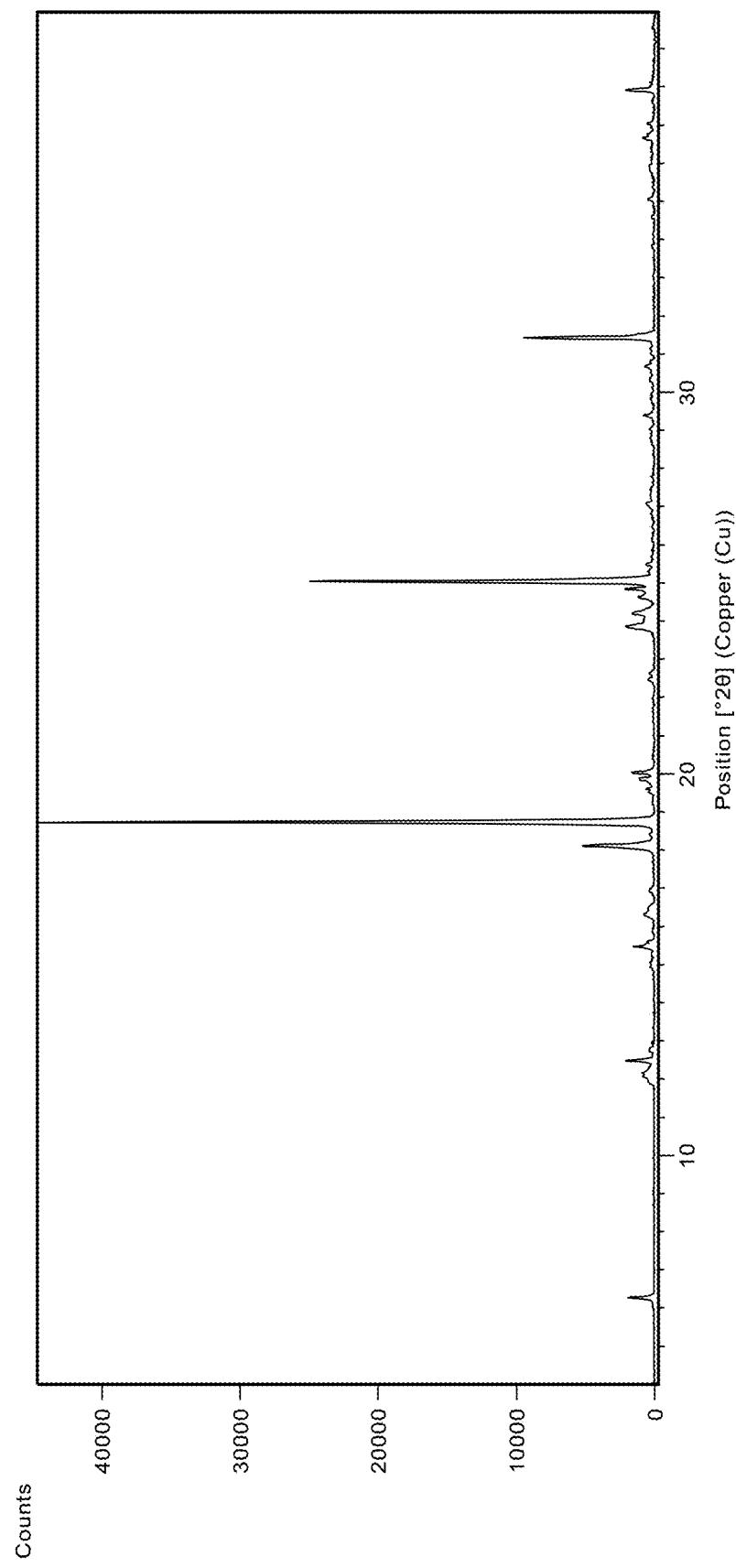
FIG. 14 shows an XRPD pattern of Compound 1 L-Tartrate Form LB.
Figure 15:
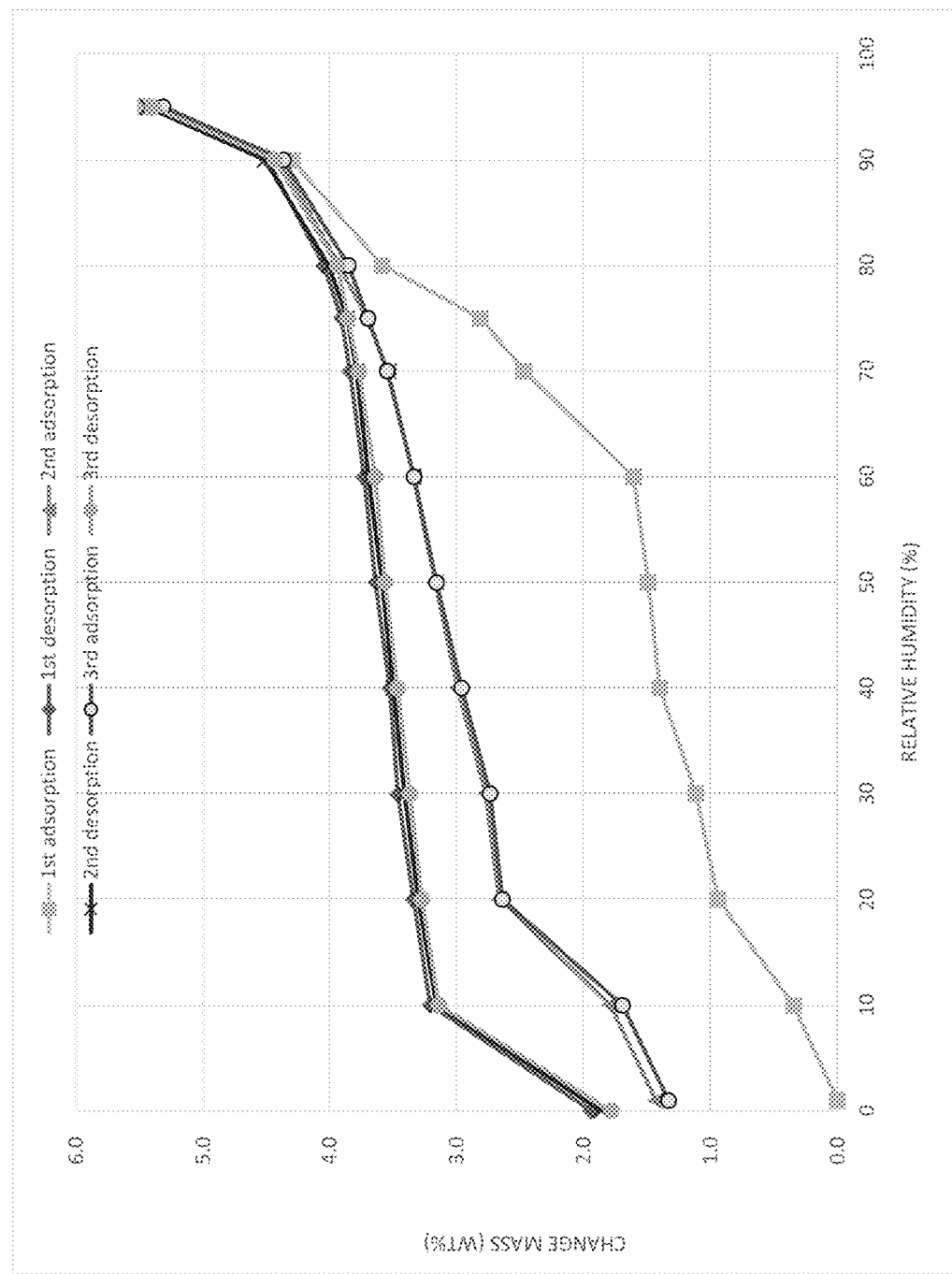
FIG. 15 shows a DVS isotherm of Compound 1 L-Tartrate Form LB.

In some embodiments, Compound 1 L-Tartrate Form LB has an XRPD pattern with characteristic peaks as substantially shown in FIG. 14 (FIG. 14). In some embodiments, Compound L-Tartrate Form LB has a DVS isotherm as substantially shown in FIG. 15 (FIG. 15).

In some embodiments, Compound 1 L-Tartrate Form LB can be isolated with a crystalline purity of at least about 80%, about 85%, about 90%, about 95%, about 96%, about 97%, about 98%, or about 99%. In some embodiments, Compound 1 L-Tartrate Form LB can be isolated with a crystalline purity greater than about 99%. In some embodiments, Compound 1 L-Tartrate Form LB can be isolated with a crystalline purity greater than about 99.9%.

In some embodiments, provided is Compound 1 L-tartrate Form LB prepared by isolating Compound 1 L-tartrate Form LB from a mixture of Compound 1, L-tartaric acid, and S1, wherein S1 is a solvent. In some embodiments, S1 is an organic solvent. In some embodiments, S1 is $C_{1-6}$ alkyl alcohol. In some embodiments, S1 is a $C_{1-6}$ alkyl ketone. In some embodiments, S1 is a mixture of organic solvents. In some embodiments, S1 is a mixture of a $C_{1-6}$ alkyl alcohol and a $C_{1-6}$ alkyl ketone. In some embodiments, S1 is a mixture of methanol and acetone.

Compound 1 L-Tartrate Form LC

In some embodiments, provided is (R)-1-(8-fluoroisochroman-1-yl)-N-methylmethanamine L-Tartrate Form LC (Compound 1 L-tartrate Form LC). In some embodiments, Compound 1 L-Tartrate Form LC is crystalline.

In some embodiments, Compound 1 L-Tartrate Form LC has characteristic XRPD peaks in terms of 2θ selected from 12.2°±0.2°, 16.5°±0.2°, and 24.8°±0.2°. In some embodiments, Compound 1 L-Tartrate Form LC has a characteristic XRPD peak in terms of 2θ at 12.2°±0.2°. In some embodiments, Compound 1 L-Tartrate Form LC has a characteristic XRPD peak in terms of 2θ at 16.5°±0.2°. In some embodiments, Compound 1 L-Tartrate Form LC has a characteristic XRPD peak in terms of 2θ at 24.8°±0.2°.

In some embodiments, Compound 1 L-Tartrate Form LC has at least one characteristic XRPD peak in terms of 2θ selected from 12.2°±0.2°, 15.4°±0.2°, 16.5°±0.2°, 18.7°±0.2°, 19.8°±0.2°, 22.6°±0.2°, 24.8°±0.2°, and 25.5°±0.2°. In some embodiments, Compound 1 L-Tartrate Form LC has at least one characteristic XRPD peak in terms of 2θ selected from 12.2°±0.2°, 12.8°±0.2°, 15.4°±0.2°, 16.5°±0.2°, 18.7°±0.2°, 19.8°±0.2°, 20.0°±0.2°, 22.4°±0.2°, 22.6°±0.2°, 24.8°±0.2°, 25.0°±0.2°, 25.5°±0.2°, and 27.1°±0.2°.

In some embodiments, Compound 1 L-Tartrate Form LC has at least two characteristic XRPD peaks in terms of 2θ selected from 12.2°±0.2°, 15.4°±0.2°, 16.5°±0.2°, 18.7°±0.2°, 19.8°±0.2°, 22.6°±0.2°, 24.8°±0.2°, and 25.5°±0.2°. In some embodiments, Compound 1 L-Tartrate Form LC has at least two characteristic XRPD peaks in terms of 2θ selected from 12.2°±0.2°, 12.8°±0.2°, 15.4°±0.2°, 16.5°±0.2°, 18.7°±0.2°, 19.8°±0.2°, 20.0°±0.2°, 22.4°±0.2°, 22.6°±0.2°, 24.8°±0.2°, 25.0°±0.2°, 25.5°±0.2°, and 27.1°±0.2°.

In some embodiments, Compound 1 L-Tartrate Form LC has at least three characteristic XRPD peaks in terms of 2θ selected from 12.2°±0.2°, 15.4°±0.2°, 16.5°±0.2°, 18.7°±0.2°, 19.8°±0.2°, 22.6°±0.2°, 24.8°±0.2°, and 25.5°±0.2°. In some embodiments, Compound 1 L-Tartrate Form LC has at least three characteristic XRPD peaks in terms of 2θ selected from 12.2°±0.2°, 12.8°±0.2°, 15.4°±0.2°, 16.5°±0.2°, 18.7°±0.2°, 19.8°±0.2°, 20.0°±0.2°, 22.4°±0.2°, 22.6°±0.2°, 24.8°±0.2°, 25.0°±0.2°, 25.5°±0.2°, and 27.1°±0.2°.

Figure 16:
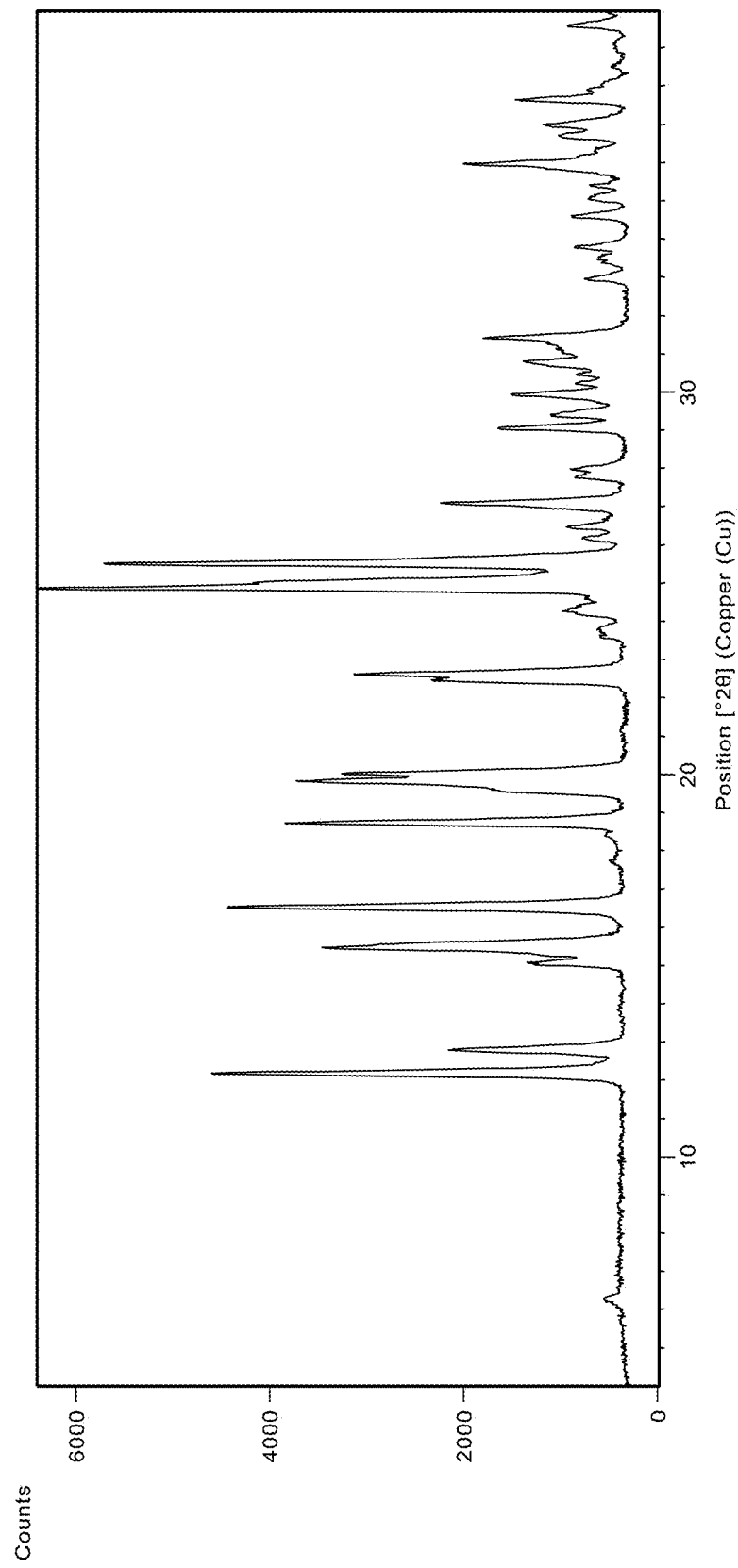
FIG. 16 shows an XRPD pattern of Compound 1 L-Tartrate Form LC.

In some embodiments, Compound 1 L-Tartrate Form LC has an XRPD pattern with characteristic peaks as substantially shown in FIG. 16 (FIG. 16).

Figure 17:
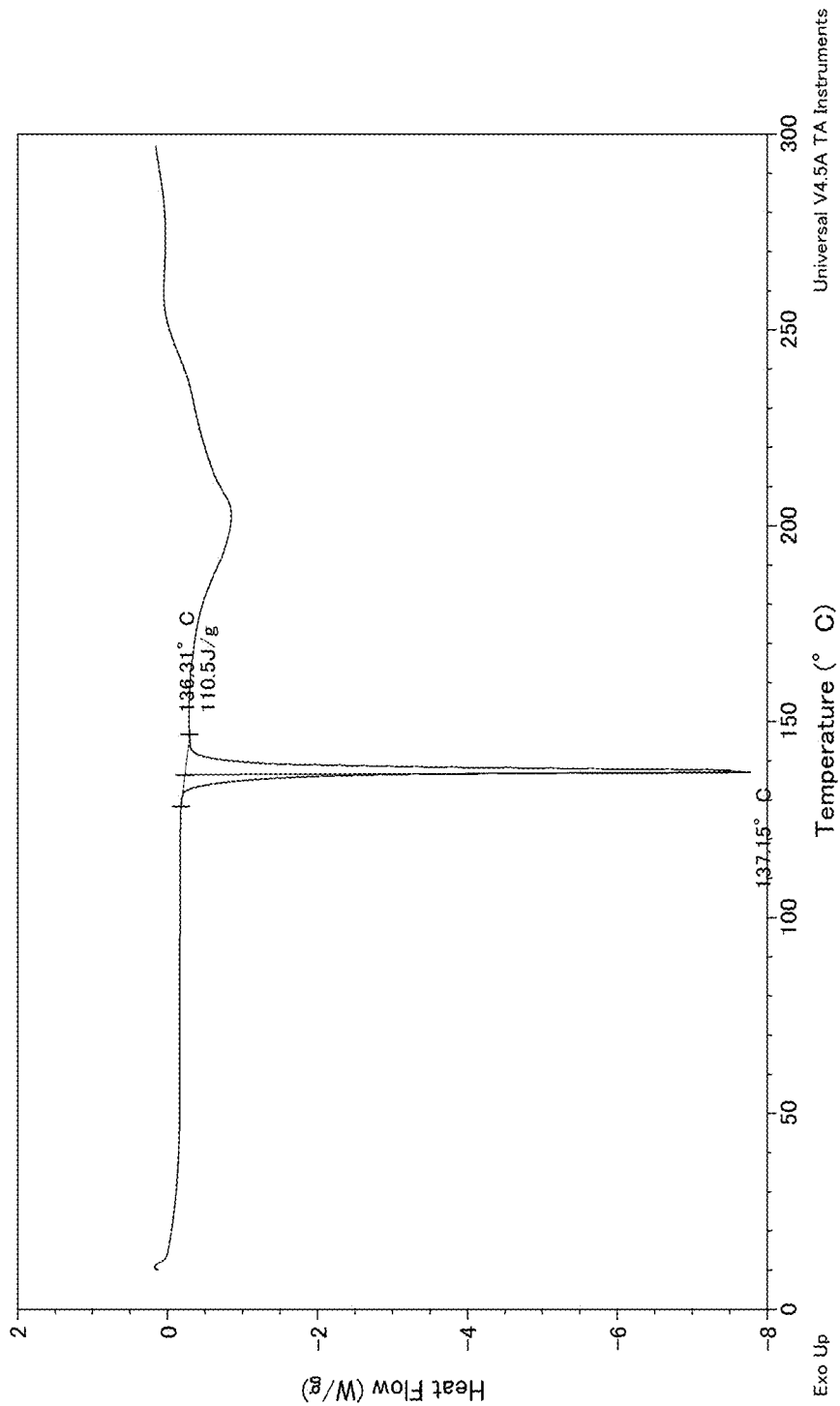
FIG. 17 shows a DSC thermogram of Compound 1 L-Tartrate Form LC.
Figure 18:
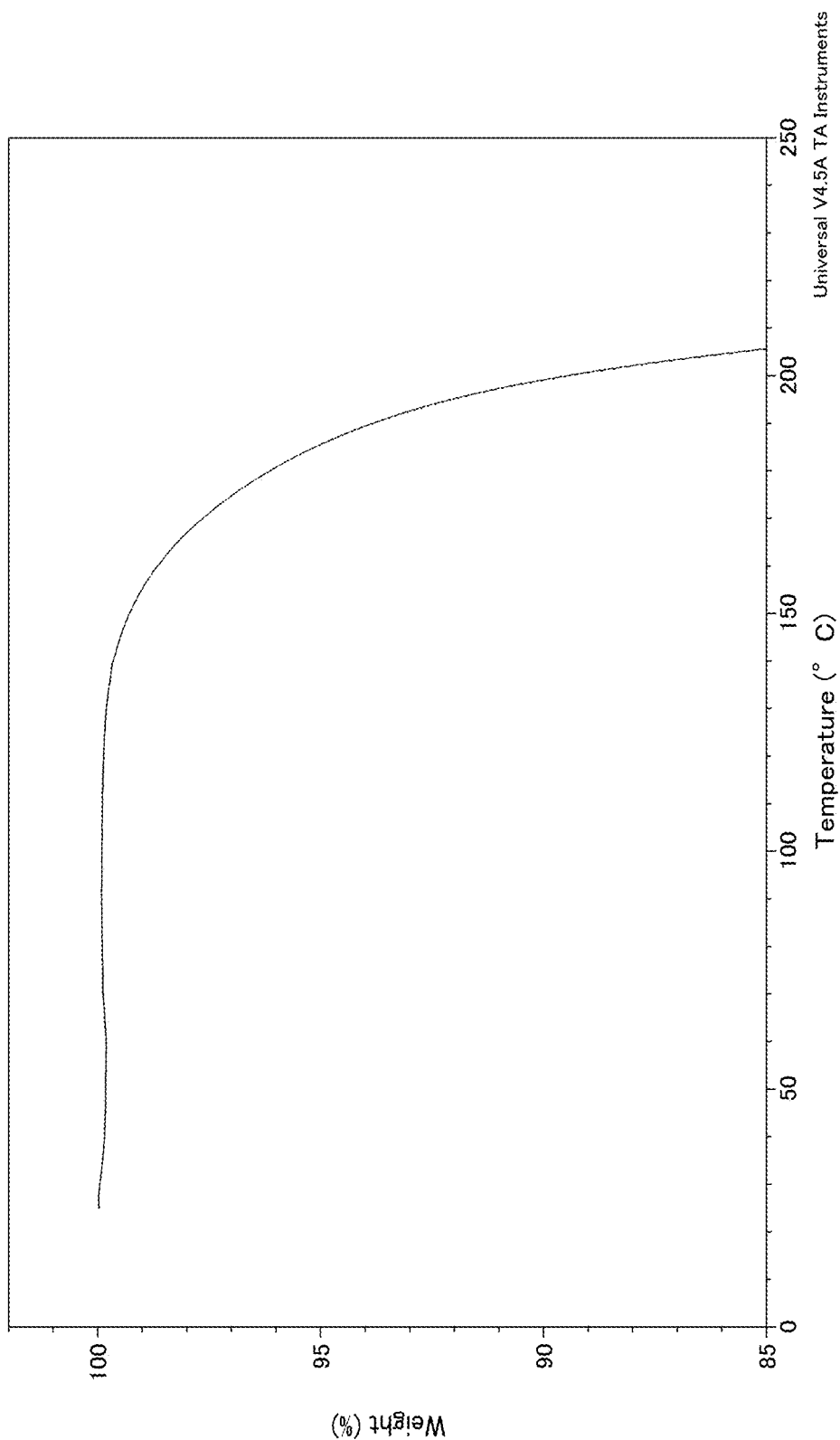
FIG. 18 shows a TGA thermogram of Compound 1 L-Tartrate Form LC.
Figure 19:
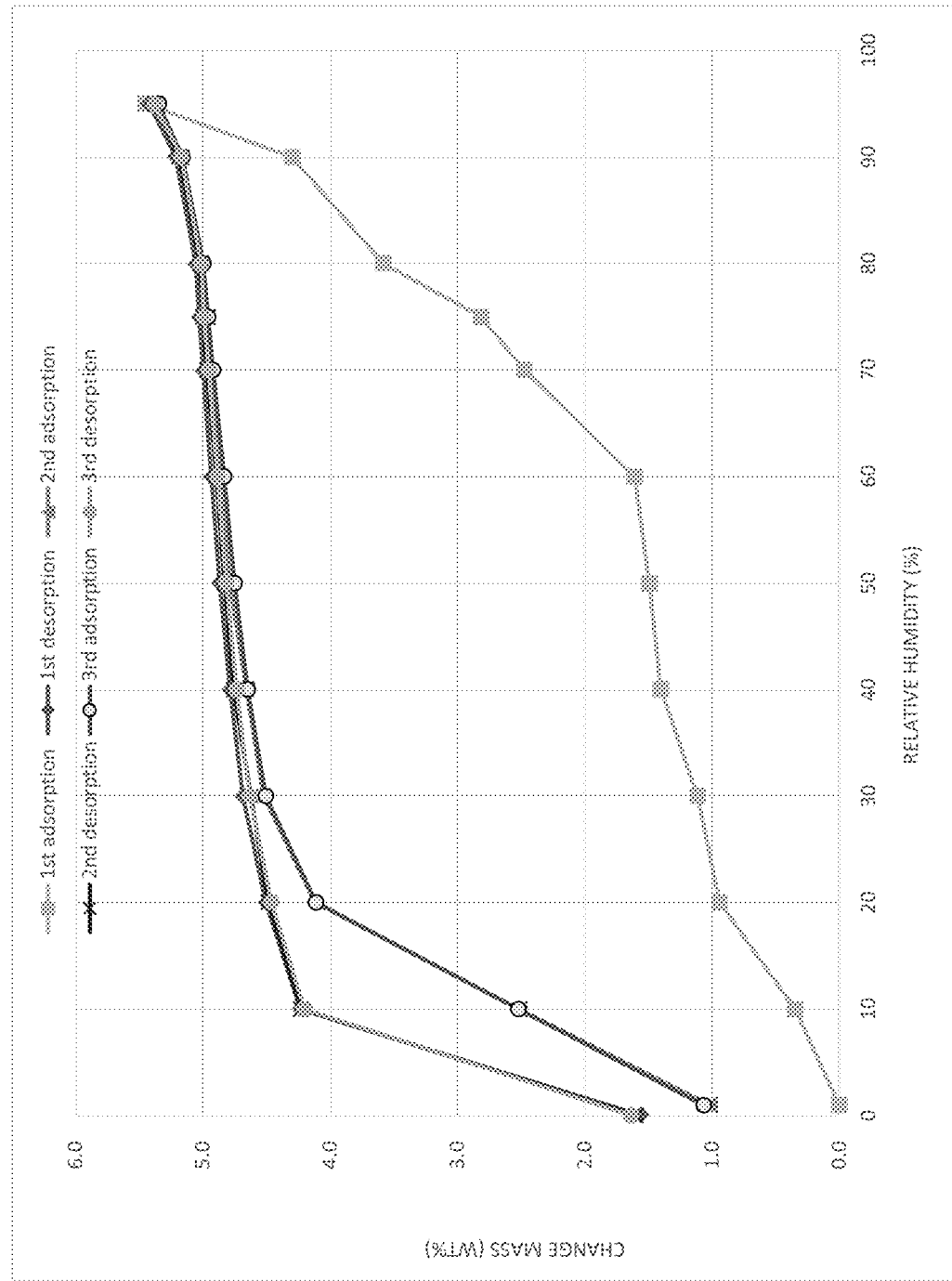
FIG. 19 shows a DVS isotherm of Compound 1 L-Tartrate Form LC.

In some embodiments, Compound 1 L-Tartrate Form LC has an endotherm peak at a temperature of about 137° C. In some embodiments, Compound 1 L-Tartrate Form LC has a DSC thermogram substantially as depicted in FIG. 17 (FIG. 17). In some embodiments, Compound 1 L-Tartrate Form LC has a TGA thermogram substantially as depicted in FIG. 18 (FIG. 18). In some embodiments, Compound 1 L-Tartrate Form LC has a DVS isotherm substantially as depicted in FIG. 19 (FIG. 19).

In some embodiments, Compound 1 L-Tartrate Form LC has at least one characteristic XRPD peak in terms of 2θ selected from 12.2°±0.2°, 16.5°±0.2°, and 24.8°±0.2°; and an endotherm peak at a temperature of about 137° C. In some embodiments, Compound 1 L-Tartrate Form LC has at least one characteristic XRPD peak in terms of 2θ selected from 12.2°±0.2°, 16.5°±0.2°, and 24.8°±0.2°; and a DSC thermogram substantially as depicted in FIG. 17 (FIG. 17). In some embodiments, Compound 1 L-Tartrate Form LC has at least one characteristic XRPD peak in terms of 2θ selected from 12.2°±0.2°, 16.5°±0.2°, and 24.8°±0.2°; and a DVS isotherm substantially as depicted in FIG. 19 (FIG. 19).

In some embodiments, Compound 1 L-Tartrate Form LC can be isolated with a crystalline purity of at least about 80%, about 85%, about 90%, about 95%, about 96%, about 97%, about 98%, or about 99%. In some embodiments, Compound 1 L-Tartrate Form LC can be isolated with a crystalline purity greater than about 99%. In some embodiments, Compound 1 L-Tartrate Form LC can be isolated with a crystalline purity greater than about 99.9%.

In some embodiments, provided is Compound 1 L-tartrate Form LB prepared by isolating Compound 1 L-tartrate Form LB from a mixture of Compound 1, L-tartaric acid, and S1, wherein S1 is a solvent. In some embodiments, S1 is an organic solvent. In some embodiments, S1 is $C_{1-6}$ alkyl alcohol. In some embodiments, S1 is $C_{1-6}$ alkyl acetate. In some embodiments, S1 is a mixture of organic solvents. In some embodiments, S1 is a mixture of a $C_{1-6}$ alkyl alcohol and a $C_{1-6}$ alkyl acetate. In some embodiments, S1 is a mixture of methanol and ethyl acetate.

Compound 1 D-Tartrate

In some embodiments, provided is (R)-1-(8-fluoroisochroman-1-yl)-N-methylmethanamine D-Tartrate (Compound 1 D-Tartrate). In some embodiments, Compound 1 D-tartrate is crystalline.

In some embodiments, Compound 1 D-Tartrate has characteristic XRPD peaks in terms of 2θ selected from 11.9°±0.2°, 16.9°±0.2°, and 17.9°±0.2°. In some embodiments, Compound 1 D-Tartrate has a characteristic XRPD peak in terms of 2θ at 11.9°±0.2°. In some embodiments, Compound 1 D-Tartrate has a characteristic XRPD peak in terms of 2θ at 16.9°±0.2°. In some embodiments, Compound 1 D-Tartrate has a characteristic XRPD peak in terms of 2θ at 17.9°±0.2°.

In some embodiments, Compound 1 D-Tartrate has characteristic XRPD peaks in terms of 2θ selected from 11.9°±0.2°, 16.9°±0.2°, 17.9°±0.2°, and 23.9°±0.2°. In some embodiments, Compound 1 D-Tartrate has at least one characteristic XRPD peak in terms of 2θ selected from 11.9°±0.2°, 16.9°±0.2°, 17.9°±0.2°, and 23.9°±0.2°.

In some embodiments, Compound 1 D-Tartrate has at least one characteristic XRPD peak in terms of 2θ selected from 11.9°±0.2°, 12.3°±0.2°, 16.1°±0.2°, 16.9°±0.2°, 17.9°±0.2°, 19.1°±0.2°, and 23.9°±0.2°. In some embodiments, Compound 1 D-Tartrate has at least one characteristic XRPD peak in terms of 2θ selected from 6.0°±0.2°, 11.9°±0.2°, 12.3°±0.2°, 13.4°±0.2°, 14.9°±0.2°, 16.10°±0.2°, 16.9°±0.2°, 17.9°±0.2°, 19.10°±0.2°, 21.6°±0.2°, 23.9°±0.2°, and 24.6°±0.2°.

In some embodiments, Compound 1 D-Tartrate has at least two characteristic XRPD peaks in terms of 2θ selected from 11.9°±0.2°, 12.3°±0.2°, 16.1°±0.2°, 16.9°±0.2°, 17.9°±0.2°, 19.1°±0.2°, and 23.9°±0.2°. In some embodiments, Compound 1 D-Tartrate has at least two characteristic XRPD peaks in terms of 2θ selected from 6.0°±0.2°, 11.9°±0.2°, 12.3°±0.2°, 13.4°±0.2°, 14.9°±0.2°, 16.1°±0.2°, 16.9°±0.2°, 17.9°±0.2°, 19.1°±0.2°, 21.6°±0.2°, 23.9°±0.2°, and 24.6°±0.2°.

In some embodiments, Compound 1 D-Tartrate has at least three characteristic XRPD peaks in terms of 2θ selected from 11.9°±0.2°, 12.3°±0.2°, 16.1°±0.2°, 16.9°±0.2°, 17.9°±0.2°, 19.1°±0.2°, and 23.9°±0.2°. In some embodiments, Compound 1 D-Tartrate has at least three characteristic XRPD peaks in terms of 2θ selected from 6.0°±0.2°, 11.9°±0.2°, 12.3°±0.2°, 13.4°±0.2°, 14.9°±0.2°, 16.1°±0.2°, 16.9°±0.2°, 17.9°±0.2°, 19.1°±0.2°, 21.6°±0.2°, 23.9°±0.2°, and 24.6°±0.2°.

Figure 20:
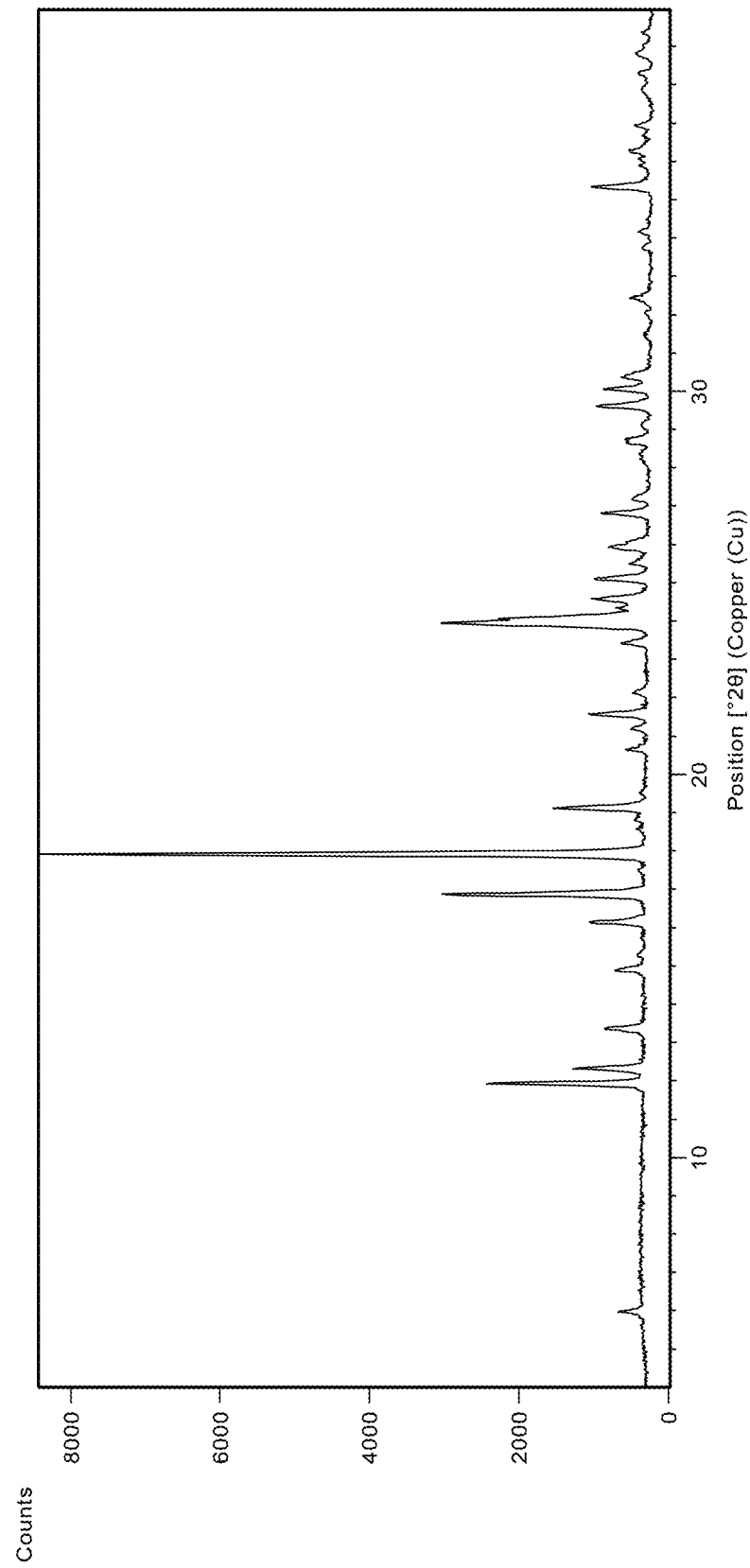
FIG. 20 shows an XRPD pattern of Compound 1 D-Tartrate.

In some embodiments, Compound 1 D-Tartrate has an XRPD pattern with characteristic peaks as substantially shown in FIG. 20 (FIG. 20).

Figure 21:
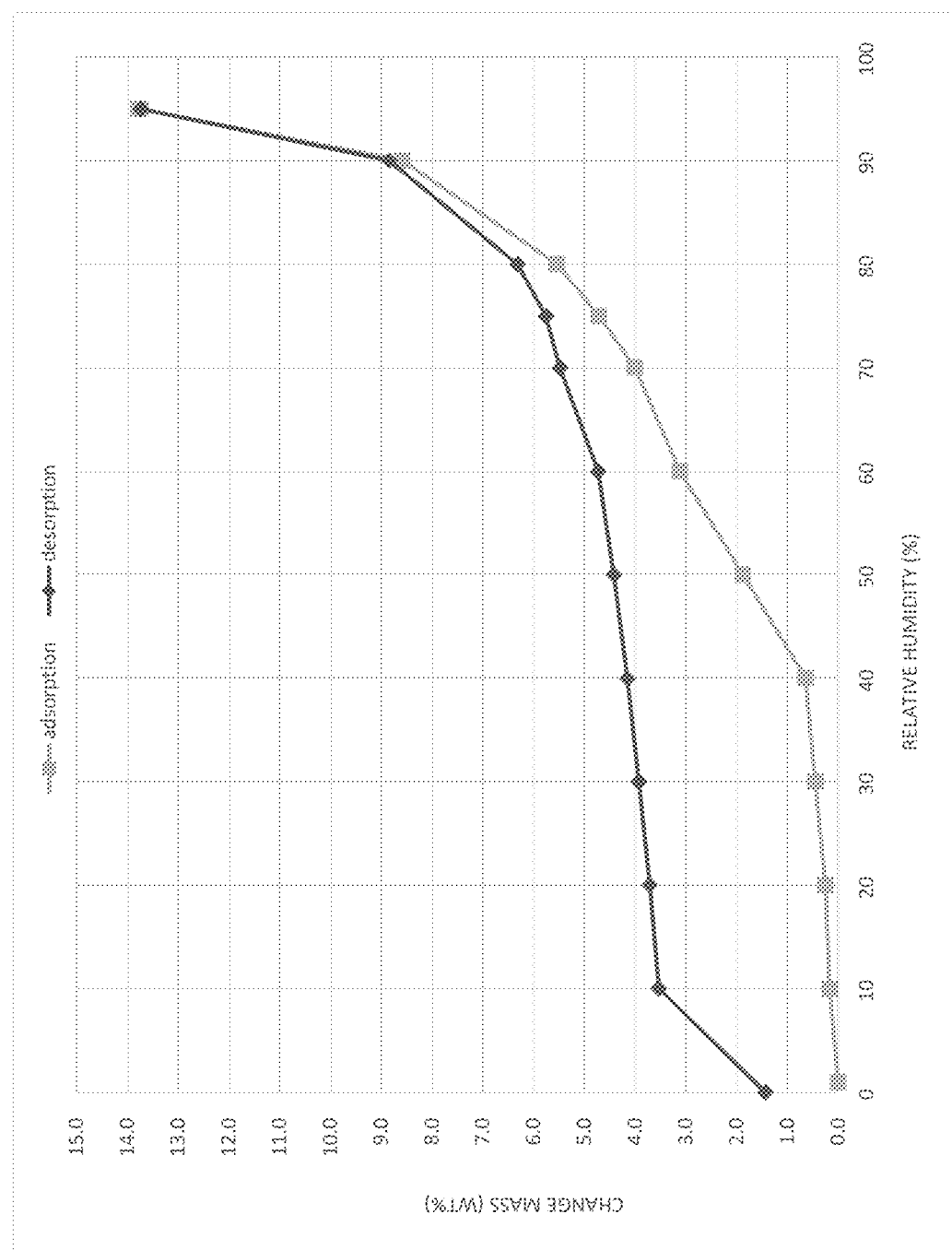
FIG. 21 shows a DVS isotherm of Compound 1 D-Tartrate.

In some embodiments, Compound 1 D-Tartrate has endotherm peaks at temperatures of about 76° C. and about 153° C. In some embodiments, Compound 1 D-Tartrate has an endotherm peak at a temperature of about 76° C. In some embodiments, Compound 1 D-Tartrate has an endotherm peak at a temperature of about 153° C. In some embodiments, Compound 1 D-Tartrate has a DVS isotherm substantially as depicted in FIG. 21 (FIG. 21).

In some embodiments, Compound 1 D-Tartrate has at least one characteristic XRPD peak in terms of 2θ selected from 11.9°±0.2°, 16.9°±0.2°, 17.9°±0.2°, and 23.9°±0.2°; and has endotherm peaks at temperatures of about 76° C. and about 153° C. In some embodiments, Compound 1 D-Tartrate has at least one characteristic XRPD peak in terms of 2θ selected from 11.9°±0.2°, 16.9°±0.2°, 17.9°±0.2°, and 23.9°±0.2°; and an endotherm peak at a temperature of about 76° C. In some embodiments, Compound 1 D-Tartrate has at least one characteristic XRPD peak in terms of 2θ selected from 11.9°±0.2°, 16.9°±0.2°, 17.9°±0.2°, and 23.9°±0.2°; and an endotherm peak at a temperature of about 153° C. In some embodiments, Compound 1 D-Tartrate has at least one characteristic XRPD peak in terms of 2θ selected from 11.9°±0.2°, 16.9°±0.2°, 17.9°±0.2°, and 23.9°±0.2°; and a DVS isotherm substantially as depicted in FIG. 21 (FIG. 21).

In some embodiments, Compound 1 D-Tartrate can be isolated with a crystalline purity of at least about 80%, about 85%, about 90%, about 95%, about 96%, about 97%, about 98%, or about 99%. In some embodiments, Compound 1 D-Tartrate can be isolated with a crystalline purity greater than about 99%. In some embodiments, Compound D-Tartrate can be isolated with a crystalline purity greater than about 99.9%.

In some embodiments, provided is Compound 1 D-Tartrate prepared by isolating Compound 1 D-Tartrate from a mixture of Compound 1, D-tartaric acid, and S1, wherein S1 is a solvent. In some embodiments, S1 is an organic solvent. In some embodiments, S1 is ether. In some embodiments, S1 is $C_{1-6}$ alkyl acetate. In some embodiments, S1 is THF. In some embodiments, S1 is ethyl acetate.

Compound 1 Fumarate

In some embodiments, provided is (R)-1-(8-fluoroisochroman-1-yl)-N-methylmethanamine fumarate (Compound 1 Fumarate). In some embodiments, Compound 1 Fumarate is crystalline.

In some embodiments, provided is Compound 1 Fumarate prepared by isolating Compound 1 Fumarate from a mixture of Compound 1, fumaric acid, and S1, wherein S1 is a solvent. In some embodiments, S1 is an organic solvent. In some embodiments, S1 is $C_{1-6}$ alkyl alcohol. In some embodiments, S1 is ether. In some embodiments, S1 is $C_{1-6}$ alkyl acetate. In some embodiments, S1 is a $C_{1-6}$ alkyl ketone. In some embodiments, S1 is a mixture of organic solvents. In some embodiments, S1 is a mixture of a $C_{1-6}$ alkyl alcohol and a $C_{1-6}$ alkyl ketone. In some embodiments, S1 is methanol. In some embodiments, S1 is THF. In some embodiments, S1 is ethyl acetate. In some embodiments, S1 is a mixture of methanol and acetone.

Compound 1 Fumarate Form FA

In some embodiments, provided is (R)-1-(8-fluoroisochroman-1-yl)-N-methylmethanamine Fumarate Form FA (Compound 1 fumarate Form FA). In some embodiments, Compound 1 Fumarate Form FA is crystalline.

In some embodiments, Compound 1 Fumarate Form FA has characteristic XRPD peaks in terms of 2θ selected from 7.7°±0.2°, 14.2°±0.2°, and 15.2°±0.2°. In some embodiments, Compound 1 Fumarate Form FA has a characteristic XRPD peak in terms of 2θ at 7.7°±0.2°. In some embodiments, Compound 1 Fumarate Form FA has a characteristic XRPD peak in terms of 2θ at 14.2°±0.2°. In some embodiments, Compound 1 Fumarate Form FA has a characteristic XRPD peak in terms of 2θ at 15.2°±0.2°.

In some embodiments, Compound 1 Fumarate Form FA has characteristic XRPD peaks in terms of 2θ selected from 7.7°±0.2°, 15.2°±0.2°, 22.9°±0.2°, and 30.7°±0.2°. In some embodiments, Compound 1 Fumarate Form FA has at least one characteristic XRPD peak in terms of 2θ selected from 7.7°±0.2°, 15.2°±0.2°, 22.9°±0.2°, and 30.7°±0.2°.

In some embodiments, Compound 1 Fumarate Form FA has at least one characteristic XRPD peak in terms of 2θ selected from 7.7°±0.2°, 13.0°±0.2°, 14.2°±0.2°, 15.2°±0.2°, 22.9°±0.2°, 24.6°±0.2°, 26.0°±0.2°, and 30.7°±0.2°. In some embodiments, Compound 1 Fumarate Form FA has at least one characteristic XRPD peak in terms of 2θ selected from 7.7°±0.2°, 12.1°±0.2°, 13.0°±0.2°, 14.2°±0.2°, 14.6°±0.2°, 15.2°±0.2°, 18.1°±0.2°, 18.8°±0.2°, 22.9°±0.2°, 24.6°±0.2°, 26.0°±0.2°, and 30.7°±0.2°.

In some embodiments, Compound 1 Fumarate Form FA has at least two characteristic XRPD peaks in terms of 2θ selected from 7.7°±0.2°, 13.0°±0.2°, 14.2°±0.2°, 15.2°±0.2°, 22.9°±0.2°, 24.6°±0.2°, 26.0°±0.2°, and 30.7°±0.2°. In some embodiments, Compound 1 Fumarate Form FA has at least two characteristic XRPD peaks in terms of 2θ selected from 7.7°±0.2°, 12.1°±0.2°, 13.0°±0.2°, 14.2°±0.2°, 14.6°±0.2°, 15.2°±0.2°, 18.1°±0.2°, 18.8°±0.2°, 22.9°±0.2°, 24.6°±0.2°, 26.0°±0.2°, and 30.7°±0.2°.

In some embodiments, Compound 1 Fumarate Form FA has at least three characteristic XRPD peaks in terms of 2θ selected from 7.7°±0.2°, 13.0°±0.2°, 14.2°±0.2°, 15.2°±0.2°, 22.9°±0.2°, 24.6°±0.2°, 26.0°±0.2°, and 30.7°±0.2°. In some embodiments, Compound 1 Fumarate Form FA has at least three characteristic XRPD peaks in terms of 2θ selected from 7.7°±0.2°, 12.1°±0.2°, 13.0°±0.2°, 14.2°±0.2°, 14.6°±0.2°, 15.2°±0.2°, 18.1°±0.2°, 18.8°±0.2°, 22.9°±0.2°, 24.6°±0.2°, 26.0°±0.2°, and 30.7°±0.2°.

Figure 22:
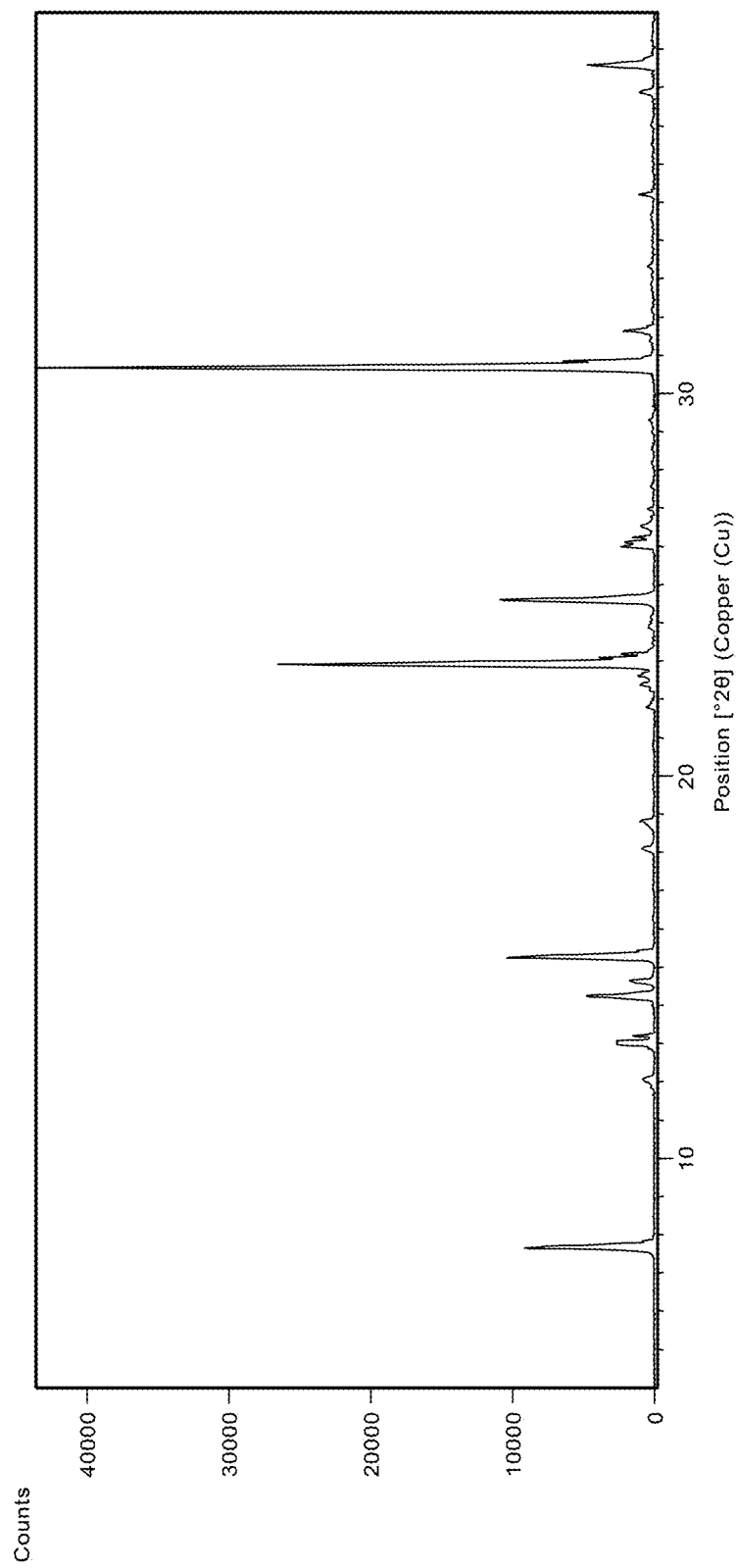
FIG. 22 shows an XRPD pattern of Compound 1 Fumarate Form FA.

In some embodiments, Compound 1 Fumarate Form FA has an XRPD pattern with characteristic peaks as substantially shown in FIG. 22 (FIG. 22).

Figure 23:
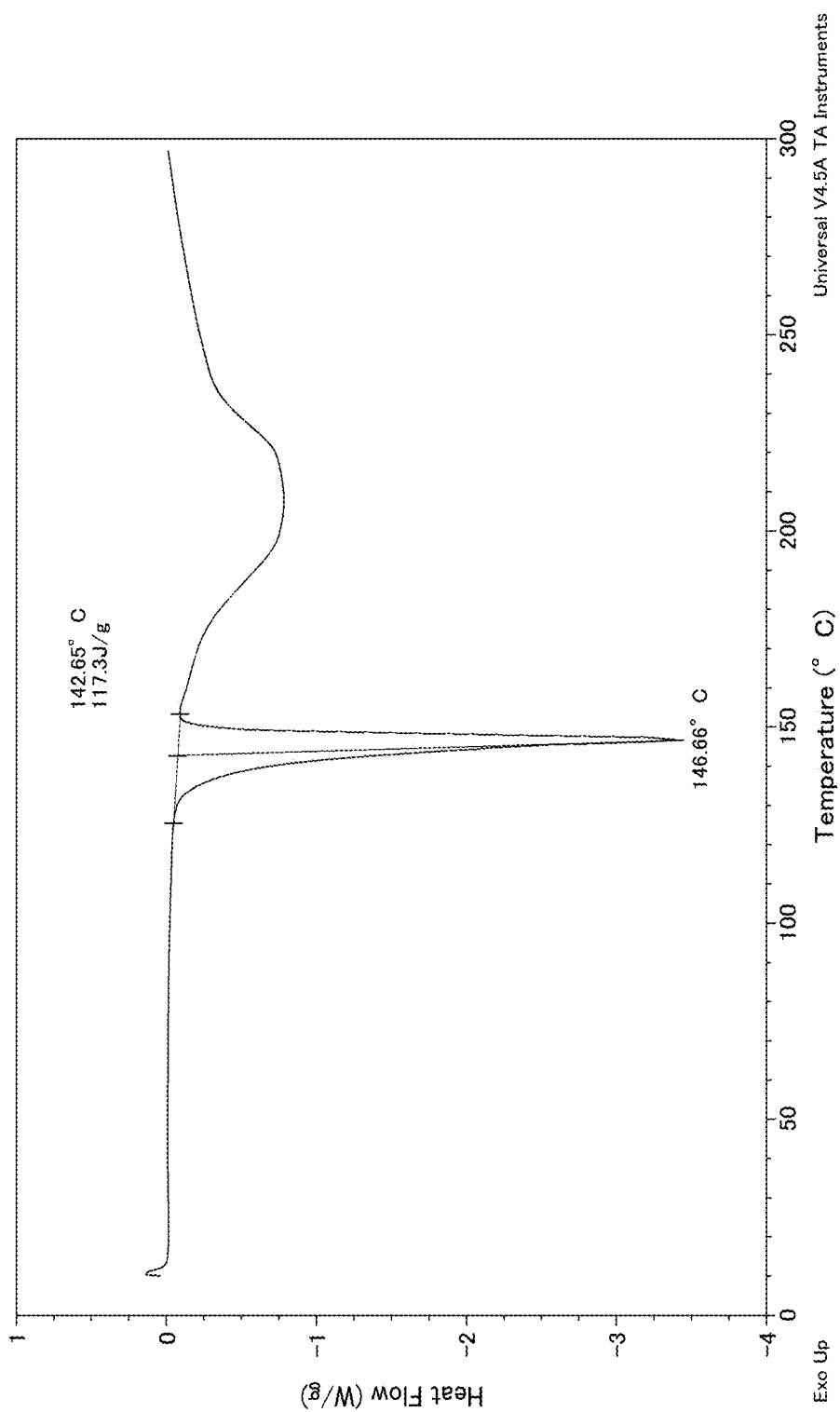
FIG. 23 shows a DSC thermogram of Compound 1 Fumarate Form FA.
Figure 24:
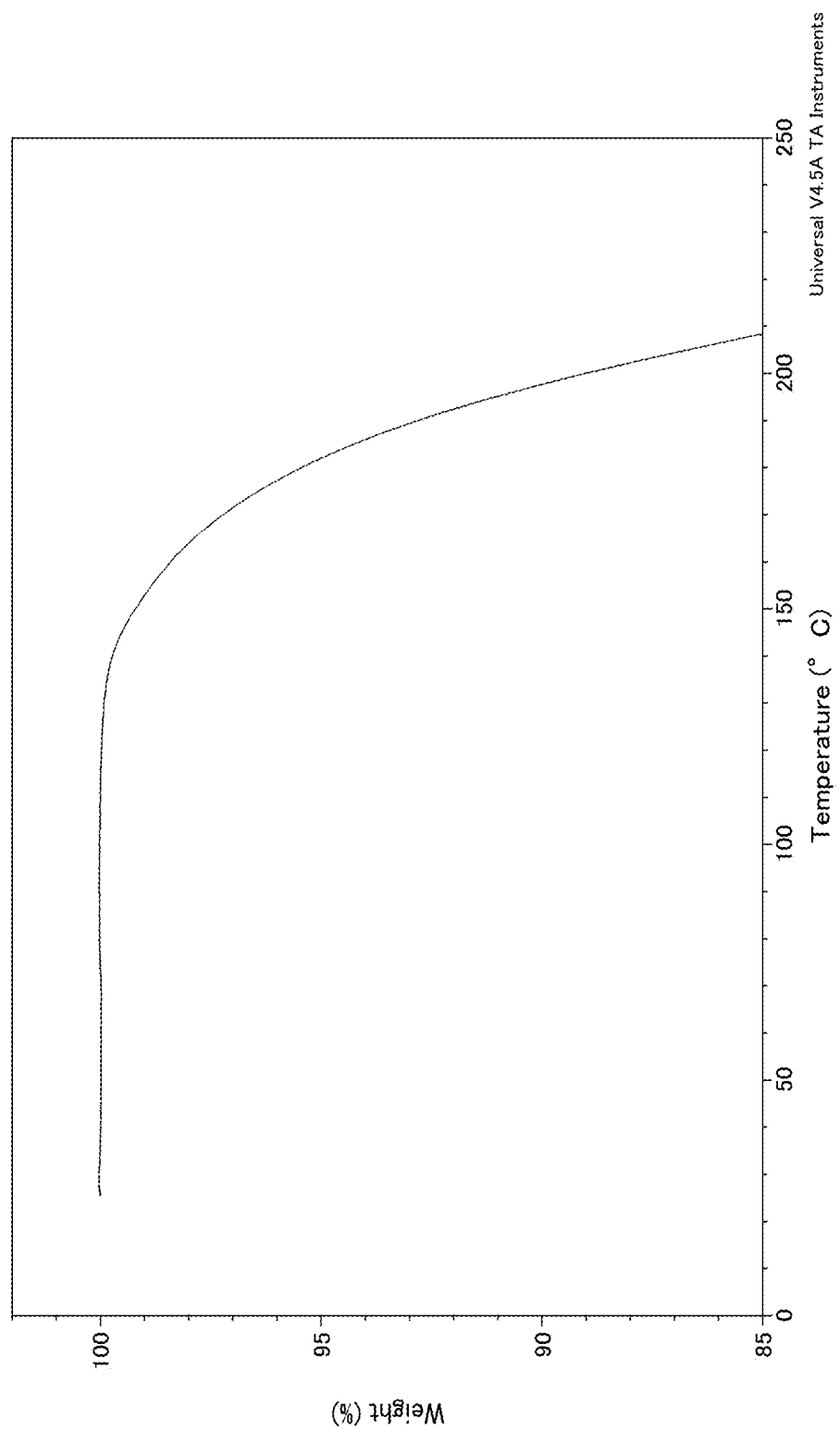
FIG. 24 shows a TGA thermogram of Compound 1 Fumarate Form FA.
Figure 25:
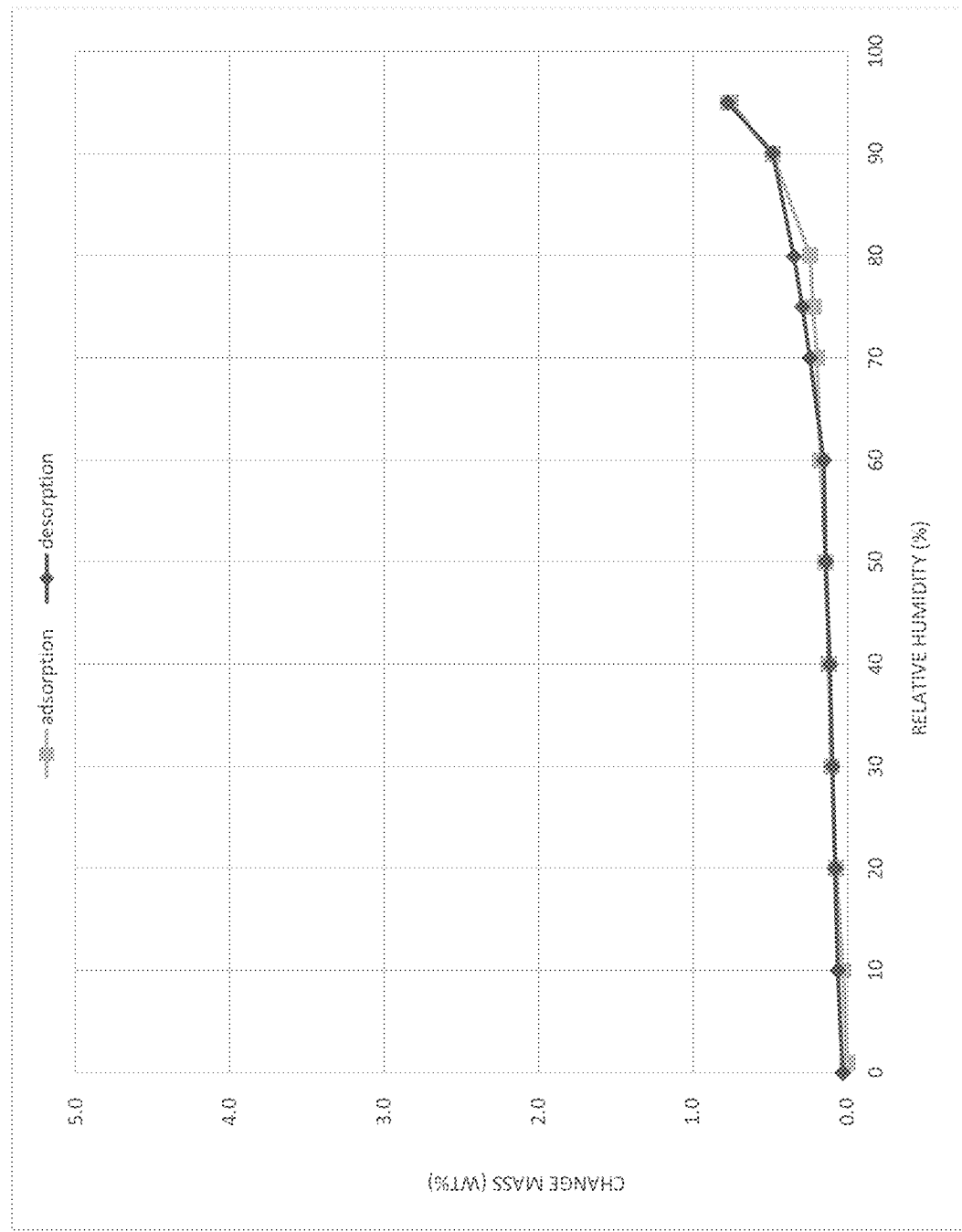
FIG. 25 shows a DVS isotherm of Compound 1 Fumarate Form FA.

In some embodiments, Compound 1 Fumarate Form FA has an endotherm peak at a temperature of about 138° C. In some embodiments, Compound 1 Fumarate Form FA has a DSC thermogram substantially as depicted in FIG. 23 (FIG. 23). In some embodiments, Compound 1 L-Fumarate Form FA has a TGA thermogram substantially as depicted in FIG. 24 (FIG. 24). In some embodiments, Compound 1 Fumarate Form FA has a DVS isotherm substantially as depicted in FIG. 25 (FIG. 25).

In some embodiments, Compound 1 Fumarate Form FA has characteristic XRPD peaks in terms of 2θ selected from 7.7°±0.2°, 14.2°±0.2°, and 15.2°±0.2°; and an endotherm peak at a temperature of about 147° C. In some embodiments, Compound 1 Fumarate Form FA has characteristic XRPD peaks in terms of 2θ selected from 7.7°±0.2°, 14.2°±0.2°, and 15.2°±0.2°; and a DSC thermogram substantially as depicted in FIG. 23 (FIG. 23). In some embodiments, Compound 1 Fumarate Form FA has characteristic XRPD peaks in terms of 2θ selected from 7.7°±0.2°, 14.2°±0.2°, and 15.2°±0.2°; and a DVS isotherm substantially as depicted in FIG. 25 (FIG. 25).

In some embodiments, Compound 1 Fumarate Form FA can be isolated with a crystalline purity of at least about 80%, about 85%, about 90%, about 95%, about 96%, about 97%, about 98%, or about 99%. In some embodiments, Compound 1 Fumarate Form FA can be isolated with a crystalline purity greater than about 99%. In some embodiments, Compound 1 Fumarate Form FA can be isolated with a crystalline purity greater than about 99.9%.

In some embodiments, provided is Compound 1 Fumarate Form FA prepared by isolating Compound 1 Fumarate Form FA from a mixture of Compound 1, fumaric acid, and S1, wherein S1 is a solvent. In some embodiments, S1 is an organic solvent. In some embodiments, S1 is $C_{1-6}$ alkyl alcohol. In some embodiments, S1 is ether. In some embodiments, S1 is a $C_{1-6}$ alkyl ketone. In some embodiments, S1 is a mixture of organic solvents. In some embodiments, S1 is a mixture of a $C_{1-6}$ alkyl alcohol and a $C_{1-6}$ alkyl ketone. In some embodiments, S1 is methanol. In some embodiments, S1 is THF. In some embodiments, S1 is a mixture of methanol and acetone.

Compound 1 Fumarate FB

In some embodiments, provided is (R)-1-(8-fluoroisochroman-1-yl)-N-methylmethanamine Fumarate Form FB (Compound 1 fumarate Form FB). In some embodiments, Compound 1 Fumarate Form FB is crystalline.

In some embodiments, Compound 1 Fumarate Form FB has characteristic XRPD peaks in terms of 2θ selected from 6.7°±0.2°, 13.8°±0.2°, and 20.2°±0.2°. In some embodiments, Compound 1 Fumarate Form FB has a characteristic XRPD peak in terms of 2θ at 6.7°±0.2°. In some embodiments, Compound 1 Fumarate Form FB has a characteristic XRPD peak in terms of 2θ at 13.8°±0.2°. In some embodiments, Compound 1 Fumarate Form FB has a characteristic XRPD peak in terms of 2θ at 20.2°±0.2°. In some embodiments, Compound 1 Fumarate Form FB has a characteristic XRPD peak in terms of 2θ at 27.0°±0.2°.

In some embodiments, Compound 1 Fumarate Form FB has at least one characteristic XRPD peak in terms of 2θ selected from 6.7°±0.2°, 13.4°±0.2°, 13.8°±0.2°, 20.2°±0.2°, 23.50°±0.2°, 25.10°±0.2°, 27.0°±0.2°, and 29.60°±0.2°. In some embodiments, Compound 1 Fumarate Form FB has at least one characteristic XRPD peak in terms of 2θ selected from 6.7°±0.2°, 13.4°±0.2°, 13.8°±0.2°, 20.2°±0.2°, 23.1°±0.2°, 23.5°±0.2°, 24.2°±0.2°, 25.1°±0.2°, 27.0°±0.2°, and 29.6°±0.2°.

In some embodiments, Compound 1 Fumarate Form FB has at least two characteristic XRPD peaks in terms of 2θ selected from 6.7°±0.2°, 13.4°±0.2°, 13.8°±0.2°, 20.2°±0.2°, 23.50°±0.2°, 25.10°±0.2°, 27.0°±0.2°, and 29.60°±0.2°. In some embodiments, Compound 1 Fumarate Form FB has at least two characteristic XRPD peaks in terms of 2θ selected from 6.7°±0.2°, 13.4°±0.2°, 13.8°±0.2°, 20.2°±0.2°, 23.1°±0.2°, 23.5°±0.2°, 24.2°±0.2°, 25.1°±0.2°, 27.0°±0.2°, and 29.6°±0.2°.

In some embodiments, Compound 1 Fumarate Form FB has at least three characteristic XRPD peaks in terms of 2θ selected from 6.7°±0.2°, 13.4°±0.2°, 13.8°±0.2°, 20.2°±0.2°, 23.50°±0.2°, 25.10°±0.2°, 27.0°±0.2°, and 29.60°±0.2°. In some embodiments, Compound 1 Fumarate Form FB has at least three characteristic XRPD peaks in terms of 2θ selected from 6.7°±0.2°, 13.4°±0.2°, 13.8°±0.2°, 20.2°±0.2°, 23.1°±0.2°, 23.5°±0.2°, 24.2°±0.2°, 25.1°±0.2°, 27.0°±0.2°, and 29.6°±0.2°.

Figure 26:
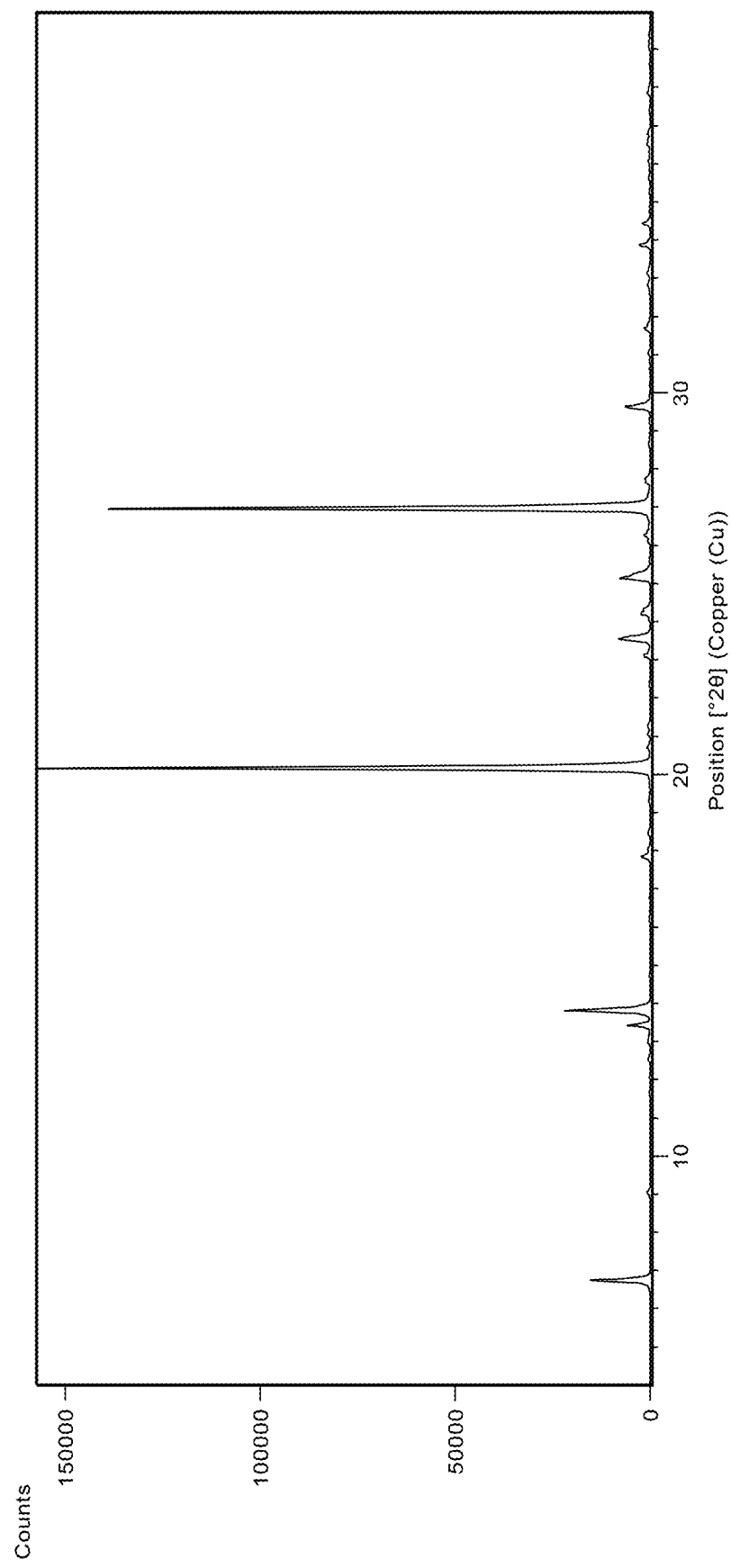
FIG. 26 shows an XRPD pattern of Compound 1 Fumarate Form FB.

In some embodiments, Compound 1 Fumarate Form FB has an XRPD pattern with characteristic peaks as substantially shown in FIG. 26 (FIG. 26).

Figure 27:
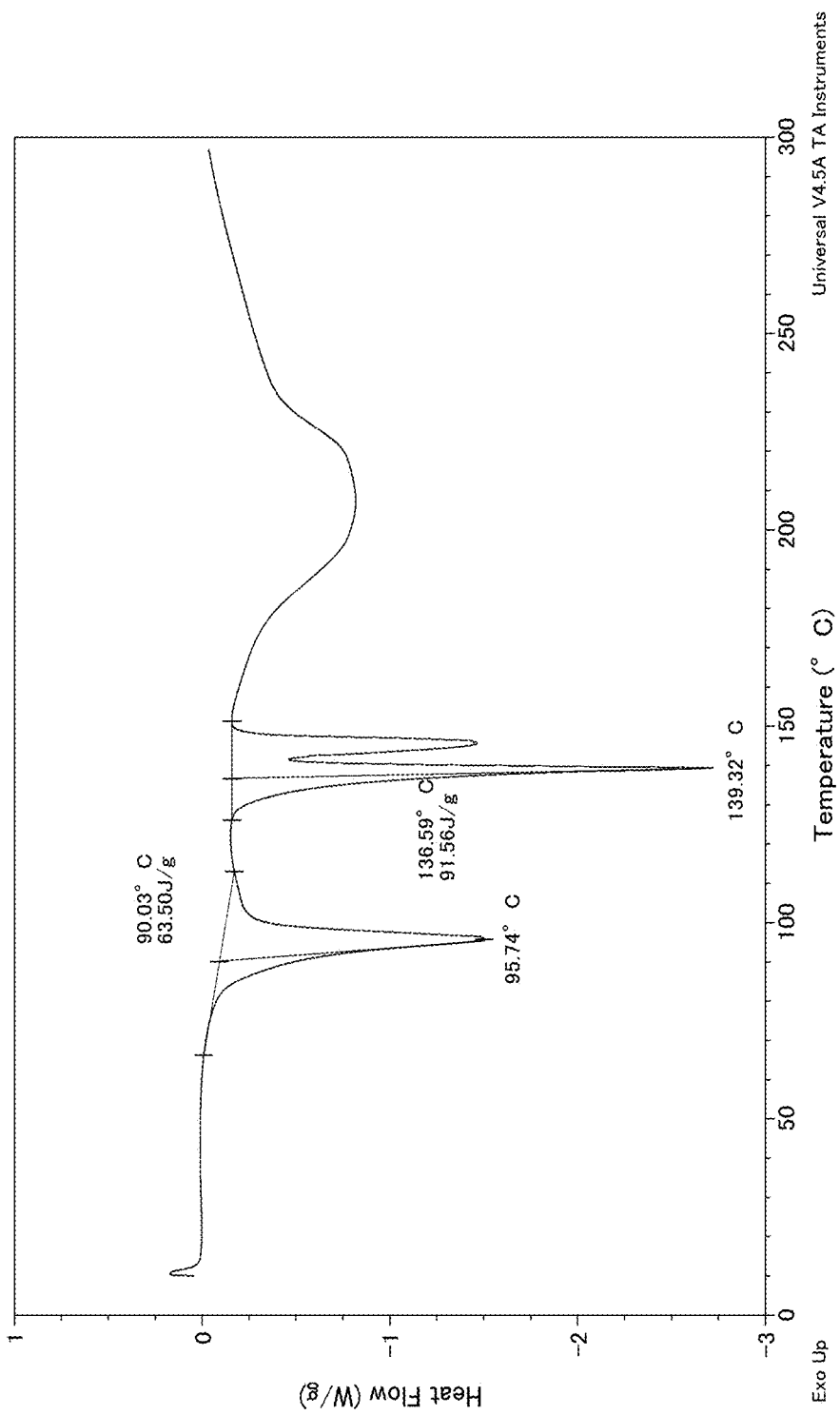
FIG. 27 shows a DSC thermogram of Compound 1 Fumarate Form FB.
Figure 28:
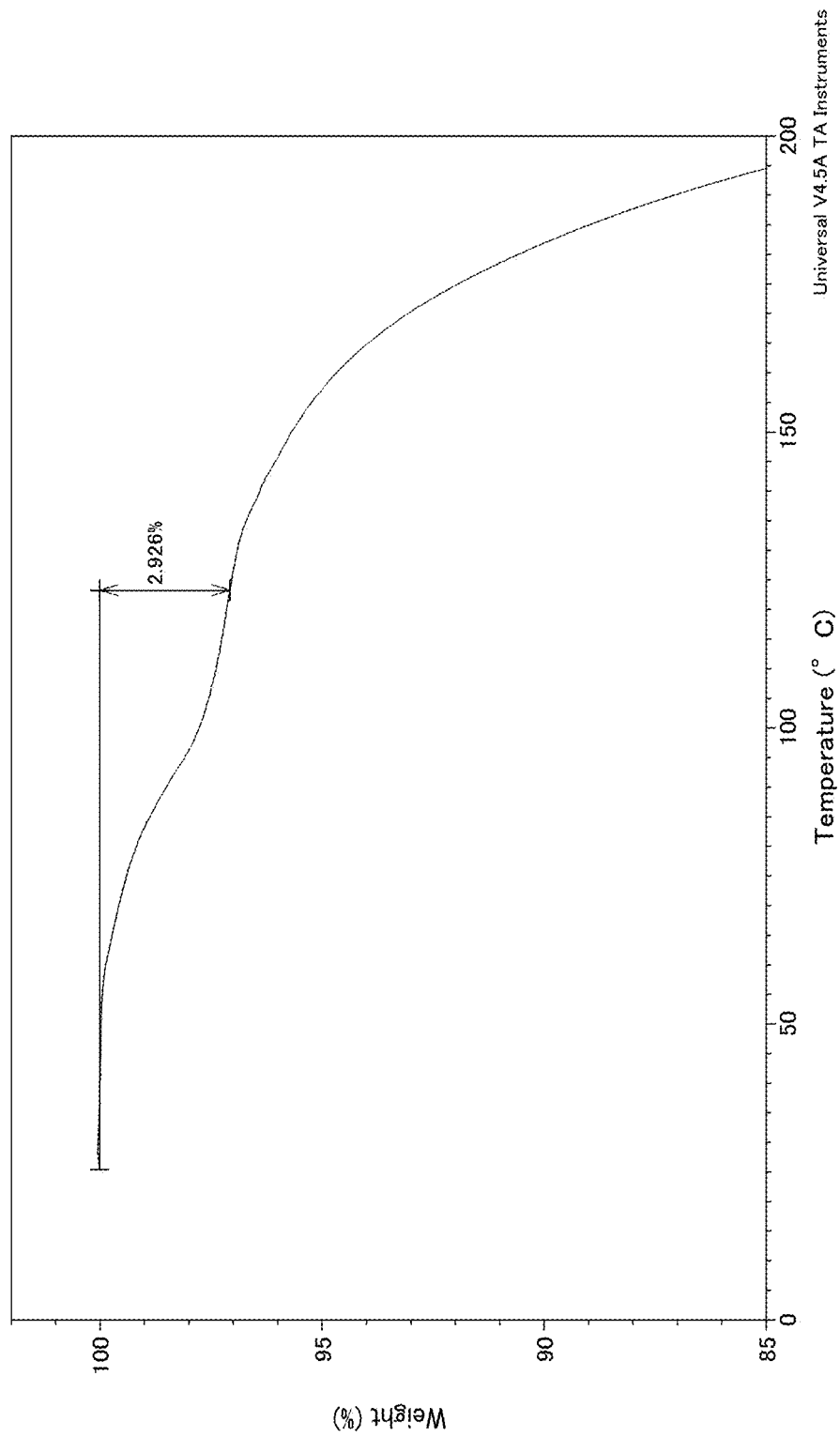
FIG. 28 shows a TGA thermogram of Compound 1 Fumarate Form FB.
Figure 29:
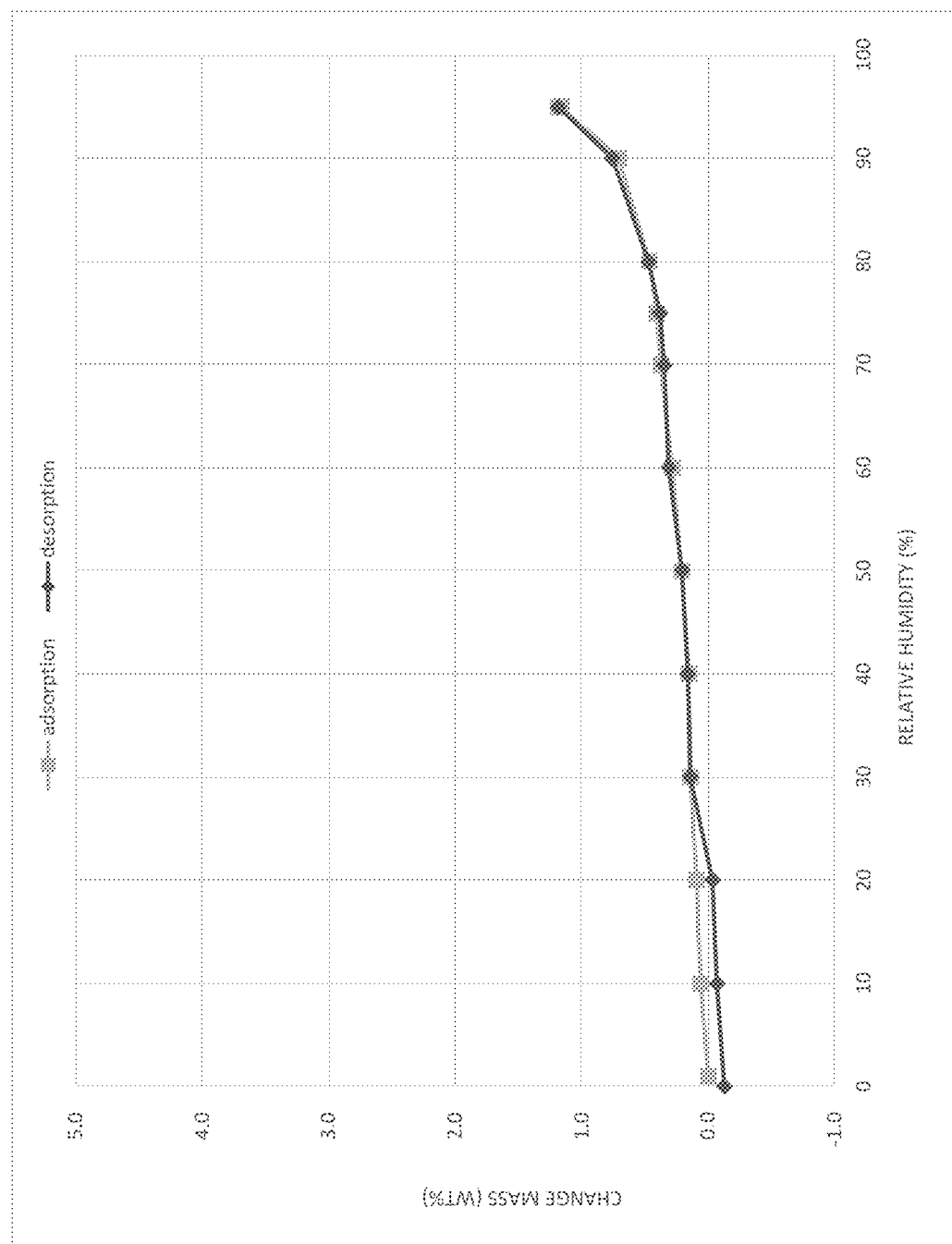
FIG. 29 shows a DVS isotherm of Compound 1 Fumarate Form FB.

In some embodiments, Compound 1 Fumarate Form FB has endotherm peaks at temperatures of about 96° C., about 139° C., and about 146° C. In some embodiments, Compound 1 Fumarate Form FB has an endotherm peak at a temperature of about 96° C. In some embodiments, Compound 1 Fumarate Form FB has an endotherm peak at a temperature of about 139° C. In some embodiments, Compound 1 Fumarate Form FB has an endotherm peak at a temperature of about 146° C. In some embodiments, Compound 1 Fumarate Form FB has a DSC thermogram substantially as depicted in FIG. 27 (FIG. 27). In some embodiments, Compound 1 Fumarate Form FB has a TGA thermogram substantially as depicted in FIG. 28 (FIG. 28). In some embodiments, Compound 1 Fumarate Form FB has a DVS isotherm substantially as depicted in FIG. 29 (FIG. 29).

In some embodiments, Compound 1 Fumarate Form FB has at least one characteristic XRPD peak in terms of 2θ selected from 6.7°±0.2°, 13.8°±0.2°, and 20.2°±0.2°; and endotherm peaks at temperatures of about 96° C., about 139° C., and about 146° C. In some embodiments, Compound 1 Fumarate Form FB has at least one characteristic XRPD peak in terms of 2θ selected from 6.7°±0.2°, 13.8°±0.2°, and 20.2°±0.2°; and an endotherm peak at a temperature of about 96° C. In some embodiments, Compound 1 Fumarate Form FB has at least one characteristic XRPD peak in terms of 2θ selected from 6.7°±0.2°, 13.8°±0.2°, and 20.2°±0.2°; and an endotherm peak at a temperature of about 139° C. In some embodiments, Compound 1 Fumarate Form FB has at least one characteristic XRPD peak in terms of 2θ selected from 6.7°±0.2°, 13.8°±0.2°, and 20.2°±0.2°; and an endotherm peak at a temperature of about 146° C. In some embodiments, Compound 1 Fumarate Form FB has at least one characteristic XRPD peak in terms of 2θ selected from 6.7°±0.2°, 13.8°±0.2°, and 20.2°±0.2°; and a DSC thermogram substantially as depicted in FIG. 27 (FIG. 27). In some embodiments, Compound 1 Fumarate Form FB has at least one characteristic XRPD peak in terms of 2θ selected from 6.7°±0.2°, 13.8°±0.2°, and 20.2°±0.2°; and a DVS isotherm substantially as depicted in FIG. 29 (FIG. 29).

In some embodiments, Compound 1 Fumarate Form FB can be isolated with a crystalline purity of at least about 80%, about 85%, about 90%, about 95%, about 96%, about 97%, about 98%, or about 99%. In some embodiments, Compound 1 Fumarate Form FB can be isolated with a crystalline purity greater than about 99%. In some embodiments, Compound 1 Fumarate Form FB can be isolated with a crystalline purity greater than about 99.9%.

In some embodiments, provided is Compound 1 Fumarate Form FB prepared by isolating Compound 1 Fumarate Form FB from a mixture of Compound 1, fumaric acid, and S1, wherein S1 is a solvent. In some embodiments, S1 is an organic solvent. In some embodiments, S1 is $C_{1-6}$ alkyl acetate. In some embodiments, S1 is ethyl acetate.

Compound 1 Citrate

In some embodiments, provided is (R)-1-(8-fluoroisochroman-1-yl)-N-methylmethanamine citrate. In some embodiments, Compound 1 Citrate is crystalline. In some embodiments, Compound 1 citrate has characteristic XRPD peaks in terms of 2θ selected from 6.5°±0.2°, 15.5°±0.2°, and 20.4°±0.2°. In some embodiments, Compound 1 Citrate has a characteristic XRPD peak in terms of 2θ at 6.5°±0.2°. In some embodiments, Compound 1 Citrate has a characteristic XRPD peak in terms of 2θ at 15.5°±0.2°. In some embodiments, Compound 1 Citrate has a characteristic XRPD peak in terms of 2θ at 20.4°±0.2°.

In some embodiments, Compound 1 Citrate has at least one characteristic XRPD peak in terms of 2θ selected from 6.5°±0.2°, 10.2°±0.2°, 13.0°±0.2°, 14.5°±0.2°, 15.5°±0.2°, 17.8°±0.2°, 19.4°±0.2°, and 20.4°±0.2°. In some embodiments, Compound 1 Citrate has at least one characteristic XRPD peak in terms of 2θ selected from 6.5°±0.2°, 10.2°±0.2°, 13.0°±0.2°, 14.5°±0.2°, 15.5°±0.2°, 16.5°±0.2°, 17.3°±0.2°, 17.8°±0.2°, 19.4°±0.2°, 20.4°±0.2°, 20.8°±0.2°, 21.2°±0.2°, 21.5°±0.2°, 22.0°±0.2°, 23.1°±0.2°, and 26.0°±0.2°.

In some embodiments, Compound 1 Citrate has at least two characteristic XRPD peaks in terms of 2θ selected from 6.5°±0.2°, 10.2°±0.2°, 13.0°±0.2°, 14.5°±0.2°, 15.5°±0.2°, 17.8°±0.2°, 19.4°±0.2°, and 20.4°±0.2°. In some embodiments, Compound 1 Citrate has at least two characteristic XRPD peaks in terms of 2θ selected from 6.5°±0.2°, 10.2°±0.2°, 13.0°±0.2°, 14.5°±0.2°, 15.5°±0.2°, 16.5°±0.2°, 17.3°±0.2°, 17.8°±0.2°, 19.4°±0.2°, 20.4°±0.2°, 20.8°±0.2°, 21.2°±0.2°, 21.5°±0.2°, 22.0°±0.2°, 23.1°±0.2°, and 26.0°±0.2°.

In some embodiments, Compound 1 Citrate has at least three characteristic XRPD peaks in terms of 2θ selected from 6.5°±0.2°, 10.2°±0.2°, 13.0°±0.2°, 14.5°±0.2°, 15.5°±0.2°, 17.8°±0.2°, 19.4°±0.2°, and 20.4°±0.2°. In some embodiments, Compound 1 Citrate has at least three characteristic XRPD peaks in terms of 2θ selected from 6.5°±0.2°, 10.2°±0.2°, 13.0°±0.2°, 14.5°±0.2°, 15.5°±0.2°, 16.5°±0.2°, 17.3°±0.2°, 17.8°±0.2°, 19.4°±0.2°, 20.4°±0.2°, 20.8°±0.2°, 21.2°±0.2°, 21.5°±0.2°, 22.0°±0.2°, 23.1°±0.2°, and 26.0°±0.2°.

Figure 30:
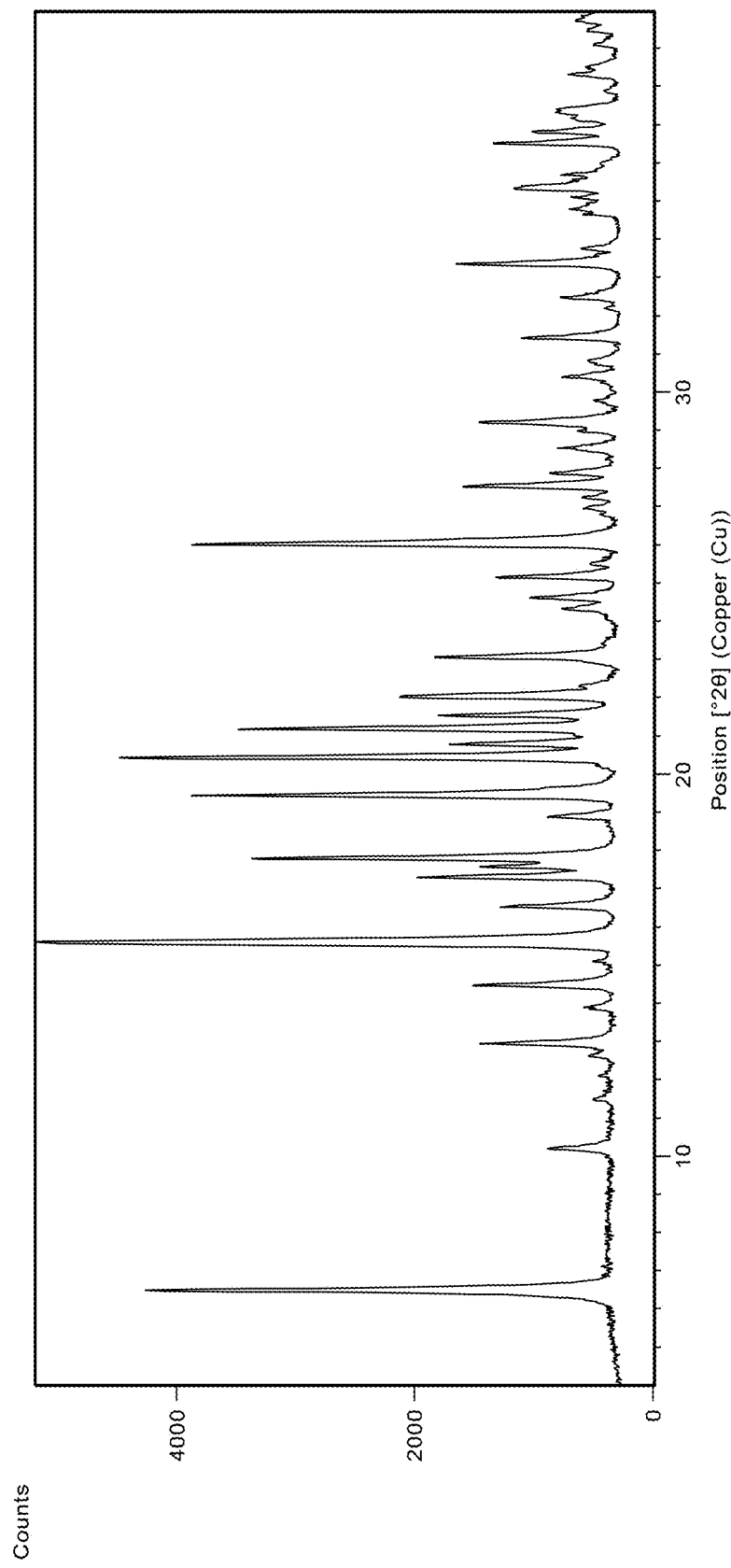
FIG. 30 shows an XRPD pattern of Compound 1 Citrate.

In some embodiments, Compound 1 Citrate has an XRPD pattern with characteristic peaks as substantially shown in FIG. 30 (FIG. 30).

Figure 31:
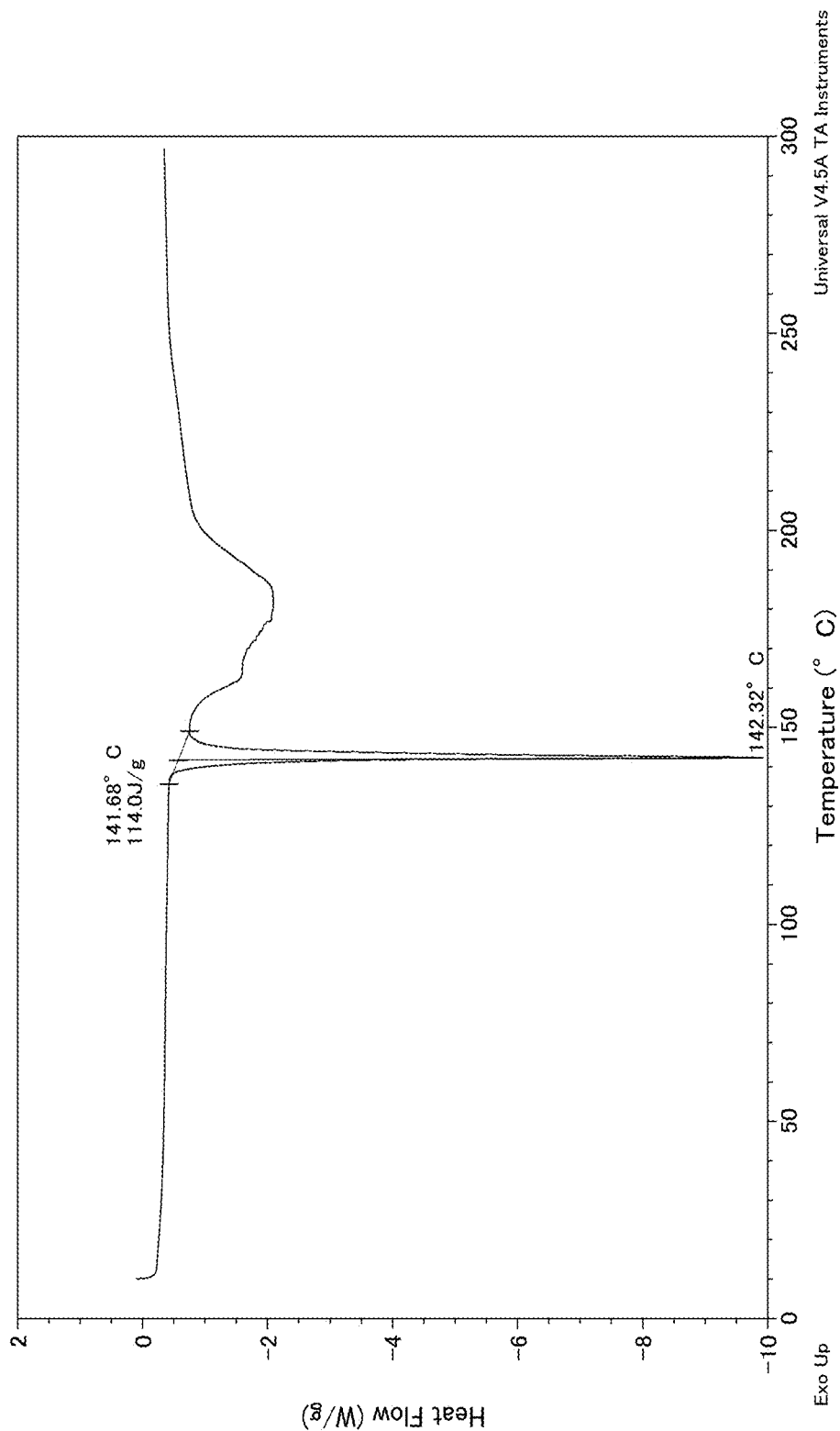
FIG. 31 shows a DSC thermogram of Compound 1 Citrate.
Figure 32:
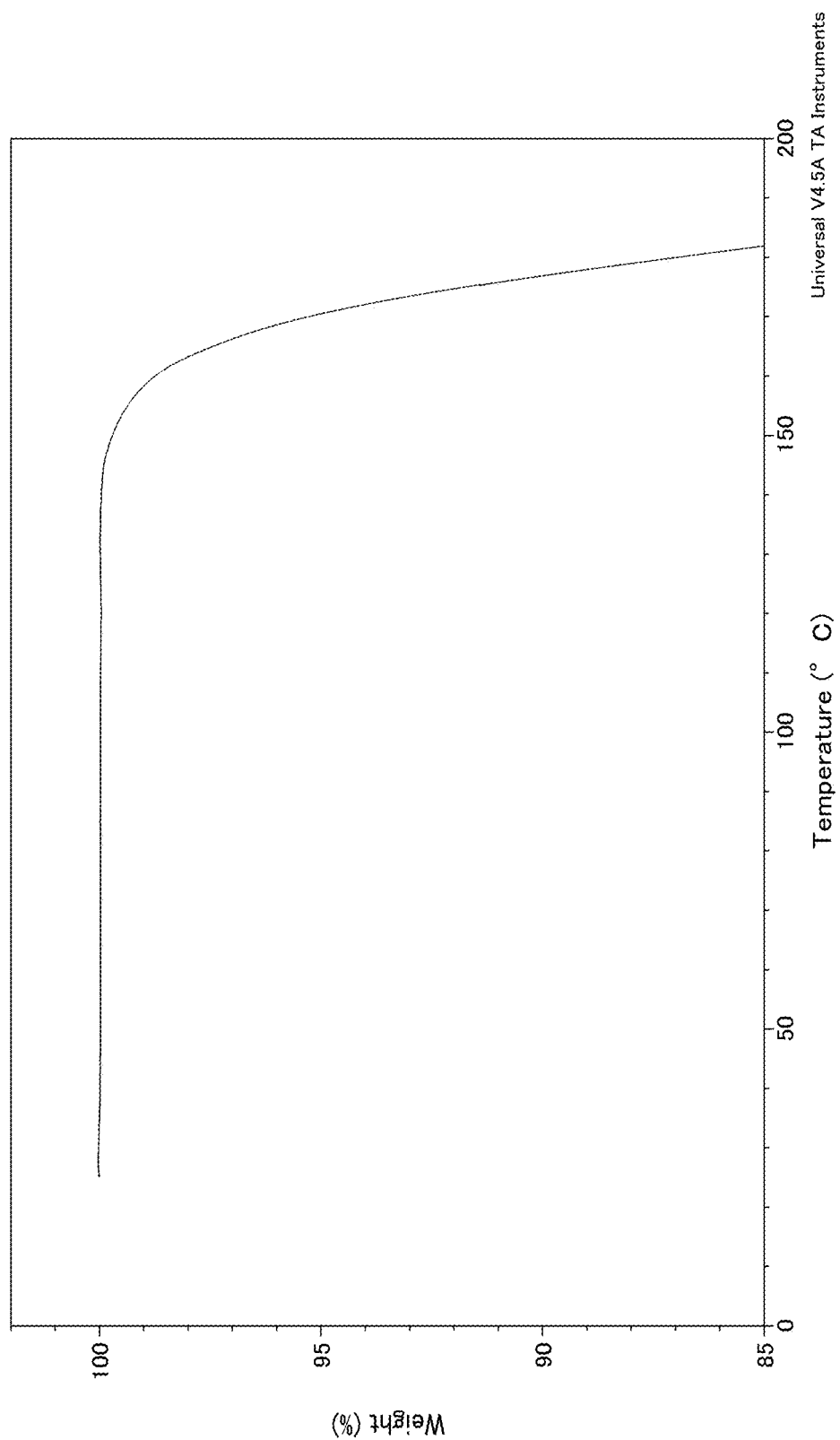
FIG. 32 shows a TGA thermogram of Compound 1 Citrate.
Figure 33:
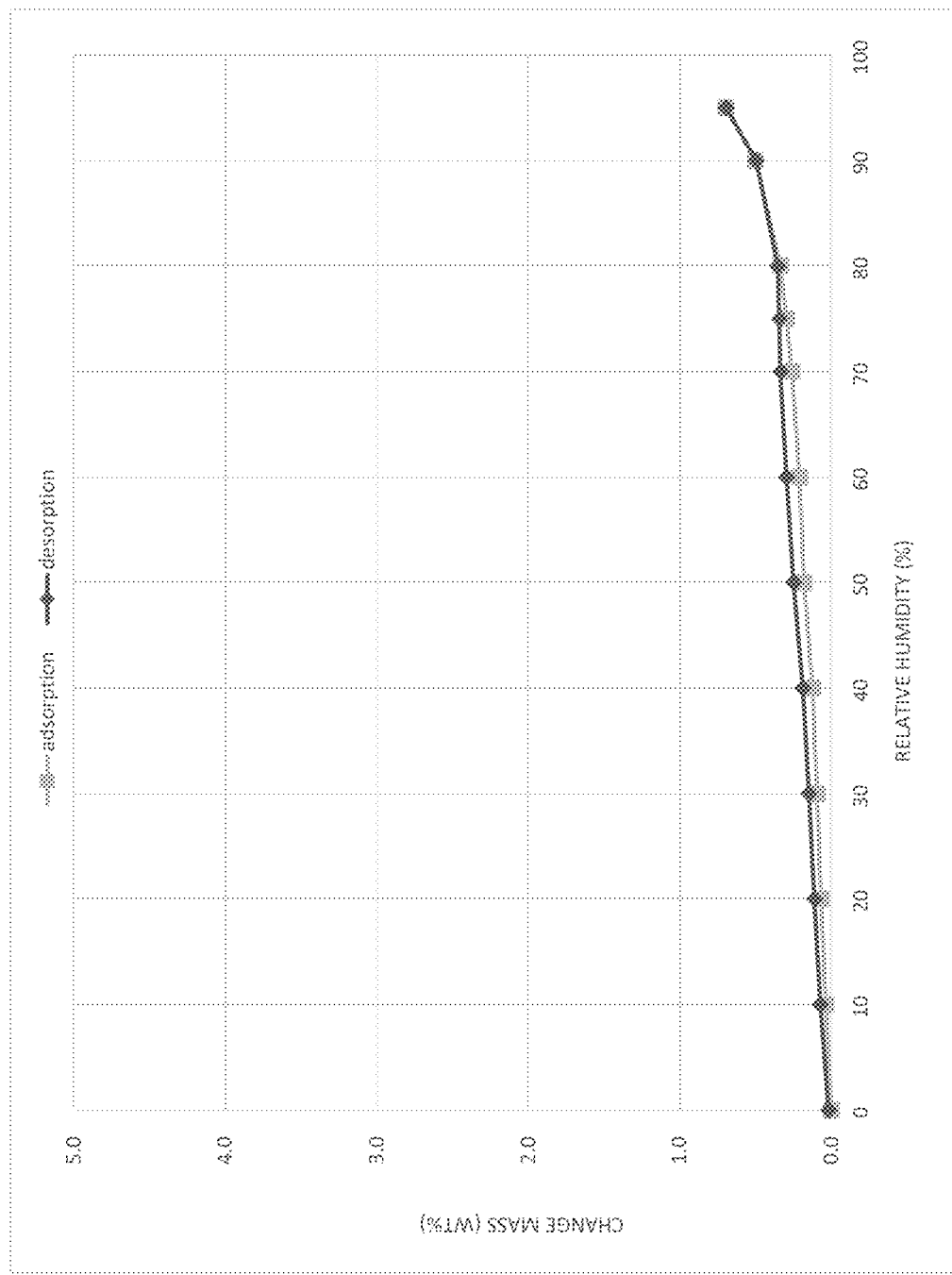
FIG. 33 shows a DVS isotherm of Compound 1 Citrate.

In some embodiments, Compound 1 Citrate has an endotherm peak at a temperature of about 142° C. In some embodiments, Compound 1 Citrate has a DSC thermogram substantially as depicted in FIG. 31 (FIG. 31). In some embodiments, Compound 1 Citrate has a TGA thermogram substantially as depicted in FIG. 32 (FIG. 32). In some embodiments, Compound 1 citrate has a DVS isotherm substantially as depicted in FIG. 33 (FIG. 33).

In some embodiments, Compound 1 Citrate has at least one characteristic XRPD peak in terms of 2θ selected from 6.5°±0.2°, 15.5°±0.2°, and 20.4°±0.2°; and an endotherm peak at a temperature of about 142° C. In some embodiments, Compound 1 Citrate has at least one characteristic XRPD peak in terms of 2θ selected from 6.5°±0.2°, 15.5°±0.2°, and 20.4°±0.2°; and a DSC thermogram substantially as depicted in FIG. 31 (FIG. 31). In some embodiments, Compound 1 Citrate has at least one characteristic XRPD peak in terms of 2θ selected from 6.5°±0.2°, 15.5°±0.2°, and 20.4°±0.2°; and a DVS isotherm substantially as depicted in FIG. 33 (FIG. 33).

In some embodiments, Compound 1 Citrate can be isolated with a crystalline purity of at least about 80%, about 85%, about 90%, about 95%, about 96%, about 97%, about 98%, or about 99%. In some embodiments, Compound 1 Citrate can be isolated with a crystalline purity greater than about 99%. In some embodiments, Compound 1 Citrate can be isolated with a crystalline purity greater than about 99.9%.

In some embodiments, provided is Compound 1 Citrate prepared by isolating Compound 1 citrate from a mixture of Compound 1, citric acid, and S1, wherein S1 is a solvent. In some embodiments, S1 is an organic solvent. In some embodiments, S1 is $C_{1-6}$ alkyl alcohol. In some embodiments, S1 is ether. In some embodiments, S1 is $C_{1-6}$ alkyl acetate. In some embodiments, S1 is a $C_{1-6}$ alkyl ketone. In some embodiments, S1 is a mixture of organic solvents. In some embodiments, S1 is a mixture of a $C_{1-6}$ alkyl alcohol and a $C_{1-6}$ alkyl ketone. In some embodiments, S1 is a mixture of a $C_{1-6}$ alkyl alcohol and a $C_{1-6}$ alkyl acetate. In some embodiments, S1 is ethyl acetate. In some embodiments, S1 is a mixture of methanol and acetone. In some embodiments, S1 is THF. In some embodiments, S1 is a mixture of methanol and ethyl acetate.

Compound 1 Succinate

In some embodiments, provided is (R)-1-(8-fluoroisochroman-1-yl)-N-methylmethanamine succinate. In some embodiments, Compound 1 Succinate is crystalline.

In some embodiments, Compound 1 Succinate has characteristic XRPD peaks in terms of 2θ selected from 6.6°±0.2°, 12.8°±0.2°, and 13.9°±0.2°. In some embodiments, Compound 1 Succinate has a characteristic XRPD peak in terms of 2θ at 6.6°±0.2°. In some embodiments, Compound 1 Succinate has a characteristic XRPD peak in terms of 2θ at 12.8°±0.2°. In some embodiments, Compound 1 Succinate has a characteristic XRPD peak in terms of 2θ at 13.9°±0.2°.

In some embodiments, Compound 1 Succinate has characteristic XRPD peaks in terms of 2θ selected from 12.8°±0.2°, 13.9°±0.2°, 19.8°±0.2°, and 26.5°±0.2°. In some embodiments, Compound 1 Succinate has at least one characteristic XRPD peak in terms of 2θ selected from 12.8°±0.2°, 13.9°±0.2°, 19.8°±0.2°, and 26.5°±0.2°.

In some embodiments, Compound 1 Succinate has at least one characteristic XRPD peak in terms of 2θ selected from 12.8°±0.2°, 13.9°±0.2°, 16.0°±0.2°, 19.2°±0.2°, 19.8°±0.2°, 21.1°±0.2°, 22.9°±0.2°, 23.3°±0.2°, 25.4°±0.2°, and 26.5°±0.2°. In some embodiments, Compound 1 Succinate has at least one characteristic XRPD peak in terms of 2θ selected from 6.60°±0.2°, 9.0°±0.2°, 11.50°±0.2°, 12.80°±0.2°, 13.9°±0.2°, 16.0°±0.2°, 19.2°±0.2°, 19.8°±0.2°, 21.1°±0.2°, 22.9°±0.2°, 23.3°±0.2°, 25.2°±0.2°, 25.4°±0.2°, and 26.5°±0.2°.

In some embodiments, Compound 1 Succinate has at least two characteristic XRPD peaks in terms of 2θ selected from 12.8°±0.2°, 13.9°±0.2°, 16.0°±0.2°, 19.2°±0.2°, 19.8°±0.2°, 21.1°±0.2°, 22.9°±0.2°, 23.3°±0.2°, 25.4°±0.2°, and 26.5°±0.2°. In some embodiments, Compound 1 Succinate has at least two characteristic XRPD peaks in terms of 2θ selected from 6.60°±0.2°, 9.0°±0.2°, 11.50°±0.2°, 12.80°±0.2°, 13.9°±0.2°, 16.0°±0.2°, 19.2°±0.2°, 19.8°±0.2°, 21.1°±0.2°, 22.9°±0.2°, 23.3°±0.2°, 25.2°±0.2°, 25.4°±0.2°, and 26.5°±0.2°.

In some embodiments, Compound 1 Succinate has at least three characteristic XRPD peaks in terms of 2θ selected from 12.8°±0.2°, 13.9°±0.2°, 16.0°±0.2°, 19.2°±0.2°, 19.8°±0.2°, 21.1°±0.2°, 22.9°±0.2°, 23.3°±0.2°, 25.4°±0.2°, and 26.5°±0.2°. In some embodiments, Compound 1 Succinate has at least three characteristic XRPD peaks in terms of 2θ selected from 6.60°±0.2°, 9.0°±0.2°, 11.50°±0.2°, 12.80°±0.2°, 13.9°±0.2°, 16.0°±0.2°, 19.2°±0.2°, 19.8°±0.2°, 21.1°±0.2°, 22.9°±0.2°, 23.3°±0.2°, 25.2°±0.2°, 25.4°±0.2°, and 26.5°±0.2°.

Figure 34:
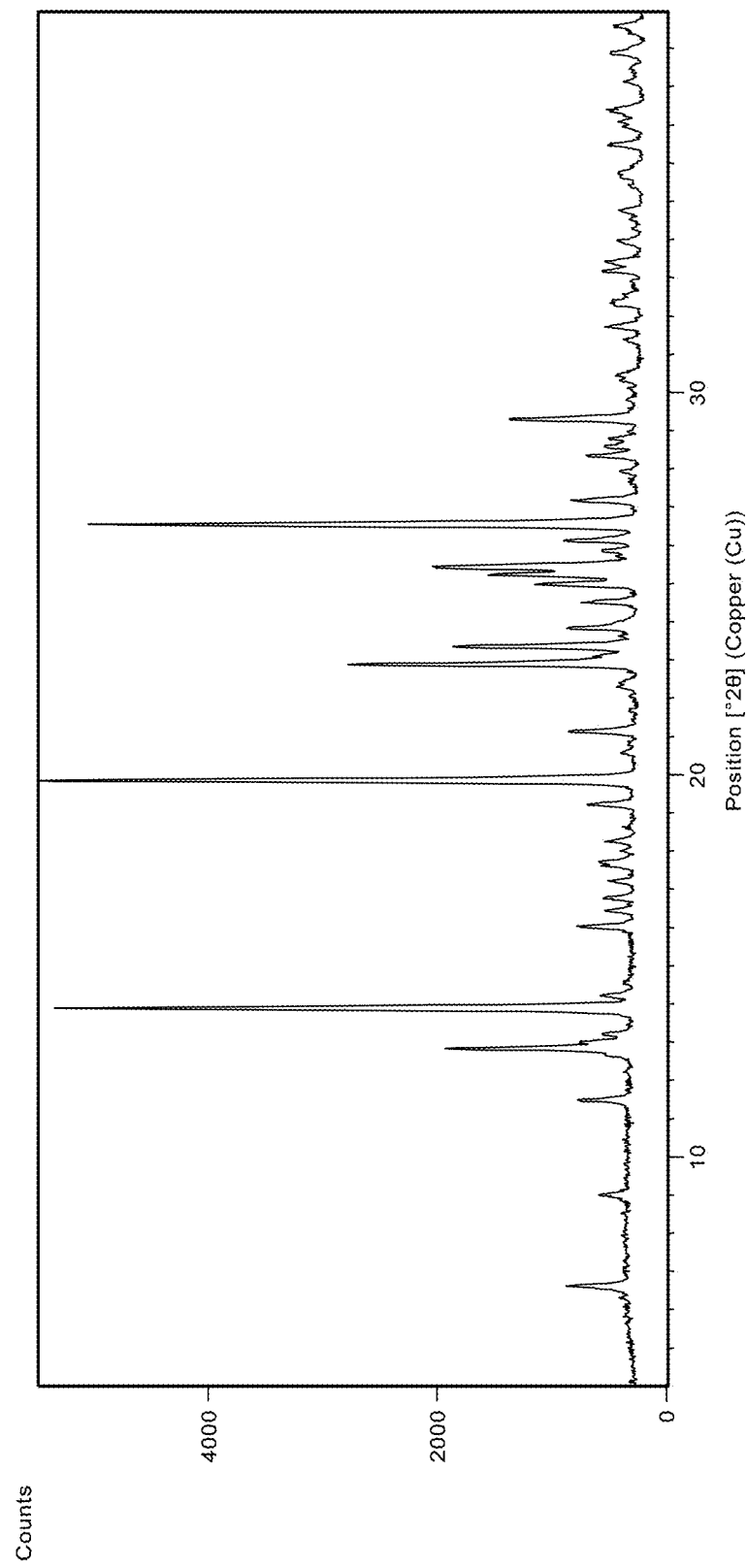
FIG. 34 shows an XRPD pattern of Compound 1 Succinate.

In some embodiments, Compound 1 Succinate has an XRPD pattern with characteristic peaks as substantially shown in FIG. 34 (FIG. 34).

Figure 35:
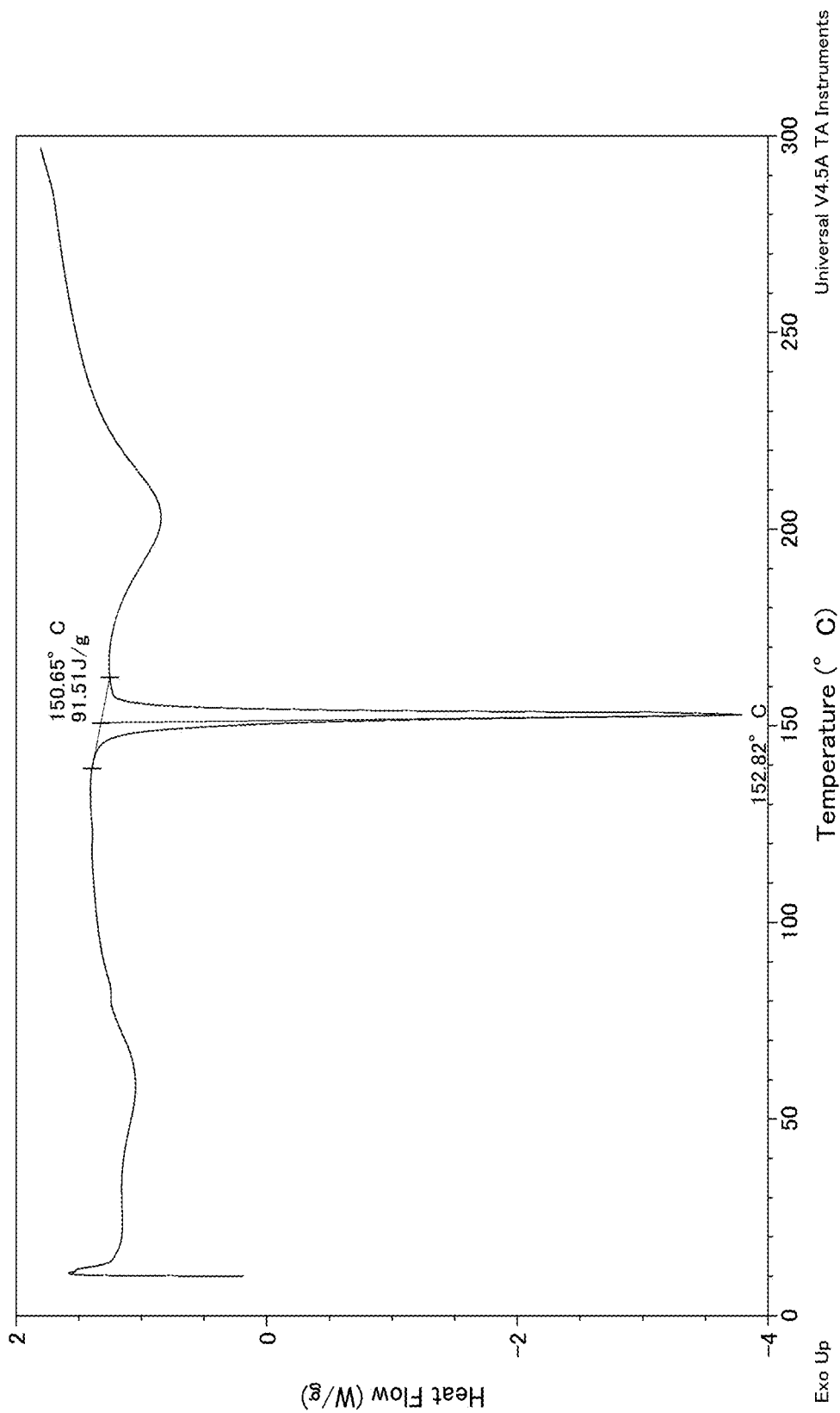
FIG. 35 shows a DSC thermogram of Compound 1 Succinate.
Figure 36:
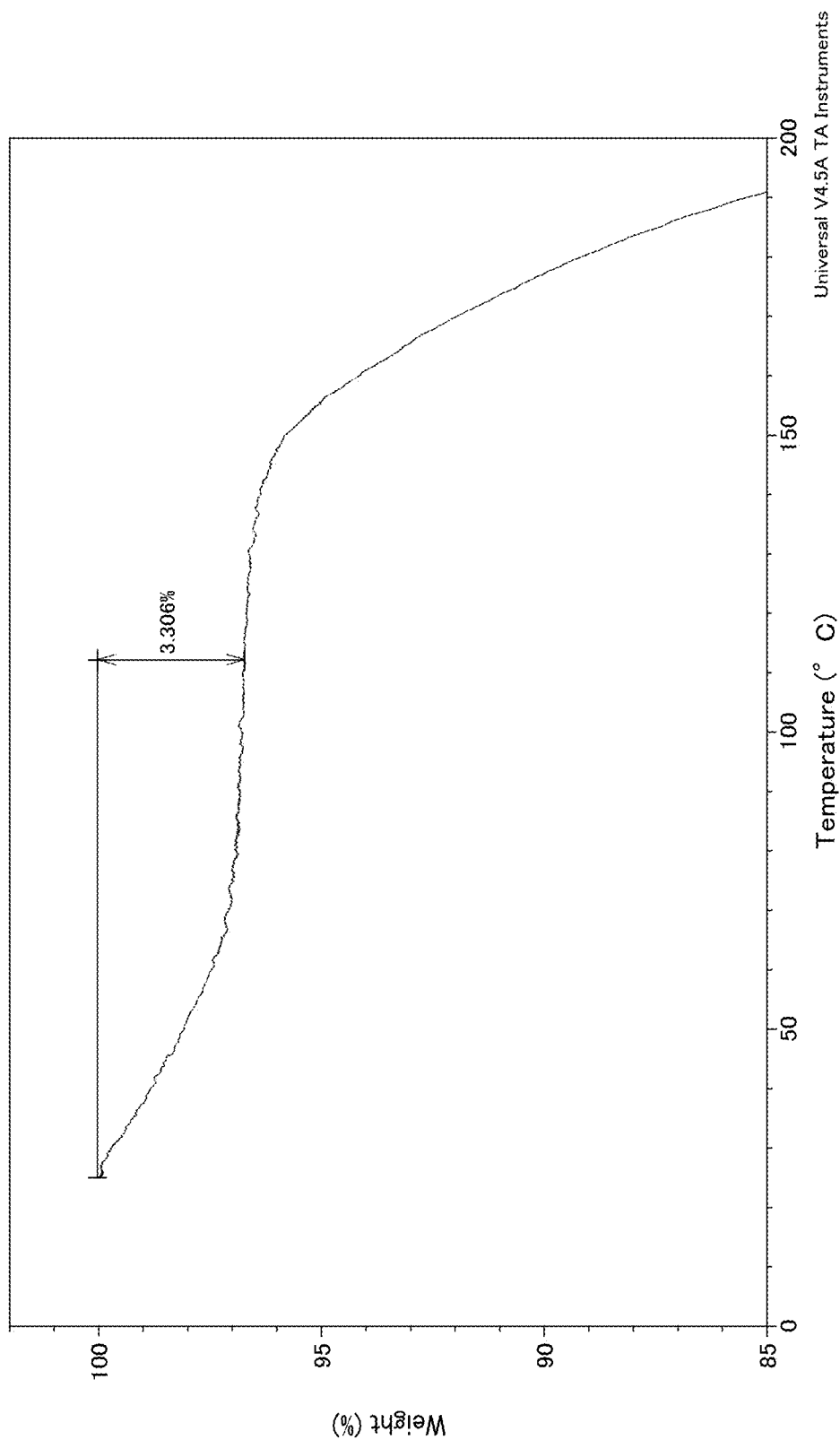
FIG. 36 shows a TGA thermogram of Compound 1 Succinate.
Figure 37:
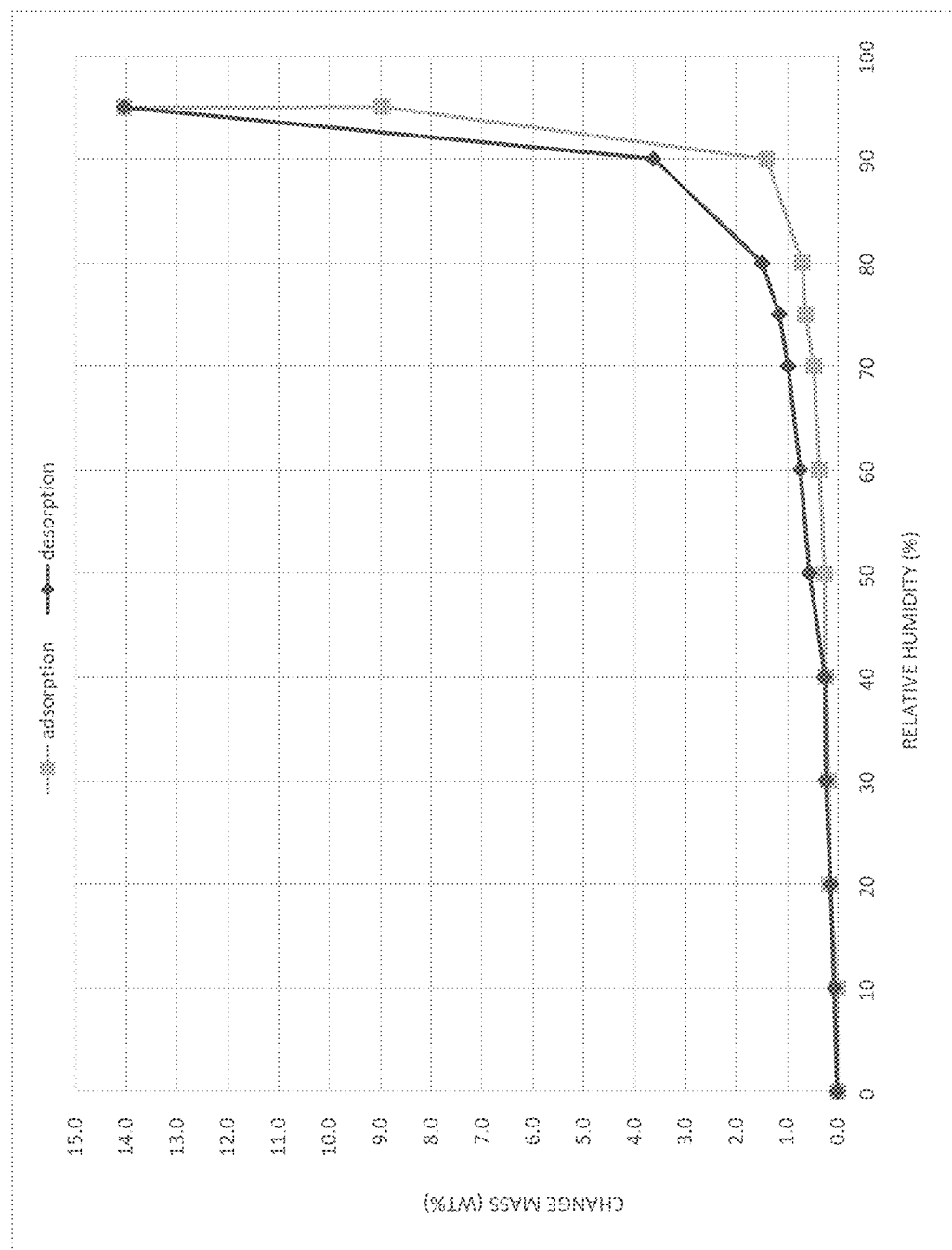
FIG. 37 shows a DVS isotherm of Compound 1 Succinate.

In some embodiments, Compound 1 Succinate has an endotherm peak at a temperature of about 153° C. In some embodiments, Compound 1 Succinate has a DSC thermogram substantially as depicted in FIG. 35 (FIG. 35). In some embodiments, Compound 1 Succinate has a TGA thermogram substantially as depicted in FIG. 36 (FIG. 36). In some embodiments, Compound 1 Succinate has a DVS isotherm substantially as depicted in FIG. 37 (FIG. 37).

In some embodiments, Compound 1 Succinate has at least one characteristic XRPD peak in terms of 2θ selected from 12.8°±0.2°, 13.9°±0.2°, 19.80°±0.2°, and 26.50°±0.2°; and an endotherm peak at a temperature of about 153° C. In some embodiments, Compound 1 succinate has at least one characteristic XRPD peak in terms of 2θ selected from 12.8°±0.2°, 13.9°±0.2°, 19.8°±0.2°, and 26.5°±0.2°; and a DSC thermogram substantially as depicted in FIG. 35 (FIG. 35). In some embodiments, Compound 1 Succinate has at least one characteristic XRPD peak in terms of 2θ selected from 12.8°±0.2°, 13.9°±0.2°, 19.80°±0.2°, and 26.50°±0.2°; and a DVS isotherm substantially as depicted in FIG. 37 (FIG. 37).

In some embodiments, Compound 1 Succinate can be isolated with a crystalline purity of at least about 80%, about 85%, about 90%, about 95%, about 96%, about 97%, about 98%, or about 99%. In some embodiments, Compound 1 Succinate can be isolated with a crystalline purity greater than about 99%. In some embodiments, Compound 1 Succinate can be isolated with a crystalline purity greater than about 99.9%.

In some embodiments, provided is Compound 1 Succinate prepared by isolating Compound 1 succinate from a mixture of Compound 1, succinic acid, and S1, wherein S1 is a solvent. In some embodiments, S1 is an organic solvent. In some embodiments, S1 is ether. In some embodiments, S1 is $C_{1-6}$ alkyl acetate. In some embodiments, S1 is THF. In some embodiments, S1 is ethyl acetate.

Compound 1 Glutarate

In some embodiments, provided is (R)-1-(8-fluoroisochroman-1-yl)-N-methylmethanamine Glutarate. In some embodiments, Compound 1 Glutarate is crystalline.

In some embodiments, Compound 1 Glutarate has characteristic XRPD peaks in terms of 2θ selected from 9.1°±0.2°, 10.6°±0.2°, and 18.2°±0.2°. In some embodiments, Compound 1 Glutarate has a characteristic XRPD peak in terms of 2θ at 9.1°±0.2°. In some embodiments, Compound 1 Glutarate has a characteristic XRPD peak in terms of 2θ at 10.6°±0.2°. In some embodiments, Compound 1 Glutarate has a characteristic XRPD peak in terms of 2θ at 18.2°±0.2°.

In some embodiments, Compound 1 Glutarate has characteristic XRPD peaks in terms of 2θ selected from 9.1°±0.2°, 10.6°±0.2°, 18.2°±0.2°, and 19.0°±0.2°. In some embodiments, Compound 1 Glutarate has at least one characteristic XRPD peak in terms of 2θ selected from 9.10°±0.2°, 10.60°±0.2°, 18.2°±0.2°, and 19.0°±0.2°.

In some embodiments, Compound 1 Glutarate has at least one characteristic XRPD peak in terms of 2θ selected from 9.1°±0.2°, 10.6°±0.2°, 18.2°±0.2°, 19.0°±0.2°, 22.5°±0.2°, 27.4°±0.2°, and 28.0°±0.2°. In some embodiments, Compound 1 Glutarate has at least one characteristic XRPD peak in terms of 2θ selected from 9.1°±0.2°, 10.6°±0.2°, 18.2°±0.2°, 19.0°±0.2°, 21.8°±0.2°, 21.9°±0.2°, 22.5°±0.2°, 25.8°±0.2°, 27.4°±0.2°, and 28.0°±0.2°.

In some embodiments, Compound 1 Glutarate has at least two characteristic XRPD peaks in terms of 2θ selected from 9.1°±0.2°, 10.6°±0.2°, 18.2°±0.2°, 19.0°±0.2°, 22.5°±0.2°, 27.4°±0.2°, and 28.0°±0.2°. In some embodiments, Compound 1 Glutarate has at least two characteristic XRPD peaks in terms of 2θ selected from 9.1°±0.2°, 10.6°±0.2°, 18.2°±0.2°, 19.0°±0.2°, 21.8°±0.2°, 21.9°±0.2°, 22.5°±0.2°, 25.8°±0.2°, 27.4°±0.2°, and 28.0°±0.2°.

In some embodiments, Compound 1 Glutarate has at least three characteristic XRPD peaks in terms of 2θ selected from 9.1°±0.2°, 10.6°±0.2°, 18.2°±0.2°, 19.0°±0.2°, 22.5°±0.2°, 27.4°±0.2°, and 28.0°±0.2°. In some embodiments, Compound 1 Glutarate has at least three characteristic XRPD peaks in terms of 2θ selected from 9.1°±0.2°, 10.6°±0.2°, 18.2°±0.2°, 19.0°±0.2°, 21.8°±0.2°, 21.9°±0.2°, 22.5°±0.2°, 25.8°±0.2°, 27.4°±0.2°, and 28.0°±0.2°.

Figure 38:
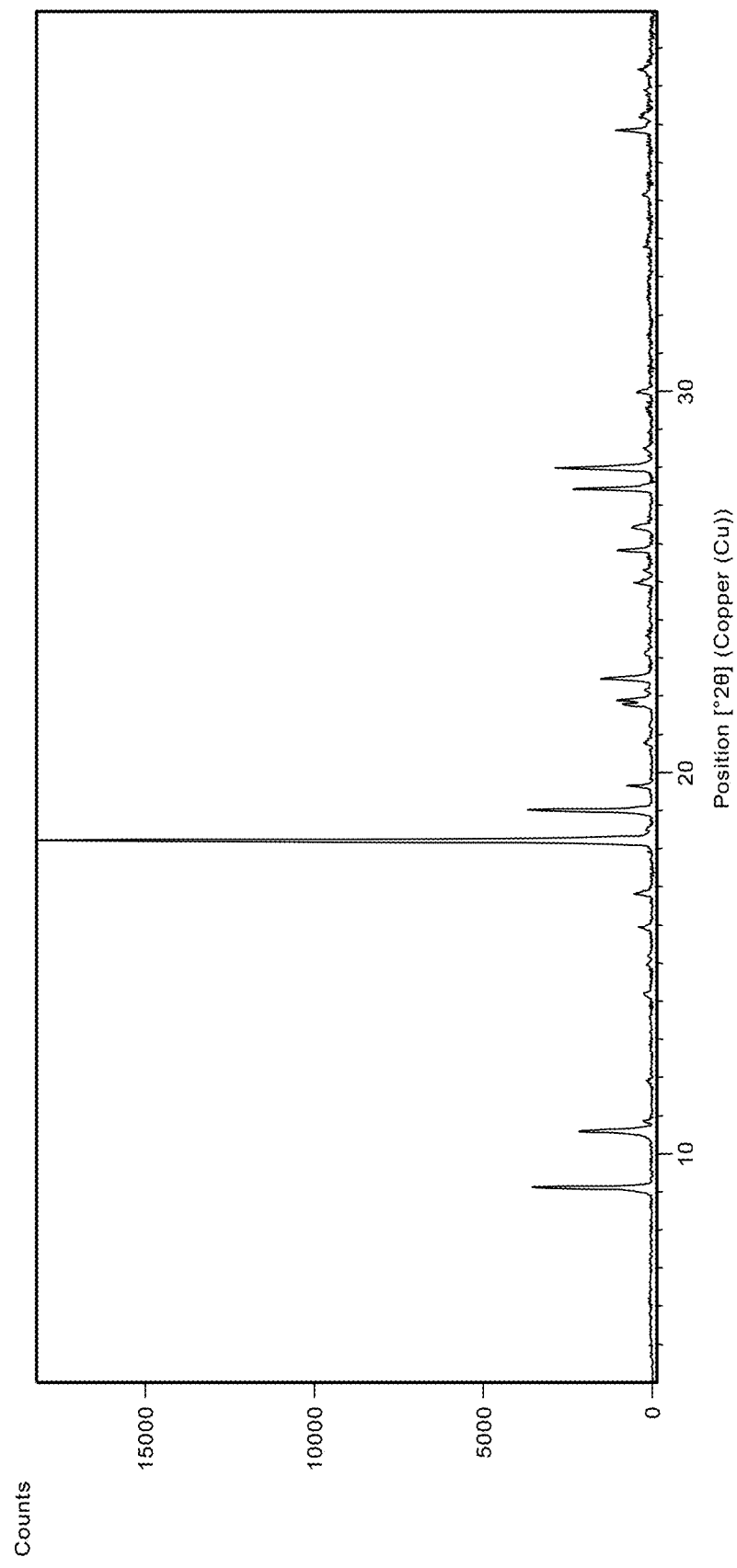
FIG. 38 shows an XRPD pattern of Compound 1 Glutarate.
Figure 39:
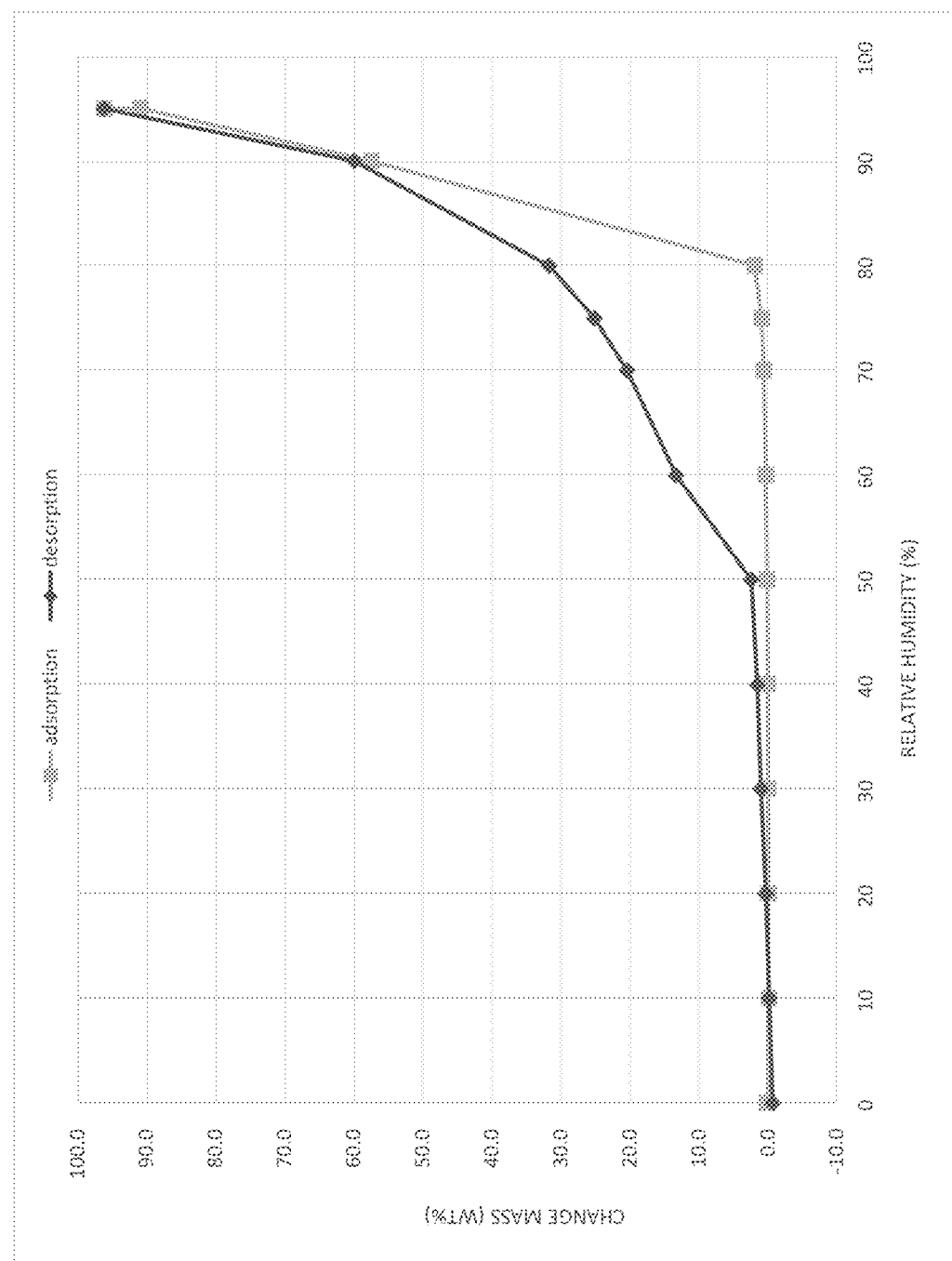
FIG. 39 shows a DVS isotherm of Compound 1 Glutarate.

In some embodiments, Compound 1 Glutarate has an XRPD pattern with characteristic peaks as substantially shown in FIG. 38 (FIG. 38). In some embodiments, Compound 1 Glutarate has a DVS isotherm as substantially shown in FIG. 39 (FIG. 39).

In some embodiments, Compound 1 Glutarate can be isolated with a crystalline purity of at least about 80%, about 85%, about 90%, about 95%, about 96%, about 97%, about 98%, or about 99%. In some embodiments, Compound 1 Glutarate can be isolated with a crystalline purity greater than about 99%. In some embodiments, Compound 1 Glutarate can be isolated with a crystalline purity greater than about 99.9%.

In some embodiments, provided is Compound 1 Glutarate prepared by isolating Compound 1 glutarate from a mixture of Compound 1, glutaric acid, and S1, wherein S1 is a solvent. In some embodiments, S1 is an organic solvent. In some embodiments, S1 is $C_{1-6}$ alkyl alcohol. In some embodiments, S1 is $C_{1-6}$ alkyl acetate. In some embodiments, S1 is a $C_{1-6}$ alkyl ketone. In some embodiments, S1 is a mixture of organic solvents. In some embodiments, S1 is a mixture of a $C_{1-6}$ alkyl alcohol and a $C_{1-6}$ alkyl ketone.

In some embodiments, S1 is a mixture of methanol and acetone. In some embodiments, S1 is THF. In some embodiments, S1 is ethyl acetate.

Compound 1 L-Malate

In some embodiments, provided is (R)-1-(8-fluoroisochroman-1-yl)-N-methylmethanamine L-Malate. In some embodiments, Compound 1 L-Malate is crystalline.

In some embodiments, Compound 1 L-Malate has characteristic XRPD peaks in terms of 2θ selected from 13.5°±0.2°, 18.8°±0.2°, and 25.2°±0.2°. In some embodiments, Compound 1 L-Malate has a characteristic XRPD peak in terms of 2θ at 13.5°±0.2°. In some embodiments, Compound 1 L-Malate has a characteristic XRPD peak in terms of 2θ at 18.8°±0.2°. In some embodiments, Compound 1 L-Malate has a characteristic XRPD peak in terms of 2θ at 25.2°±0.2°.

In some embodiments, Compound 1 L-Malate has at least one characteristic XRPD peak in terms of 2θ selected from 13.5°±0.2°, 14.4°±0.2°, 15.2°±0.2°, 18.8°±0.2°, 23.8°±0.2°, 24.8°±0.2°, and 25.2°±0.2°. In some embodiments, Compound 1 L-Malate has at least one characteristic XRPD peak in terms of 2θ selected from 13.5°±0.2°, 14.4°±0.2°, 15.2°±0.2°, 17.7°±0.2°, 18.8°±0.2°, 22.4°±0.2°, 23.8°±0.2°, 24.6°±0.2°, 24.8°±0.2°, and 25.2°±0.2°.

In some embodiments, Compound 1 L-Malate has at least two characteristic XRPD peaks in terms of 2θ selected from 13.5°±0.2°, 14.4°±0.2°, 15.2°±0.2°, 18.8°±0.2°, 23.8°±0.2°, 24.8°±0.2°, and 25.2°±0.2°. In some embodiments, Compound 1 L-Malate has at least two characteristic XRPD peaks in terms of 2θ selected from 13.5°±0.2°, 14.4°±0.2°, 15.2°±0.2°, 17.7°±0.2°, 18.8°±0.2°, 22.4°±0.2°, 23.8°±0.2°, 24.6°±0.2°, 24.8°±0.2°, and 25.2°±0.2°.

In some embodiments, Compound 1 L-Malate has at least three characteristic XRPD peaks in terms of 2θ selected from 13.5°±0.2°, 14.4°±0.2°, 15.2°±0.2°, 18.8°±0.2°, 23.8°±0.2°, 24.8°±0.2°, and 25.2°±0.2°. In some embodiments, Compound 1 L-Malate has at least three characteristic XRPD peaks in terms of 2θ selected from 13.5°±0.2°, 14.4°±0.2°, 15.2°±0.2°, 17.7°±0.2°, 18.8°±0.2°, 22.4°±0.2°, 23.8°±0.2°, 24.6°±0.2°, 24.8°±0.2°, and 25.2°±0.2°.

Figure 40:
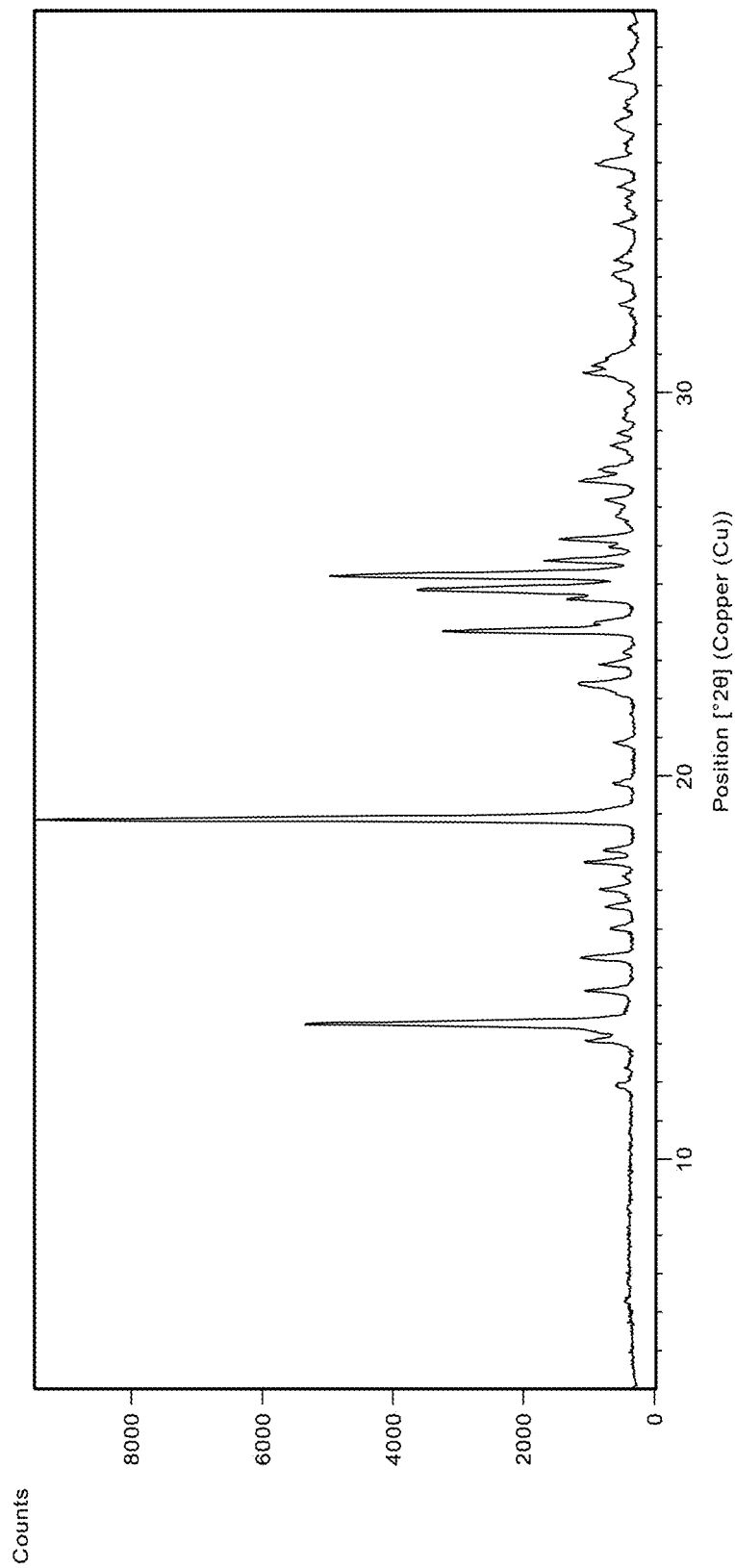
FIG. 40 shows an XRPD pattern of Compound 1 L-Malate.

In some embodiments, Compound 1 L-Malate has an XRPD pattern with characteristic peaks as substantially shown in FIG. 40 (FIG. 40).

Figure 41:
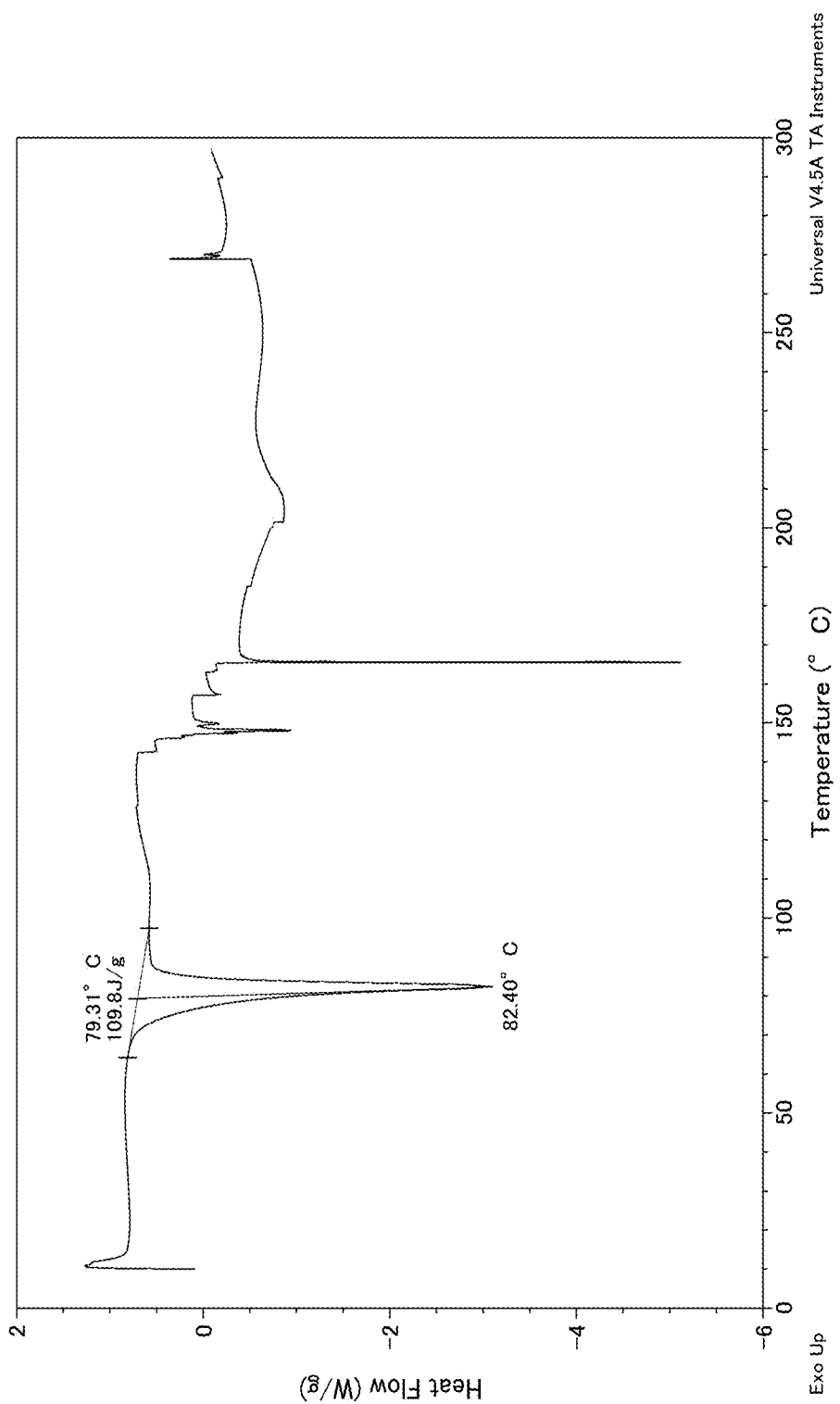
FIG. 41 shows a DSC thermogram of Compound 1 L-Malate.
Figure 42:
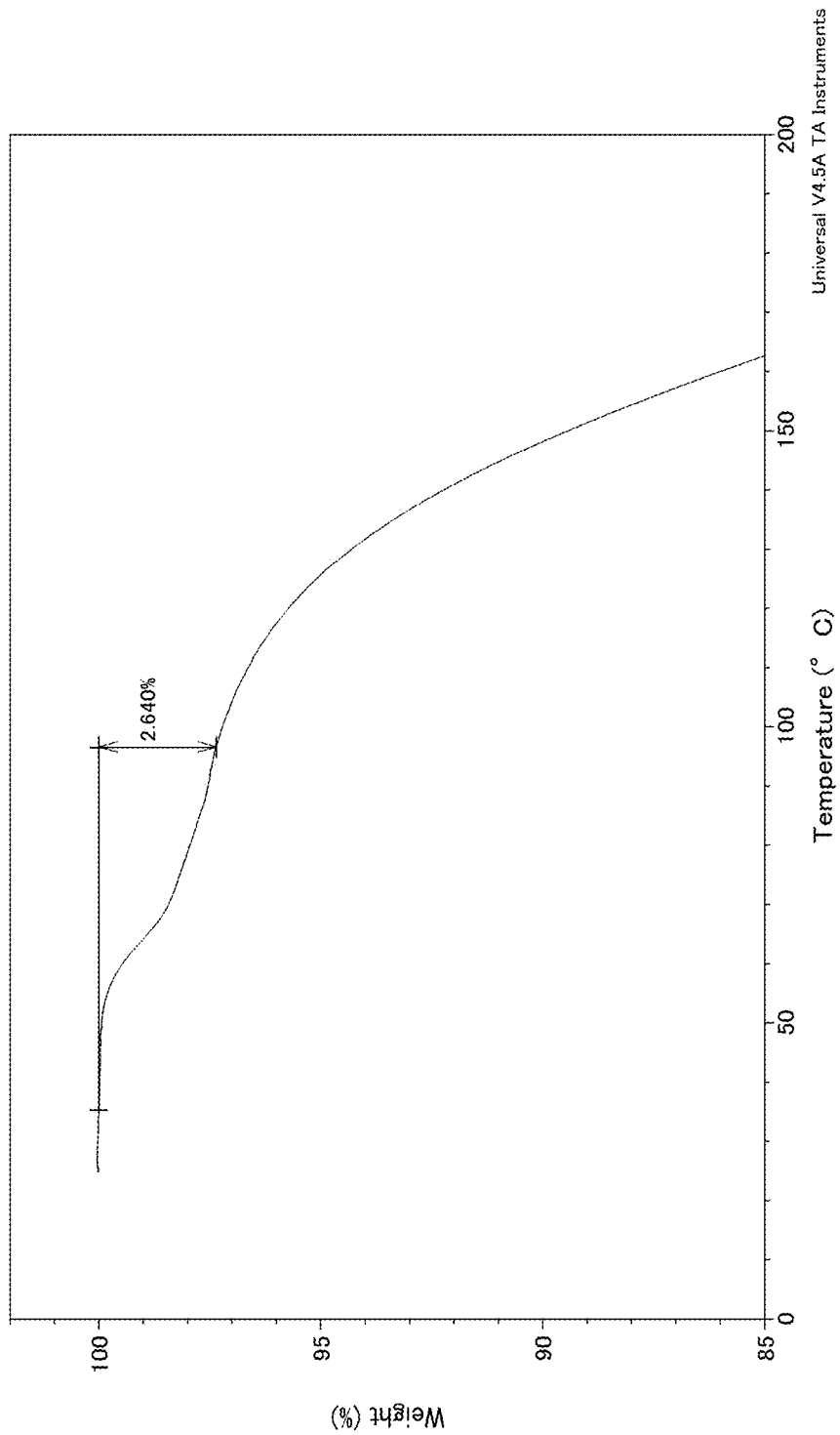
FIG. 42 shows a TGA thermogram of Compound 1 L-Malate.
Figure 43:
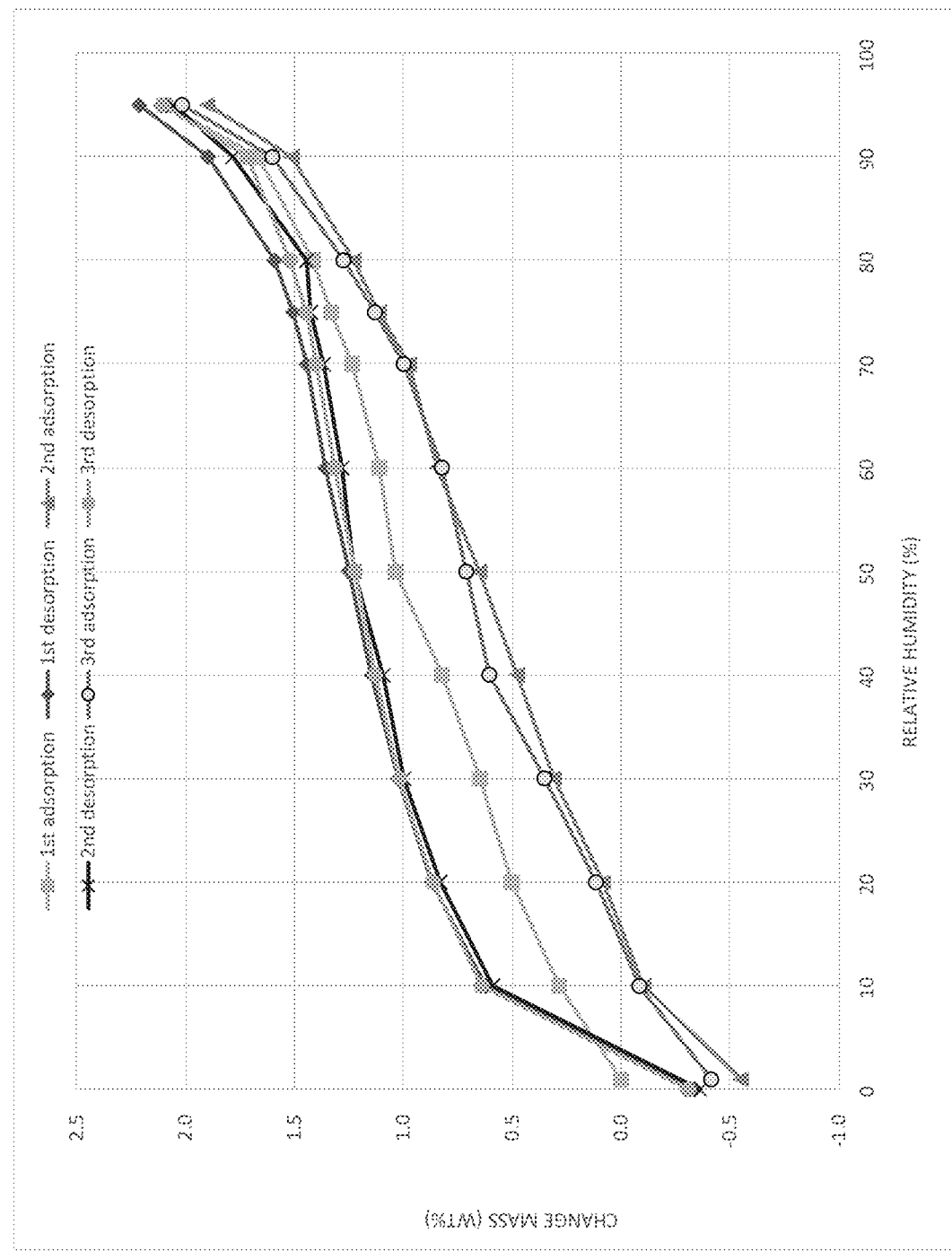
FIG. 43 shows a DVS isotherm of Compound 1 L-Malate.

In some embodiments, Compound 1 L-Malate has an endotherm peak at a temperature of about 82° C. In some embodiments, Compound 1 L-Malate has a DSC thermogram substantially as depicted in FIG. 41 (FIG. 41). In some embodiments, Compound 1 L-L-Malate has a TGA thermogram substantially as depicted in FIG. 42 (FIG. 42). In some embodiments, Compound 1 L-Malate has a DVS isotherm substantially as depicted in FIG. 43 (FIG. 43).

In some embodiments, Compound 1 L-Malate has at least one characteristic XRPD peak in terms of 2θ selected from 13.5°±0.2°, 18.8°±0.2°, and 25.2°±0.2°; and an endotherm peak at a temperature of about 82° C. In some embodiments, Compound 1 L-Malate has at least one characteristic XRPD peak in terms of 2θ selected from 13.5°±0.2°, 18.8°±0.2°, and 25.2°±0.2°; and a DSC thermogram substantially as depicted in FIG. 41 (FIG. 41). In some embodiments, Compound 1 L-Malate has at least one characteristic XRPD peak in terms of 2θ selected from 13.5°±0.2°, 18.8°±0.2°, and 25.2°±0.2°; and a DVS isotherm substantially as depicted in FIG. 43 (FIG. 43).

In some embodiments, Compound 1 L-Malate can be isolated with a crystalline purity of at least about 80%, about 85%, about 90%, about 95%, about 96%, about 97%, about 98%, or about 99%. In some embodiments, Compound 1 L-Malate can be isolated with a crystalline purity greater than about 99%. In some embodiments, Compound 1 L-Malate can be isolated with a crystalline purity greater than about 99.9%.

In some embodiments, provided is Compound 1 L-Malate prepared by isolating Compound 1 L-malate from a mixture of Compound 1, L-malic acid, and S1, wherein S1 is a solvent. In some embodiments, S1 is an organic solvent. In some embodiments, S1 is $C_{1-6}$ alkyl alcohol. In some embodiments, S1 is ether. In some embodiments, S1 is $C_{1-6}$ alkyl acetate. In some embodiments, S1 is methanol. In some embodiments, S1 is THF. In some embodiments, S1 is ethyl acetate.

Compound 1 Besylate

In some embodiments, provided is (R)-1-(8-fluoroisochroman-1-yl)-N-methylmethanamine Besylate. In some embodiments, Compound 1 Besylate is crystalline. In some embodiments, Compound 1 Besylate has characteristic XRPD peaks in terms of 2θ selected from 6.0°±0.2°, 12.0°±0.2°, and 24.1°±0.2°. In some embodiments, Compound 1 Besylate has a characteristic XRPD peak in terms of 2θ at 6.0°±0.2°. In some embodiments, Compound 1 Besylate has a characteristic XRPD peak in terms of 2θ at 12.0°±0.2°. In some embodiments, Compound 1 Besylate has a characteristic XRPD peak in terms of 2θ at 24.1°±0.2°.

In some embodiments, Compound 1 Besylate has at least one characteristic XRPD peak in terms of 2θ selected from 6.0°±0.2°, 12.0°±0.2°, 16.6°±0.2°, 24.1°±0.2°, 26.8°±0.2°, and 30.3°±0.2°. In some embodiments, Compound 1 Besylate has at least one characteristic XRPD peak in terms of 2θ selected from 6.0°±0.2°, 12.0°±0.2°, 16.4°±0.2°, 16.6°±0.2°, 19.0°±0.2°, 21.2°±0.2°, 22.2°±0.2°, 23.2°±0.2°, 24.10°±0.2°, 26.8°±0.2°, and 30.3°±0.2°.

In some embodiments, Compound 1 Besylate has at least two characteristic XRPD peaks in terms of 2θ selected from 6.0°±0.2°, 12.0°±0.2°, 16.6°±0.2°, 24.1°±0.2°, 26.8°±0.2°, and 30.3°±0.2°. In some embodiments, Compound 1 Besylate has at least two characteristic XRPD peaks in terms of 2θ selected from 6.0°±0.2°, 12.0°±0.2°, 16.4°±0.2°, 16.6°±0.2°, 19.0°±0.2°, 21.2°±0.2°, 22.2°±0.2°, 23.2°±0.2°, 24.10°±0.2°, 26.8°±0.2°, and 30.3°±0.2°.

In some embodiments, Compound 1 Besylate has at least three characteristic XRPD peaks in terms of 2θ selected from 6.0°±0.2°, 12.0°±0.2°, 16.6°±0.2°, 24.1°±0.2°, 26.8°±0.2°, and 30.3°±0.2°. In some embodiments, Compound 1 Besylate has at least three characteristic XRPD peaks in terms of 2θ selected from 6.0°±0.2°, 12.0°±0.2°, 16.4°±0.2°, 16.6°±0.2°, 19.0°±0.2°, 21.2°±0.2°, 22.2°±0.2°, 23.2°±0.2°, 24.10°±0.2°, 26.8°±0.2°, and 30.3°±0.2°.

Figure 44:
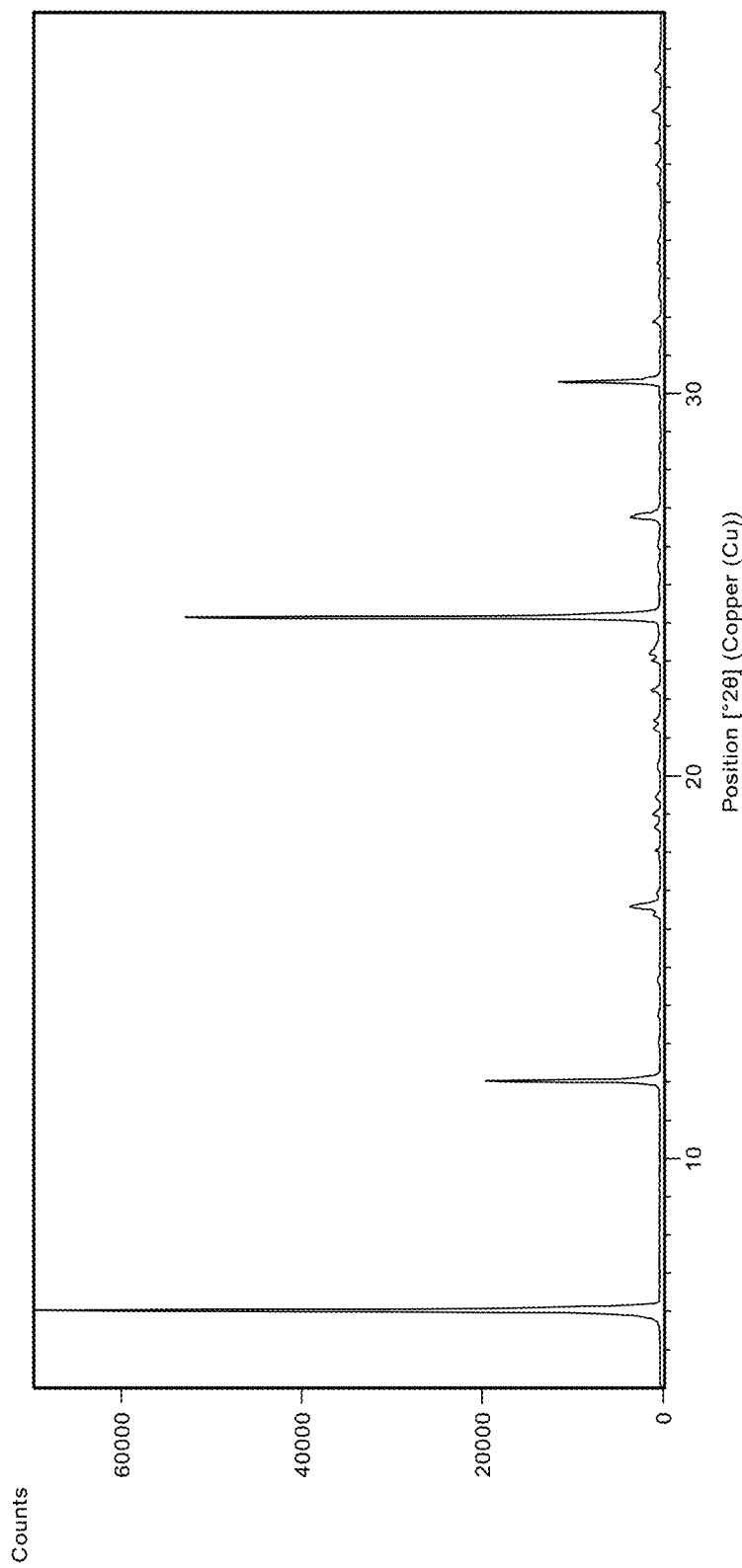
FIG. 44 shows an XRPD pattern of Compound 1 Besylate.

In some embodiments, Compound 1 Besylate has an XRPD pattern with characteristic peaks as substantially shown in FIG. 44 (FIG. 44).

Figure 45:
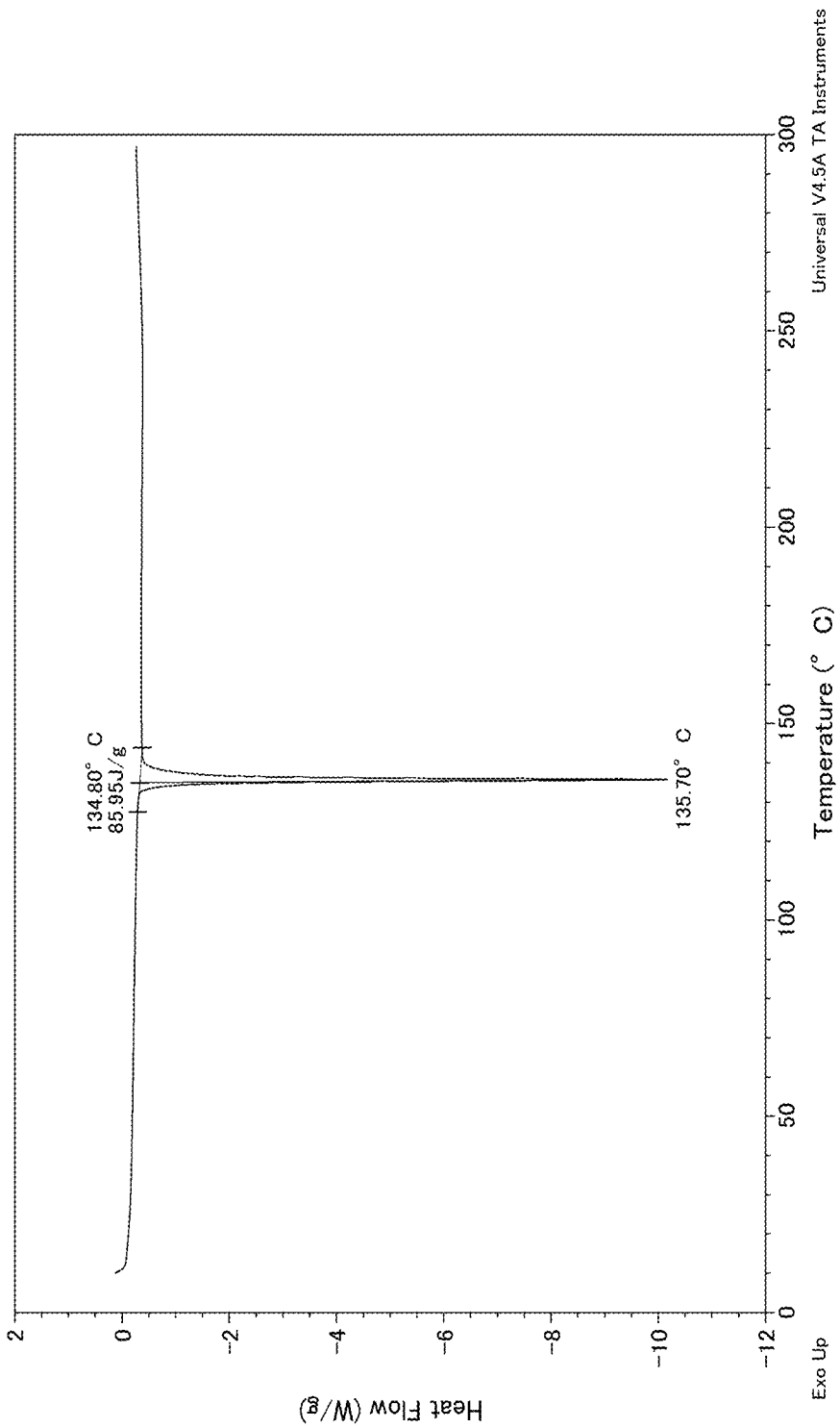
FIG. 45 shows a DSC thermogram of Compound 1 Besylate.
Figure 46:
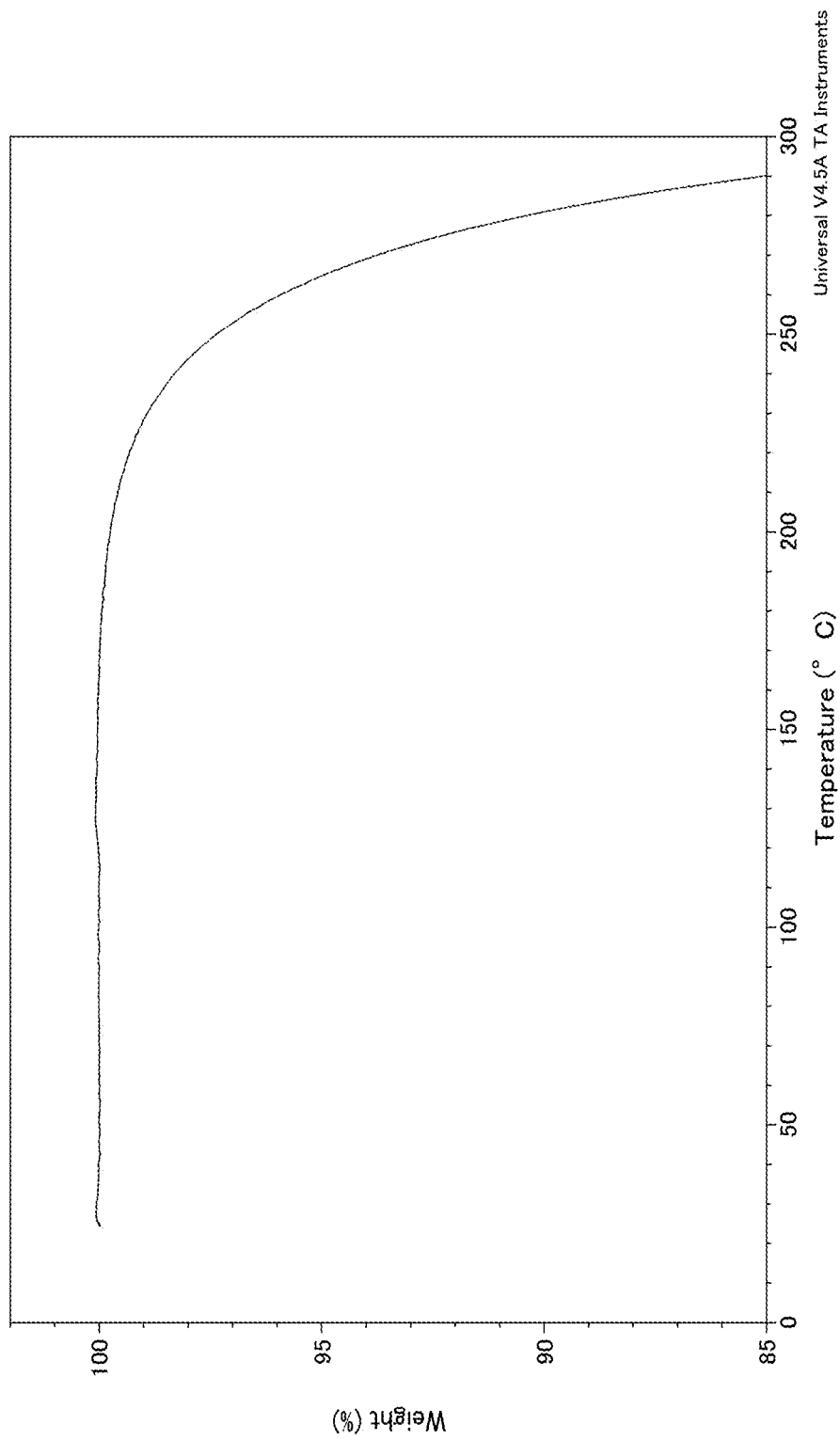
FIG. 46 shows a TGA thermogram of Compound 1 Besylate.
Figure 47:
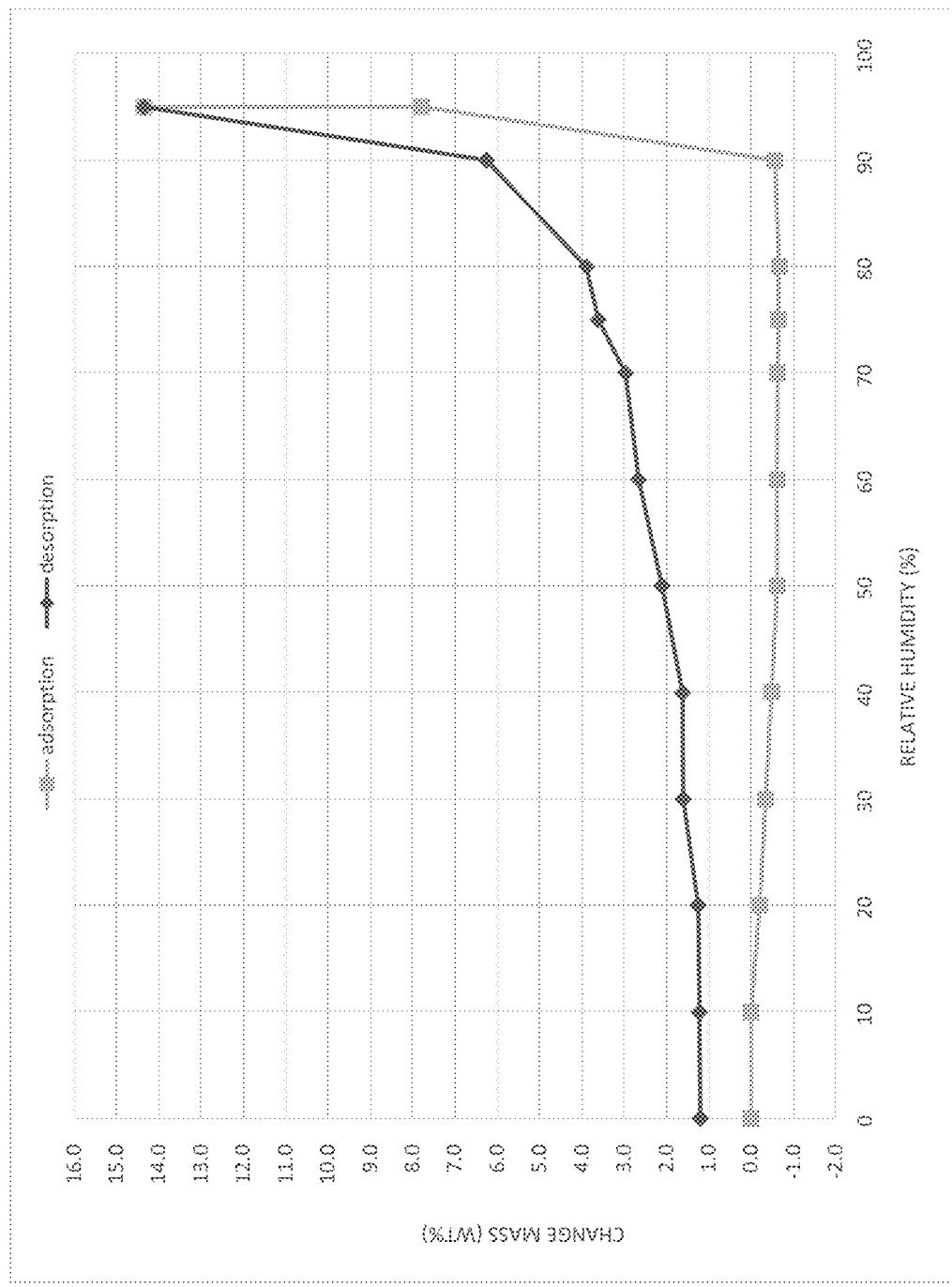
FIG. 47 shows a DVS isotherm of Compound 1 Besylate.

In some embodiments, Compound 1 Besylate has an endotherm peak at a temperature of about 136° C. In some embodiments, Compound 1 Besylate has a DSC thermogram substantially as depicted in FIG. 45 (FIG. 45). In some embodiments, Compound 1 Besylate has a TGA thermogram substantially as depicted in FIG. 46 (FIG. 46). In some embodiments, Compound 1 Besylate has a DVS isotherm substantially as depicted in FIG. 47 (FIG. 47).

In some embodiments, Compound 1 Besylate has at least one characteristic XRPD peak in terms of 2θ selected from 6.0°±0.2°, 12.0°±0.2°, and 24.1°±0.2°; and an endotherm peak at a temperature of about 136° C. In some embodiments, Compound 1 Besylate has at least one characteristic XRPD peak in terms of 2θ selected from 6.0°±0.2°, 12.0°±0.2°, and 24.1°±0.2°; and a DSC thermogram substantially as depicted in FIG. 45 (FIG. 45). In some embodiments, Compound 1 Besylate has at least one characteristic XRPD peak in terms of 2θ selected from 6.0°±0.2°, 12.0°±0.2°, and 24.1°±0.2°; and a DVS isotherm substantially as depicted in FIG. 47 (FIG. 47).

In some embodiments, Compound 1 Besylate can be isolated with a crystalline purity of at least about 80%, about 85%, about 90%, about 95%, about 96%, about 97%, about 98%, or about 99%. In some embodiments, Compound 1 Besylate can be isolated with a crystalline purity greater than about 99%. In some embodiments, Compound 1 Besylate can be isolated with a crystalline purity greater than about 99.9%.

In some embodiments, provided is Compound 1 Besylate prepared by isolating Compound 1 Besylate from a mixture of Compound 1, benzenesulfonic acid, and S1, wherein S1 is a solvent. In some embodiments, S1 is an organic solvent. In some embodiments, S1 is $C_{1-6}$ alkyl alcohol. In some embodiments, S1 is ether. In some embodiments, S1 is $C_{1-6}$ alkyl acetate. In some embodiments, S1 is a $C_{1-6}$ alkyl ketone. In some embodiments, S1 is a mixture of organic solvents. In some embodiments, S1 is a mixture of a $C_{1-6}$ alkyl alcohol and a $C_{1-6}$ alkyl ketone. In some embodiments, S1 is ethyl acetate. In some embodiments, S1 is THF. In some embodiments, S1 is a mixture of methanol and acetone.

Compound 1 Tosylate

In some embodiments, provided is (R)-1-(8-fluoroisochroman-1-yl)-N-methylmethanamine tosylate (Compound 1 Tosylate).

In some embodiments, provided is Compound 1 Tosylate prepared by isolating Compound 1 Tosylate from a mixture of Compound 1, p-toluenesulfonic acid, and S1, wherein S1 is a solvent. In some embodiments, S1 is an organic solvent. In some embodiments, S1 is $C_{1-6}$ alkyl alcohol. In some embodiments, S1 is ether. In some embodiments, S1 is $C_{1-6}$ alkyl acetate. In some embodiments, S1 is a $C_{1-6}$ alkyl ketone. In some embodiments, S1 is a mixture of organic solvents. In some embodiments, S1 is a mixture of a $C_{1-6}$ alkyl alcohol and a $C_{1-6}$ alkyl ketone. In some embodiments, S1 is methanol. In some embodiments, S1 is THF. In some embodiments, S1 is ethyl acetate. In some embodiments, S1 is a mixture of methanol and acetone.

Process for Preparation of Compound 1 and Compound 1 Phosphate

Provided herein are also processes for preparing Compound 1 or a salt thereof. A process of preparing Compound 1 is described in U.S. Pat. No. 10,196,403, the entirety of which is incorporated herein by reference. The processes for preparing Compound 1 or a salt thereof provided herein have certain advantages over the processes currently disclosed in the art. For example, the processes described herein demonstrate good scalability, yields, and stereochemical selectivity. The processes described herein include a chiral resolution by crystallization, which avoids chiral separation by HPLC, and is therefore more amenable for manufacture on a multi-kilogram scale.

Provided herein is a process of preparing (R)-1-(8-fluoroisochroman-1-yl)-N-methylmethanamine phosphate (Compound 1 Phosphate), having the structure:

Compound 1 Phospate wherein the process comprises:
(a) reacting a compound of Formula III having the structure:

Formula III or a salt thereof, wherein X is halo, with N-methylaminoacetaldehyde dimethylacetal (Compound 4) having the structure:

Compound 4 in the presence of A1, wherein A1 is an acid, to provide a compound of Formula II, having the structure:

Formula II or a salt thereof, wherein X is halo;
(b) hydrogenating a compound of Formula II, or a salt thereof, in the presence of a metal catalyst to provide 1-(8-fluoroisochroman-1-yl)-N-methylmethanamine (Racemic Compound 1) having the structure:

Racemic Compound 1

(c) reacting Racemic Compound 1 with dibenzoyl-L-tartaric acid in the presence of S3, wherein S3 is a solvent, to provide (R)-1-(8-fluoroisochroman-1-yl)-N-methylmethanamine dibenzoyl-L-tartrate (Compound 1 dibenzoyl-L-tartate) having the structure:

Compound 1

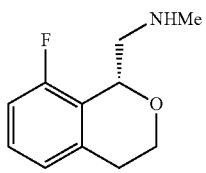 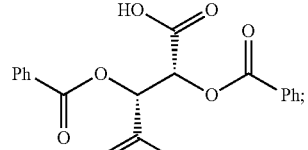

dibenzoyl-L-tartate (d) reacting Compound 1 dibenzoyl-L-tartrate with B1, wherein B1 is a base, to provide Compound 1 having the structure:

Compound 1

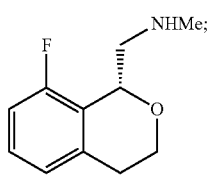

and (e) reacting Compound 1 with phosphoric acid to provide Compound 1 Phosphate.

Provided herein is a process of preparing Compound 1 having the structure:

Compound 1

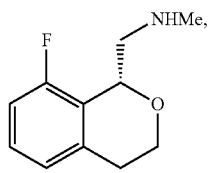

wherein the process comprises:

(a) reacting a compound of Formula III having the structure:

Formula III

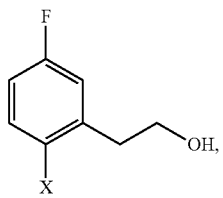

or a salt thereof, wherein X is halo, with N-methylaminoacetaldehyde dimethylacetal (Compound 4) having the structure:

Compound 4

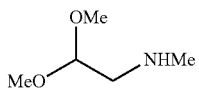

in the presence of A1, wherein A1 is an acid, to provide a compound of Formula II, having the structure:

Formula II

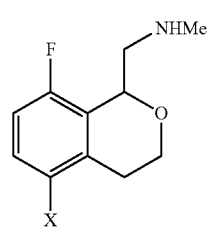

or a salt thereof, wherein X is halo;

(b) hydrogenating a compound of Formula II, or a salt thereof, in the presence of a metal catalyst to provide 1-(8-fluoroisochroman-1-yl)-N-methylmethanamine (Racemic Compound 1) having the structure:

Racemic Compound 1

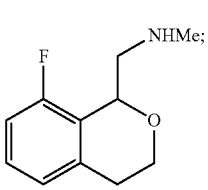

(c) reacting Racemic Compound 1 with dibenzoyl-L-tartaric acid in the presence of S3, wherein S3 is a solvent, to provide (R)-1-(8-fluoroisochroman-1-yl)-N-methylmethanamine dibenzoyl-L-tartrate (Compound 1 dibenzoyl-L-tartrate) having the structure:

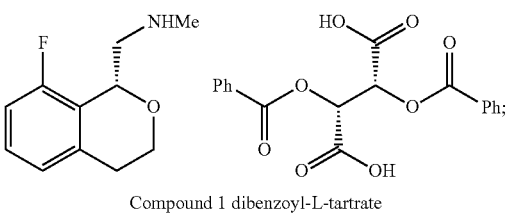 [SMILES: CNC[C@@H]1OCCc2cccc(F)c21 ; O=C(O[C@@H](C(=O)O)[C@@H](OC(=O)c1ccccc1)C(=O)O)c1ccccc1]

Compound 1 dibenzoyl-L-tartrate and (d) reacting Compound 1 dibenzoyl-L-tartrate with B1, wherein B1 is a base, to provide Compound 1.

In some embodiments, provided is a process of preparing Compound 1, wherein the process comprises:

(a) hydrogenating a compound of Formula II, or a salt thereof, in the presence of a metal catalyst to provide Racemic Compound 1;

(b) reacting Racemic Compound 1 with dibenzoyl-L-tartaric acid in the presence of S3, wherein S3 is a solvent, to provide Compound 1 dibenzoyl-L-tartrate; and (c) reacting Compound 1 dibenzoyl-L-tartrate with B1, wherein B1 is a base, to provide Compound 1.

In some embodiments, provided is a process of preparing Compound 1, wherein the process comprises:

(a) reacting Racemic Compound 1 with dibenzoyl-L-tartaric acid in the presence of S3, wherein S3 is a solvent, to provide Compound 1 dibenzoyl-L-tartrate; and (c) reacting Compound 1 dibenzoyl-L-tartrate with B1, wherein B1 is a base, to provide Compound 1.

Provided herein is a process of preparing (R)-1-(8-fluoroisochroman-1-yl)-N-methylmethanamine phosphate (Compound 1 Phosphate), having the structure:

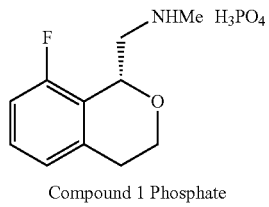

Compound 1 Phosphate comprising reacting (R)-1-(8-fluoroisochroman-1-yl)-N-methylmethanamine (Compound 1) having the structure:

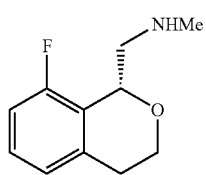

Compound 1 with phosphoric acid. In some embodiments, Compound 1 phosphate is crystalline.

In some embodiments, the phosphoric acid is an aqueous solution of phosphoric acid. In some embodiments, the aqueous solution of phosphoric acid is about 80% to about 95% aqueous solution of phosphoric acid by weight. In some embodiments, the aqueous solution of phosphoric acid is about 87% aqueous solution of phosphoric acid by weight.

In some embodiments, the reacting of Compound 1 with phosphoric acid is carried out in the presence of S1a, wherein S1a is a solvent. In some embodiments, S1a is a polar aprotic solvent, water, or a mixture thereof. In some embodiments, the polar aprotic solvent of S1 is acetonitrile. In some embodiments, S1a is a mixture of acetonitrile and water.

In some embodiments, the reacting of Compound 1 with phosphoric acid is carried out at a temperature between about 15° C. and about 25° C. In some embodiments, the reacting of Compound 1 with phosphoric acid is carried out at about 20° C. In some embodiments, between about 1 and about 5 molar equivalents of phosphoric acid are used per molar equivalent of Compound 1. In some embodiments, about 1 molar equivalent of phosphoric acid is used per molar equivalent of Compound 1.

Compound 1 can be prepared by a process comprising reacting (R)-1-(8-fluoroisochroman-1-yl)-N-methylmethanamine dibenzoyl-L-tartrate (Compound 1 dibenzoyl-L-tartrate) having the structure:

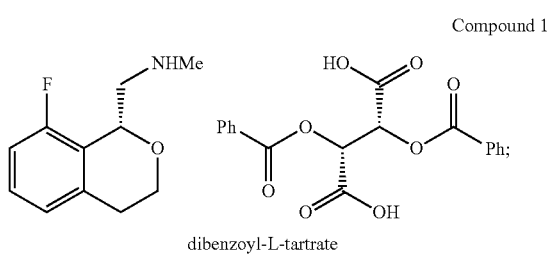 [SMILES: CNC[C@@H]1OCCc2cccc(F)c21 ; O=C(O[C@@H](C(=O)O)[C@@H](OC(=O)c1ccccc1)C(=O)O)c1ccccc1]

dibenzoyl-L-tartrate with B1, wherein B1 is a base.

In some embodiments, B1 is an alkali hydroxide base. In some embodiments, B1 is potassium hydroxide. In some embodiments, B1 is an aqueous solution of potassium hydroxide. In some embodiments, the aqueous solution of potassium hydroxide is about 10% to about 20% aqueous solution of potassium hydroxide by weight. In some embodiments, the aqueous solution of potassium hydroxide is about 14% aqueous solution of potassium hydroxide by weight.

In some embodiments, the reacting of Compound 1 dibenzoyl-L-tartrate and the base is carried out in the presence of S2, wherein S2 is a solvent. In some embodiments, S2 is a polar aprotic solvent. In some embodiments, the polar aprotic solvent is an ether. In some embodiments, S2 is tert-butyl methyl ether.

In some embodiments, the reacting of Compound 1 dibenzoyl-L-tartrate and B1 is carried out at a temperature between about 20° C. and about 30° C. In some embodiments, the reacting of Compound 1 dibenzoyl-L-tartrate and the base is carried out at a temperature of about 23° C. In some embodiments, between about 0.5 and about 5 molar equivalents of B1 are used per molar equivalent of Compound 1 dibenzoyl-L-tartrate. In some embodiments, between about 1 and about 3 molar equivalents of B1 are used per molar equivalent of Compound 1 dibenzoyl-L-tartrate. In some embodiments, between about 1 and about 2 molar equivalents of B1 are used per molar equivalent of Compound 1 dibenzoyl-L-tartrate. In some embodiments, about 1 molar equivalent of B1 is used per molar equivalent of Compound 1 dibenzoyl-L-tartrate.

In some embodiments, the reacting of Compound 1 dibenzoyl-L-tartrate with B1 is further carried out in the presence of sodium chloride. In some embodiments, about 1 to about 10 molar equivalents of sodium chloride are used per molar equivalent of Compound 1 dibenzoyl-L-tartrate. In some embodiments, about 5 molar equivalents of sodium chloride are used per molar equivalent of Compound 1 dibenzoyl-L-tartrate.

(R)-1-(8-fluoroisochroman-1-yl)-N-methylmethanamine dibenzoyl-L-tartrate (Compound 1 dibenzoyl-L-tartrate) can be prepared by a process comprising reacting 1-(8-fluoroisochroman-1-yl)-N-methylmethanamine (Racemic Compound 1) having the structure:

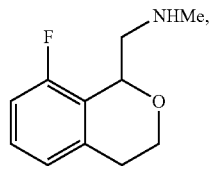 [SMILES: CNCC1OCCc2cccc(F)c21]

with dibenzoyl-L-tartaric acid, in the presence of S3, wherein S3 is a solvent.

In some embodiments, S3 is a polar protic solvent. In some embodiments, S3 is $C_{1-6}$ alkyl-OH. In some embodiments, S3 is methanol. In some embodiments, S3 is a mixture of methanol and water. In some embodiments, the reacting is carried out at a temperature from about 20° C. to about 70° C. In some embodiments, the precipitating is carried out at a temperature of about 20° C. In some embodiments, about 1 to about 5 molar equivalents of dibenzoyl-L-tartaric acid are used per molar equivalent of Racemic Compound 1. In some embodiments, about 1 molar equivalent of dibenzoyl-L-tartaric acid is used per molar equivalent of Racemic Compound 1.

The process of preparing Compound 1 dibenzoyl L-tartrate can further comprise precipitating Compound 1 dibenzoyl-L-tartrate from a mixture comprising: Racemic Compound 1, dibenzoyl-L-tartaric acid, and S3. In some embodiments, S3 is methanol. In some embodiments, S3 is a mixture of methanol and water.

The process of preparing Compound 1 dibenzoyl L-tartrate can further comprise isolating Compound 1 dibenzoyl-L-tartrate from S3a, wherein S3a is a solvent. In some embodiments, S3a is polar protic solvent. In some embodiments, S3a is $C_{1-6}$ alkyl-OH. In some embodiments, S3a is methanol. In some embodiments, the isolating of Compound 1 dibenzoyl-L-tartrate is carried out at a temperature of about 10° C. to about 65° C.

1-(8-fluoroisochroman-1-yl)-N-methylmethanamine (Racemic Compound 1) can be prepared by a process comprising hydrogenating a compound of Formula II, having the structure:

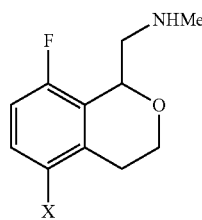

or a salt thereof, wherein X is halo, in the presence of a metal catalyst.

In some embodiments, the compound of Formula II is Compound 2 is 1-(5-bromo-8-fluoroisochroman-1-yl)-N-methylmethanamine trifluoromethanesulfonate (Compound 2) having the structure:

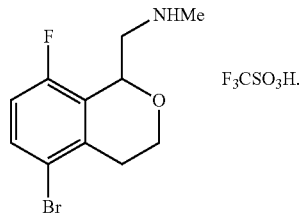 [SMILES: CNCC1OCCc2c(Br)ccc(F)c21 ; "F3CSO3H."]

In some embodiments, the metal catalyst is palladium on activated carbon. In some embodiments, the hydrogenating of a compound of Formula II is carried out at a hydrogen pressure of about 2 to about 10 bar. In some embodiments, the hydrogenating of a compound of Formula II is carried out at a hydrogen pressure of about 5 bar.

In some embodiments, the hydrogenating of a compound of Formula II is carried out at a temperature between about 20° C. and about 30° C. In some embodiments, the hydrogenating of a compound of Formula II is carried out at a temperature of about 25° C.

In some embodiments, the hydrogenating of a compound of Formula II is carried out in the presence of S4, wherein S4 is a solvent. In some embodiments, S4 is a polar protic solvent, In some embodiments, S4 is $C_{1-6}$ alkyl-OH. In some embodiments, S4 is methanol.

In some embodiments, the hydrogenating of a compound of Formula II is carried out in the presence of B2, wherein B2 is a base. In some embodiments, B2 is a carbonate base. In some embodiments, B2 is potassium carbonate. In some embodiments, B2 is an aqueous solution of potassium carbonate. In some embodiments, the aqueous solution of potassium carbonate is about 5% potassium carbonate by weight.

The compound of Formula II can be prepared by reacting a compound of Formula III having the structure:

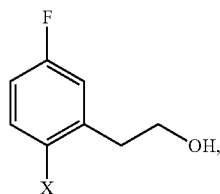

or a salt thereof, wherein X is halo,
with N-methylaminoacetaldehyde dimethylacetal (Compound 4) having the structure:

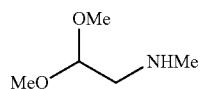

in the presence of A1, wherein A1 is an acid.

In some embodiments, the compound of Formula III is 2-(2-bromo-5-fluorophenyl)ethan-1-ol (Compound 3) having the structure:

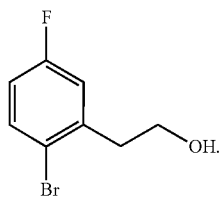

In some embodiments, A1 is trifluoromethanesulfonic acid. In some embodiments, the reacting of the compound of Formula III and Compound 4 is carried out in the presence of S5, wherein S5 is a solvent. In some embodiments, S5 is a halogenated solvent. In some embodiments, S5 is dichloromethane.

In some embodiments, the reacting of the compound of Formula III and Compound 4 is carried out a temperature between about 0° C. and about 35° C. In some embodiments, the reacting of the compound of Formula III and Compound 4 is carried out a temperature of about 30° C. In some embodiments, about 1.2 molar equivalents of Compound 4 are used per molar equivalent of the compound of Formula III. In some embodiments, about 4 molar equivalents of A1 are used per molar equivalent of the compound of Formula III.

It is appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

The reactions of the processes described herein can be carried out in air or under an inert atmosphere. Typically, reactions containing reagents or products that are substantially reactive with air can be carried out using air-sensitive synthetic techniques that are well known to the skilled artisan.

The processes described herein can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), or mass spectrometry; or by chromatography such as high performance liquid chromatography (HPLC) or thin layer chromatography. The compounds obtained by the reactions can be purified by any suitable method known in the art. For example, chromatography (medium pressure) on a suitable adsorbent (e.g., silica gel, alumina and the like), HPLC, or preparative thin layer chromatography; distillation; sublimation; trituration, or recrystallization. The purity of the compounds, in general, are determined by physical methods such as measuring the melting point (in case of a solid), obtaining a NMR spectrum, or performing a HPLC separation. If the melting point decreases, if unwanted signals in the NMR spectrum are decreased, or if extraneous peaks in an HPLC trace are removed, the compound can be said to have been purified. In some embodiments, the compounds are substantially purified.

Method of Use

In some embodiments, the disclosure provides a method for treating a neurological or psychiatric disease or disorder in a subject, comprising administering to the subject an effective amount of a compound of this disclosure (or its pharmaceutically acceptable salt), or composition comprising a compound of this disclosure (or its pharmaceutically acceptable salt). Neurological and/or psychiatric diseases and disorders can exhibit a variety of psychiatric and behavioral symptoms, including apathy, depression, anxiety, cognitive impairment, psychosis, aggression, agitation, poor impulse control and sleep disruptions.

In one embodiment, the neurological or psychiatric disease or disorder is bipolar disorder, anxiety, depression, Alzheimer's disease with agitation, Alzheimer's disease with aggression, Alzheimer's disease agitation or Alzheimer's disease with agitation aggression.

In one embodiment, the neurological or psychiatric disease or disorder is bipolar disorder, anxiety, depression, dementia, Alzheimer's disease, Alzheimer's disease with agitation, Alzheimer's disease with aggression, Alzheimer's disease agitation or Alzheimer's disease with agitation aggression, a neurocognitive disorder, a neurocognitive disorder with behavioral and psychological symptoms.

In one embodiment, the neurological or psychiatric disease or disorder are behavioral and psychological symptoms of a neurocognitive disorder including dementia and Alzheimer's disease. The behavioral and psychological symptoms include disturbances in perception, thought content, mood, or behaviors including delusions (distressing beliefs), hallucinations, psychoses, agitation (easily upset, repeating questions, arguing or complaining, hoarding, pacing, inappropriate screaming, crying out, disruptive sounds, rejection of care leaving home), aggression (physical or verbal), depression or dysphoria, anxiety (worrying, shadowing), apathy or indifference, disinhibition (socially inappropriate behavior, sexually inappropriate behavior, irritability or lability, motor disturbance (repetitive activities without purpose, wandering, rummaging, night-time behaviors (waking and getting up at night) impulsivity, attentional deficits, executive dysfunction.

Assays were used herein to identify representative candidate treatments. Examples of candidate treatments include, without limitation, treatment of Alzheimer's disease with agitation, Alzheimer's disease with aggression, Alzheimer's disease agitation and Alzheimer's disease with agitation aggression. Aggression and agitation are common symptoms in neurological and psychiatric diseases and disorders. Aggression and agitation have been associated with hyperactivity in subcortical brain regions, which can be modelled in animals using psychostimulants (e.g., PCP, Amphetamine). For example, psychostimulants induce hyperlocomotor activity (HLA) in animals. Antipsychotics (e.g., haloperidol, clozapine and risperidone) have been shown to reduce psychostimulant-induced HLA and are efficacious against agitation in Alzheimer's disease. Other drugs used off-label, or are currently under study in clinical trials, for agitation in Alzheimer's disease are mood stabilizers, such as lithium (which also decreases Amphetamine-induced HLA), and antidepressants (e.g., citalopram). Antidepressants demonstrate activity in assays such as the forced swim and tail suspension tests. Therefore, the aforementioned assays were helpful in identifying candidate treatments for agitation in Alzheimer's disease and agitation/aggression in other neurological and psychiatric diseases and disorders.

In one embodiment, provided is a method of treating a bipolar disorder in a subject in need thereof, comprising the step of administering to said subject an effective amount of the compound according to formula I or a pharmaceutically acceptable salt thereof.

In one embodiment, provided is a method of treating anxiety in a subject in need thereof, comprising the step of administering to said subject an effective amount of the compound according to formula I or a pharmaceutically acceptable salt thereof.

In some embodiments, the neurological or psychiatric disease or disorder is selected from a psychosis, including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (e.g., phencyclidine, ketamine and other dissociative anesthetics, amphetamine and other psychostimulants and cocaine) psychosis, psychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both positive, negative, and cognitive symptoms of schizophrenia and other psychoses; cognitive disorders including dementia (semantic dementia, frontotemporal dementia, dementia with depressive features, persisting, subcortical dementia, dementia with Lewy Bodies, Parkinsonism-ALS Dementia Complex, and dementia associated with Alzheimer's disease, ischemia, multi-infarct dementia, trauma, vascular problems, stroke, HIV disease, Parkinson's disease, Huntington's disease, Down syndrome, Pick's disease, Creutzfeldt-Jacob disease, perinatal hypoxia, or substance abuse), delirium, amnestic disorders or age related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); eating disorders such as obesity, bulimia nervosa, pica and compulsive eating disorders; bipolar disorders, including bipolar I disorder, bipolar II disorder, cyclothymic disorder, substance/medication-induced bipolar and related disorders, bipolar and related disorder due to another medical condition, other specified bipolar and related disorder, and unspecified bipolar and related disorders, depressive disorders including unipolar depression, seasonal depression and post-partum depression, atypical depression, catatonic depression, elderly depression, endogenous depression, melancholic depression, perinatal depression, situational depression, chronic depression, premenstrual syndrome (PMS) and premenstrual dysphoric disorder (PDD), mood disorders due to a general medical condition, and substance-induced mood disorders; attention, learning and development disorders such as pervasive developmental disorder including autistic disorder, attention disorders including attention-deficit hyperactivity disorder (ADHD) and conduct disorder, disorders such as autism and autism spectrum disorders (including Asperger's syndrome, pervasive developmental disorder, Rett Syndrome and Fragile X Syndrome), depression, benign forgetfulness, childhood learning disorders, specific learning disorders, intellectual development disorders, and closed head injury; movement disorders and symptoms, including tremors, dyskinesia, dystonia, tics, dysphonia, ataxia, myoclonus, Essential Tremor, Tardive Dyskinesia, Restless Leg Syndrome, Tourette Syndrome, Multiple System Atrophy, Multiple Sclerosis, Huntington's Disease, Parkinson's Disease and Atypical Parkinsonisms; epilepsy; urinary incontinence; neuronal damage including ocular damage, retinopathy or macular degeneration of the eye, tinnitus, hearing impairment and loss, and brain edema; emesis; and sleep disorders including insomnia, disturbed sleep, jet lag, hypersomnia, cataplexy, sleep apnea, obstructive sleep apnea, REM sleep behavior disorder, Restless Leg Syndrome, periodic limb movement disorder, circadian rhythm sleep disorders, delayed sleep phase disorder, sleepwalking, night terrors, bed wetting, rapid eye movement sleep behavior disorder, shift work sleep disorder, excessive daytime sleepiness, non-24-hour sleep-wake disorder, sleep paralysis and narcolepsy.

In some embodiments, the neurological or psychiatric disease or disorder is Alzheimer's disease, Parkinson's disease, depression, cognitive impairment, stroke, schizophrenia, Down syndrome, or Fetal Alcohol Syndrome. In some embodiments, the neurological or psychiatric disorder is Alzheimer's disease. In some embodiments, the neurological or psychiatric disorder is Parkinson's disease. In some embodiments, the neurological or psychiatric disorder is depression. In some embodiments, the neurological or psychiatric disorder is cognitive impairment. In some embodiments, the cognitive impairment is cognitive dysfunction associated with depression, for example, major depressive disorder. In some embodiments, the neurological or psychiatric disorder is stroke. In some embodiments, the neurological or psychiatric disorder is schizophrenia. In some embodiments, the neurological or psychiatric disorder is Down syndrome. In some embodiments, the neurological or psychiatric disorder is Fetal Alcohol Syndrome.

In some embodiments, the neurological or psychiatric disease or disorder is bipolar disorder. Bipolar disorders (including both bipolar I and bipolar II) are serious psychiatric disorders that have a prevalence of approximately 2% of the population, and affects both genders alike. It is a relapsing-remitting condition characterized by cycling between elevated (i.e., manic) and depressed moods, which distinguishes it from other disorders such as major depressive disorder and schizophrenia. Bipolar I is defined by the occurrence of a full manic episode, although most individuals experience significant depression. Symptoms of mania include elevated or irritable mood, hyperactivity, grandiosity, decreased need for sleep, racing thoughts and in some cases, psychosis. The depressive episodes are characterized by anhedonia, sad mood, hopelessness, poor self-esteem, diminished concentration and lethargy. Bipolar II is defined as the occurrence of a major depressive episode and hypomanic (less severe mania) episode although subjects spend considerably more time in the depressive state. Other related conditions include cyclothymic disorder.

In some embodiments, the neurological or psychiatric disease or disorder is schizophrenia. Schizophrenia is a disorder of unknown origin, which usually appears for the first time in early adulthood and is marked by characteristics such as psychotic symptoms, phasic progression and development, and/or deterioration in social behavior and professional capability. Characteristic psychotic symptoms are disorders of thought content (e.g., multiple, fragmentary, incoherent, implausible or simply delusional contents, or ideas of persecution) and of mentality (e.g., loss of association, flight of imagination, incoherence up to incomprehensibility), as well as disorders of perceptibility (e.g., hallucinations), emotions (e.g., superficial or inadequate emotions), self-perceptions, intentions, impulses, and/or inter-human relationships, and psychomotoric disorders (e.g., catatonia). Other symptoms are also associated with this disorder. Schizophrenia is classified into subgroups: the paranoid type, characterized by delusions and hallucinations and absence of thought disorder, disorganized behavior, and affective flattening; the disorganized type, also named "hebephrenic schizophrenia," in which thought disorder and flat affect are present together; the catatonic type, in which prominent psychomotor disturbances are evident, and symptoms may include catatonic stupor and waxy flexibility; and the undifferentiated type, in which psychotic symptoms are present but the criteria for paranoid, disorganized, or catatonic types have not been met. The symptoms of schizophrenia normally manifest themselves in three broad categories: positive, negative and cognitive symptoms. Positive symptoms are those which represent an "excess" of normal experiences, such as hallucinations and delusions. Negative symptoms are those where the subject suffers from a lack of normal experiences, such as anhedonia and lack of social interaction. The cognitive symptoms relate to cognitive impairment in schizophrenics, such as lack of sustained attention and deficits in decision making.

In some embodiments, the neurological or psychiatric disease or disorder is anxiety disorder. Anxiety disorders are characterized by fear, worry, and uneasiness, usually generalized and unfocused as an overreaction to a situation. Anxiety disorders differ in the situations or types of objects that induce fear, anxiety, or avoidance behavior, and the associated cognitive ideation. Anxiety differs from fear in that anxiety is an emotional response to a perceived future threat while fear is associated with a perceived or real immediate threat. They also differ in the content of the associated thoughts or beliefs. Examples of anxiety disorders include separation anxiety disorder, selective mutism, specific phobia, social anxiety disorder (social phobia), panic disorder, panic attack specifier, agoraphobia, generalized anxiety disorder, substance/medication-induced anxiety disorder, anxiety disorder due to another medical condition, illness anxiety disorder, social (pragmatic) communication disorder, other specified anxiety disorder, and unspecified anxiety disorder; stressor-related disorders, including reactive attachment disorder, disinhibited social engagement disorder, posttraumatic stress disorder (PTSD), acute stress disorder, and adjustment disorders.

Cognitive impairment includes a decline in cognitive functions or cognitive domains, e.g., working memory, attention and vigilance, verbal learning and memory, visual learning and memory, reasoning and problem solving (e.g., executive function, speed of processing and/or social cognition). In particular, cognitive impairment may indicate deficits in attention, disorganized thinking, slow thinking, difficulty in understanding, poor concentration, impairment of problem solving, poor memory, difficulties in expressing thoughts, and/or difficulties in integrating thoughts, feelings and behavior, or difficulties in extinction of irrelevant thoughts.

In some embodiments, the neurological or psychiatric disease or disorder involves a deficit in cognition (cognitive domains as defined by the DSM-5 are: complex attention, executive function, learning and memory, language, perceptual-motor, social cognition). In some embodiments, the neurological or psychiatric disorder is associated with a deficit in dopamine signaling. In some embodiments, the neurological or psychiatric disorder is associated with basal ganglia dysfunction. In some embodiments, the neurological or psychiatric disorder is associated with dysregulated locomotor activity. In some embodiments, the neurological or psychiatric disorder is associated with impairment of prefrontal cortex functioning.

In some embodiments, the present disclosure provides a method of treating one or more symptoms of a neurological and/or psychiatric disease or disorder provided herein. Such diseases or disorders include mood disorders, including bipolar I disorder, bipolar II disorder, mania, cyclothymic disorder, substance/medication-induced bipolar and related disorders, bipolar and related disorder due to another medical condition, other specified bipolar and related disorder, and unspecified bipolar and related disorders; psychotic disorders, including schizophrenia, schizophrenia spectrum disorder, acute schizophrenia, chronic schizophrenia, NOS schizophrenia, schizoid personality disorder, schizotypal personality disorder, delusional disorder, psychosis, psychotic disorder, brief psychotic disorder, shared psychotic disorder, psychotic disorder due to a general medical condition, drug-induced psychosis (e.g., cocaine, alcohol, amphetamine), schizoaffective disorder, agitation, aggression, delirium, catalepsy, catatonia, dissociative identity disorder, paranoid personality disorder, psychotic depression, Schizotypical Personality Disorder, Childhood Disintegrative Disorder (Heller's Syndrome), Disintegrative Psychosis, Dissociative Amnesia, Somatic Symptom Disorder, Parkinson's psychosis, excitative psychosis, Tourette's syndrome, and organic or NOS psychosis; depressive disorders, including disruptive mood dysregulation disorder, major depressive disorder (MDD) (including major depressive episode), dysthymia, persistent depressive disorder (dysthymia), treatment resistant depression, premenstrual dysphoric disorder, substance/medication-induced depressive disorder, depressive disorder due to another medical condition, other specified depressive disorder, and unspecified depressive disorder; anxiety disorders; and other disorders including substance abuse or dependency (e.g., nicotine, alcohol, cocaine), addiction, internet gaming disorder, eating disorders, behavior disorder, seizure, vertigo, epilepsy, agitation, aggression, neurodegenerative disease, Alzheimer's disease, Parkinson's disease, dyskinesias, Huntington's disease, dementia, premenstrual dysphoria, attention deficit disorder (ADD) and attention deficit hyperactivity disorder (ADHD)), hyperkinetic syndrome, autism, autism spectrum disorder, obsessive-compulsive disorder, pain, fibromyalgia, migraine, cognitive impairment, movement disorder, restless leg syndrome (RLS), multiple sclerosis, Primary Progressive Multiple Sclerosis, Parkinson's disease, Huntington's disease, dyskinesias multiple sclerosis, sleep disorder, sleep apnea, narcolepsy, excessive daytime sleepiness, jet lag, drowsy side effect of medications, insomnia, sexual dysfunction, hypertension, emesis, Lesche-Nyhane disease, Wilson's disease, Rett syndrome, and Huntington's chorea. In some embodiments, the neurological and/or psychiatric disorders include agitation and aggression.

In some embodiments, the agitation and aggression are associated with Alzheimer's disease, Parkinson's disease, and/or autism.

In some embodiments, the agitation is associated with psychiatric disorders such as depression and schizophrenia.

In some embodiments, the neurological and/or psychiatric disease or disorders are obsessive-compulsive disorder and related disorders (e.g., body dysmorphic disorder, hoarding disorder, trichotillomania, excoriation disorder).

In some embodiments, the neurological and/or psychiatric diseases or disorders are disruptive, impulse-control, and conduct disorders including oppositional defiant disorder, intermittent explosive disorder, conduct disorder, antisocial personality disorder, pyromania, kleptomania, other specified disruptive, impulse-control, and conduct disorder, unspecified disruptive, impulse-control, and conduct disorder.

Depressive disorders include major depressive disorder and dysthymia, and are associated with depressed mood (sadness), poor concentration, insomnia, fatigue, appetite disturbances, excessive guilt and thoughts of suicide.

In some embodiments, the present disclosure provides a method of treating one or more symptoms including depression (e.g., major depressive disorder or dysthymia); bipolar disorder, seasonal affective disorder; cognitive deficit; sleep related disorder (e.g., sleep apnea, insomnia, narcolepsy, cataplexy) including those sleep disorders which are produced by psychiatric conditions; chronic fatigue syndrome; anxieties (e.g., general anxiety disorder, social anxiety disorder, panic disorder); obsessive compulsive disorder; postmenopausal vasomotor symptoms (e.g., hot flashes, night sweats); neurodegenerative disease (e.g., Parkinson's disease, Alzheimer's disease, amyotrophic lateral sclerosis, primary lateral sclerosis, progressive muscular atrophy, progressive bulbar (atrophy) palsy, pseudobulbar palsy spinal muscular atrophy diseases (e.g., SMA type I, also called Werdnig-Hoffmann disease, SMA type II, SMA type III, also called Kugelberg-Welander disease, and Kennedy Disease, also called progressive spinobulbar muscular atrophy), Hallervorden-Spatz disease, Seitelberger disease (Infantile Neuroaxonal Dystrophy), adrenoleukodystrophy, Alexander Disease, autosomal dominant cerebellar ataxia (ADCA), pure autonomic failure (Bradbury-Eggleston Syndrome), CADASIL Syndrome, and neuronal ceroids lipofuscinose disorders such as Batten Disease (Spielmeyer-Vogt-Sjogren)); manic disorder; dysthymic disorder; and obesity.

In some embodiments, a depressive disorder is associated with acute suicidality or suicide ideation. The United States Food and Drug Administration has adopted a "black box" label warning indicating that antidepressants may increase the risk of suicidal thinking and behavior in some children, adolescents and young adults (up to age 24) with a depressive disorder such as MDD. In some embodiments, a provided compound does not increase the risk of suicidal thinking and/or behavior in children, adolescents and/or young adults with a depressive disorder, e.g., with MDD. In some embodiments, the present disclosure provides a method of treating one or more symptoms of a depressive disorder (e.g., MDD) in children, adolescents and/or young adults without increasing the risk of suicidal thinking and/or behavior.

In some embodiments, the present disclosure provides a method of treating one or more symptoms including senile dementia, Early Onset Alzheimer's disease, Alzheimer's type dementia, cognition, memory loss, amnesia/amnestic syndrome, disturbances of consciousness, coma, lowering of attention, speech disorder, agnosia, aphasia, apraxia, Mild Cognitive Impairment (MCI), benign forgetfulness, mild neurocognitive disorder, major neurocognitive disorder, neurocognitive disorder due to disease (e.g., Huntington's Disease, Parkinson's disease, Prion Disease, Traumatic Brain Injury, HIV or AIDS), Binswanger's Disease (subcortical leukoencephalopathy), and Capgras Syndrome.

In some embodiments, the present disclosure provides a method of treating one or more symptoms of pain, e.g., neuropathic pain, sensitization accompanying neuropathic pain, or inflammatory pain. In some embodiments, the pain is neuropathic pain, including post herpetic (or post-shingles) neuralgia, reflex sympathetic dystrophy/causalgia or nerve trauma, phantom limb pain, carpal tunnel syndrome, and peripheral neuropathy (such as diabetic neuropathy or neuropathy arising from chronic alcohol use). In some embodiments, the pain is acute pain, nociceptive pain, arthritis pain, rheumatoid arthritis, osteoarthritis, joint pain, muscoskeletal pain, back pain, dorsalgia, bulging disc, hip pain, visceral pain, headache, tension headache, acute tension headache, chronic tension headache, chronic cluster headache, common migraine, classic migraine, cluster headache, mixed headache, posttraumatic headache, eye strain headache, Short-lasting Unilateral Neuralgiform (SUNCT) headache, SUNCT Syndrome, herpes zoster, acute herpes zoster, shingles, postherpetic neuralgia (shingles), causalgia, central pain, central pain syndrome, chronic back pain, neuralgia, neuropathic pain syndrome, neuropathy, diabetic neuropathy, diabetes-related neuropathy, diabetes-related nerve pain, fibrositis, peripheral neuropathy caused by chemotherapy, peripheral nerve disease, peripheral neuropathy, nerve pain, nerve trauma, sensitization accompanying neuropathic pain, complex regional pain syndrome, compression neuropathy, craniofacial pain, chronic joint pain, chronic knee pain, chronic pain syndrome, cancer pain, trigeminal neuralgia, tic doloreaux, reflex sympathetic causalgia, painful peripheral neuropathy, spinal nerve injury, arachnoiditis, spinal pain, Bernhardt-Roth Syndrome (meralgia parasthetica), carpal tunnel syndrome, cerebrospinal fluid syndrome, Charcot-Marie-tooth disease, hereditary motor and sensory neuropathy, peroneal muscular atrophy, cluster-tic syndrome, coccygeal pain syndromes, compartment syndrome, degenerative disc disease, failed back surgery syndrome, genito-pelvic pain/penetration disorder, gout, inflammatory pain, lumbar radiculopathy, neuroma (painful scar), pain associated with multiple sclerosis, pelvic floor disorders, phantom limb pain, piriformis syndrome, psychogenic pain, radicular pain syndrome, Raeder's syndrome, referred pain, reflex sympathetic dystrophy syndrome, sciatica, sciatica pain, scoliosis, slipped disc, somatic pain, spinal stenosis, stiff-person syndrome/stiff-man syndrome, stump pain, sympathetically maintained pain, tolosa-hunt syndrome, whiplash, or pain associated with Lyme disease.

In some embodiments, the present disclosure provides a method of treating one or more symptoms including obesity; migraine or migraine headache; and sexual dysfunction, in men or women, including without limitation sexual dysfunction caused by psychological and/or physiological factors, erectile dysfunction, premature ejaculation, vaginal dryness, lack of sexual excitement, inability to obtain orgasm, and psycho-sexual dysfunction, including without limitation, inhibited sexual desire, inhibited sexual excitement, inhibited female orgasm, inhibited male orgasm, functional dyspareunia, functional vaginismus, and atypical psychosexual dysfunction.

In some embodiments, the present disclosure provides a method of suppressing rapid eye movement (REM) during both sleep and daytime equivalent.

In some embodiments, the present disclosure provides a method of suppressing or eliminating pathological or excessive REM during the night or daytime equivalent.

In some embodiments, the present disclosure provides a method of treating one or more symptoms including cataplexy (sudden involuntary transient bouts of muscle weakness or paralysis while awake); nighttime sleep disturbance/sleep fragmentation associated with narcolepsy or other conditions; sleep paralysis associated with narcolepsy or other conditions; hypnagogic and hypnapompic hallucinations associated with narcolepsy or other conditions; and excessive daytime sleepiness associated with narcolepsy, sleep apnea or shift work disorder and other medical conditions such as cancer, chronic fatigue syndrome and fibromyalgia.

In some embodiments, the present disclosure provides a method of treating one or more symptoms of movement diseases or disorders, including akinesias, akinetic-rigid syndromes, dyskinesias and dystonias. Examples of akinesias and akinetic-rigid syndromes include Parkinson's disease, drug-induced Parkinsonism, postencephalitic Parkinsonism, secondary Parkinsonism, Parkinson plus syndromes, atypical Parkinsonism, idiopathic Parkinsonism, progressive supranuclear palsy, multiple system atrophy, corticobasal degeneration, Parkinsonism-ALS dementia complex and basal ganglia calcification, medication-induced Parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, muscular spasms and disorders associated with muscular spasticity or weakness including tremors. Examples of dyskinesias include drug (e.g. L-DOPA) induced dyskinesia tremor (such as rest tremor, postural tremor, intention tremor), chorea (such as Sydenham's chorea, Huntington's disease, benign hereditary chorea, neuroacanthocytosis, symptomatic chorea, drug-induced chorea and hemiballism), myoclonus (including generalized myoclonus and focal myoclonus), tics (including simple tics, complex tics and symptomatic tics). Examples of dystonias include generalized dystonia, idiopathic dystonia, drug-induced dystonia, symptomatic dystonia, paroxymal dystonia, focal dystonia, blepharospasm, oromandibular dystonia, spasmodic dysphonia, spasmodic torticollis, axial dystonia, dystonic writer's cramp and hemiplegic dystonia. Other examples of movement diseases or disorders include stereotypic movement disorder, persistent (chronic) motor disorder, medication-Induced movement disorder, psychogenic movement disorders, substance/medication-induced movement disorder, extrapyramidal movement disorders, hyperkinetic movement disorders, hypokinetic movement disorders, alternating hemiplegia, Angelman syndrome, Hallervorden-Spatz Disease, ataxia, dentate cerebellar ataxia, ataxia telangiectasia (Louis-Bar syndrome), Friedreich's Ataxia, hereditary spinal ataxia, hereditary spinal sclerosis, Machado-Joseph Disease, spinocerebellar ataxia, progressive myoclonic ataxia, athetosis, ballismus, blepharospasm (eye twitching), cerebral palsy, tardive dystonia, tardive dyskinesia, idiopathic torsion dystonia, torsion dystonia, focal dystonia, idiopathic familial dystonia, Idiopathic non-familial dystonia, cervical dystonia (spasmodic torticollis), primary dystonia, orofacial dystonia, developmental coordination disorder, bulbospinal muscular atrophy (Kennedy's Disease), Shy-Drager Syndrome, and Stiff-Person (Stiff-Man) Syndrome.

In some embodiments, the present disclosure provides a method of treating one or more symptoms of epilepsy and/or seizures, including abdominal epilepsy, absence seizure, acquired epilepsy, acquired epileptiform aphasia, Aicardi syndrome, Alpers' disease, Alpers-Huttenlocher syndrome, Angelman syndrome, benign focal epilepsy, benign focal epilepsy of childhood, benign intracranial hypertension, benign rolandic epilepsy (BRE), CDKL5 disorder, childhood absence epilepsy, dentate cerebellar ataxia, Doose syndrome, Dravet syndrome, dyscognitive focal seizure, epilepsy with grand mal seizures, epilepsy with myoclonic-absences, epileptic hemiplegia, febrile seizures, focal seizure, frontal lobe epilepsy, generalized tonic-clonic seizures, genetic epilepsy, Glut1 deficiency syndrome, hypothalamic hamartoma, idiopathic epilepsy, idiopathic generalized epilepsy, idiopathic localization-related epilepsies, idiopathic partial epilepsy, idiopathic seizure, juvenile absence epilepsy, juvenile myoclonic epilepsy, Lafora disease, Lafora progressive myoclonus epilepsy, Landau-Kleffner syndrome, Lassueur-Graham-Little syndrome, Lennox syndrome, Lennox-Gastaut syndrome, medically refractory epilepsy, mesial-temporal lobe sclerosis, myoclonic seizure, neonatal epilepsy, occipital lobe epilepsy, Ohtahara syndrome, Panayiotopoulos syndrome, parietal lobe epilepsy, PCDH19 epilepsy, photosensitive epilepsy, progressive myoclonic epilepsies, Rasmussen's encephalitis, Rasmussen's syndrome, refractory epilepsy, seizure disorder, status epilepticus, Sturge-Weber syndrome, symptomatic generalized epilepsy, symptomatic partial epilepsy, TBCK-related ID syndrome, temporal lobe epilepsy, temporal lobe seizures, tonic-clonic seizure, West syndrome, tremor, cerebellar tremor, cerebellar outflow tremor, intention tremor, essential tremor, benign essential tremor, Parkinsonian tremor, and medication-induced postural tremor.

Pharmaceutical Compositions

According to an embodiment, the disclosure provides a composition comprising Compound 1 or salts thereof (or crystalline forms, hydrates, or solvates thereof) and a pharmaceutically acceptable carrier, adjuvant, or vehicle. In some embodiments, the amount of Compound 1 in compositions of this disclosure is such that is effective to treat, prevent, and/or manage various neurological and/or psychiatric diseases, disorders and/or symptoms in a subject. In some embodiments, a composition of this disclosure is formulated for administration to a subject in need of such composition. In some embodiments, a composition of this disclosure is formulated for oral administration to a subject.

As used herein, the term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

In certain embodiments, provided herein is a composition (e.g., a pharmaceutical composition) comprising Compound 1 or salts thereof (or crystalline forms, hydrates, or solvates thereof) and a pharmaceutically acceptable excipient or carrier. In some embodiments, provided herein is a method of treating neurological or psychiatric diseases and disorders in a subject in need thereof in a subject, comprising administering an effective amount of Compound 1 or salts thereof (or crystalline forms, hydrates, or solvates thereof) or a pharmaceutical composition described herein. Examples of carriers and excipients are well known to those skilled in the art and are described in detail in, e.g., Ansel, Howard C, et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present disclosure or pharmaceutical composition thereof) or aid in the manufacturing of the pharmaceutical product (i.e., medicament).

Compositions of the present disclosure may be administered orally, parenterally, by inhalation, topically, rectally, nasally, buccally, sublingually, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. Pharmaceutically acceptable compositions of this disclosure may be orally administered in any orally acceptable dosage form including capsules, tablets, aqueous suspensions or solutions.

The amount of Compound 1 or salts thereof (or crystalline forms, hydrates, or solvates thereof) that may be combined with the carrier materials to produce a composition in a single dosage form will vary depending upon a variety of factors, including the host treated and the particular mode of administration. It should also be understood that a specific dosage and treatment regimen for any particular subject will depend upon a variety of factors, including the activity of the specific form of Compound 1 employed, the age, body weight, general health, sex, diet, time of administration, rate of excretion, drug combination, and the judgment of the treating physician and the severity of the particular disease being treated.

Combination Therapies

In some embodiments, the present disclosure provides a method of treating a neurological and/or psychiatric disease or disorder described herein, comprising administering a compound of the disclosure in conjunction with one or more pharmaceutical agents. Suitable pharmaceutical agents that may be used in combination with Compound 1 or salts thereof (or crystalline forms, hydrates, or solvates thereof) include anti-Parkinson's drugs, anti-Alzheimer's drugs, antidepressants, anti-psychotics, anti-ischemics, CNS depressants, anti-cholinergics, nootropics, epilepsy medication, attention (e.g., ADD/ADHD) medications, sleep-promoting medications, wakefulness-promoting medications, and pain medications. In some embodiments, suitable pharmaceutical agents are anxiolytics.

Suitable anti-Parkinson's drugs include dopamine replacement therapy (e.g. L-DOPA, carbidopa, COMT inhibitors such as entacapone or tolcapone), dopamine agonists (e.g. D1 agonists, D2 agonists, mixed D1/D2 agonists, bromocriptine, pergolide, cabergoline, ropinirole, pramipexole, piribedil, or apomorphine in combination with domperidone), histamine H2 antagonists, monoamine oxidase inhibitors (such as selegiline, rasagiline, safinamide and tranylcypromine), certain atypical antipsychotics such as pimavanserin (a non-dopaminergic atypical antipsychotic and inverse agonist of the serotonin 5-HT2A receptor), and amantadine.

In some embodiments, Compound 1 or salts thereof (or crystalline forms, hydrates, or solvates thereof) can be used in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexyl)hydrochloride, COMT inhibitors such as entacapone or tolcapone, MAO A/B inhibitors, antioxidants, A2a adenosine receptor antagonists, cholinergic agonists, MDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexole are commonly used in a non-salt form.

Suitable anti-Alzheimer's drugs include beta-secretase inhibitors, gamma-secretase inhibitors, cholinesterase inhibitors such as donepezil, galantamine or rivastigmine, HMG-CoA reductase inhibitors, NSAID's including ibuprofen, vitamin E, and anti-amyloid antibodies. In some embodiments, an anti-Alzheimer's drug is memantine.

Suitable anti-depressants and anti-anxiety agents include norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, a-adrenoreceptor antagonists, neurokinin-1 receptor antagonists, atypical anti-depressants, benzodiazepines, 5-HT1 A agonists or antagonists, especially 5-HT1 A partial agonists, and corticotropin releasing factor (CRF) antagonists.

Specific suitable anti-depressant and anti-anxiety agents include amitriptyline, clomipramine, doxepin, imipramine and trimipramine; amoxapine, desipramine, citalopram, escitalopram, maprotiline, nortriptyline and protriptyline; fluoxetine, fluvoxamine, paroxetine and sertraline; isocarboxazid, phenelzine, tranylcypromine and selegiline; moclobemide: venlafaxine; desvenlafaxine, duloxetine; aprepitant; bupropion, vilazodone, mirtazapine, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, reboxetine, vortioxetine, clorazepate, and ketamine and pharmaceutically acceptable salts thereof. In some embodiments, suitable anti-depressant and anti-anxiety agents are tianeptine, or pharmaceutically acceptable salts thereof.

Suitable anti-psychotic and mood stabilizer agents include D2 antagonists, 5HT2A antagonists, atypical antipsychotics, lithium, and anticonvulsants.

Specific suitable anti-psychotic and mood stabilizer agents include chlorpromazine, fluphenazine, haloperidol, amisulpride, perphenazine, thioridazine, trifluoperazine, aripiprazole, asenapine, clozapine, olanzapine, paliperidone, brexpiprazole, paliperidone, cariprazine, pimavanserin, illoperidone, lumateperone, MIN-101, quetiapine, risperidone, ziprasidone, lurasidone, flupentixol, levomepromazine, pericyazine, perphenazine, pimozide, prochlorperazine, zuclopenthixol, olanzapine and fluoxetine, lithium, carbamazepine, lamotrigine, valproic acid, iloperidone, thiothixene, gabapentin, tiagabine and pharmaceutically acceptable salts thereof.

Suitable epilepsy medications include levetiracetam, oxcarbazepine, clobazam, retigabine, zonisamide, felbamate, esclicarbazepine acetate, lacosamide, carbamazepine, tiagabine, methsuximide, progabide, valproic acid, lamotrigine, brivaracetam, rufinamide, topiramate and perampanel.

Suitable attention medications include methyl phenidate, atomoxetine, guanfacine, D-amphetamine, lisdexamphetamine, methylamphetamine, and clonidine.

Suitable sleep-promoting medications include ramelteon, triazolam, zopiclone, eszopiclone, Zolpidem, temazepam, and trazodone.

Suitable wakefulness-promoting medications include Modafinil, D-Amphetamine, caffeine, and armodafinil.

Suitable pain medications include dextromethorphan, tapentadol, buprenorphine, codeine, fentanyl, hydrocodone, hydromorphone, morphine, naloxegol, oxycodone, tramadol, gabapentil, difluprednate, pregabalin, acetyl salicyclic acid, bromfenac, diclofenac, diflunisal, indomethacin, ketorolac, meoxican, and naproxen.

In some embodiments, compounds and compositions of the disclosure may be used in combination with other therapies. Suitable therapies include psychotherapy, cognitive behavioral therapy, electroconvulsive therapy, transcranial magnetic stimulation, vagus nerve stimulation, and deep-brain stimulation.

The exact amount required will vary from subject to subject, depending on the species, age, and general condition of the subject, the severity of the condition, the particular agent, its mode of administration, and the like. The compounds and compositions of the disclosure are preferably formulated in dosage unit form for ease of administration and uniformity of dosage. The expression "dosage unit form" as used herein refers to a physically discrete unit of agent appropriate for the subject to be treated. It will be understood, however, that the total daily usage of the compounds and compositions of the present disclosure will be decided by the attending physician within the scope of sound medical judgment.

The pharmaceutically acceptable compositions of this disclosure can be administered to humans and other animals orally, rectally, parenterally, intracisternally, intravaginally, intraperitoneally, topically (as by powders, ointments, or drops), bucally, sublingually, as an oral or nasal spray, or the like, depending on the severity of the infection being treated. In some embodiments, Compound 1 or salts thereof (or crystalline forms, hydrates, or solvates thereof) may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

In some embodiments, a combination of two or more therapeutic agents may be administered together with Compound 1 or salts thereof (or crystalline forms, hydrates, or solvates thereof). In some embodiments, a combination of three or more therapeutic agents may be administered with Compound 1 or salts thereof (or crystalline forms, hydrates, or solvates thereof).

Other examples of agents the compounds and compositions of this disclosure may also be combined with include: vitamins and nutritional supplements, antiemetics (e.g. 5-HT3 receptor antagonists, dopamine antagonists, K1 receptor antagonists, histamine receptor antagonists, cannabinoids, benzodiazepines, or anticholinergics), agents for treating Multiple Sclerosis (MS) such as beta interferon (e.g., Avonex® and Rebif®, dalfampridine, alemtuzumab), Copaxone®, and mitoxantrone; treatments for Huntington's disease such as tetrabenazine; treatments for asthma such as albuterol and Singulair®; anti-inflammatory agents such as corticosteroids, T F blockers, IL-1 RA, azathioprine, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, agents for treating cardiovascular disease such as beta-blockers, ACE inhibitors, diuretics, nitrates, calcium channel blockers, and statins, fibrates, cholesterol absorption inhibitors, bile acid sequestrants, and niacin; agents for treating liver disease such as corticosteroids, cholestyramine, interferons, and anti-viral agents; agents for treating blood disorders such as corticosteroids, anti-leukemic agents, and growth factors; agents for treating immunodeficiency disorders such as gamma globulin; and anti-diabetic agents such as biguanides (metformin, phenformin, buformin), thiazolidinediones (rosiglitazone, pioglitazone, troglitazone), sulfonylureas (tolbutamide, acetohexamide, tolazamide, chlorpropamide, glipizide, glyburide, glimepiride, gliclazide), meglitinides (repaglinide, nateglinide), alpha-glucosidase inhibitors (miglitol, acarbose), incretin mimetics (exenatide, liraglutide, taspoglutide), gastric inhibitory peptide analogs, DPP-4 inhibitors (vildagliptin, sitagliptin, saxagliptin, linagliptin, alogliptin), amylin analogs (pramlintide), and insulin and insulin analogs.

In some embodiments, Compound 1 or salts thereof (or crystalline forms, hydrates, or solvates thereof) are administered in combination with an antisense agent, a monoclonal or polyclonal antibody, or an siRNA therapeutic.

Those additional agents may be administered separately from an inventive compound-containing composition, as part of a multiple dosage regimen. Alternatively, those agents may be part of a single dosage form, mixed together with a compound of this disclosure in a single composition. If administered as part of a multiple dosage regime, the two active agents may be submitted simultaneously, sequentially or within a period of time from one another, normally within five hours from one another.

As used herein, the term "combination," "combined," and related terms refers to the simultaneous or sequential administration of therapeutic agents in accordance with this disclosure. For example, Compound 1 or salts thereof (or crystalline forms, hydrates, or solvates thereof) may be administered with another therapeutic agent simultaneously or sequentially in separate unit dosage forms or together in a single unit dosage form. Accordingly, the present disclosure provides a single unit dosage form comprising Compound 1 or salts thereof (or crystalline forms, hydrates, or solvates thereof), an additional therapeutic agent, and a pharmaceutically acceptable carrier, adjuvant, or vehicle.

The amount of both, an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this disclosure should be formulated so that a dosage of between 0.01-100 mg/kg body weight/day of an inventive can be administered.

In those compositions which comprise an additional therapeutic agent, that additional therapeutic agent and Compound 1 or salts thereof (or crystalline forms, hydrates, or solvates thereof) may act synergistically. Therefore, the amount of additional therapeutic agent in such compositions will be less than that required in a monotherapy utilizing only that therapeutic agent. In such compositions a dosage of between 0.01-100 mg/kg body weight/day of the additional therapeutic agent can be administered.

The amount of additional therapeutic agent present in the compositions of this disclosure will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In some embodiments, the present disclosure provides a medicament comprising Compound 1 or salts thereof (or crystalline forms, hydrates, or solvates thereof), and a pharmaceutically acceptable carrier, adjuvant, or vehicle.

In some embodiments, the present disclosure provides the use of Compound 1 or salts thereof (or crystalline forms, hydrates, or solvates thereof) in the manufacture of a medicament for the treatment of a neurological and/or psychiatric disease or disorder.

EXAMPLES

Example 1: Preparation of Salts of Compound 1

The free base of Compound 1 (500 mg) was dissolved in MeOH (34 mL). The solution was divided into 33 vials (resulting in a 15 mg scale of Compound 1). To each vial, the appropriate counter ion (0.95 equivalents) was added and dissolved by the screening solvent listed in Table 1. The solution was heated at 60° C. for 1 h and then allowed to cool undisturbed at room temperature. Each vial was opened and allowed to stand at room temperature (slow evaporation). In several cases, acetone or EtOAc additive were added to vials and allowed to stand at room temperature, allowing for slow evaporation. Results of the solvent screen are shown below in Table 1. Further, certain experiments were performed on a larger scale, as shown in Table 1.

TABLE 1

Solvent screen

| Entry | Acid (0.95 equivalents rel. to Compound 1) | Scale (amount of Compound 1) | Screening Solvent | Solvent Additive for slow evaporation | Notes On Product |
|---|---|---|---|---|---|
| 1 | HCl | 15 mg | MeOH | — | — |
| 2 | HCl | 15 mg | THF | — | Crystalline - Form HA |
| 3 | HCl | 15 mg | EtOAc | — | Crystalline - Form HA |
| 4 | H$_3$PO$_4$ | 15 mg | MeOH + Acetone | — | Crystalline |
| 5 | H$_3$PO$_4$ | 15 mg | THF | — | Crystalline |
| 6 | H$_3$PO$_4$ | 15 mg | EtOAc | — | Crystalline |
| 7 | H$_3$PO$_4$ | 200 mg | MeOH (1 mL) + EtOAc (5 mL) | acetone | Crystalline |
| 8 | H$_3$PO$_4$ | 1000 mg | MeOH (7 mL) + EtOAc (35 mL) | acetone | Crystalline |
| 9 | L-Tartaric acid | 15 mg | MeOH + acetone | | Crystalline - Form LB |
| 10 | L-Tartaric acid | 15 mg | THF | | Crystalline - Form LA |
| 11 | L-Tartaric acid | 15 mg | EtOAc | | Crystalline - Form LA |
| 12 | L-Tartaric acid | 100 mg | MeOH (1 mL) + EtOAc (5 mL), 100 mg scale | acetone | Crystalline - Form LC |
| 13 | L-Tartaric acid | 100 mg | MeOH (1 mL) + EtOAc (5 mL); 100 mg scale | EtOAc | Crystalline - Form LC |
| 14 | D-Tartaric acid | 15 mg | MeOH + acetone | | — |
| 15 | D-Tartaric acid | 15 mg | THF | | Crystalline |
| 16 | D-Tartaric acid | 15 mg | EtOAc | | Crystalline |
| 17 | Fumaric acid | 15 mg | MeOH | | Crystalline - Form FA |
| 18 | Fumaric acid | 15 mg | THF | | Crystalline - Form FA |
| 19 | Fumaric acid | 15 mg | EtOAc | | Crystalline - Form FB |
| 20 | Fumaric acid | 200 mg | MeOH (1 mL) + Acetone (5 mL) | Acetone | Crystalline - Form FA |
| 21 | Citric Acid | 15 mg | MeOH + acetone | | Crystalline |
| 22 | Citric Acid | 15 mg | THF | | — |
| 23 | Citric Acid | 15 mg | EtOAc | | Crystalline |
| 24 | Citric Acid | 100 mg | MeOH (1 mL) + EtOAc (5 mL) | Acetone | Crystalline |
| 25 | TsOH | 15 mg | MeOH + acetone | | — |
| 26 | TsOH | 15 mg | THF | | — |
| 27 | TsOH | 15 mg | EtOAc | | — |
| 28 | Succinic acid | 15 mg | MeOH + acetone | | — |
| 29 | Succinic acid | 15 mg | THF | | Crystalline |
| 30 | Succinic acid | 15 mg | EtOAc | | Crystalline |
| 31 | Glutaric acid | 15 mg | MeOH + acetone | | Crystalline |
| 32 | Glutaric acid | 15 mg | THF | | — |
| 33 | Glutaric acid | 15 mg | EtOAc | | — |
| 34 | L-malic acid | 15 mg | MeOH | | Crystalline |
| 35 | L-malic acid | 15 mg | THF | | Crystalline |
| 36 | L-malic acid | 15 mg | EtOAC | | Crystalline |
| 37 | BsOH | 15 mg | MeOH + acetone | | — |
| 38 | BsOH | 15 mg | THF | | — |
| 39 | BsOH | 15 mg | EtOAc | | Crystalline |

Example 2. Synthesis of Free Base

Saturated sodium bicarbonate water (15 ml) and water (5 ml) was added to Compound 1 hydrochloride (600 mg). The solution was extracted with chloroform (15 mL, 3 times). The organic extract was washed with brine (20 ml) and evaporated. The free base of Compound 1 was isolated as an oil (approx. 500 mg).

Example 3. Compound 1 Hydrochloride Form HA

The XRPD spectrum for Compound 1 Hydrochloride HA is provided in FIG. 1 (FIG. 1) and the corresponding peak data is provided below in Table 2.

TABLE 2

XRPD Peak Data for Compound 1 Hydrochloride Form HA

| Pos. [°2θ] | FWHM Left [°2θ] | Area [cts*°2θ] | d-spacing [Å] | Height [cts] | Rel. Int. [%] |
|---|---|---|---|---|---|
| 6.7 | 0.1 | 7.0 | 13.1 | 43.1 | 0.6 |
| 8.6 | 0.2 | 46.6 | 10.3 | 214.3 | 2.7 |
| 9.4 | 0.1 | 1072.7 | 9.4 | 7887.4 | 100.0 |
| 10.3 | 0.2 | 24.8 | 8.6 | 91.1 | 1.2 |
| 11.4 | 0.1 | 196.4 | 7.7 | 1443.9 | 18.3 |
| 12.5 | 0.3 | 16.7 | 7.1 | 38.4 | 0.5 |
| 13.6 | 0.2 | 11.6 | 6.5 | 53.1 | 0.7 |
| 14.2 | 0.1 | 192.1 | 6.2 | 1412.5 | 17.9 |
| 15.1 | 0.1 | 328.7 | 5.9 | 2417.1 | 30.6 |
| 16.0 | 0.2 | 9.9 | 5.5 | 45.7 | 0.6 |
| 17.2 | 0.1 | 329.2 | 5.2 | 2420.3 | 30.7 |
| 17.6 | 0.1 | 442.4 | 5.0 | 2710.9 | 34.4 |
| 17.9 | 0.2 | 16.6 | 5.0 | 76.4 | 1.0 |
| 18.8 | 0.1 | 87.4 | 4.7 | 535.5 | 6.8 |
| 19.2 | 0.1 | 116.1 | 4.6 | 609.6 | 7.7 |
| 20.1 | 0.2 | 57.1 | 4.4 | 262.4 | 3.3 |
| 20.6 | 0.1 | 30.9 | 4.3 | 189.5 | 2.4 |
| 20.9 | 0.2 | 37.8 | 4.3 | 173.5 | 2.2 |
| 21.5 | 0.2 | 25.4 | 4.1 | 93.5 | 1.2 |
| 22.1 | 0.1 | 49.6 | 4.0 | 303.9 | 3.9 |
| 23.1 | 0.1 | 55.2 | 3.8 | 405.7 | 5.1 |
| 23.6 | 0.1 | 21.2 | 3.8 | 129.9 | 1.7 |
| 24.3 | 0.1 | 204.0 | 3.7 | 1250.3 | 15.9 |
| 24.8 | 0.1 | 41.2 | 3.6 | 303.0 | 3.8 |
| 25.2 | 0.1 | 24.4 | 3.5 | 149.6 | 1.9 |
| 25.6 | 0.1 | 76.5 | 3.5 | 562.3 | 7.1 |
| 25.8 | 0.1 | 170.3 | 3.4 | 894.7 | 11.3 |
| 26.2 | 0.2 | 269.3 | 3.4 | 824.9 | 10.5 |
| 27.0 | 0.1 | 615.1 | 3.3 | 3768.7 | 47.8 |
| 27.7 | 0.1 | 66.1 | 3.2 | 405.1 | 5.1 |
| 28.0 | 0.1 | 38.5 | 3.2 | 283.1 | 3.6 |
| 28.3 | 0.1 | 90.9 | 3.2 | 668.5 | 8.5 |
| 28.6 | 0.1 | 99.9 | 3.1 | 734.3 | 9.3 |
| 29.8 | 0.1 | 27.2 | 3.0 | 166.4 | 2.1 |
| 30.1 | 0.1 | 31.8 | 3.0 | 195.0 | 2.5 |
| 30.5 | 0.1 | 79.8 | 2.9 | 488.7 | 6.2 |
| 31.7 | 0.1 | 83.3 | 2.8 | 612.1 | 7.8 |
| 32.2 | 0.2 | 58.9 | 2.8 | 270.7 | 3.4 |
| 32.8 | 0.2 | 40.3 | 2.7 | 148.3 | 1.9 |
| 33.0 | 0.1 | 8.7 | 2.7 | 53.1 | 0.7 |
| 33.5 | 0.2 | 22.6 | 2.7 | 69.3 | 0.9 |
| 34.0 | 0.2 | 20.0 | 2.6 | 73.6 | 0.9 |
| 34.5 | 0.1 | 17.1 | 2.6 | 104.6 | 1.3 |
| 35.6 | 0.1 | 174.9 | 2.5 | 1286.0 | 16.3 |
| 36.4 | 0.1 | 16.7 | 2.5 | 102.1 | 1.3 |
| 38.3 | 0.2 | 42.6 | 2.3 | 195.5 | 2.5 |
| 38.6 | 0.2 | 41.2 | 2.3 | 189.3 | 2.4 |
| 39.5 | 0.1 | 16.5 | 2.3 | 100.9 | 1.3 |

A DSC thermogram for Form HA is shown in FIG. 2 (FIG. 2). The thermogram is characterized by endotherm peaks at temperatures of about 99° C. and about 187° C. FIG. 3 (FIG. 3) shows a thermogravimetric analysis (TGA) thermogram of Form HA. FIG. 4 (FIG. 4) shows a dynamic vapor sorption (DVS) isotherm of Form HA.

Example 4. Compound 1 Hydrochloride Form HB

The XRPD spectrum for Compound 1 Hydrochloride HB is provided in FIG. 5 (FIG. 5) and the corresponding peak data is provided below in Table 3.

TABLE 3

XRPD Peak Data for Compound 1 Hydrochloride Form HB

| Pos. [°2θ] | FWHM Left [°2θ] | Area [cts*°2θ] | d-spacing [Å] | Height [cts] | Rel. Int. [%] |
|---|---|---|---|---|---|
| 8.6 | 0.2 | 139.5 | 10.2 | 640.9 | 28.7 |
| 9.6 | 0.1 | 189.2 | 9.2 | 1391.2 | 62.3 |
| 10.3 | 0.1 | 364.2 | 8.6 | 2231.9 | 100.0 |
| 12.6 | 0.1 | 146.9 | 7.0 | 1079.8 | 48.4 |
| 13.6 | 0.2 | 57.1 | 6.5 | 174.8 | 7.8 |
| 14.7 | 0.2 | 314.0 | 6.0 | 1442.9 | 64.7 |
| 16.5 | 0.1 | 99.9 | 5.4 | 524.9 | 23.5 |
| 17.3 | 0.1 | 296.0 | 5.1 | 2176.4 | 97.5 |
| 17.6 | 0.2 | 80.4 | 5.0 | 369.3 | 16.6 |
| 18.3 | 0.1 | 67.1 | 4.8 | 493.1 | 22.1 |
| 19.5 | 0.1 | 45.3 | 4.6 | 277.8 | 12.5 |
| 19.7 | 0.1 | 44.1 | 4.5 | 269.9 | 12.1 |
| 20.1 | 0.2 | 75.8 | 4.4 | 278.7 | 12.5 |
| 21.1 | 0.2 | 45.3 | 4.2 | 208.2 | 9.3 |
| 22.0 | 0.3 | 82.6 | 4.0 | 216.9 | 9.7 |
| 23.1 | 0.2 | 55.5 | 3.9 | 255.0 | 11.4 |
| 23.8 | 0.1 | 188.1 | 3.7 | 988.1 | 44.3 |
| 24.4 | 0.2 | 239.1 | 3.6 | 732.6 | 32.8 |
| 25.3 | 0.1 | 98.4 | 3.5 | 516.6 | 23.1 |
| 26.3 | 0.2 | 116.7 | 3.4 | 536.5 | 24.0 |
| 26.6 | 0.1 | 60.5 | 3.4 | 370.5 | 16.6 |
| 26.9 | 0.1 | 151.8 | 3.3 | 1116.3 | 50.0 |
| 27.1 | 0.1 | 154.7 | 3.3 | 1137.6 | 51.0 |
| 27.4 | 0.1 | 102.1 | 3.3 | 625.5 | 28.0 |
| 28.9 | 0.2 | 112.0 | 3.1 | 514.8 | 23.1 |
| 29.7 | 0.2 | 38.9 | 3.0 | 119.2 | 5.3 |
| 30.3 | 0.2 | 52.0 | 2.9 | 238.7 | 10.7 |
| 31.7 | 0.2 | 75.6 | 2.8 | 278.1 | 12.5 |
| 32.6 | 0.2 | 45.0 | 2.7 | 165.5 | 7.4 |
| 33.3 | 0.5 | 87.3 | 2.7 | 133.7 | 6.0 |
| 34.8 | 0.3 | 85.5 | 2.6 | 196.5 | 8.8 |
| 35.6 | 0.2 | 59.0 | 2.5 | 271.3 | 12.2 |
| 38.8 | 0.2 | 42.7 | 2.3 | 130.8 | 5.9 |

FIG. 6 (FIG. 6) shows a dynamic vapor sorption (DVS) isotherm of Form HB.

Example 5. Compound 1 Phosphate

The XRPD spectrum for Compound 1 Phosphate is provided in FIG. 7 (FIG. 7) and the corresponding peak data is provided below in Table 4.

TABLE 4

XRPD Peak Data for Compound 1 Phosphate

| Pos. [°2θ] | FWHM Left [°2θ] | Area [cts*°2θ] | d-spacing [Å] | Height [cts] | Rel. Int. [%] |
|---|---|---|---|---|---|
| 4.6 | 0.1 | 1876.4 | 19.4 | 13796.8 | 99.4 |
| 9.1 | 0.1 | 665.0 | 9.7 | 4890.0 | 35.2 |
| 13.6 | 0.1 | 36.5 | 6.5 | 335.3 | 2.4 |
| 14.0 | 0.1 | 40.3 | 6.3 | 296.0 | 2.1 |
| 15.2 | 0.1 | 10.6 | 5.8 | 97.6 | 0.7 |
| 15.7 | 0.1 | 79.4 | 5.6 | 583.5 | 4.2 |
| 16.2 | 0.1 | 28.8 | 5.5 | 264.9 | 1.9 |
| 18.2 | 0.1 | 1887.7 | 4.9 | 13880.4 | 100.0 |
| 19.1 | 0.1 | 59.7 | 4.6 | 548.4 | 4.0 |
| 19.8 | 0.1 | 9.5 | 4.5 | 87.6 | 0.6 |
| 21.2 | 0.1 | 20.5 | 4.2 | 187.9 | 1.4 |
| 22.3 | 0.1 | 77.0 | 4.0 | 707.7 | 5.1 |
| 22.8 | 0.1 | 1005.6 | 3.9 | 9242.6 | 66.6 |
| 23.1 | 0.1 | 44.5 | 3.8 | 408.6 | 2.9 |
| 23.4 | 0.1 | 24.7 | 3.8 | 181.9 | 1.3 |
| 24.0 | 0.1 | 12.4 | 3.7 | 75.8 | 0.6 |
| 24.8 | 0.1 | 82.3 | 3.6 | 605.3 | 4.4 |
| 25.2 | 0.1 | 33.0 | 3.5 | 242.5 | 1.8 |
| 25.5 | 0.1 | 16.6 | 3.5 | 152.6 | 1.1 |
| 26.0 | 0.1 | 121.0 | 3.4 | 1111.9 | 8.0 |

TABLE 4-continued

XRPD Peak Data for Compound 1 Phosphate

| Pos. [°2θ] | FWHM Left [°2θ] | Area [cts*°2θ] | d-spacing [Å] | Height [cts] | Rel. Int. [%] |
|---|---|---|---|---|---|
| 26.8 | 0.1 | 12.3 | 3.3 | 150.8 | 1.1 |
| 27.0 | 0.1 | 17.7 | 3.3 | 130.0 | 0.9 |
| 27.4 | 0.1 | 154.5 | 3.3 | 1419.7 | 10.2 |
| 27.7 | 0.1 | 20.0 | 3.2 | 183.7 | 1.3 |
| 28.2 | 0.1 | 14.7 | 3.2 | 134.9 | 1.0 |
| 29.4 | 0.1 | 10.5 | 3.0 | 64.5 | 0.5 |
| 29.6 | 0.1 | 9.1 | 3.0 | 55.9 | 0.4 |
| 30.1 | 0.1 | 103.4 | 3.0 | 760.0 | 5.5 |
| 30.7 | 0.1 | 14.0 | 2.9 | 128.2 | 0.9 |
| 31.0 | 0.1 | 59.6 | 2.9 | 438.6 | 3.2 |
| 31.3 | 0.1 | 12.9 | 2.9 | 79.2 | 0.6 |
| 32.1 | 0.1 | 41.8 | 2.8 | 384.3 | 2.8 |
| 33.5 | 0.2 | 9.1 | 2.7 | 28.0 | 0.2 |
| 34.1 | 0.1 | 24.0 | 2.6 | 176.4 | 1.3 |
| 34.9 | 0.1 | 32.7 | 2.6 | 300.7 | 2.2 |
| 35.2 | 0.1 | 16.5 | 2.5 | 151.3 | 1.1 |
| 36.4 | 0.1 | 8.2 | 2.5 | 50.3 | 0.4 |
| 36.8 | 0.1 | 25.9 | 2.4 | 190.1 | 1.4 |
| 37.8 | 0.1 | 18.5 | 2.4 | 135.8 | 1.0 |
| 38.3 | 0.1 | 16.1 | 2.3 | 118.0 | 0.9 |
| 38.8 | 0.1 | 62.1 | 2.3 | 456.3 | 3.3 |
| 39.0 | 0.1 | 75.9 | 2.3 | 558.4 | 4.0 |
| 39.3 | 0.1 | 11.0 | 2.3 | 101.0 | 0.7 |
| 40.9 | 0.1 | 13.5 | 2.2 | 123.9 | 0.9 |
| 41.3 | 0.1 | 10.5 | 2.2 | 64.1 | 0.5 |
| 41.6 | 0.2 | 13.7 | 2.2 | 63.0 | 0.5 |
| 43.4 | 0.1 | 22.4 | 2.1 | 205.8 | 1.5 |
| 45.1 | 0.1 | 13.6 | 2.0 | 125.1 | 0.9 |
| 45.5 | 0.2 | 9.5 | 2.0 | 34.8 | 0.3 |
| 45.9 | 0.1 | 23.7 | 2.0 | 174.3 | 1.3 |
| 46.5 | 0.1 | 9.0 | 2.0 | 82.8 | 0.6 |
| 48.0 | 0.1 | 31.5 | 1.9 | 289.5 | 2.1 |
| 49.0 | 0.1 | 15.2 | 1.9 | 93.1 | 0.7 |
| 49.4 | 0.1 | 14.1 | 1.8 | 86.3 | 0.6 |
| 50.8 | 0.2 | 10.8 | 1.8 | 33.0 | 0.2 |
| 51.5 | 0.1 | 13.6 | 1.8 | 124.9 | 0.9 |
| 52.3 | 0.1 | 10.8 | 1.7 | 99.0 | 0.7 |
| 52.5 | 0.1 | 13.7 | 1.7 | 126.1 | 0.9 |
| 52.9 | 0.1 | 72.9 | 1.7 | 446.8 | 3.2 |
| 53.9 | 0.1 | 9.2 | 1.7 | 112.4 | 0.8 |
| 56.3 | 0.1 | 6.4 | 1.6 | 33.5 | 0.2 |
| 57.3 | 0.1 | 9.1 | 1.6 | 55.7 | 0.4 |
| 58.6 | 0.1 | 17.9 | 1.6 | 109.4 | 0.8 |
| 60.3 | 0.2 | 8.9 | 1.5 | 27.3 | 0.2 |
| 62.4 | 0.4 | 16.0 | 1.5 | 29.4 | 0.2 |
| 63.9 | 0.2 | 5.7 | 1.5 | 17.6 | 0.1 |
| 64.4 | 0.1 | 5.9 | 1.4 | 36.1 | 0.3 |

A DSC thermogram for Compound 1 Phosphate is shown in FIG. 8 (FIG. 8). The thermogram is characterized by an endotherm peak at a temperature of about 213° C. FIG. 9 (FIG. 9) shows a thermogravimetric analysis (TGA) thermogram of Compound 1 Phosphate. FIG. 10 (FIG. 10) shows a dynamic vapor sorption (DVS) isotherm of Compound 1 Phosphate.

Example 6. Compound 1 L-Tartrate Form LA

The XRPD spectrum for Compound 1 Form LA is provided in FIG. 11 (FIG. 11) and the corresponding peak data is provided below in Table 5.

TABLE 5

XRPD Peak Data for Compound 1 L-Tartrate Form LA

| Pos. [°2θ] | FWHM Left [°2θ] | Area [cts*°2θ] | d-spacing [Å] | Height [cts] | Rel. Int. [%] |
|---|---|---|---|---|---|
| 4.7 | 0.5 | 15.1 | 18.8 | 23.2 | 0.1 |
| 5.1 | 0.2 | 7.5 | 17.3 | 27.6 | 0.1 |
| 6.1 | 0.2 | 91.6 | 14.6 | 336.6 | 1.2 |
| 9.1 | 0.2 | 55.6 | 9.8 | 255.4 | 0.9 |
| 12.1 | 0.2 | 570.4 | 7.3 | 2621.2 | 9.5 |
| 12.4 | 0.2 | 161.8 | 7.2 | 743.5 | 2.7 |
| 12.8 | 0.2 | 55.3 | 6.9 | 203.4 | 0.7 |
| 13.4 | 0.2 | 65.3 | 6.6 | 240.0 | 0.9 |
| 14.1 | 0.2 | 85.6 | 6.3 | 314.8 | 1.1 |
| 15.0 | 0.2 | 286.0 | 5.9 | 1051.5 | 3.8 |
| 15.9 | 0.1 | 58.1 | 5.6 | 427.5 | 1.6 |
| 16.4 | 0.3 | 407.9 | 5.4 | 1071.2 | 3.9 |
| 16.9 | 0.1 | 170.1 | 5.2 | 1042.1 | 3.8 |
| 17.1 | 0.1 | 177.0 | 5.2 | 1301.4 | 4.7 |
| 18.1 | 0.2 | 7483.7 | 4.9 | 27513.5 | 100.0 |
| 19.3 | 0.1 | 182.5 | 4.6 | 958.4 | 3.5 |
| 19.9 | 0.1 | 96.3 | 4.5 | 590.0 | 2.1 |
| 20.5 | 0.3 | 192.8 | 4.3 | 506.3 | 1.8 |
| 21.1 | 0.1 | 23.5 | 4.2 | 144.1 | 0.5 |
| 21.7 | 0.2 | 172.9 | 4.1 | 635.8 | 2.3 |
| 22.1 | 0.2 | 74.1 | 4.0 | 340.4 | 1.2 |
| 22.5 | 0.2 | 34.9 | 3.9 | 160.3 | 0.6 |
| 23.0 | 0.2 | 144.9 | 3.9 | 443.8 | 1.6 |
| 23.9 | 0.2 | 910.0 | 3.7 | 4182.2 | 15.2 |
| 24.2 | 0.1 | 1554.5 | 3.7 | 11430.2 | 41.5 |
| 24.8 | 0.1 | 381.4 | 3.6 | 2003.3 | 7.3 |
| 25.8 | 0.2 | 92.7 | 3.5 | 426.0 | 1.6 |
| 26.2 | 0.1 | 60.4 | 3.4 | 370.1 | 1.4 |
| 27.0 | 0.1 | 361.4 | 3.3 | 1897.9 | 6.9 |
| 27.2 | 0.1 | 306.0 | 3.3 | 2249.8 | 8.2 |
| 27.6 | 0.2 | 162.1 | 3.2 | 744.8 | 2.7 |
| 28.4 | 0.1 | 220.1 | 3.1 | 1156.1 | 4.2 |
| 29.0 | 0.2 | 220.8 | 3.1 | 811.7 | 3.0 |
| 29.4 | 0.2 | 94.4 | 3.0 | 433.8 | 1.6 |
| 29.8 | 0.1 | 166.3 | 3.0 | 1019.1 | 3.7 |
| 30.3 | 0.1 | 236.2 | 2.9 | 1736.9 | 6.3 |
| 30.7 | 0.2 | 142.4 | 2.9 | 523.6 | 1.9 |
| 31.2 | 0.2 | 76.2 | 2.9 | 280.3 | 1.0 |
| 31.8 | 0.2 | 52.2 | 2.8 | 191.8 | 0.7 |
| 32.7 | 0.2 | 94.2 | 2.7 | 346.3 | 1.3 |
| 33.1 | 0.2 | 83.3 | 2.7 | 255.2 | 0.9 |
| 33.5 | 0.2 | 67.1 | 2.7 | 246.6 | 0.9 |
| 34.1 | 0.2 | 120.2 | 2.6 | 441.8 | 1.6 |
| 34.4 | 0.1 | 74.6 | 2.6 | 457.2 | 1.7 |
| 34.9 | 0.1 | 21.1 | 2.6 | 129.4 | 0.5 |
| 35.6 | 0.2 | 163.1 | 2.5 | 749.4 | 2.7 |
| 36.6 | 0.2 | 239.8 | 2.5 | 1101.8 | 4.0 |
| 37.1 | 0.1 | 171.4 | 2.4 | 900.0 | 3.3 |
| 38.3 | 0.1 | 63.9 | 2.3 | 391.6 | 1.4 |
| 38.6 | 0.1 | 134.4 | 2.3 | 823.8 | 3.0 |
| 39.0 | 0.2 | 50.3 | 2.3 | 154.1 | 0.6 |

A DSC thermogram for Form LA is shown in FIG. 12 (FIG. 12). The thermogram is characterized by endotherm peaks at temperatures of about 89° C. and about 138° C. FIG. 13 (FIG. 13) shows a thermogravimetric analysis (TGA) thermogram of Compound 1 L-Tartrate Form LA. FIG. 14 (FIG. 14) shows a dynamic vapor sorption (DVS) isotherm of Form LA.

Example 7. Compound 1 L-Tartrate Form LB

The XRPD spectrum for Compound 1 L-Tartrate Form LB is provided in FIG. 15 (FIG. 15) and the corresponding peak data is provided below in Table 6.

TABLE 6

XRPD Peak Data for Compound 1 L-Tartrate Form LB

| Pos. [°2θ] | FWHM Left [°2θ] | Area [cts*°2θ] | d-spacing [Å] | Height [cts] | Rel. Int. [%] |
|---|---|---|---|---|---|
| 4.3 | 0.5 | 9.5 | 20.7 | 14.6 | 0.0 |
| 6.3 | 0.1 | 269.5 | 14.1 | 1651.3 | 4.2 |
| 8.9 | 0.7 | 33.5 | 9.9 | 38.4 | 0.1 |
| 11.9 | 0.1 | 66.9 | 7.4 | 410.0 | 1.1 |
| 12.1 | 0.2 | 221.2 | 7.3 | 813.2 | 2.1 |
| 12.5 | 0.1 | 302.4 | 7.1 | 1853.2 | 4.7 |
| 12.8 | 0.1 | 60.1 | 6.9 | 368.0 | 0.9 |
| 13.4 | 0.2 | 19.1 | 6.6 | 58.5 | 0.2 |
| 14.1 | 0.1 | 8.5 | 6.3 | 51.9 | 0.1 |
| 14.9 | 0.2 | 82.8 | 5.9 | 253.6 | 0.7 |
| 15.5 | 0.1 | 222.5 | 5.7 | 1363.3 | 3.5 |
| 15.9 | 0.1 | 28.6 | 5.6 | 175.2 | 0.5 |
| 16.3 | 0.2 | 186.9 | 5.4 | 763.5 | 2.0 |
| 16.5 | 0.1 | 65.6 | 5.4 | 402.0 | 1.0 |
| 16.9 | 0.1 | 63.5 | 5.2 | 389.1 | 1.0 |
| 18.1 | 0.1 | 717.7 | 4.9 | 5276.8 | 13.5 |
| 18.7 | 0.1 | 6395.4 | 4.7 | 39187.7 | 100.0 |
| 19.2 | 0.2 | 34.3 | 4.6 | 157.5 | 0.4 |
| 19.6 | 0.1 | 65.8 | 4.5 | 403.0 | 1.0 |
| 19.9 | 0.1 | 146.2 | 4.5 | 1074.9 | 2.7 |
| 20.0 | 0.1 | 227.2 | 4.4 | 1391.9 | 3.6 |
| 20.5 | 0.2 | 30.5 | 4.3 | 93.6 | 0.2 |
| 22.0 | 0.2 | 38.5 | 4.0 | 118.1 | 0.3 |
| 22.5 | 0.1 | 59.3 | 4.0 | 435.9 | 1.1 |
| 22.6 | 0.1 | 50.8 | 3.9 | 373.3 | 1.0 |
| 23.9 | 0.2 | 459.3 | 3.7 | 2110.9 | 5.4 |
| 24.2 | 0.1 | 224.6 | 3.7 | 1651.5 | 4.2 |
| 24.6 | 0.1 | 154.1 | 3.6 | 1132.8 | 2.9 |
| 25.0 | 0.1 | 3586.6 | 3.6 | 21976.5 | 56.1 |
| 27.1 | 0.2 | 123.6 | 3.3 | 568.0 | 1.5 |
| 28.4 | 0.1 | 12.9 | 3.1 | 78.7 | 0.2 |
| 28.8 | 0.3 | 94.4 | 3.1 | 247.9 | 0.6 |
| 29.4 | 0.1 | 114.3 | 3.0 | 700.1 | 1.8 |
| 29.8 | 0.2 | 43.4 | 3.0 | 199.5 | 0.5 |
| 30.3 | 0.1 | 61.7 | 2.9 | 323.9 | 0.8 |
| 30.7 | 0.2 | 137.7 | 2.9 | 632.9 | 1.6 |
| 31.0 | 0.2 | 64.8 | 2.9 | 298.0 | 0.8 |
| 31.4 | 0.1 | 1318.4 | 2.8 | 8078.3 | 20.6 |
| 33.1 | 0.2 | 28.4 | 2.7 | 104.5 | 0.3 |
| 33.8 | 0.2 | 48.9 | 2.6 | 149.7 | 0.4 |
| 34.0 | 0.1 | 10.2 | 2.6 | 74.8 | 0.2 |
| 34.1 | 0.2 | 25.3 | 2.6 | 77.6 | 0.2 |
| 34.6 | 0.1 | 29.1 | 2.6 | 178.5 | 0.5 |
| 35.1 | 0.1 | 77.6 | 2.6 | 475.3 | 1.2 |
| 35.9 | 0.2 | 99.2 | 2.5 | 364.7 | 0.9 |
| 36.4 | 0.1 | 38.0 | 2.5 | 232.9 | 0.6 |
| 36.7 | 0.2 | 173.5 | 2.4 | 797.3 | 2.0 |
| 37.0 | 0.1 | 79.1 | 2.4 | 484.8 | 1.2 |
| 37.7 | 0.2 | 23.6 | 2.4 | 108.3 | 0.3 |
| 37.9 | 0.1 | 279.5 | 2.4 | 2055.0 | 5.2 |
| 38.9 | 0.2 | 1.6 | 2.3 | 5.8 | 0.0 |
| 39.6 | 0.1 | 18.1 | 2.3 | 110.8 | 0.3 |

FIG. 16 (FIG. 16) shows a dynamic vapor sorption (DVS) isotherm of Form LB.

Example 8. Compound 1 L-Tartrate Form LC

The XRPD spectrum for Compound 1 L-Tartrate Form LC is provided in FIG. 17 (FIG. 17) and the corresponding peak data is provided below in Table 7.

TABLE 7

XRPD Peak Data for Compound 1 L-Tartrate Form LC

| Pos. [°2θ] | FWHM Left [°2θ] | Area [cts*°2θ] | d-spacing [Å] | Height [cts] | Rel. Int. [%] |
|---|---|---|---|---|---|
| 6.3 | 0.2 | 57.4 | 14.1 | 175.8 | 3.0 |
| 12.2 | 0.2 | 908.8 | 7.3 | 4176.6 | 70.7 |
| 12.8 | 0.2 | 389.8 | 6.9 | 1791.5 | 30.3 |
| 15.0 | 0.1 | 168.1 | 5.9 | 882.8 | 15.0 |
| 15.4 | 0.1 | 420.8 | 5.7 | 3093.9 | 52.4 |
| 16.5 | 0.2 | 1001.8 | 5.4 | 4092.4 | 69.3 |
| 18.7 | 0.2 | 825.8 | 4.7 | 3373.2 | 57.1 |
| 19.5 | 0.1 | 179.9 | 4.5 | 1102.1 | 18.7 |
| 19.8 | 0.1 | 646.7 | 4.5 | 3396.4 | 57.5 |
| 20.0 | 0.1 | 557.8 | 4.4 | 2929.7 | 49.6 |
| 22.4 | 0.1 | 290.2 | 4.0 | 1777.9 | 30.1 |
| 22.6 | 0.2 | 614.3 | 3.9 | 2822.9 | 47.8 |
| 23.7 | 0.3 | 107.2 | 3.8 | 246.2 | 4.2 |
| 24.2 | 0.3 | 211.4 | 3.7 | 555.1 | 9.4 |
| 24.8 | 0.1 | 963.6 | 3.6 | 5904.1 | 100.0 |
| 25.0 | 0.1 | 697.9 | 3.6 | 3665.6 | 62.1 |
| 25.5 | 0.2 | 1163.6 | 3.5 | 5347.3 | 90.6 |
| 26.2 | 0.2 | 97.8 | 3.4 | 449.6 | 7.6 |
| 26.5 | 0.1 | 99.7 | 3.4 | 611.0 | 10.4 |
| 27.1 | 0.1 | 356.3 | 3.3 | 1871.2 | 31.7 |
| 27.8 | 0.1 | 83.2 | 3.2 | 509.6 | 8.6 |
| 28.0 | 0.1 | 85.6 | 3.2 | 524.7 | 8.9 |
| 29.0 | 0.2 | 286.3 | 3.1 | 1315.9 | 22.3 |
| 29.4 | 0.1 | 102.3 | 3.0 | 752.4 | 12.7 |
| 29.9 | 0.2 | 259.2 | 3.0 | 1191.2 | 20.2 |
| 30.8 | 0.2 | 282.3 | 2.9 | 1037.7 | 17.6 |
| 31.4 | 0.1 | 199.3 | 2.8 | 1465.7 | 24.8 |
| 32.9 | 0.1 | 68.5 | 2.7 | 419.4 | 7.1 |
| 33.4 | 0.7 | 131.0 | 2.7 | 150.5 | 2.6 |
| 33.8 | 0.1 | 86.4 | 2.7 | 529.2 | 9.0 |
| 34.6 | 0.1 | 75.8 | 2.6 | 557.2 | 9.4 |
| 35.0 | 0.2 | 121.9 | 2.6 | 373.3 | 6.3 |
| 35.4 | 0.1 | 52.4 | 2.5 | 385.6 | 6.5 |
| 36.0 | 0.1 | 273.1 | 2.5 | 1673.6 | 28.4 |
| 36.6 | 0.1 | 104.7 | 2.5 | 641.3 | 10.9 |
| 37.0 | 0.1 | 139.8 | 2.4 | 856.8 | 14.5 |
| 37.6 | 0.2 | 277.9 | 2.4 | 1135.3 | 19.2 |
| 39.6 | 0.1 | 114.0 | 2.3 | 598.9 | 10.1 |

A DSC thermogram for Form LC is shown in FIG. 18 (FIG. 18). The thermogram is characterized by an endotherm peak at a temperature of about 137° C. FIG. 19 (FIG. 19) shows a thermogravimetric analysis (TGA) thermogram of Compound 1 L-Tartrate Form LC. FIG. 20 (FIG. 20) shows a dynamic vapor sorption (DVS) isotherm of Form LC.

Example 9. Compound 1 D-Tartrate

The XRPD spectrum for Compound 1 D-Tartrate is provided in FIG. 22 (FIG. 22) and the corresponding peak data is provided below in Table 8.

TABLE 8

XRPD Peak Data for Compound 1 D-Tartrate

| Pos. [°2θ] | FWHM Left [°2θ] | Area [cts*°2θ] | d-spacing [Å] | Rel. Int. [%] |
|---|---|---|---|---|
| 6.0 | 0.2 | 71.0 | 14.8 | 4.0 |
| 11.9 | 0.1 | 286.4 | 7.4 | 25.7 |
| 12.3 | 0.1 | 129.2 | 7.2 | 11.6 |
| 13.4 | 0.2 | 115.0 | 6.6 | 6.5 |
| 14.9 | 0.1 | 57.0 | 5.9 | 4.3 |
| 16.1 | 0.1 | 120.8 | 5.5 | 9.1 |
| 16.9 | 0.1 | 432.0 | 5.3 | 32.4 |
| 17.9 | 0.1 | 1112.7 | 4.9 | 100.0 |

TABLE 8-continued

XRPD Peak Data for Compound 1 D-Tartrate

| Pos. [°2θ] | FWHM Left [°2θ] | Area [cts*°2θ] | d-spacing [Å] | Rel. Int. [%] |
|---|---|---|---|---|
| 19.1 | 0.1 | 202.7 | 4.6 | 15.2 |
| 20.6 | 0.1 | 41.3 | 4.3 | 3.1 |
| 21.2 | 0.1 | 32.2 | 4.2 | 2.4 |
| 21.6 | 0.1 | 125.1 | 4.1 | 9.4 |
| 22.1 | 0.2 | 37.8 | 4.0 | 2.1 |
| 23.4 | 0.1 | 57.1 | 3.8 | 4.3 |
| 23.9 | 0.1 | 523.8 | 3.7 | 33.6 |
| 24.6 | 0.1 | 102.0 | 3.6 | 9.2 |
| 25.1 | 0.2 | 167.0 | 3.5 | 8.3 |
| 25.9 | 0.1 | 86.3 | 3.4 | 6.5 |
| 26.8 | 0.1 | 87.1 | 3.3 | 7.8 |
| 27.2 | 0.2 | 59.7 | 3.3 | 2.7 |
| 28.7 | 0.2 | 78.5 | 3.1 | 3.5 |
| 29.6 | 0.1 | 106.2 | 3.0 | 8.0 |
| 30.1 | 0.1 | 84.6 | 3.0 | 7.6 |
| 30.4 | 0.2 | 96.6 | 2.9 | 4.3 |
| 31.5 | 0.3 | 31.9 | 2.8 | 0.9 |
| 32.4 | 0.2 | 57.6 | 2.8 | 3.2 |
| 33.8 | 0.2 | 22.5 | 2.7 | 1.3 |
| 34.2 | 0.2 | 43.8 | 2.6 | 1.6 |
| 35.3 | 0.1 | 150.3 | 2.5 | 9.7 |
| 36.3 | 0.2 | 62.3 | 2.5 | 3.5 |
| 36.9 | 0.1 | 33.8 | 2.4 | 2.5 |
| 38.3 | 0.2 | 35.1 | 2.3 | 2.0 |
| 38.8 | 0.2 | 45.1 | 2.3 | 2.5 |

A DSC thermogram for Compound 1 D-Tartrate is shown in FIG. 23 (FIG. 23). The thermogram is characterized by endotherm peaks at temperatures of about 76° C. and about 153° C. FIG. 23 (FIG. 23) shows a thermogravimetric analysis (TGA) thermogram of Compound 1 D-Tartrate. FIG. 24 (FIG. 24) shows a dynamic vapor sorption (DVS) isotherm of Compound 1 D-Tartrate.

Example 10. Compound 1 Fumarate Form FA

The XRPD spectrum for Compound 1 Fumarate FA is provided in FIG. 25 (FIG. 25) and the corresponding peak data is provided below in Table 9.

TABLE 9

XRPD Peak Data for Compound 1 Fumarate Form FA

| Pos. [°2θ] | FWHM Left [°2θ] | Area [cts*°2θ] | d-spacing [Å] | Height [cts] | Rel. Int. [%] |
|---|---|---|---|---|---|
| 5.0 | 0.3 | 7.1 | 17.7 | 16.4 | 0.0 |
| 7.7 | 0.2 | 2022.3 | 11.5 | 9293.7 | 21.3 |
| 11.3 | 0.2 | 8.6 | 7.8 | 26.3 | 0.1 |
| 12.1 | 0.2 | 161.3 | 7.3 | 741.3 | 1.7 |
| 13.0 | 0.1 | 429.8 | 6.8 | 2633.3 | 6.0 |
| 14.2 | 0.1 | 911.3 | 6.2 | 4786.2 | 11.0 |
| 14.6 | 0.1 | 339.9 | 6.0 | 1784.9 | 4.1 |
| 15.2 | 0.1 | 1404.9 | 5.8 | 10330.6 | 23.7 |
| 15.9 | 0.2 | 13.6 | 5.6 | 62.5 | 0.1 |
| 16.2 | 0.2 | 18.9 | 5.5 | 69.5 | 0.2 |
| 17.1 | 0.2 | 22.9 | 5.2 | 105.2 | 0.2 |
| 18.1 | 0.2 | 183.7 | 4.9 | 844.0 | 1.9 |
| 18.8 | 0.1 | 126.3 | 4.7 | 928.9 | 2.1 |
| 19.1 | 0.1 | 6.2 | 4.6 | 38.1 | 0.1 |
| 19.3 | 0.1 | 5.6 | 4.6 | 34.3 | 0.1 |
| 19.9 | 0.3 | 32.9 | 4.5 | 75.5 | 0.2 |
| 20.8 | 0.1 | 15.2 | 4.3 | 92.9 | 0.2 |
| 21.8 | 0.2 | 115.7 | 4.1 | 531.7 | 1.2 |
| 22.4 | 0.1 | 135.0 | 4.0 | 993.0 | 2.3 |
| 22.6 | 0.1 | 162.7 | 3.9 | 996.7 | 2.3 |
| 22.9 | 0.1 | 4216.3 | 3.9 | 25835.4 | 59.3 |
| 23.9 | 0.2 | 85.0 | 3.7 | 390.4 | 0.9 |
| 24.2 | 0.1 | 42.2 | 3.7 | 258.7 | 0.6 |
| 24.6 | 0.1 | 1727.3 | 3.6 | 10583.8 | 24.3 |
| 25.0 | 0.1 | 5.0 | 3.6 | 30.7 | 0.1 |
| 25.5 | 0.1 | 2.0 | 3.5 | 12.0 | 0.0 |
| 26.0 | 0.2 | 500.3 | 3.4 | 2299.2 | 5.3 |
| 26.5 | 0.2 | 193.7 | 3.4 | 890.0 | 2.0 |
| 27.0 | 0.1 | 61.1 | 3.3 | 374.5 | 0.9 |
| 27.2 | 0.1 | 16.6 | 3.3 | 101.5 | 0.2 |
| 27.6 | 0.2 | 55.7 | 3.2 | 170.6 | 0.4 |
| 28.2 | 0.1 | 22.4 | 3.2 | 164.6 | 0.4 |
| 28.6 | 0.1 | 25.1 | 3.1 | 153.9 | 0.4 |
| 29.0 | 0.1 | 27.7 | 3.1 | 203.7 | 0.5 |
| 29.3 | 0.2 | 74.8 | 3.0 | 343.9 | 0.8 |
| 30.1 | 0.1 | 4.5 | 3.0 | 33.2 | 0.1 |
| 30.7 | 0.1 | 7109.3 | 2.9 | 43561.8 | 100.0 |
| 31.6 | 0.2 | 441.0 | 2.8 | 2026.5 | 4.7 |
| 32.2 | 0.1 | 27.6 | 2.8 | 169.2 | 0.4 |
| 32.8 | 0.4 | 93.0 | 2.7 | 170.9 | 0.4 |
| 33.3 | 0.1 | 68.3 | 2.7 | 418.2 | 1.0 |
| 34.6 | 0.2 | 48.2 | 2.6 | 177.1 | 0.4 |
| 35.2 | 0.1 | 165.4 | 2.5 | 1013.5 | 2.3 |
| 35.9 | 0.2 | 20.1 | 2.5 | 74.0 | 0.2 |
| 37.0 | 0.1 | 35.8 | 2.4 | 263.0 | 0.6 |
| 37.9 | 0.1 | 175.8 | 2.4 | 1077.3 | 2.5 |
| 38.6 | 0.2 | 1019.2 | 2.3 | 4684.0 | 10.8 |
| 39.7 | 0.2 | 24.5 | 2.3 | 112.4 | 0.3 |

A DSC thermogram for Form FA is shown in FIG. 26 (FIG. 26). The thermogram is characterized by an endotherm peak at a temperature of about 147° C. FIG. 27 (FIG. 27) shows a thermogravimetric analysis (TGA) thermogram of Compound 1 Fumarate Form FA. FIG. 28 (FIG. 28) shows a dynamic vapor sorption (DVS) isotherm of Form FA.

Example 11. Compound 1 Fumarate Form FB

The XRPD spectrum for Compound 1 Fumarate FB is provided in FIG. 29 (FIG. 29) and the corresponding peak data is provided below in Table 10.

TABLE 10

XRPD Peak Data for Compound 1 Fumarate Form FB

| Pos. [°2θ] | FWHM Left [°2θ] | Area [cts*°2θ] | d-spacing [Å] | Height [cts] | Rel. Int. [%] |
|---|---|---|---|---|---|
| 4.7 | 0.5 | 18.2 | 18.9 | 27.9 | 0.0 |
| 6.7 | 0.1 | 2225.1 | 13.1 | 13634.5 | 9.2 |
| 9.0 | 0.1 | 118.6 | 9.8 | 871.7 | 0.6 |
| 9.7 | 0.1 | 5.6 | 9.1 | 41.3 | 0.0 |
| 11.1 | 0.1 | 7.2 | 8.0 | 44.1 | 0.0 |
| 11.7 | 0.2 | 49.6 | 7.6 | 182.4 | 0.1 |
| 12.1 | 0.1 | 31.3 | 7.3 | 191.5 | 0.1 |
| 12.5 | 0.2 | 152.2 | 7.1 | 699.5 | 0.5 |
| 13.0 | 0.2 | 207.1 | 6.8 | 634.3 | 0.4 |
| 13.4 | 0.1 | 868.4 | 6.6 | 5321.2 | 3.6 |
| 13.8 | 0.1 | 3273.3 | 6.4 | 20057.1 | 13.6 |
| 14.7 | 0.1 | 30.2 | 6.0 | 185.3 | 0.1 |
| 15.9 | 0.1 | 7.8 | 5.6 | 48.0 | 0.0 |
| 16.2 | 0.1 | 52.0 | 5.5 | 318.6 | 0.2 |
| 17.8 | 0.2 | 506.6 | 5.0 | 2328.1 | 1.6 |
| 18.4 | 0.1 | 102.2 | 4.8 | 626.3 | 0.4 |
| 19.3 | 0.1 | 85.3 | 4.6 | 448.1 | 0.3 |
| 20.2 | 0.1 | 24120.6 | 4.4 | 147797.7 | 100.0 |
| 20.7 | 0.1 | 135.2 | 4.3 | 828.2 | 0.6 |

TABLE 10-continued

XRPD Peak Data for Compound 1 Fumarate Form FB

| Pos. [°2θ] | FWHM Left [°2θ] | Area [cts*°2θ] | d-spacing [Å] | Height [cts] | Rel. Int. [%] |
|---|---|---|---|---|---|
| 21.1 | 0.1 | 104.2 | 4.2 | 638.7 | 0.4 |
| 21.2 | 0.1 | 85.5 | 4.2 | 628.5 | 0.4 |
| 22.3 | 0.2 | 38.0 | 4.0 | 174.6 | 0.1 |
| 23.1 | 0.1 | 270.2 | 3.8 | 1655.6 | 1.1 |
| 23.5 | 0.1 | 1093.1 | 3.8 | 8037.4 | 5.4 |
| 24.2 | 0.1 | 316.6 | 3.7 | 2328.0 | 1.6 |
| 25.1 | 0.1 | 1032.5 | 3.5 | 7592.1 | 5.1 |
| 26.1 | 0.1 | 85.6 | 3.4 | 629.7 | 0.4 |
| 26.3 | 0.1 | 246.2 | 3.4 | 1508.5 | 1.0 |
| 27.0 | 0.1 | 22016.7 | 3.3 | 134906.2 | 91.3 |
| 27.7 | 0.2 | 408.1 | 3.2 | 1250.3 | 0.9 |
| 28.6 | 0.2 | 73.0 | 3.1 | 335.3 | 0.2 |
| 29.2 | 0.2 | 47.6 | 3.1 | 218.9 | 0.2 |
| 29.6 | 0.1 | 1056.9 | 3.0 | 6476.2 | 4.4 |
| 30.2 | 0.1 | 28.5 | 3.0 | 174.7 | 0.1 |
| 31.0 | 0.1 | 102.4 | 2.9 | 537.6 | 0.4 |
| 31.7 | 0.1 | 256.7 | 2.8 | 1573.0 | 1.1 |
| 32.6 | 0.1 | 24.5 | 2.7 | 150.0 | 0.1 |
| 32.8 | 0.1 | 122.3 | 2.7 | 749.7 | 0.5 |
| 33.1 | 0.1 | 111.4 | 2.7 | 819.1 | 0.6 |
| 33.9 | 0.1 | 395.1 | 2.6 | 2905.2 | 2.0 |
| 34.4 | 0.1 | 257.4 | 2.6 | 1893.0 | 1.3 |
| 35.0 | 0.2 | 25.8 | 2.6 | 95.0 | 0.1 |
| 35.3 | 0.1 | 37.1 | 2.5 | 194.8 | 0.1 |
| 35.6 | 0.2 | 95.5 | 2.5 | 438.8 | 0.3 |
| 36.1 | 0.1 | 112.4 | 2.5 | 688.5 | 0.5 |
| 36.5 | 0.2 | 168.2 | 2.5 | 773.1 | 0.5 |
| 36.8 | 0.2 | 107.5 | 2.4 | 493.8 | 0.3 |
| 37.4 | 0.2 | 58.1 | 2.4 | 213.8 | 0.1 |
| 37.9 | 0.1 | 132.2 | 2.4 | 809.9 | 0.6 |
| 38.6 | 0.2 | 42.2 | 2.3 | 129.3 | 0.1 |
| 39.0 | 0.1 | 60.0 | 2.3 | 367.4 | 0.3 |

A DSC thermogram for Form FB is shown in FIG. 30 (FIG. 30). The thermogram is characterized by endotherm peaks at temperatures of about 96° C., about 139° C., and about 146° C. FIG. 31 (FIG. 31) shows a thermogravimetric analysis (TGA) thermogram of Compound 1 Fumarate Form FB. FIG. 32 (FIG. 32) shows a dynamic vapor sorption (DVS) isotherm of Form FB.

Example 12. Compound 1 Citrate

The XRPD spectrum for Compound 1 Citrate is provided in FIG. 33 (FIG. 33) and the corresponding peak data is provided below in Table 11.

TABLE 11

XRPD Peak Data for Compound 1 Citrate

| Pos. [°2θ] | FWHM Left [°2θ] | Area [cts*°2θ] | d-spacing [Å] | Height [cts] | Rel. Int. [%] |
|---|---|---|---|---|---|
| 6.5 | 0.1 | 638.9 | 13.6 | 3915.0 | 91.1 |
| 10.2 | 0.1 | 70.4 | 8.7 | 517.3 | 12.0 |
| 11.5 | 0.2 | 41.4 | 7.7 | 126.8 | 3.0 |
| 13.0 | 0.2 | 226.0 | 6.8 | 1038.5 | 24.2 |
| 13.9 | 0.2 | 43.2 | 6.4 | 198.5 | 4.6 |
| 14.5 | 0.1 | 160.4 | 6.1 | 1179.6 | 27.5 |
| 15.5 | 0.2 | 1052.1 | 5.7 | 4297.6 | 100.0 |
| 16.5 | 0.1 | 152.9 | 5.4 | 936.6 | 21.8 |
| 17.3 | 0.1 | 272.8 | 5.1 | 1671.6 | 38.9 |
| 17.8 | 0.1 | 414.1 | 5.0 | 3044.9 | 70.9 |
| 18.9 | 0.1 | 103.1 | 4.7 | 541.2 | 12.6 |
| 19.4 | 0.1 | 472.0 | 4.6 | 3470.7 | 80.8 |
| 20.4 | 0.1 | 778.0 | 4.3 | 4086.1 | 95.1 |
| 20.8 | 0.1 | 226.2 | 4.3 | 1385.8 | 32.3 |
| 21.2 | 0.1 | 511.2 | 4.2 | 3132.6 | 72.9 |
| 21.5 | 0.2 | 290.8 | 4.1 | 1336.5 | 31.1 |
| 22.0 | 0.2 | 416.0 | 4.0 | 1699.3 | 39.5 |
| 23.1 | 0.1 | 249.5 | 3.9 | 1528.8 | 35.6 |
| 24.3 | 0.2 | 85.8 | 3.7 | 394.4 | 9.2 |
| 24.6 | 0.1 | 87.3 | 3.6 | 641.8 | 14.9 |
| 25.1 | 0.1 | 161.9 | 3.5 | 992.2 | 23.1 |
| 26.0 | 0.1 | 569.5 | 3.4 | 3489.4 | 81.2 |
| 27.0 | 0.1 | 39.3 | 3.3 | 241.0 | 5.6 |
| 27.2 | 0.1 | 40.4 | 3.3 | 247.3 | 5.8 |
| 27.5 | 0.1 | 195.6 | 3.2 | 1198.4 | 27.9 |
| 27.9 | 0.1 | 85.5 | 3.2 | 523.6 | 12.2 |
| 28.5 | 0.2 | 91.5 | 3.1 | 420.3 | 9.8 |
| 29.2 | 0.1 | 184.4 | 3.1 | 1129.8 | 26.3 |
| 30.4 | 0.2 | 90.1 | 2.9 | 413.9 | 9.6 |
| 30.8 | 0.2 | 47.3 | 2.9 | 217.4 | 5.1 |
| 31.4 | 0.1 | 124.7 | 2.8 | 763.9 | 17.8 |
| 32.5 | 0.1 | 56.1 | 2.8 | 412.5 | 9.6 |
| 33.3 | 0.1 | 211.8 | 2.7 | 1297.9 | 30.2 |
| 33.8 | 0.1 | 46.2 | 2.7 | 283.3 | 6.6 |
| 34.8 | 0.2 | 91.0 | 2.6 | 278.6 | 6.5 |
| 35.3 | 0.1 | 138.9 | 2.5 | 850.8 | 19.8 |
| 36.5 | 0.1 | 136.9 | 2.5 | 1006.8 | 23.4 |
| 36.8 | 0.1 | 89.2 | 2.4 | 656.2 | 15.3 |
| 37.4 | 0.2 | 118.6 | 2.4 | 435.9 | 10.1 |
| 38.3 | 0.1 | 50.5 | 2.3 | 309.5 | 7.2 |

A DSC thermogram for Compound 1 Citrate is shown in FIG. 34 (FIG. 34). The thermogram is characterized by an endotherm peak at a temperature of about 142° C. FIG. 35 (FIG. 35) shows a thermogravimetric analysis (TGA) thermogram of Compound 1 Citrate. FIG. 36 (FIG. 36) shows a dynamic vapor sorption (DVS) isotherm of Compound 1 Citrate.

Example 13. Compound 1 Succinate

The XRPD spectrum for Compound 1 Succinate is provided in FIG. 37 (FIG. 37) and the corresponding peak data is provided below in Table 12.

TABLE 12

XRPD Peak Data for Compound 1 Succinate

| Pos. [°2θ] | FWHM Left [°2θ] | Area [cts*°2θ] | d-spacing [Å] | Height [cts] | Rel. Int. [%] |
|---|---|---|---|---|---|
| 6.6 | 0.1 | 78.4 | 13.3 | 576.5 | 11.0 |
| 9.0 | 0.2 | 59.6 | 9.8 | 273.7 | 5.2 |
| 11.5 | 0.1 | 79.6 | 7.7 | 487.5 | 9.3 |
| 12.8 | 0.1 | 223.3 | 6.9 | 1641.8 | 31.4 |
| 13.9 | 0.1 | 690.8 | 6.4 | 5079.1 | 97.2 |
| 14.2 | 0.1 | 47.7 | 6.2 | 292.3 | 5.6 |
| 16.0 | 0.1 | 81.8 | 5.5 | 501.4 | 9.6 |
| 16.4 | 0.1 | 40.7 | 5.4 | 249.1 | 4.8 |
| 16.8 | 0.1 | 40.4 | 5.3 | 247.3 | 4.7 |
| 17.2 | 0.1 | 35.5 | 5.1 | 217.3 | 4.2 |
| 17.7 | 0.2 | 87.6 | 5.0 | 268.5 | 5.1 |
| 18.3 | 0.1 | 39.8 | 4.9 | 243.6 | 4.7 |
| 19.2 | 0.1 | 79.4 | 4.6 | 417.1 | 8.0 |
| 19.8 | 0.1 | 852.5 | 4.5 | 5223.5 | 100.0 |
| 21.1 | 0.1 | 97.2 | 4.2 | 595.9 | 11.4 |
| 22.9 | 0.1 | 343.9 | 3.9 | 2528.7 | 48.4 |
| 23.3 | 0.1 | 304.5 | 3.8 | 1599.1 | 30.6 |
| 23.8 | 0.1 | 80.9 | 3.7 | 594.6 | 11.4 |
| 24.5 | 0.1 | 73.2 | 3.6 | 448.7 | 8.6 |
| 25.0 | 0.1 | 148.6 | 3.6 | 910.6 | 17.4 |

TABLE 12-continued

XRPD Peak Data for Compound 1 Succinate

| Pos. [°2θ] | FWHM Left [°2θ] | Area [cts*°2θ] | d-spacing [Å] | Height [cts] | Rel. Int. [%] |
|---|---|---|---|---|---|
| 25.2 | 0.1 | 177.8 | 3.5 | 1307.4 | 25.0 |
| 25.4 | 0.1 | 340.4 | 3.5 | 1787.6 | 34.2 |
| 25.9 | 0.1 | 50.0 | 3.4 | 306.3 | 5.9 |
| 26.1 | 0.1 | 84.1 | 3.4 | 618.3 | 11.8 |
| 26.5 | 0.1 | 913.2 | 3.4 | 4796.2 | 91.8 |
| 27.2 | 0.2 | 118.0 | 3.3 | 542.4 | 10.4 |
| 28.3 | 0.1 | 69.6 | 3.1 | 426.7 | 8.2 |
| 29.3 | 0.1 | 184.3 | 3.0 | 1129.3 | 21.6 |
| 30.4 | 0.2 | 50.7 | 2.9 | 155.2 | 3.0 |
| 31.7 | 0.1 | 45.2 | 2.8 | 277.0 | 5.3 |
| 32.3 | 0.2 | 51.0 | 2.8 | 234.3 | 4.5 |
| 33.2 | 0.1 | 53.2 | 2.7 | 325.9 | 6.2 |
| 33.4 | 0.1 | 47.8 | 2.7 | 293.1 | 5.6 |
| 33.9 | 0.2 | 40.5 | 2.6 | 186.3 | 3.6 |
| 34.8 | 0.2 | 52.5 | 2.6 | 160.9 | 3.1 |
| 35.8 | 0.2 | 61.6 | 2.5 | 188.8 | 3.6 |
| 36.5 | 0.2 | 62.0 | 2.5 | 285.0 | 5.5 |
| 37.4 | 0.2 | 81.7 | 2.4 | 250.3 | 4.8 |
| 38.9 | 0.1 | 43.8 | 2.3 | 268.1 | 5.1 |
| 39.6 | 0.2 | 51.2 | 2.3 | 235.1 | 4.5 |

A DSC thermogram for Compound 1 Succinate is shown in FIG. 38 (FIG. 38). The thermogram is characterized by an endotherm peak at a temperature of about 153° C. FIG. 39 (FIG. 39) shows a thermogravimetric analysis (TGA) thermogram of Compound 1 Succinate. FIG. 40 (FIG. 40) shows a dynamic vapor sorption (DVS) isotherm of Compound 1 Succinate.

Example 14. Compound 1 Glutarate

The XRPD spectrum for Compound 1 Glutarate is provided in FIG. 41 (FIG. 41) and the corresponding peak data is provided below in Table 13.

TABLE 13

XRPD Peak Data for Compound 1 Glutarate

| Pos. [°2θ] | FWHM Left [°2θ] | Area [cts*°2θ] | d-spacing [Å] | Height [cts] | Rel. Int. [%] |
|---|---|---|---|---|---|
| 9.1 | 0.1 | 487.6 | 9.7 | 3585.4 | 21.0 |
| 9.7 | 0.2 | 4.3 | 9.1 | 13.1 | 0.1 |
| 10.6 | 0.1 | 409.4 | 8.4 | 2150.4 | 12.6 |
| 11.3 | 0.2 | 7.3 | 7.8 | 33.6 | 0.2 |
| 11.9 | 0.2 | 28.2 | 7.4 | 129.6 | 0.8 |
| 12.7 | 0.1 | 7.5 | 7.0 | 55.1 | 0.3 |
| 14.2 | 0.1 | 37.5 | 6.2 | 230.0 | 1.4 |
| 15.0 | 0.2 | 31.0 | 5.9 | 142.4 | 0.8 |
| 15.9 | 0.1 | 74.0 | 5.6 | 388.5 | 2.3 |
| 16.8 | 0.1 | 85.0 | 5.3 | 520.6 | 3.1 |
| 18.2 | 0.1 | 2781.0 | 4.9 | 17040.5 | 100.0 |
| 18.6 | 0.1 | 18.4 | 4.8 | 134.9 | 0.8 |
| 19.0 | 0.1 | 503.2 | 4.7 | 3700.2 | 21.7 |
| 19.6 | 0.1 | 96.8 | 4.5 | 593.4 | 3.5 |
| 20.8 | 0.1 | 33.4 | 4.3 | 204.5 | 1.2 |
| 21.8 | 0.1 | 110.8 | 4.1 | 678.8 | 4.0 |
| 21.9 | 0.1 | 136.5 | 4.1 | 836.7 | 4.9 |
| 22.5 | 0.1 | 209.4 | 4.0 | 1539.6 | 9.0 |
| 23.1 | 0.2 | 58.2 | 3.8 | 214.0 | 1.3 |
| 23.6 | 0.1 | 17.4 | 3.8 | 106.3 | 0.6 |
| 25.0 | 0.2 | 97.3 | 3.6 | 446.9 | 2.6 |
| 25.3 | 0.1 | 39.1 | 3.5 | 239.3 | 1.4 |
| 25.8 | 0.1 | 135.9 | 3.4 | 999.2 | 5.9 |
| 26.4 | 0.1 | 74.2 | 3.4 | 545.5 | 3.2 |
| 27.4 | 0.1 | 368.3 | 3.2 | 2256.9 | 13.2 |
| 28.0 | 0.1 | 451.6 | 3.2 | 2767.2 | 16.2 |

TABLE 13-continued

XRPD Peak Data for Compound 1 Glutarate

| Pos. [°2θ] | FWHM Left [°2θ] | Area [cts*°2θ] | d-spacing [Å] | Height [cts] | Rel. Int. [%] |
|---|---|---|---|---|---|
| 28.5 | 0.1 | 25.9 | 3.1 | 190.2 | 1.1 |
| 29.5 | 0.1 | 19.8 | 3.0 | 121.5 | 0.7 |
| 30.0 | 0.1 | 56.1 | 3.0 | 412.6 | 2.4 |
| 30.3 | 0.1 | 10.1 | 3.0 | 61.6 | 0.4 |
| 31.5 | 0.2 | 27.9 | 2.8 | 85.5 | 0.5 |
| 32.9 | 0.2 | 40.1 | 2.7 | 123.0 | 0.7 |
| 33.8 | 0.1 | 32.2 | 2.6 | 197.0 | 1.2 |
| 35.2 | 0.1 | 42.2 | 2.6 | 258.5 | 1.5 |
| 35.6 | 0.2 | 26.2 | 2.5 | 80.1 | 0.5 |
| 36.8 | 0.1 | 148.0 | 2.4 | 1088.0 | 6.4 |
| 37.2 | 0.2 | 65.1 | 2.4 | 299.2 | 1.8 |
| 37.9 | 0.1 | 33.6 | 2.4 | 246.9 | 1.5 |
| 38.5 | 0.1 | 59.6 | 2.3 | 365.3 | 2.1 |
| 39.5 | 0.1 | 8.8 | 2.3 | 54.1 | 0.3 |

FIG. 42 (FIG. 42) shows a dynamic vapor sorption (DVS) isotherm of Compound 1 Glutarate.

Example 15. Compound 1 L-Malate

The XRPD spectrum for Compound 1 L-Malate is provided in FIG. 43 (FIG. 43) and the corresponding peak data is provided below in Table 14.

TABLE 14

XRPD Peak Data for Compound 1 L-Malate

| Pos. [°2θ] | FWHM Left [°2θ] | Area [cts*°2θ] | d-spacing [Å] | Height [cts] | Rel. Int. [%] |
|---|---|---|---|---|---|
| 11.9 | 0.1 | 37.7 | 7.4 | 231.0 | 2.6 |
| 13.1 | 0.1 | 93.8 | 6.8 | 689.9 | 7.8 |
| 13.5 | 0.2 | 1102.0 | 6.5 | 5064.2 | 57.0 |
| 14.4 | 0.1 | 97.7 | 6.2 | 718.5 | 8.1 |
| 15.2 | 0.2 | 171.4 | 5.8 | 787.6 | 8.9 |
| 16.0 | 0.1 | 59.5 | 5.5 | 312.4 | 3.5 |
| 16.6 | 0.1 | 58.5 | 5.3 | 429.9 | 4.8 |
| 17.0 | 0.1 | 69.6 | 5.2 | 512.0 | 5.8 |
| 17.7 | 0.1 | 121.5 | 5.0 | 744.3 | 8.4 |
| 18.1 | 0.1 | 73.3 | 4.9 | 449.4 | 5.1 |
| 18.8 | 0.2 | 1935.1 | 4.7 | 8893.1 | 100.0 |
| 19.8 | 0.1 | 49.1 | 4.5 | 300.6 | 3.4 |
| 20.9 | 0.1 | 43.5 | 4.3 | 320.2 | 3.6 |
| 22.4 | 0.2 | 179.9 | 4.0 | 826.6 | 9.3 |
| 22.9 | 0.2 | 105.8 | 3.9 | 486.1 | 5.5 |
| 23.8 | 0.1 | 539.5 | 3.7 | 2833.7 | 31.9 |
| 24.6 | 0.1 | 138.8 | 3.6 | 1020.8 | 11.5 |
| 24.8 | 0.2 | 856.5 | 3.6 | 3148.9 | 35.4 |
| 25.2 | 0.2 | 1082.7 | 3.5 | 4422.7 | 49.7 |
| 25.6 | 0.1 | 241.8 | 3.5 | 1269.7 | 14.3 |
| 26.2 | 0.1 | 217.6 | 3.4 | 1142.8 | 12.9 |
| 26.8 | 0.2 | 89.7 | 3.3 | 274.7 | 3.1 |
| 27.2 | 0.1 | 61.3 | 3.3 | 450.6 | 5.1 |
| 27.7 | 0.1 | 134.8 | 3.2 | 826.1 | 9.3 |
| 28.0 | 0.2 | 105.8 | 3.2 | 486.4 | 5.5 |
| 28.6 | 0.2 | 75.7 | 3.1 | 347.8 | 3.9 |
| 28.9 | 0.1 | 39.8 | 3.1 | 244.1 | 2.7 |
| 29.4 | 0.4 | 74.8 | 3.0 | 137.4 | 1.6 |
| 30.5 | 0.1 | 104.3 | 2.9 | 767.2 | 8.6 |
| 32.3 | 0.1 | 36.3 | 2.8 | 222.7 | 2.5 |
| 33.1 | 0.2 | 75.5 | 2.7 | 277.5 | 3.1 |
| 33.4 | 0.2 | 74.1 | 2.7 | 272.6 | 3.1 |
| 34.4 | 0.2 | 58.7 | 2.6 | 269.7 | 3.0 |
| 34.8 | 0.3 | 51.2 | 2.6 | 117.6 | 1.3 |
| 35.4 | 0.2 | 63.3 | 2.5 | 194.1 | 2.2 |
| 35.9 | 0.2 | 123.8 | 2.5 | 568.9 | 6.4 |
| 37.1 | 0.3 | 124.8 | 2.4 | 286.8 | 3.2 |
| 37.5 | 0.3 | 49.2 | 2.4 | 113.1 | 1.3 |

TABLE 14-continued

XRPD Peak Data for Compound 1 L-Malate

| Pos. [°2θ] | FWHM Left [°2θ] | Area [cts*°2θ] | d-spacing [Å] | Height [cts] | Rel. Int. [%] |
|---|---|---|---|---|---|
| 38.2 | 0.3 | 157.5 | 2.4 | 361.9 | 4.1 |
| 39.5 | 0.2 | 18.1 | 2.3 | 83.2 | 0.9 |

A DSC thermogram for Compound 1 L-Malate is shown in FIG. 44 (FIG. 44). The thermogram is characterized by an endotherm peak at a temperature of about 82° C. FIG. 45 (FIG. 45) shows a thermogravimetric analysis (TGA) thermogram of Compound 1 L-Malate. FIG. 46 (FIG. 46) shows a dynamic vapor sorption (DVS) isotherm of Compound 1 L-Malate.

Example 16. Compound 1 Besylate

The XRPD spectrum for Compound 1 Besylate is provided in FIG. 47 (FIG. 47) and the corresponding peak data is provided below in Table 15.

TABLE 15

XRPD Peak Data for Compound 1 Besylate

| Pos. [°2θ] | FWHM Left [°2θ] | Area [cts*°2θ] | d-spacing [Å] | Height [cts] | Rel. Int. [%] |
|---|---|---|---|---|---|
| 6.0 | 0.1 | 9260.8 | 14.6 | 56745.2 | 100.0 |
| 12.0 | 0.2 | 3664.6 | 7.4 | 16841.2 | 29.7 |
| 13.0 | 0.2 | 42.2 | 6.8 | 155.1 | 0.3 |
| 13.8 | 0.2 | 58.7 | 6.4 | 179.7 | 0.3 |
| 14.7 | 0.2 | 67.1 | 6.0 | 246.6 | 0.4 |
| 16.4 | 0.1 | 90.9 | 5.4 | 668.0 | 1.2 |
| 16.6 | 0.2 | 711.3 | 5.3 | 3269.0 | 5.8 |
| 16.9 | 0.1 | 54.1 | 5.2 | 331.6 | 0.6 |
| 18.1 | 0.1 | 73.6 | 4.9 | 451.0 | 0.8 |
| 18.6 | 0.1 | 81.6 | 4.8 | 600.1 | 1.1 |
| 19.0 | 0.1 | 102.1 | 4.7 | 750.5 | 1.3 |
| 19.4 | 0.1 | 70.5 | 4.6 | 518.7 | 0.9 |
| 20.3 | 0.2 | 91.9 | 4.4 | 281.6 | 0.5 |
| 21.2 | 0.1 | 101.0 | 4.2 | 742.6 | 1.3 |
| 21.4 | 0.1 | 94.2 | 4.1 | 692.3 | 1.2 |
| 22.2 | 0.1 | 126.7 | 4.0 | 931.6 | 1.6 |
| 23.2 | 0.1 | 160.2 | 3.8 | 1177.8 | 2.1 |
| 24.1 | 0.1 | 7880.7 | 3.7 | 48288.4 | 85.1 |
| 24.9 | 0.2 | 54.1 | 3.6 | 165.6 | 0.3 |
| 25.5 | 0.2 | 77.2 | 3.5 | 236.6 | 0.4 |
| 26.0 | 0.2 | 58.2 | 3.4 | 267.6 | 0.5 |
| 26.8 | 0.1 | 450.2 | 3.3 | 3310.2 | 5.8 |
| 28.6 | 0.2 | 31.5 | 3.1 | 115.8 | 0.2 |
| 29.6 | 0.2 | 24.0 | 3.0 | 110.1 | 0.2 |
| 30.3 | 0.1 | 1661.3 | 2.9 | 10179.2 | 17.9 |
| 31.9 | 0.2 | 174.8 | 2.8 | 803.5 | 1.4 |
| 34.0 | 0.1 | 47.0 | 2.6 | 345.3 | 0.6 |
| 34.6 | 0.2 | 26.0 | 2.6 | 119.4 | 0.2 |
| 35.5 | 0.1 | 52.8 | 2.5 | 323.7 | 0.6 |
| 36.0 | 0.1 | 67.0 | 2.5 | 410.6 | 0.7 |
| 36.6 | 0.2 | 108.9 | 2.5 | 333.6 | 0.6 |
| 37.4 | 0.1 | 119.7 | 2.4 | 880.4 | 1.6 |
| 38.4 | 0.1 | 107.9 | 2.3 | 661.2 | 1.2 |

A DSC thermogram for Compound 1 Besylate is shown in FIG. 48 (FIG. 48). The thermogram is characterized by an endotherm peak at a temperature of about 136° C. FIG. 49 (FIG. 49) shows a thermogravimetric analysis (TGA) thermogram of Compound 1 Besylate. FIG. 50 (FIG. 50) shows a dynamic vapor sorption (DVS) isotherm of Compound 1 Besylate.

Example 17. Stability Study

Each sample was stored at 60° C. and 60° C. 75% RH for 1 month. Each sample was measured at 20 days and 1 month by HPLC. HPLC conditions are described below.

Column: Waters XSelect CSH C18, 4.6×150 mm, 3.5 μm
MPA: 50 mM HClO4 in water (pH=3)
MPB: MeOH/acetonitrile (9:1)
Wavelength: 215 nm
Column Temp: 40° C.
Flow: 1 mL/min
Gradient:

| 0 min | 10% MPB |
|---|---|
| 12 min | 24% MPB |
| 20 min | 90% MPB |
| 20 min | 90% MPB |
| 21 min | 10% MPB |
| 31 min | 10% MPB |

The results of the stability are shown in Table 16 below.

TABLE 16

Stability Study Results

| | HCl | $H_3PO_4$ | L-Tartaric | Fumaric acid | Citric acid | Freebase |
|---|---|---|---|---|---|---|
| Initial | 98.94 | 99.20 | 99.10 | 99.48 | 99.08 | 98.28 |
| 20 day at 60° C. | 98.50 | 99.20 | 99.13 | 99.54 | 99.10 | 76.57 |
| 1 month at 60° C. | 98.89 | 99.23 | 99.14 | 99.60 | 99.16 | 62.18 |
| 20 days at 60° C. 75% RH | 99.07 | 99.20 | 99.23 | 99.67 | 98.34 | — |
| 1 month at 60° C. 75% RH | 99.05 | 99.24 | 99.23 | 99.64 | 97.73 | 5.83 |

The freebase (amorphous) of Compound 1 was unstable at 60° C. and 60° C. 75% RH. The other salts (Hydrochloride, Phosphate, L-tartrate, Fumarate, citrate) were stable.

Example 18. Phosphate Polymorph Screen

Compound 1 Phosphate was subjected to three forms of polymorph screening: solvent screening, slurry screening, and rapid cool screening. The procedures for each screening are provided below.

Solvent Screening:

Compound 1 Phosphate (5 mg) was put into a small glass vial and solvents were added until the sample was dissolved at 90° C. or boiling point. Maximum volume of solvent was 500 μL. The solution or suspension was heated for 1 h, allowed to cool undisturbed at room temperature overnight, and cooled at 5° C. for 3 days. Un-precipitated samples were opened and allowed to stand at room temperature until dryness (slow evaporation). The precipitated solids were filtered by sintering filter plate, and measured directly by XRPD on the plate.

Slurry Screening:

Compound 1 Phosphate (10 mg) was put into a small glass vial and organic solvents mixed with water were added. The samples were then suspended at room temperature or 50° C. and shaken for 4 to 10 days. The suspensions were filtered. The collected solids were analyzed by XRPD to determine polymorphic form.

Rapid Cool Screening:

Compound 1 Phosphate (10 mg) was dissolved at 90° C. or boiling point. The solution was cooled at 0° C. rapidly. After 1 h, solution was cooled at −20° C. for 3 days. The precipitated crystals were filtered. Recovered solids were analyzed by XRPD to determine polymorphic form.

From the screening studies (over 75 trials), only one polymorph (Compound 1 Phosphate as described in Example 5) was identified.

Example 19. Synthesis of Compound 1 and Compound 1 Phosphate

Step 1. Preparation of 1-(5-bromo-8-fluoroisochroman-1-yl)-N-methylmethanamine trifluoromethanesulfonate

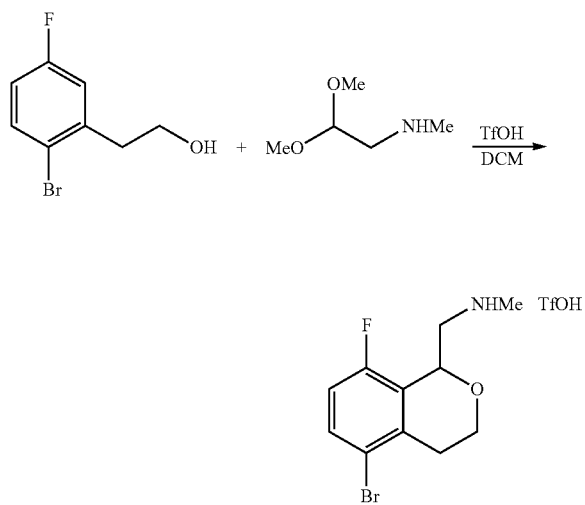

A solution of 2-(2-bromo-5-fluorophenyl)ethan-1-ol (200 g, 913 mmol) and N-methylaminoacetaldehyde dimethylacetal (130 g, 1091 mmol) in dichloromethane (300 mL) was cooled to 0° C. and trifluoromethanesulfonic acid (554 g, 3691 mmol) was added over 1 h while maintaining the temperature below 35° C. with external cooling. The mixture was warmed to 30° C. and stirred at 30° C. for 23 h. The mixture was cooled to 20° C. and methanol (33 mL), dichloromethane (1275 mL) and tert-butyl methyl ether (1358 mL) were added. The precipitate was collected by suction filtration. The solids were washed with a solution consisting of 1:1 (v/v) dichloromethane and tert-butyl methyl ether (1830 mL) and dried under vacuum (>28" Hg) at 45° C. for 21 h to give 1-(5-bromo-8-fluoroisochroman-1-yl)-N-methylmethanamine trifluoromethanesulfonate (339 g, 87% yield) as a tan powder. MS (ESI): m/z 274, 276 [M+H]$^+$; $^1$H-NMR (400 MHz, DMSO-$d_6$): [ppm 8.65 (br s, 1H), 8.54 (br s, 1H), 7.67 (dd, J=8.80, 5.28 Hz, 1H), 7.15 (dd, J=9.98, 8.80 Hz, 1H), 5.21 (dd, J=9.78, 2.35 Hz, 1H), 4.06 (dt, J=12.03, 5.92 Hz, 1H), 3.89 (dt, J=11.93, 5.18 Hz, 1H), 3.50-3.38 (m, 1H), 3.31 (br s, 1H), 2.73 (t, J=5.67 Hz, 2H), 2.64 (br s, 3H); $^{13}$C-NMR (100 MHz, DMSO-$d_6$): [ppm 158.91, 156.48, 136.20, 136.16, 132.57, 132.48, 123.37, 123.20, 119.20, 119.17, 115.34, 115.10, 66.59, 59.63, 49.09, 49.04, 33.01, 28.75, 28.73.

Step 2. Preparation of (R)-1-(8-fluoroisochroman-1-yl)-N-methylmethanaminium (2R,3R)-2,3-bis(benzoyloxy)-3-carboxypropanoate

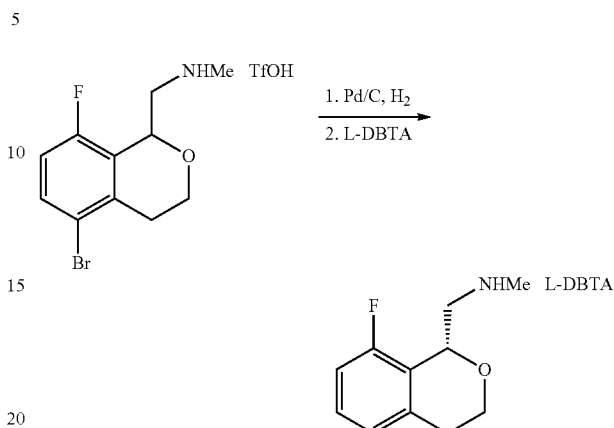

A solution of 1-(5-bromo-8-fluoroisochroman-1-yl)-N-methylmethanamine trifluoromethanesulfonate (300 g, 707 mmol), palladium, 10 wt. % (dry basis) on activated carbon, 50% water (1.2 g), methanol (1006 mL) and 5 wt. % aq. potassium carbonate (1059 g) was hydrogenated at 25° C., 5 bar hydrogen pressure, for 1 h. The pressure was released, and the solution was filtered through a 5-micron disposable polypropylene in-line filter cartridge which was rinsed with a solution consisting of 1:1 (v/v) methanol and water (540 g). The solution was concentrated under reduced pressure to a final volume of 1200 mL. To the mixture was added tert-butyl methyl ether (893 mL) and 20 wt. % aq. potassium hydroxide (185 mL). The mixture was stirred for 10 minutes at 20° C. The stirring was stopped and the phases were separated. The aqueous phase was extracted with tert-butyl methyl ether (649 mL). The combined organic layers were concentrated under reduced pressure to a final volume of 450 mL. To the solution was added SDA (specially denatured alcohol) 3A ethanol (851 mL). The solution was concentrated under reduced pressure to a final volume of 675 mL. The solution (solution A) was held for further processing. In a separate vessel was added dibenzoyl-L-tartaric acid (252 g, 703 mmol), SDA 3A ethanol (2704 mL) and deionized water (69 mL). The mixture was heated to approximately 70° C. and solution A was added over 9 minutes, which resulted in precipitation. The mixture was stirred at approximately 70° C. for 45 minutes then cooled to 20° C. over approximately 2.5 h. The precipitate was collected by suction filtration. The solids were washed with SDA 3A ethanol (960 mL) and dried under vacuum (>28" Hg) at 45° C. for 17 h to give (R)-1-(8-fluoroisochroman-1-yl)-N-methylmethanaminium (2R,3R)-2,3-bis(benzoyloxy)-3-carboxypropanoate (181 g, 46% yield) as a white solid.

Alternative resolving agents, other than dibenzoyl-L-tartaric acid were explored, but most were found to not be suitable or practical for various reasons (e.g., availability, cost, performance). Such resolving agents include (R)-mandelic acid, L-tartaric acid, and L-malic acid. However, N-acetyl-D-leucine was found to provide the desired (R)-isomer in approximately 91:9 ratio and approximately 17% yield.

The optical purity of intermediate (R)-1-(8-fluoroisochroman-1-yl)-N-methylmethanaminium (2R,3R)-2,3-bis(benzoyloxy)-3-carboxypropanoate was enriched to 96.4% de by performing the following recrystallization procedure.

To (R)-1-(8-fluoroisochroman-1-yl)-N-methylmethanaminium (2R,3R)-2,3-bis(benzoyloxy)-3-carboxypropanoate (177 g, 320 mmol) was added methanol (3578 mL) and the solution was concentrated at atmospheric pressure to a final volume of 1326 mL which resulted in crystallization. The temperature of the slurry was adjusted to approximately 62° C. and stirring was continued for 20 min. The slurry was cooled to 10° C. over 2 h and the solids were collected by suction filtration. The solids were washed with cold (10° C.) methanol (675 mL) and dried under vacuum (>28" Hg) at 45° C. overnight to give (R)-1-(8-fluoroisochroman-1-yl)-N-methylmethanaminium (2R,3R)-2,3-bis(benzoyloxy)-3-carboxypropanoate (136 g, 77% yield) as a white solid. MS (ESI): m/z 196 [M+H]$^+$; $^1$H-NMR (400 MHz, DMSO-d$_6$): [ppm 8.03-7.85 (m, 4H), 7.70-7.55 (m, 2H), 7.54-7.43 (m, 4H), 7.27 (td, J=7.92, 6.06 Hz, 1H), 7.11-6.89 (m, 2H), 5.67 (s, 2H), 5.15 (dd, J=9.98, 2.93 Hz, 1H), 3.92 (ddd, J=11.84, 7.34, 4.70 Hz, 1H), 3.69 (dt, J=11.54, 4.99 Hz, 1H), 3.36-3.24 (m, 1H), 3.22-3.04 (m, 1H), 2.80-2.61 (m, 2H), 2.54 (s, 3H); $^{13}$C-NMR (100 MHz, DMSO-d$_6$): [ppm 168.21, 164.89, 159.56, 157.13, 136.87, 136.82, 133.37, 129.60, 129.23, 128.88, 128.80, 128.65, 125.10, 125.07, 120.58, 120.43, 114.57, 113.07, 112.87, 72.47, 66.71, 59.65, 49.22, 49.17, 32.62, 27.28, 27.26.

Step 3. Preparation of (R)-1-(8-fluoroisochroman-1-yl)-N-methylmethanamine phosphate

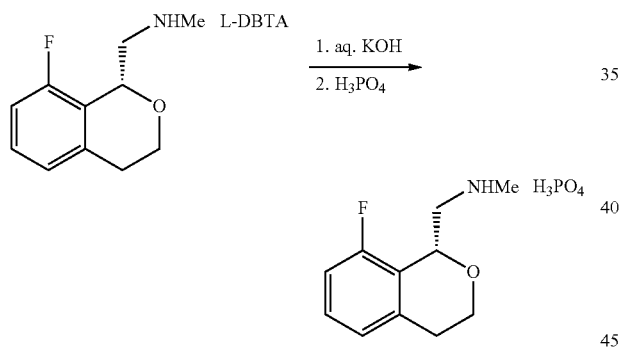

To a mixture of compound (R)-1-(8-fluoroisochroman-1-yl)-N-methylmethanaminium (2R,3R)-2,3-bis(benzoyloxy)-3-carboxypropanoate (75 g, 135.5 mmol) and tert-butyl methyl ether (223 mL) was added a solution consisting of 14 wt. % aq. potassium hydroxide (120 mL) and sodium chloride (15 g). The mixture was stirred for 10 minutes at 23-25° C. The stirring was stopped and the phases were separated. The aqueous phase was extracted with tert-butyl methyl ether (2×78 mL). The combined organic layers were concentrated under reduced pressure to a final volume of 90 mL. The solution was cooled to approximately 48° C. and acetonitrile (288 ml) was added. The solution was concentrated at atmospheric pressure to a final volume of approx. 210 mL. The mixture was cooled to 20° C. and acetonitrile (97 mL) and DI water (23 mL) were added. To this was added at 20° C. a solution consisting of 87% by weight aq. H$_3$PO$_4$ (16.9 g) and acetonitrile (81 mL). The product precipitated during the addition. The slurry was stirred for 3 h at 20° C. and the solids were collected by suction filtration. The solids were washed with a solution consisting of acetonitrile (135 mL) and DI water (8 mL) and dried under vacuum (>28" Hg) at 55° C. overnight to give (R)-1-(8-fluoroisochroman-1-yl)-N-methylmethanamine phosphate (36 g, 89% yield) as a white crystalline solid, which is Compound 1 Phosphate as characterized in Example 5. MS (ESI): m/z 196 [M+H]$^+$; $^1$H-NMR (400 MHz, D$_2$O): [ppm 7.27 (td, J=7.83, 5.87 Hz, 1H), 7.03 (d, J=7.25 Hz, 1H), 6.97 (dd, J=10.37, 8.80 Hz, 1H), 5.25 (t, J=5.87 Hz, 1H), 4.04 (dt, J=11.74, 5.87 Hz, 1H), 3.91-3.80 (m, 1H), 3.47 (d, J=5.87 Hz, 2H); 2.83 (t, J=5.48 Hz, 2H), 2.75 (s, 3H); $^{13}$C-NMR (100 MHz, D$_2$O with 5% methanol-d$_4$): [ppm 161.09, 158.67, 138.10, 138.07, 130.51, 130.42, 126.19, 126.16, 120.28, 120.13, 114.37, 114.17, 68.33, 62.15, 51.39, 51.34, 34.05, 28.38, 28.35.

Step 4. Recrystallization of (R)-1-(8-fluoroisochroman-1-yl)-N-methylmethanamine phosphate Using Water Acetone

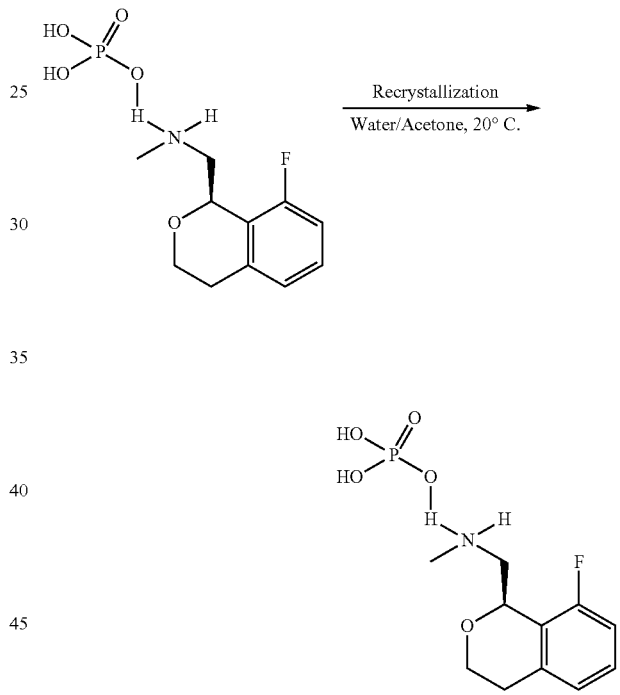

19.5 g of the product of (R)-1-(8-fluoroisochroman-1-yl)-N-methylmethanamine phosphate from step 3 was dissolved in 70 g water at 20° C., and then 30 g acetone was charged into the process stream to make the 16.3 wt % starting solution. The solution passed through the polish filter to remove any insoluble matters. Then dosing 600 g acetone into the solution within around 1 hour. The product crystallized out during the addition. The slurry was stirred at least 30 min at 20° C. and the solids were collected by suction filtration. The solids were washed with a binary solvents acetone (54 g) and DI water (6 g) and dried under vacuum (>28" Hg) at 55° C. overnight to give (R)-1-(8-fluoroisochroman-1-yl)-N-methylmethanamine phosphate (18.1 g, 93% yield) as a white crystalline solid.

Step 4. Recrystallization of (R)-1-(8-fluoroisochroman-1-yl)-N-methylmethanamine phosphate Using Water Acetonitrile

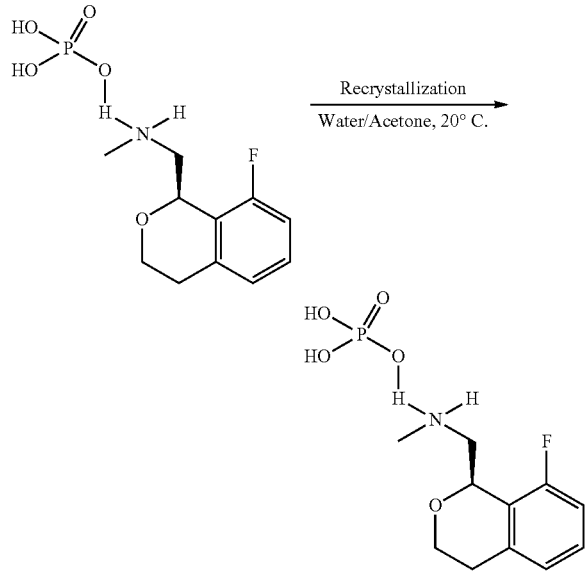

35.0 g of the product of (R)-1-(8-fluoroisochroman-1-yl)-N-methylmethanamine phosphate from step 3 was dissolved in 70 g water at 20° C., and then 30 g acetonitrile was charged into the process stream to make the 25.9 wt % starting solution. The solution passed through the polish filter to remove any insoluble matters. Then dosing 600 g acetonitrile into the solution within around 1 hour. The product crystallized out during the addition. The slurry was stirred at least 30 min at 20° C. and the solids were collected by suction filtration. The solids were washed with a binary solvents acetonitrile (90 g) and DI water (10 g) and dried under vacuum (>28" Hg) at 55° C. overnight to give (R)-1-(8-fluoroisochroman-1-yl)-N-methylmethanamine phosphate (31.2 g, 89% yield) as a white crystalline solid.

Various preferred embodiments [A] to [DY] of the invention can be described in the text below:

EMBODIMENT A

A salt, which is:
(R)-1-(8-fluoroisochroman-1-yl)-N-methylmethanamine phosphate (Compound 1 Phosphate);
(R)-1-(8-fluoroisochroman-1-yl)-N-methylmethanamine L-tartrate (Compound 1 L-Tartrate);
(R)-1-(8-fluoroisochroman-1-yl)-N-methylmethanamine D-tartrate (Compound 1 D-Tartrate);
(R)-1-(8-fluoroisochroman-1-yl)-N-methylmethanamine fumarate (Compound 1 Fumarate);
(R)-1-(8-fluoroisochroman-1-yl)-N-methylmethanamine citrate (Compound 1 Citrate);
(R)-1-(8-fluoroisochroman-1-yl)-N-methylmethanamine succinate (Compound 1 Succinate);
(R)-1-(8-fluoroisochroman-1-yl)-N-methylmethanamine glutarate (Compound 1 Glutarate);
(R)-1-(8-fluoroisochroman-1-yl)-N-methylmethanamine L-malate (Compound 1 L-Malate);
(R)-1-(8-fluoroisochroman-1-yl)-N-methylmethanamine besylate (Compound 1 Besylate); or
(R)-1-(8-fluoroisochroman-1-yl)-N-methylmethanamine tosylate (Compound 1 Tosylate);
or a hydrate or solvate thereof.

EMBODIMENT B

The salt of Embodiment [B] above, or according to other embodiments of the invention, wherein the salt is a solid form.

EMBODIMENT C

The salt of Embodiment [A] or [B] above, or according to other embodiments of the invention, wherein the salt is (R)-1-(8-fluoroisochroman-1-yl)-N-methylmethanamine phosphate (Compound 1 Phosphate).

EMBODIMENT D

The salt of Embodiment [C] above, or according to other embodiments of the invention, wherein Compound 1 Phosphate is crystalline.

EMBODIMENT E

The salt of Embodiment [D] above, or according to other embodiments of the invention, wherein the salt has characteristic XRPD peaks in terms of 2θ selected from 4.6°±0.2°, 9.10°±0.2°, and 18.2°±0.2°.

EMBODIMENT F

The salt of Embodiment [D] above, or according to other embodiments of the invention, wherein the salt has at least one characteristic XRPD peak in terms of 2θ selected from 4.6°±0.2°, 9.1°±0.2°, 15.7°±0.2°, 18.2°±0.2°, 22.3°±0.2°, 22.8°±0.2°, and 24.8°±0.2°.

EMBODIMENT G

The salt of Embodiment [D] above, or according to other embodiments of the invention, wherein the salt has at least two characteristic XRPD peaks in terms of 2θ selected from 4.6°±0.2°, 9.1°±0.2°, 15.7°±0.2°, 18.2°±0.2°, 22.3°±0.2°, 22.8°±0.2°, and 24.8°±0.2°.

EMBODIMENT H

The salt of Embodiment [D] above, or according to other embodiments of the invention, wherein the salt has at least three characteristic XRPD peaks in terms of 2θ selected from 4.6°±0.2°, 9.1°±0.2°, 15.7°±0.2°, 18.2°±0.2°, 22.3°±0.2°, 22.8°±0.2°, and 24.8°±0.2°.

EMBODIMENT I

The salt of any one of Embodiments [D] through [H] above, or according to other embodiments of the invention, wherein the salt has an XRPD pattern with characteristic peaks as substantially shown in FIG. 6 (FIG. 6).

EMBODIMENT J

The salt of any one of Embodiments [D] through [I] above, or according to other embodiments of the invention, wherein the salt has an endotherm peak at a temperature of about 213° C.

EMBODIMENT K

The salt of any one of Embodiments [D] through [J] above, or according to other embodiments of the invention, wherein the salt has a DSC thermogram substantially as depicted in FIG. 7 (FIG. 7).

EMBODIMENT L

The salt of any one of Embodiments [D] through [K] above, or according to other embodiments of the invention, wherein the salt has a DVS isotherm substantially as depicted in FIG. 9 (FIG. 9).

EMBODIMENT M

The salt of Embodiment [A] or [B] above, or according to other embodiments of the invention, wherein the salt is (R)-1-(8-fluoroisochroman-1-yl)-N-methylmethanamine L-tartrate (Compound 1 L-Tartrate).

EMBODIMENT N

The salt of Embodiment [M] above, or according to other embodiments of the invention, wherein Compound 1 L-tartrate is crystalline.

EMBODIMENT O

The salt of Embodiment [N] above, or according to other embodiments of the invention, having Form LA.

EMBODIMENT P

The salt of Embodiment [O] above, or according to other embodiments of the invention, wherein Form LA has characteristic XRPD peaks in terms of 2θ selected from 12.1°±0.2°, 18.1°±0.2°, and 24.2°±0.2°.

EMBODIMENT Q

The salt of Embodiment [N] or [O] above, or according to other embodiments of the invention, wherein Form LA has an XRPD pattern with characteristic peaks as substantially shown in FIG. 10 (FIG. 10).

EMBODIMENT R

The salt of Embodiment [N] above, or according to other embodiments of the invention, having Form LB.

EMBODIMENT S

The salt of Embodiment [R] above, or according to other embodiments of the invention, wherein Form LB has characteristic XRPD peaks in terms of 2θ selected from 18.7°±0.2°, 25.0°±0.2°, and 31.4°±0.2°.

EMBODIMENT T

The salt of Embodiment [R] or [S] above, or according to other embodiments of the invention, wherein Form LB has an XRPD pattern with characteristic peaks as substantially shown in FIG. 14 (FIG. 14).

EMBODIMENT U

The salt of Embodiment [N] above, or according to other embodiments of the invention, having Form LC.

EMBODIMENT V

The salt of Embodiment [U] above, or according to other embodiments of the invention, wherein Form LC has characteristic XRPD peaks in terms of 2θ selected from 12.2°±0.2°, 16.5°±0.2°, and 24.8°±0.2°.

EMBODIMENT W

The salt of Embodiment [U] or [V] above, or according to other embodiments of the invention, wherein Form LC has an XRPD pattern with characteristic peaks as substantially shown in FIG. 16 (FIG. 16).

EMBODIMENT X

The salt of Embodiment [A] or [B] above, or according to other embodiments of the invention, wherein the salt is (R)-1-(8-fluoroisochroman-1-yl)-N-methylmethanamine D-tartrate (Compound 1 D-tartrate).

EMBODIMENT Y

The salt of Embodiment [X] above, or according to other embodiments of the invention, wherein Compound 1 D-tartrate is crystalline.

EMBODIMENT Z

The salt of Embodiment [Y] above, or according to other embodiments of the invention, wherein the salt has characteristic XRPD peaks in terms of 2θ selected from 11.9°±0.2°, 16.9°±0.2°, and 17.9°±0.2°.

EMBODIMENT AA

The salt of Embodiment [Y] or [Z] above, or according to other embodiments of the invention, wherein the salt has an XRPD pattern with characteristic peaks as substantially shown in FIG. 20 (FIG. 20).

EMBODIMENT AB

The salt of Embodiment [A] or [B] above, or according to other embodiments of the invention, wherein the salt is (R)-1-(8-fluoroisochroman-1-yl)-N-methylmethanamine fumarate (Compound 1 L-Fumarate).

EMBODIMENT AC

The salt of Embodiment [AB] above, or according to other embodiments of the invention, wherein Compound 1 Fumarate is crystalline.

EMBODIMENT AD

The salt of Embodiment [AC] above, or according to other embodiments of the invention, having Form FA.

EMBODIMENT AE

The Embodiment [AD] above, or according to other embodiments of the invention, wherein Form FA has characteristic XRPD peaks in terms of 2θ selected from 7.7°±0.2°, 14.2°±0.2°, and 15.2°±0.2°.

EMBODIMENT AF

The salt of Embodiment [AD] or [AE] above, or according to other embodiments of the invention, wherein Form FA has an XRPD pattern with characteristic peaks as substantially shown in FIG. 22 (FIG. 22).

EMBODIMENT AG

The salt of Embodiment [AC] above, or according to other embodiments of the invention, having Form FB.

EMBODIMENT AH

The salt of Embodiment [AG] above, or according to other embodiments of the invention, wherein Form FB has characteristic XRPD peaks in terms of 2θ selected from 6.7°±0.2°, 13.8°±0.2°, and 20.2°±0.2°.

EMBODIMENT AI

The salt of Embodiment [AG] or [AH] above, or according to other embodiments of the invention, wherein Form FB has an XRPD pattern with characteristic peaks as substantially shown in FIG. 26 (FIG. 26).

EMBODIMENT AJ

The salt of Embodiment [A] or [B] above, or according to other embodiments of the invention, wherein the salt is (R)-1-(8-fluoroisochroman-1-yl)-N-methylmethanamine citrate (Compound 1 Citrate).

EMBODIMENT AK

The salt of Embodiment [AJ] above, or according to other embodiments of the invention, wherein Compound 1 Citrate is crystalline.

EMBODIMENT AL

The Embodiment [AK] above, or according to other embodiments of the invention, wherein the salt has characteristic XRPD peaks in terms of 2θ selected from 6.5°±0.2°, 15.5°±0.2°, and 20.4°±0.2°.

EMBODIMENT AM

The salt of Embodiment [AK] or [AL] above, or according to other embodiments of the invention, wherein the salt has an XRPD pattern with characteristic peaks as substantially shown in FIG. 30 (FIG. 30).

EMBODIMENT AN

The salt of Embodiment [A] or [B] above, or according to other embodiments of the invention, wherein the salt is (R)-1-(8-fluoroisochroman-1-yl)-N-methylmethanamine succinate (Compound 1 Succinate).

EMBODIMENT AO

The salt of Embodiment [AN] above, or according to other embodiments of the invention, wherein Compound 1 Succinate is crystalline.

EMBODIMENT AP

The salt of Embodiment [AO] above, or according to other embodiments of the invention, wherein the salt has characteristic XRPD peaks in terms of 2θ selected from 6.6°±0.2°, 12.8°±0.2°, and 13.9°±0.2°.

EMBODIMENT AQ

The salt of Embodiment [AO] or [AP] above, or according to other embodiments of the invention, wherein the salt has an XRPD pattern with characteristic peaks as substantially shown in FIG. 34 (FIG. 34).

EMBODIMENT AR

The salt of Embodiment [A] or [B] above, or according to other embodiments of the invention, wherein the salt is (R)-1-(8-fluoroisochroman-1-yl)-N-methylmethanamine glutarate (Compound 1 Glutarate).

EMBODIMENT AS

The salt of Embodiment [AR] above, or according to other embodiments of the invention, wherein Compound 1 Glutarate is crystalline.

EMBODIMENT AT

The salt of Embodiment [AS] above, or according to other embodiments of the invention, wherein the salt has characteristic XRPD peaks in terms of 2θ selected from 9.1°±0.2°, 10.6°±0.2°, and 18.2°±0.2°.

EMBODIMENT AU

The salt of Embodiment [AS] or [AT] above, or according to other embodiments of the invention, wherein the salt has an XRPD pattern with characteristic peaks as substantially shown in FIG. 38 (FIG. 38).

EMBODIMENT AV

The salt of Embodiment [A] or [B] above, or according to other embodiments of the invention, wherein the salt is (R)-1-(8-fluoroisochroman-1-yl)-N-methylmethanamine L-malate (Compound 1 L-Malate).

EMBODIMENT AW

The salt of Embodiment [AV] above, or according to other embodiments of the invention, wherein Compound 1 L-Malate is crystalline.

EMBODIMENT AX

The salt of Embodiment [AW] above, or according to other embodiments of the invention, wherein the salt has characteristic XRPD peaks in terms of 2θ selected from 13.5°±0.2°, 18.8°±0.2°, and 25.2°±0.2°.

EMBODIMENT AY

The salt of Embodiment [AW] or [AX] above, or according to other embodiments of the invention, wherein the salt has an XRPD pattern with characteristic peaks as substantially shown in FIG. 40 (FIG. 40).

EMBODIMENT AZ

The salt of Embodiment [A] or [B] above, or according to other embodiments of the invention, wherein the salt is (R)-1-(8-fluoroisochroman-1-yl)-N-methylmethanamine besylate (Compound 1 Besylate).

EMBODIMENT BA

The salt of Embodiment [AZ] above, or according to other embodiments of the invention, wherein Compound 1 Besylate is crystalline.

EMBODIMENT BB

The salt of Embodiment [BA] above, or according to other embodiments of the invention, wherein the salt has characteristic XRPD peaks in terms of 2θ selected from 6.0°±0.2°, 12.0°±0.2°, and 24.10°±0.2°.

EMBODIMENT BC

The salt of Embodiment [BA] or [BB] above, or according to other embodiments of the invention, wherein the salt has an XRPD pattern with characteristic peaks as substantially shown in FIG. 44 (FIG. 44).

EMBODIMENT BD

The salt of Embodiment [A] above, or according to other embodiments of the invention, wherein the salt is (R)-1-(8-fluoroisochroman-1-yl)-N-methylmethanamine tosylate (Compound 1 Tosylate).

EMBODIMENT BE

A salt, which is: (R)-1-(8-fluoroisochroman-1-yl)-N-methylmethanamine hydrochloride (Compound 1 Hydrochloride); or a hydrate or solvate thereof, wherein the salt is crystalline and having Form HA or Form HB.

EMBODIMENT BF

The salt of Embodiment [BE] above, or according to other embodiments of the invention, having Form HA.

EMBODIMENT BG

The salt of Embodiment [BF] above, or according to other embodiments of the invention, wherein Form HA has characteristic XRPD peaks in terms of 2θ selected from 9.4°±0.2°, 11.4±0.2°, and 15.10°±0.2°.

EMBODIMENT BH

The salt of Embodiment [BF] above, or according to other embodiments of the invention, wherein Form HA has characteristic XRPD peaks in terms of 2θ selected from 9.4°±0.2°, 11.4±0.2°, 15.1°±0.2°, 17.2°±0.2°, and 17.6°±0.2°.

EMBODIMENT BI

The salt of Embodiment [BF] above, or according to other embodiments of the invention, wherein Form HA has at least one characteristic XRPD peak in terms of 2θ selected from 9.4°±0.2°, 11.4°±0.2°, 14.2°±0.2°, 15.1°±0.2°, 17.2°±0.2°, 17.6°±0.2°, and 27.0°±0.2°.

EMBODIMENT BJ

The salt of Embodiment [BF] above, or according to other embodiments of the invention, wherein Form HA has at least two characteristic XRPD peaks in terms of 2θ selected from 9.4°±0.2°, 11.4°±0.2°, 14.2°±0.2°, 15.1°±0.2°, 17.2°±0.2°, 17.6°±0.2°, and 27.0°±0.2°.

EMBODIMENT BK

The salt of Embodiment [BF] above, or according to other embodiments of the invention, wherein Form HA has at least three characteristic XRPD peaks in terms of 2θ selected from 9.4°±0.2°, 11.4°±0.2°, 14.2°±0.2°, 15.1°±0.2°, 17.2°±0.2°, 17.6°±0.2°, and 27.0°±0.2°.

EMBODIMENT BL

The salt of any one of Embodiments [BE] to [BK] above, or according to other embodiments of the invention, wherein Form HA has an XRPD pattern with characteristic peaks as substantially shown in FIG. 1 (FIG. 1).

EMBODIMENT BM

The salt of any one of Embodiments [BE] to [BL] above, or according to other embodiments of the invention, wherein Form HA has endotherm peaks at temperatures of about 99° C. and about 187° C.

EMBODIMENT BN

The salt of any one of Embodiments [BE] to [BM] above, or according to other embodiments of the invention, wherein Form HA has a DSC thermogram substantially as depicted in FIG. 2 (FIG. 2).

EMBODIMENT BO

The salt of any one of Embodiments [BE] to [BN] above, or according to other embodiments of the invention, wherein Form HA has a DVS isotherm substantially as depicted in FIG. 4 (FIG. 4).

EMBODIMENT BP

The salt of Embodiment [BE] above, or according to other embodiments of the invention, having Form HB.

EMBODIMENT BQ

The salt of Embodiment [BP] above, or according to other embodiments of the invention, wherein Form HB has characteristic XRPD peaks in terms of 2θ selected from 8.6°±0.2°, 9.6°±0.2°, and 10.3°±0.2°.

EMBODIMENT BR

The salt of Embodiment [BP] above, or according to other embodiments of the invention, wherein Form HB has characteristic XRPD peaks in terms of 2θ selected from 8.6°±0.2°, 9.6°±0.2°, 10.3°±0.2°, and 17.3°±0.2°.

EMBODIMENT BS

The salt of Embodiment [BP] above, or according to other embodiments of the invention, wherein Form HB has at least one characteristic XRPD peak in terms of 2θ selected from 8.6°±0.2°, 9.6°±0.2°, 10.3°±0.2°, 12.6°±0.2°, 14.7°±0.2°, 17.3°±0.2°, and 23.8°±0.2°.

EMBODIMENT BT

The salt of Embodiment [BP] above, or according to other embodiments of the invention, wherein Form HB has at least two characteristic XRPD peaks in terms of 2θ selected from 8.6°±0.2°, 9.6°±0.2°, 10.3°±0.2°, 12.6°±0.2°, 14.7°±0.2°, 17.3°±0.2°, and 23.8°±0.2°.

EMBODIMENT BU

The salt of Embodiment [BP] above, or according to other embodiments of the invention, wherein Form HB has at least three characteristic XRPD peaks in terms of 2θ selected from 8.6°±0.2°, 9.6°±0.2°, 10.3°±0.2°, 12.6°±0.2°, 14.7°±0.2°, 17.3°±0.2°, and 23.8°±0.2°.

EMBODIMENT BV

The salt of any one of Embodiments [BP] to [BU] above, or according to other embodiments of the invention, wherein Form HB has an XRPD pattern with characteristic peaks as substantially shown in FIG. 5 (FIG. 5).

EMBODIMENT BW

A pharmaceutical composition comprising the salt of any one of Embodiments [A] to [BV] above, or according to other embodiments of the invention, and a pharmaceutically acceptable excipient.

EMBODIMENT BX

A method for treating a neurological or psychiatric disease or disorder in a subject in need thereof, comprising administering to said subject an effective amount of the salt of any one of Embodiments [A] to [BV] above, or the pharmaceutical composition of

EMBODIMENT BW above, or according to other embodiments of the invention.

EMBODIMENT BY

The method according to Embodiment [BX] above, or according to other embodiments of the invention, wherein the neurological or psychiatric disease or disorder is depression, bipolar disorder, pain, schizophrenia, or other psychotic diseases, obsessive compulsive disorder, addiction, social disorder, attention deficit hyperactivity disorder, an anxiety disorder, a movement disorder, epilepsy, autism or cognitive disease or disorder.

EMBODIMENT BZ

The method according to Embodiment [BX] above, or according to other embodiments of the invention, wherein the neurological or psychiatric disease or disorder is depression.

EMBODIMENT CA

The method according to Embodiment [BZ] above, or according to other embodiments of the invention, wherein the depression is treatment-resistant depression (TRD), major depressive disorder (MDD), unipolar depression, bipolar depression or depression associated with another disease or disorder.

EMBODIMENT CB

The method according to Embodiment [BX] above, or according to other embodiments of the invention, wherein said neurological disease or disorder is selected from Alzheimer's disease and Parkinson's disease.

EMBODIMENT CC

The method according to Embodiment [CB] above, or according to other embodiments of the invention, wherein said Alzheimer's disease is Alzheimer's disease with agitation, Alzheimer's disease with aggression, Alzheimer's disease agitation or Alzheimer's disease with agitation aggression.

EMBODIMENT CD

A method of treating agitation in a subject in need thereof, comprising administering to said subject an effective amount of the salt of any one of Embodiments [A] to [BV] above, or the pharmaceutical composition of [Embodiment BW] above, or according to other embodiments of the invention.

EMBODIMENT CE

A method of treating agitation associated with a neurological or psychiatric disease or disorder in a subject in need thereof, comprising administering to said subject an effective amount of the salt of any one of Embodiments [A] to [BV] above, or the pharmaceutical composition of [Embodiment BW] above, or according to other embodiments of the invention.

EMBODIMENT CF

A process of preparing (R)-1-(8-fluoroisochroman-1-yl)-N-methylmethanamine phosphate (Compound 1 Phosphate), having the structure:

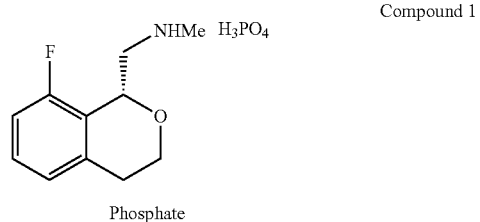

Compound 1 Phosphate comprising reacting (R)-1-(8-fluoroisochroman-1-yl)-N-methylmethanamine (Compound 1) having the structure:

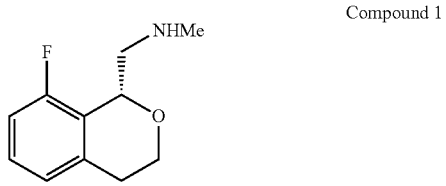 [SMILES: CNC[C@@H]1OCCc2cccc(F)c21]

Compound 1 with phosphoric acid.

EMBODIMENT CG

The process of Embodiment [CF] above, or according to other embodiments of the invention, wherein the phosphoric acid is an aqueous solution of phosphoric acid.

EMBODIMENT CH

The process of Embodiment [CF] above, or according to other embodiments of the invention, wherein the aqueous solution of phosphoric acid is an about 80% to about 95% aqueous solution of phosphoric acid by weight.

EMBODIMENT CI

The process of Embodiment [CF] above, or according to other embodiments of the invention, wherein the aqueous solution of phosphoric acid is an about 87% aqueous solution of phosphoric acid by weight.

EMBODIMENT CJ

The process of any one of Embodiments [CF] to [CI] above, or according to other embodiments of the invention, wherein the reacting of Compound 1 with phosphoric acid is carried out in the presence of S1a, wherein S1a is a solvent.

EMBODIMENT CK

The process of Embodiment [CJ] above, or according to other embodiments of the invention, wherein S1a is a mixture of acetonitrile and water.

EMBODIMENT CL

The process of Embodiment [CJ] above, or according to other embodiments of the invention, wherein S1a is a mixture of acetone and water.

EMBODIMENT CM

The process of Embodiment [CJ] above, or according to other embodiments of the invention, wherein S1a is a polar aprotic solvent, water, or a mixture thereof.

EMBODIMENT CN

The process of any one of Embodiments [CF] to [CM] above, or according to other embodiments of the invention, wherein between about 1 and about 5 molar equivalents of phosphoric acid are used per molar equivalent of Compound 1.

EMBODIMENT CO

The process of any one of Embodiments [CF] to [CN] above, or according to other embodiments of the invention, wherein Compound 1 is prepared by a process comprising reacting (R)-1-(8-fluoroisochroman-1-yl)-N-methylmethanamine dibenzoyl-L-tartrate (Compound 1 dibenzoyl-L-tartrate) having the structure:

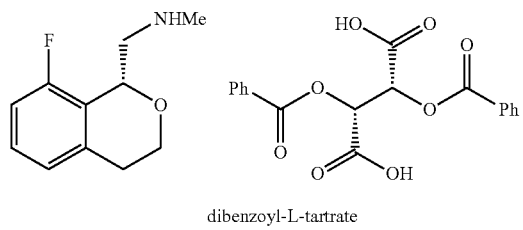

dibenzoyl-L-tartrate with B1, wherein B1 is a base.

EMBODIMENT CP

A process of preparing (R)-1-(8-fluoroisochroman-1-yl)-N-methylmethanamine (Compound 1) comprising reacting (R)-1-(8-fluoroisochroman-1-yl)-N-methylmethanamine dibenzoyl-L-tartrate (Compound 1 dibenzoyl-L-tartrate) having the structure:

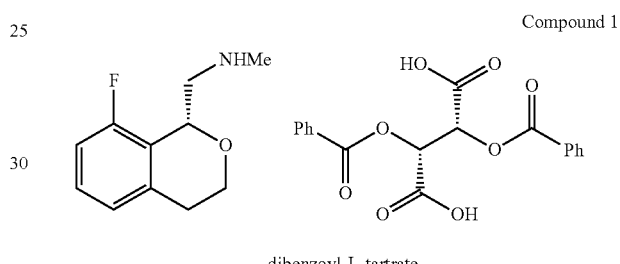

dibenzoyl-L-tartrate with B1, wherein B1 is a base.

EMBODIMENT CQ

The process of Embodiment [CO] or [CP] above, or according to other embodiments of the invention, wherein B1 is an alkali hydroxide base.

EMBODIMENT CR

The process of Embodiment [CO] or [CP] above, or according to other embodiments of the invention, wherein B1 is potassium hydroxide.

EMBODIMENT CS

The process of Embodiment [CO] or [CP] above, or according to other embodiments of the invention, wherein B1 is an aqueous solution of potassium hydroxide.

EMBODIMENT CT

The process of Embodiment [CS] above, or according to other embodiments of the invention, wherein the aqueous solution of potassium hydroxide is an about 10% to about 20% aqueous solution of potassium hydroxide by weight.

EMBODIMENT CU

The process of Embodiment [CS] above, or according to other embodiments of the invention, wherein the aqueous

87 solution of potassium hydroxide is an about 14% aqueous solution of potassium hydroxide by weight.

EMBODIMENT CV

The process of any one of Embodiments [CO] to [CU] above, or according to other embodiments of the invention, wherein the reacting of Compound 1 dibenzoyl-L-tartrate and the base is carried out in the presence of S2, wherein S2 is a solvent.

EMBODIMENT CW

The process of Embodiment [CV] above, or according to other embodiments of the invention, wherein S2 is a polar aprotic solvent.

EMBODIMENT CX

The process of any one of Embodiments [CO] to [CW] above, or according to other embodiments of the invention, wherein between about 0.5 and about 5 molar equivalents of B1 are used per molar equivalent of Compound 1 dibenzoyl-L-tartrate.

EMBODIMENT CY

The process of any one of Embodiments [CO] to [CX] above, or according to other embodiments of the invention, wherein the reacting of Compound 1 dibenzoyl-L-tartrate with B1 is further carried out in the presence of sodium chloride.

EMBODIMENT CZ

The process of any one of Embodiments [CO] to [CY] above, or according to other embodiments of the invention, wherein about 1 to about 10 molar equivalents of sodium chloride are used per molar equivalent of Compound 1 dibenzoyl-L-tartrate.

EMBODIMENT DA

A process for preparing (R)-1-(8-fluoroisochroman-1-yl)-N-methylmethanamine dibenzoyl-L-tartrate (Compound 1 dibenzoyl-L-tartrate), comprising reacting 1-(8-fluoroisochroman-1-yl)-N-methylmethanamine (Racemic Compound 1) having the structure:

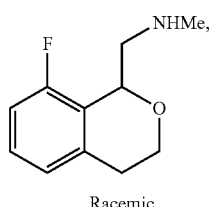

Compound 1

Racemic with dibenzoyl-L-tartaric acid in the presence of S3, wherein S3 is a solvent.

88

EMBODIMENT DB

The process of Embodiment [DA] above, or according to other embodiments of the invention, wherein S3 is a polar protic solvent.

EMBODIMENT DC

The process of Embodiment [DA] above, or according to other embodiments of the invention, wherein S3 is a mixture of methanol and water.

EMBODIMENT DD

The process of any one of Embodiments [DA] to [DC] above, or according to other embodiments of the invention, wherein about 1 to about 5 molar equivalents of dibenzoyl-L-tartaric acid are used per molar equivalent of Racemic Compound 1.

EMBODIMENT DE

The process of any one of Embodiments [DA] to [DD] above, or according to other embodiments of the invention, further comprising precipitating Compound 1 dibenzoyl-L-tartrate from a mixture comprising: Racemic Compound 1, dibenzoyl-L-tartaric acid, and S3.

EMBODIMENT DF

The process of any one of Embodiments [DA] to [DE] above, or according to other embodiments of the invention, further comprising isolating Compound 1 dibenzoyl-L-tartrate from S3a, wherein S3a is a solvent.

EMBODIMENT DG

The process of Embodiment [DF] above, or according to other embodiments of the invention, wherein S3a is methanol.

EMBODIMENT DH

The process of any one of Embodiments [DA] to [DG] above, or according to other embodiments of the invention, wherein 1-(8-fluoroisochroman-1-yl)-N-methylmethanamine (Racemic Compound 1) is prepared by a process comprising hydrogenating a compound of Formula II, having the structure:

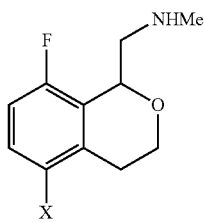

Formula II or a salt thereof, wherein X is halo, in the presence of a metal catalyst.

EMBODIMENT DI

The process of Embodiment [DH] above, or according to other embodiments of the invention, wherein the compound of Formula II is 1-(5-bromo-8-fluoroisochroman-1-yl)-N-methylmethanamine trifluoromethanesulfonate (Compound 2) having the structure:

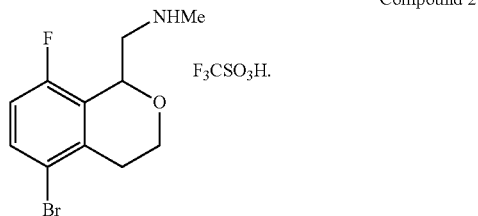

Compound 2

EMBODIMENT DJ

The process of Embodiment [DH] or [DI] above, or according to other embodiments of the invention, wherein the metal catalyst is palladium on activated carbon.

EMBODIMENT DK

The process of any one of Embodiments [DH] to [DJ] above, or according to other embodiments of the invention, wherein the hydrogenating of the compound of Formula II is carried out at a hydrogen pressure of about 2 to about 10 bar.

EMBODIMENT DL

The process of any one of Embodiments [DH] to [DK] above, or according to other embodiments of the invention, wherein the hydrogenating of the compound of Formula II is carried out at a hydrogen pressure of about 5 bar.

EMBODIMENT DM

The process of any one of Embodiments [DH] to [DL] above, or according to other embodiments of the invention, wherein the hydrogenating of the compound of Formula II is carried out in the presence of S4, wherein S4 is a solvent.

EMBODIMENT DN

The process of Embodiment [DM] above, or according to other embodiments of the invention, wherein S4 is a polar protic solvent.

EMBODIMENT DO

The process of any one of Embodiments [DH] to [DN] above, or according to other embodiments of the invention, wherein the hydrogenating of the compound of Formula II is carried out in the presence of B2, wherein B2 is a base.

EMBODIMENT DP

The process of Embodiment [DO] above, or according to other embodiments of the invention, wherein B2 is a carbonate base.

EMBODIMENT DQ

The process of Embodiment [DO] above, or according to other embodiments of the invention, wherein B2 is potassium carbonate.

EMBODIMENT DR

The process of Embodiment [DO] above, or according to other embodiments of the invention, wherein B2 is an aqueous solution of potassium carbonate.

EMBODIMENT DS

The process of any one of Embodiments [DH] to [DR] above, or according to other embodiments of the invention, wherein the compound of Formula II is prepared by reacting a compound of Formula III having the structure:

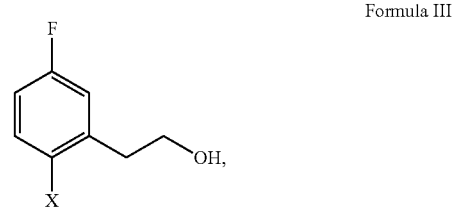

Formula III or a salt thereof, wherein X is halo, with N-methylamino-acetaldehyde dimethylacetal (Compound 4) having the structure:

Compound 4 in the presence of A1, wherein A1 is an acid.

EMBODIMENT DT

The process of Embodiment [DS] above, or according to other embodiments of the invention, wherein the compound of Formula III is 2-(2-bromo-5-fluorophenyl)ethan-1-ol (Compound 3) having the structure:

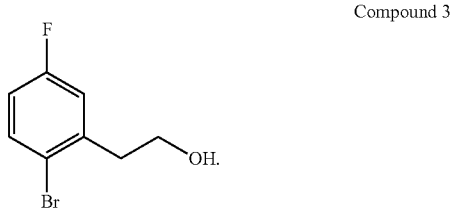 [SMILES: OCCc1cc(F)ccc1Br]

Compound 3

EMBODIMENT DU

The process of claim Embodiment [DS] or [DT] above, or according to other embodiments of the invention, wherein A1 is trifluoromethanesulfonic acid.

EMBODIMENT DV

The process of any one of Embodiments [DS] to [DU] above, or according to other embodiments of the invention, wherein the reacting of the compound of Formula III and Compound 4 is carried out in the presence of S5, wherein S5 is a solvent.

EMBODIMENT DW

The process of Embodiment [DV] above, or according to other embodiments of the invention, wherein S5 is a halogenated solvent.

EMBODIMENT DX

The process of any one of Embodiments [DS] to [DW] above, or according to other embodiments of the invention, wherein about 1.2 molar equivalents of Compound 4 are used per molar equivalent of the compound of Formula III.

EMBODIMENT DY

Compound 1 Phosphate prepared by the process of any one of Embodiments [CF] to [CO] above, or according to other embodiments of the invention, wherein Compound 1 Phosphate is crystalline.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A salt, which is:
crystalline (R)-1-(8-fluoroisochroman-1-yl)-N-methylmethanamine phosphate (Compound 1 Phosphate); or a hydrate or solvate thereof.

2. The salt of claim 1, wherein the salt has characteristic XRPD peaks in terms of 2θ selected from 4.6°±0.2°, 9.1°±0.2°, and 18.2°±0.2°.

3. The salt of claim 1, wherein the salt has at least one characteristic XRPD peak in terms of 2θ selected from 4.6°±0.2°, 9.1°±0.2°, 15.7°±0.2°, 18.2°±0.2°, 22.3°±0.2°, 22.8°±0.2°, and 24.8°±0.2°.

4. The salt of claim 1, wherein the salt has at least two characteristic XRPD peaks in terms of 2θ selected from 4.6°±0.2°, 9.1°±0.2°, 15.7°±0.2°, 18.2°±0.2°, 22.3°±0.2°, 22.8°±0.2°, and 24.8°±0.2°.

5. The salt of claim 1, wherein the salt has at least three characteristic XRPD peaks in terms of 2θ selected from 4.6°±0.2°, 9.1°±0.2°, 15.7°±0.2°, 18.2°±0.2°, 22.3°±0.2°, 22.8°±0.2°, and 24.8°±0.2°.

6. The salt of claim 1, wherein the salt has an XRPD pattern with characteristic peaks as substantially shown in FIG. 6.

7. The salt of claim 1, wherein the salt has an endotherm peak at a temperature of about 213° C.

8. The salt of claim 1, wherein the salt has a DSC thermogram substantially as depicted in FIG. 7.

9. The salt of claim 1, wherein the salt has a DVS isotherm substantially as depicted in FIG. 9.

10. A pharmaceutical composition comprising the salt of claim 1 and a pharmaceutically acceptable excipient.

11. A method for treating a neurological or psychiatric disease or disorder in a subject in need thereof, comprising administering to said subject an effective amount of the salt of claim 1.

12. The method according to claim 11, wherein the neurological or psychiatric disease or disorder is depression, bipolar disorder, pain, schizophrenia, or other psychotic diseases, obsessive compulsive disorder, addiction, social disorder, attention deficit hyperactivity disorder, an anxiety disorder, a movement disorder, epilepsy, autism or cognitive disease or disorder.

13. The method according to claim 11, wherein the neurological or psychiatric disease or disorder is depression.

14. The method according to claim 13, wherein the depression is treatment-resistant depression (TRD), major depressive disorder (MDD), unipolar depression, bipolar depression or depression associated with another disease or disorder.

15. The method according to claim 11, wherein said neurological disease or disorder is selected from Alzheimer's disease and Parkinson's disease.

16. The method according to claim 15, wherein said Alzheimer's disease is Alzheimer's disease with agitation, Alzheimer's disease with aggression, Alzheimer's disease agitation or Alzheimer's disease with agitation aggression.

17. A method of treating agitation in a subject in need thereof, comprising administering to said subject an effective amount of the salt of claim 1.

18. A method of treating agitation associated with a neurological or psychiatric disease or disorder in a subject in need thereof, comprising administering to said subject an effective amount of the salt of claim 1.

19. A process of preparing (R)-1-(8-fluoroisochroman-1-yl)-N-methylmethanamine phosphate (Compound 1 Phosphate), having the structure:

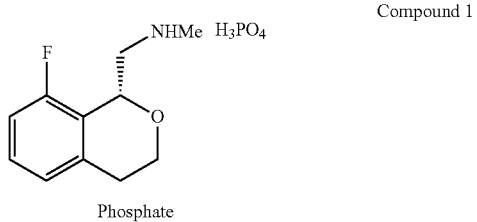

Compound 1 Phosphate comprising reacting (R)-1-(8-fluoroisochroman-1-yl)-N-methylmethanamine (Compound 1) having the structure:

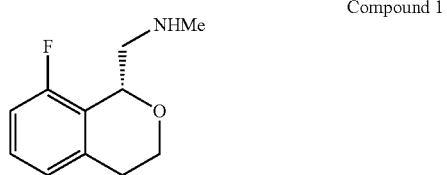 [SMILES: CNC[C@@H]1OCCc2cccc(F)c21]

Compound 1 with phosphoric acid.

20. A process of preparing (R)-1-(8-fluoroisochroman-1-yl)-N-methylmethanamine (Compound 1) comprising reacting (R)-1-(8-fluoroisochroman-1-yl)-N-methylmethanamine dibenzoyl-L-tartrate (Compound 1 dibenzoyl-L-tartrate) having the structure:

with B1, wherein B1 is a base.

21. A process for preparing (R)-1-(8-fluoroisochroman-1-yl)-N-methylmethanamine dibenzoyl-L-tartrate (Compound 1 dibenzoyl-L-tartrate), comprising reacting 1-(8-fluoroisochroman-1-yl)-N-methylmethanamine (Racemic Compound 1) having the structure:

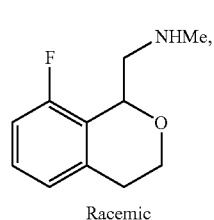

Racemic Compound 1 with dibenzoyl-L-tartaric acid in the presence of S3, wherein S3 is a solvent.

22. Compound 1 Phosphate prepared by the process of claim 19, wherein Compound 1 Phosphate is crystalline.

* * * * *

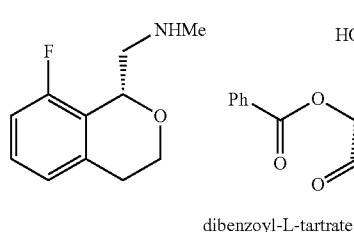

Compound 1 · dibenzoyl-L-tartrate